(12) United States Patent
Miyamoto et al.

(10) Patent No.: US 8,445,509 B2
(45) Date of Patent: May 21, 2013

(54) FUSED HETEROCYCLIC DERIVATIVES AND USE THEREOF

(75) Inventors: Naoki Miyamoto, Tsukuba (JP); Shigemitsu Matsumoto, Tsukuba (JP); Shinichi Imamura, Tsukuba (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 333 days.

(21) Appl. No.: 12/990,760

(22) PCT Filed: May 7, 2009

(86) PCT No.: PCT/JP2009/058962
§ 371 (c)(1),
(2), (4) Date: Nov. 2, 2010

(87) PCT Pub. No.: WO2009/136663
PCT Pub. Date: Nov. 12, 2009

(65) Prior Publication Data
US 2011/0046169 A1 Feb. 24, 2011

(30) Foreign Application Priority Data

May 8, 2008 (JP) .................................. 2008-122789
Dec. 1, 2008 (JP) .................................. 2008-306661

(51) Int. Cl.
*A61K 31/44* (2006.01)
*C07D 491/02* (2006.01)
*C07D 498/02* (2006.01)

(52) U.S. Cl.
USPC ........................................... 514/300; 546/121

(58) Field of Classification Search
USPC .................. 514/274, 300, 301, 303; 546/121, 546/114, 119; 548/163; 544/316
See application file for complete search history.

(56) References Cited

U.S. PATENT DOCUMENTS

| | | | |
|---|---|---|---|
| 4,096,264 A | 6/1978 | Bochis et al. | |
| 4,177,274 A | 12/1979 | Bochis et al. | |
| 4,237,300 A | 12/1980 | Bochis et al. | |
| 8,034,812 B2 * | 10/2011 | Sakai et al. | 514/248 |
| 8,044,049 B2 * | 10/2011 | Sakai et al. | 514/248 |
| 8,273,741 B2 * | 9/2012 | Sakai et al. | 514/248 |
| 2009/0137595 A1 | 5/2009 | Sakai et al. | |
| 2010/0029619 A1 | 2/2010 | Uchikawa et al. | |
| 2010/0216810 A1 | 8/2010 | Okaniwa et al. | |

FOREIGN PATENT DOCUMENTS

| | | | |
|---|---|---|---|
| EP | 2 181 987 | | 5/2010 |
| EP | 2 184 285 | | 5/2010 |
| JP | 52-73896 | | 6/1977 |
| WO | 02/44156 | | 6/2002 |
| WO | 2005/118587 | | 12/2005 |
| WO | 2009/025358 | | 2/2006 |
| WO | 2007/004749 | | 1/2007 |
| WO | 2008/016131 | | 2/2008 |
| WO | 2008/016192 | | 2/2008 |
| WO | 2009096435 | * | 2/2008 |
| WO | 2008/150015 | | 12/2008 |
| WO | 2009/028629 | | 3/2009 |
| WO | 2008016192 | * | 8/2009 |
| WO | 2010/064611 | | 6/2010 |
| WO | 2010/064722 | | 6/2010 |

OTHER PUBLICATIONS

Baselga et al., Nature, vol. 10, No. 8, (2004), pp. 786-787.*

* cited by examiner

*Primary Examiner* — Niloofar Rahmani
(74) *Attorney, Agent, or Firm* — Hamre, Schumann, Mueller & Larson, P.C.

(57) ABSTRACT

The present invention provides a fused heterocyclic derivative having a strong kinase inhibitory activity and use thereof. The present invention relates to a compound represented by the formula

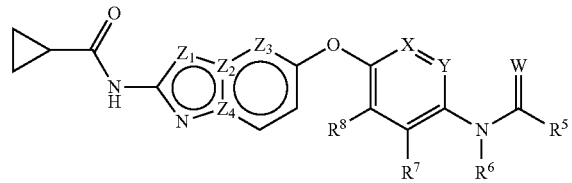

wherein each symbol is as defined in the present specification, or a salt thereof.

8 Claims, No Drawings

FUSED HETEROCYCLIC DERIVATIVES AND USE THEREOF

TECHNICAL FIELD

The present invention relates to a fused heterocyclic derivative having a potent kinase inhibitory activity and useful for the prophylaxis or treatment of cancer and the like, and use thereof.

BACKGROUND OF THE INVENTION

For a solid tumor to grow to a certain size or above, angiogenesis is essential for ensuring sufficient supply of nutrition and oxygen to cancer cell (see, for example, Non Patent Literature 1). One of the important factors causing angiogenesis toward tumor, a vascular endothelial growth factor (VEGF) is known. VEGF is bound to a vascular endothelial growth factor receptor (VEGFR) expressed on vascular endothelial cells and transmits signal for cell proliferation (see, for example, Non Patent Literature 2). Accordingly, inhibition of the VEGF-VEGFR signal transduction system is considered to enable suppression of angiogenesis and tumor growth (see, for example, Non Patent Literature 3). Moreover, since tumor blood vessels are involved in cancer hematogenous metastasis, inhibition of angiogenesis is considered to be effective for suppression of cancer metastasis.

Hepatocyte growth factor (HGF) is known to promote growth of vascular endothelial cell via its receptor (c-Met), and cause angiogenesis (see, for example, Non Patent Literature 4). It has been clarified that c-Met is highly expressed in various types of cancers (colorectal cancer, gastric cancer, lung cancer, kidney cancer, breast cancer, ovary cancer, prostate cancer and the like), and is deeply involved in the growth and survival of cancer cells (see, for example, Non Patent Literature 5). Therefore, cancer cell growth is expected to be suppressed by inhibiting c-Met. Moreover, activation of c-Met is also involved in the invasion and metastasis of cancer cells (see, for example, Non Patent Literature 6), and inhibition of c-Met is considered to be effective for the prevention of invasion or metastasis of cancer.

Tyrosine Kinase with Immunoglobulin and Epidermal Growth homology domain 2 (TIE2) is a receptor of angiopoietin (angiopoietin 1 and angiopoietin 2), mainly expressed in vascular endothelial cells and is known to be indispensable for the development of blood vessels in the fetal stages (see, for example, Non Patent Literature 7). It has been reported that inhibition of binding of angiopoietin with solubilized form TIE2 etc. decreases tumor blood vessel density and suppresses tumor growth in non-clinical model (see, for example, Non Patent Literature 8). The system of angiopoietin TIE2 is suggested to play a key role in the tumor angiogenesis, along with the VEGF-VEGFR system. Therefore, inhibition of TIE2 is considered to suppress angiogenesis as well as tumor growth.

Fms Like Tyrosine Kinase 3 (FLT3) is mutated most frequently in acute myelocytic leukemia (AML), and is known to be constitutively activated even in the absence of a ligand, by length mutation (FLT3-ITD mutation) of transmembrane portion, which is called Internal Tandem Duplication (ITD), or activated mutation of tyrosine kinase portion (see, for example, Non Patent Literature 9). It is considered that signals from FLT3 activate downstream AKT, extracellular signal regulated kinase (ERK), signal transducer and activator of transcription (STATS), and are involved in the growth of leukemia cells and suppression of differentiation (see, for example, Non Patent Literature 10). Particularly, the FLT3-ITD mutation observed in 20-30% of AML patients has been reported to correlate with poor life prognosis (see, for example, Non Patent Literature 11). Therefore, inhibition of FLT3 is considered to suppress growth of leukemia cells.

As compounds inhibiting kinase including VEGFR and c-Met, phthalazine derivatives (see, for example, Patent Literature 1), pyrrole-substituted 2-indolinone derivatives (see, for example, Patent Literature 2), quinazoline derivatives (see, for example, Patent Literature 3), ω-carboxyaryl-substituted diphenylurea derivatives (see, for example, Patent Literature 4), quinoline derivatives and quinazoline derivatives (see, for example, Patent Literature 5), nitrogen-containing aromatic ring derivatives (see, for example, Patent Literature 6), quinoline derivatives and quinazoline derivative (see, for example, Patent Literature 7) and the like are known.

CITATION LIST

Patent Literature

PTL 1: WO98/35958
PTL 2: WO01/60814
PTL 3: WO01/32651
PTL 4: WO00/42012
PTL 5: WO00/43366
PTL 6: WO02/32872
PTL 7: WO03/000660

Non Patent Literature

NPL 1: New England Journal of Medicine, 1971, vol. 285, No. 21, pages 1182-1186
NPL 2: Endocrine Reviews, 1997, vol. 18, No. 1, pages 4-25
NPL 3: Drug Discovery Today, 2001, vol. 6, No. 19, pages 1005-1024
NPL 4: EXS, 1997, vol. 79, pages 193-208
NPL 5: Cytokine & Growth Factor Reviews, 2002, vol. 13, No. 1, pages 41-59
NPL 6: Nature Reviews Molecular Cell Biology, 2003, vol. 4, No. 12, pages 915-925
NPL 7: Genes and Development, 1994, vol. 8, No. 16, pages 1897-1909
NPL 8: The Journal of Clinical investigation, 1997, No. 100, No. 8, pages 2072-2078
NPL 9: Leukemia, 1996, vol. 10, No. 12, pages 1911-1918
NPL 10: Blood, 2000, vol. 96, No. 12, pages 3907-3914
NPL 11: Blood, 2001, vol. 98, No. 6, pages 1752-1759

SUMMARY OF INVENTION

Technical Problem

A kinase inhibitor superior in the affinity for kinase, efficacy expression, pharmacokinetics, solubility, interaction with other pharmaceutical products, safety and stability is expected to show a therapeutically superior effect. At present, however, such inhibitor superior in the affinity for kinase, and sufficiently satisfactory in the efficacy expression, pharmacokinetics, solubility, interaction with other pharmaceutical products, safety and stability has not been found. Thus, there is a demand for the development of a compound having a superior kinase inhibitory activity, and sufficiently satisfactory as a pharmaceutical product. Accordingly, an object of the present invention is to provide a compound having a superior kinase inhibitory activity, low toxic and sufficiently satisfactory as a pharmaceutical product.

Solution to Problem

The present inventors have conducted intensive studies in an attempt to solve the above-mentioned problems and found that a compound represented by the following formula or a salt thereof has a superior kinase inhibitory activity, which resulted in the completion of the present invention.

Accordingly, the present invention provides the following.

[1] A compound represented by the formula (I):

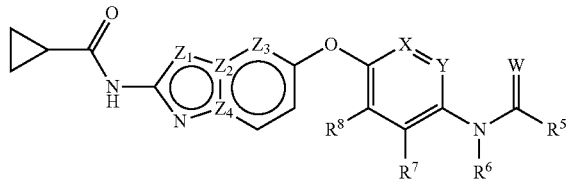

wherein $Z_1$, $Z_2$, $Z_3$ and $Z_4$ are in the following combination:

$(Z_1,Z_2,Z_3,Z_4)$=$(CR^1,N,CR^2,C)$, (N,N,$CR^2$,C), (N,C,$CR^2$,N)

(S,C,$CR^2$,C), or (S,C,N,C);

$R^1$ and $R^2$ are the same or different and each is (1) a hydrogen atom, (2) a halogen atom, (3) a group bonded via a carbon atom, (4) a group bonded via a nitrogen atom, (5) a group bonded via an oxygen atom, or (6) a group bonded via a sulfur atom;

W is O or S;

X is $CR^3$ ($R^3$ is a hydrogen atom, a halogen atom or $C_{1-6}$ alkyl), or N;

Y is $CR^4$ ($R^4$ is a hydrogen atom, a halogen atom or $C_{1-6}$ alkyl), or N;

$R^5$ is (1) $C_{3-6}$ cycloalkyl optionally having one $C_{6-10}$ aryl-aminocarbonyl optionally having 1 to 3 substituents selected from a halogen atom and $C_{1-6}$ alkyl, (2) $C_{1-6}$ alkyl-carbonylamino optionally having one $C_{6-10}$ aryl, (3) $C_{1-6}$ alkoxy optionally having one $C_{6-10}$ aryl, or (4) a nitrogen-containing heterocyclic group or an N-oxide thereof optionally having 1 to 4 substituents selected from (a) $C_{6-10}$ aryl optionally having 1 to 3 substituents selected from a halogen atom and $C_{1-6}$ alkyl, (b) $C_{1-6}$ alkyl optionally having 1 to 3 halogen atoms, and (c) oxo;

$R^6$ is a hydrogen atom;

$R^7$ is a hydrogen atom, a halogen atom or $C_{1-6}$ alkyl; and $R^8$ is a hydrogen atom, a halogen atom or $C_{1-6}$ alkyl, or a salt thereof (to be referred to as "compound (I)" in the present specification);

[2] a compound represented by the formula

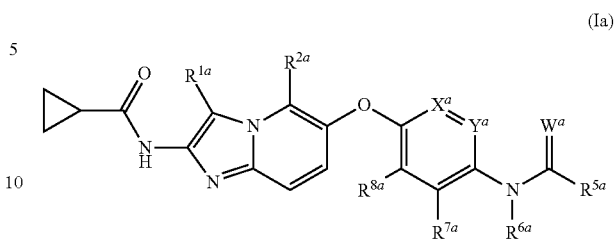

wherein $R^{1a}$ and $R^{2a}$ are the same or different and each is (1) a hydrogen atom, (2) a halogen atom, (3) a group bonded via a carbon atom, (4) a group bonded via a nitrogen atom, (5) a group bonded via an oxygen atom, or (6) a group bonded via a sulfur atom;

$W^a$ is O or S;

$X^a$ is $CR^{3a}$ ($R^{3a}$ is a hydrogen atom, a halogen atom or $C_{1-6}$ alkyl), or N;

$Y^a$ is $CR^{4a}$ ($R^{4a}$ is a hydrogen atom, a halogen atom or $C_{1-6}$ alkyl), or N;

$R^{5a}$ is (1) $C_{3-6}$ cycloalkyl optionally having one $C_{6-10}$ aryl-aminocarbonyl optionally having 1 to 3 substituents selected from a halogen atom and $C_{1-6}$ alkyl, (2) $C_{1-6}$ alkyl-carbonylamino optionally having one $C_{6-10}$ aryl, (3) $C_{1-6}$ alkoxy optionally having one $C_{6-10}$ aryl, or (4) a nitrogen-containing heterocyclic group or an N-oxide thereof optionally having 1 to 4 substituents selected from (a) $C_{6-10}$ aryl optionally having 1 to 3 substituents selected from a halogen atom and $C_{1-6}$ alkyl, (b) $C_{1-6}$ alkyl optionally having 1 to 3 halogen atoms, and (c) oxo;

$R^{6a}$ is a hydrogen atom;

$R^{7a}$ is a hydrogen atom, a halogen atom or $C_{1-6}$ alkyl;

$R^{8a}$ is a hydrogen atom, a halogen atom or $C_{1-6}$ alkyl, or a salt thereof (to be referred to as "compound (Ia)" in the present specification);

[3] the compound of the above-mentioned [2] wherein $R^{1a}$ is a hydrogen atom, a fluorine atom or methyl;

$R^{2a}$ is a hydrogen atom;

$W^a$ is O or S;

$X^a$ is CH, CF, CCl, C(CH$_3$) or N;

$Y^a$ is CH, CF, CCl, C(CH$_3$) or N;

$R^{5a}$ is (1) cyclopropyl optionally having one phenylaminocarbonyl optionally having 1 to 3 substituents selected from a fluorine atom and methyl, (2) acetylamino optionally having one phenyl, (3) methoxy optionally having one phenyl, (4) tert-butoxy, or (5) a nitrogen-containing heterocyclic group or an N-oxide thereof optionally having 1 to 4 substituents selected from (a) phenyl optionally having 1 to 3 substituents selected from a fluorine atom, a chlorine atom, a bromine atom, methyl and isopropyl, (b) methyl optionally having 1 to 3 fluorine atoms, (c) ethyl optionally having 1 to 3 fluorine atoms, (d) isopropyl, and (e) oxo;

$R^{6a}$ is a hydrogen atom;

$R^{7a}$ is a hydrogen atom; and $R^{8a}$ is a hydrogen atom;

[4] N-[4-({2-[(cyclopropylcarbonyl)amino]imidazo[1,2-a]pyridin-6-yl}oxy)-3-fluorophenyl]-N'-phenylcyclopropane-1,1-dicarboxamide or a salt thereof;

[5] N-[4-({2-[(cyclopropylcarbonyl)amino]imidazo[1,2-a]pyridin-6-yl}oxy)-3-fluorophenyl]-6-methyl-2-oxo-1-phenyl-1,2-dihydropyridine-3-carboxamide or a salt thereof;

[6] N-[4-({2-[(cyclopropylcarbonyl)amino]imidazo[1,2-a]pyridin-6-yl}oxy)-3-fluorophenyl]-1-(4-fluorophenyl)-6-methyl-2-oxo-1,2-dihydropyridine-3-carboxamide or a salt thereof;

[7] N-[5-({2-[(cyclopropylcarbonyl)amino]imidazo[1,2-a]pyridin-6-yl}oxy)pyridin-2-yl]-6-(4-fluorophenyl)-5-methylpyridine-2-carboxamide 1-oxide or a salt thereof;

[8] a prodrug of the compound of the above-mentioned [1];

[9] a pharmaceutical agent comprising the compound of the above-mentioned [1] or a prodrug thereof;

[10] the pharmaceutical agent of the above-mentioned [9], which is a kinase inhibitor;

[11] the pharmaceutical agent of the above-mentioned [9], which is an agent for the prophylaxis or treatment of cancer;

[12] a method for the prophylaxis or, treatment of cancer, which comprises administering an effective amount of the compound of the above-mentioned [1] or a prodrug thereof to the mammal;

[13] use of the compound of the above-mentioned [1] or a prodrug thereof for the production of an agent for the prophylaxis or treatment of cancer; and the like.

Advantageous Effects of Invention

The compound (I) and a prodrug thereof have a strong inhibitory activity against kinases such as vascular endothelial growth factor receptor, hepatocyte growth factor receptor, angiopoietin receptor, Fms Like Tyrosine Kinase 3 (FLT3), platelet-derived growth factor receptor and the like, and have a strong angiogenesis inhibitory activity, cancer cell proliferation inhibitory action and the like. Therefore, they can provide clinically useful agents for the prophylaxis or treatment of cancer, cancer growth inhibitors or cancer invasion and/or metastasis suppressors. Moreover, compound (I) and a prodrug thereof can provide clinically useful agents for the prophylaxis or treatment of applications to diseases other than cancer, such as chronic rheumatism, diabetic retinopathy and the like, and have excellent efficacy expression, pharmacokinetics, solubility, interaction with other pharmaceutical products, safety and stability.

DETAILED DESCRIPTION OF THE INVENTION

The present invention is explained in detail in the following.

In the present specification, the term "halogen atom" means a fluorine atom, a chlorine atom, a bromine atom or an iodine atom.

In the present specification, the term "$C_{1-6}$ alkyl" means, for example, methyl, ethyl, propyl, isopropyl, butyl, isobutyl, sec-butyl, tert-butyl, pentyl, hexyl and the like.

In the present specification, the term "$C_{3-6}$ cycloalkyl" means, for example, cyclopropyl, cyclobutyl, cyclopentyl, cyclohexyl and the like.

In the present specification, the term "$C_{6-10}$ aryl" means, for example, phenyl, naphthyl and the like.

In the present specification, the term "$C_{1-6}$ alkoxy" means methoxy, ethoxy, propoxy, isopropoxy, butoxy, isobutoxy, sec-butoxy, tert-butoxy and the like.

In the present specification, the term "$C_{1-6}$ alkyl-carbonylamino" means, for example, acetylamino, ethylcarbonylamino, propylcarbonylamino, isopropylcarbonylamino, butylcarbonylamino, isobutylcarbonylamino, sec-butylcarbonylamino, tert-butylcarbonylamino and the like.

In the present specification, the term "$C_{6-10}$ aryl-aminocarbonyl" means, for example, phenylaminocarbonyl, naphthylaminocarbonyl and the like.

In the present specification, the term "heterocyclic group" means, for example, a monocyclic aromatic heterocyclic group, a fused aromatic heterocyclic group or a nonaromatic heterocyclic group.

The "monocyclic aromatic heterocyclic group" means, for example, a 5- to 7-membered (preferably 5- or 6-membered) monocyclic aromatic heterocyclic group containing, as a ring constituting atom besides carbon atom, 1 to 4 hetero atoms selected from an oxygen atom, a sulfur atom (optionally oxidized) and a nitrogen atom, and the like. Examples thereof include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl, 5-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-4-yl), tetrazolyl (e.g., tetrazol-1-yl, tetrazol-5-yl), triazinyl (e.g., 1,3,5-triazin-2-yl) and the like.

The fused aromatic heterocyclic group includes a 9- to 12-membered fused aromatic heterocyclic group formed by fusion of a 5- to 7-membered monocyclic aromatic heterocyclic group containing, as ring-constituting atom besides carbon atom, 1 to 4 heteroatoms selected from an oxygen atom, a sulfur atom (optionally oxidized) and a nitrogen atom, and the like, and $C_{6-10}$ aryl and the like; a 8- to 12-membered fused aromatic heterocyclic group formed by fusion of 5- to 7-membered monocyclic aromatic heterocyclic groups, and the like. Examples thereof include quinolyl (e.g., 2-quinolyl, 3-quinolyl, 4-quinolyl), isoquinolyl (e.g., 1-isoquinolyl, 3-isoquinolyl, 4-isoquinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), isobenzofuryl (e.g., 1-isobenzofuryl, 3-isobenzofuryl), benzothienyl (e.g., 2-benzothienyl, 3-benzothienyl), isobenzothienyl (e.g., 1-isobenzothienyl, 3-isobenzothienyl), benzoxazolyl (e.g., 2-benzoxazolyl), benzothiazolyl (e.g., 2-benzothiazolyl, 5-benzothiazolyl, 6-benzothiazolyl), benzimidazolyl (e.g., benzimidazol-1-yl, benzimidazol-2-yl, benzimidazol-5-yl), indolyl (e.g., indol-1-yl, indol-2-yl, indol-3-yl, indol-4-yl, indol-5-yl, indol-6-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl), imidazopyrazinyl (e.g., 1H-imidazo[4,5-b]pyrazin-2-yl), benzisoxazolyl (e.g., benzisoxazol-3-yl), benzotriazolyl (e.g., 1H-1,2,3-benzotriazol-5-yl), benzopyrazolyl (e.g., benzopyrazol-5-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

Examples of the "nonaromatic heterocyclic group" include a 3- to 8-membered nonaromatic heterocyclic group containing, as a ring constituting atom besides carbon atom, 1 to 4 hetero atoms selected from an oxygen atom, a sulfur atom (optionally oxidized) and a nitrogen atom, and the like. Examples thereof include oxiranyl (e.g., 2-oxiranyl), azetidinyl (e.g., 1-azetidinyl, 2-azetidinyl, 3-azetidinyl), oxetanyl (e.g., 2-oxetanyl, 3-oxetanyl), thietanyl (e.g., 2-thietanyl, 3-thietanyl), pyrrolidinyl (e.g., 1-pyrrolidinyl, 2-pyrrolidinyl, 3-pyrrolidinyl), tetrahydrofuryl (e.g., 2-tetrahydrofuryl, 3-tetrahydrofuryl), thioranyl (e.g., 2-thioranyl, 3-thioranyl), piperidinyl (e.g., 1-piperidinyl, 2-piperidinyl, 3-piperidinyl, 4-piperidinyl), tetrahydropyranyl (e.g., 2-tetrahydropyranyl, 3-tetrahydropyranyl, 4-tetrahydropyranyl), thianyl (e.g., 2-thianyl, morpholinyl (e.g., 2-morpholinyl, 3-morpholinyl, 4-morpholinyl), thiomorpholinyl (e.g., 2-thiomorpholinyl, 3-thiomorpholinyl, 4-thiomorpholinyl), piperazinyl (e.g., 1-piperazinyl, 2-piperazinyl), azepanyl (e.g., 1-azepanyl, 3-azepanyl), oxepanyl (e.g., 3-oxepanyl), thiepanyl (e.g., 3-thiepanyl), oxazepanyl (e.g., 1,4-oxazepan-4-yl, 1,4-oxazepan-5-yl), thiazepanyl (e.g., 1,4-thiazepan-4-yl, 1,4-thiazepan-5-yl), azocanyl (e.g., 1-azocanyl, 4-azocanyl), oxocanyl (e.g., 4-oxocanyl), thiocanyl (e.g., 4-thiocanyl), oxazocanyl (e.g., 1,4-oxazocan-5-yl), thioazocanyl (e.g., 1,4-thioazocan-5-yl), dioxinyl (e.g., 1,4-dioxin-2-yl), dihydropyrazolyl (e.g., 2,3-dihydropyrazol-1-yl, 2,3-dihydropyrazol-3-yl, 2,3-dihydropyrazol-4-yl, 2,3-dihydropyrazol-5-yl), hexahydropyrimidinyl (e.g., hexahydropyrimidin-1-yl, hexahydropyrimidin-2-yl, hexahydropyrimidin-4-yl, hexahydropyrimidin-5-yl), tetrahydropyrimidinyl (e.g., 1,2,3,4-tetrahydropyrimidin-1-yl, 1,2,3,4-tetrahydropyrimidin-2-yl, 1,2,5,6-tetrahydropyrimidin-1-yl, 1,2,5,6-tetrahydropyrimidin-2-yl), dihydropyrimidinyl (e.g., 1,2-dihydropyrimidin-1-yl, 1,2-dihydropyrimidin-2-yl), tetrahydropyridyl (e.g., 1,2,3,4-tetrahydropyridin-1-yl, 1,2,3,4-tetrahydropyridin-2-yl, 1,2,5,6-tetrahydropyridin-1-yl, 1,2,5,6-tetrahydropyridin-2-yl), dihydropyridyl (e.g., 1,2-dihydropyridin-1-yl, 1,2-dihydropyridin-2-yl, 1,2-dihydropyridin-3-yl, 1,2-dihydropyridin-4-yl), tetrahydroimidazolyl (e.g., tetrahydroimidazol-1-yl, tetrahydroimidazol-2-yl, tetrahydroimidazol-4-yl), dihydroimidazolyl (e.g., 4,5-dihydroimidazol-1-yl, 4,5-dihydroimidazol-2-yl, 4,5-dihydroimidazol-4-yl, 4,5-dihydroimidazol-5-yl) and the like.

In the present specification, the term "group bonded via a carbon atom" means, for example, cyano, a hydrocarbon group optionally having substituent(s), a heterocyclic group bonded via a carbon atom optionally having substituent(s) and the like.

Examples of the "hydrocarbon group optionally having substituent(s)" include alkyl optionally having substituent(s), alkenyl optionally having substituent(s), alkynyl optionally having substituent(s), cycloalkyl optionally having substituent(s), cycloalkenyl optionally having substituent(s), aryl optionally having substituent(s), cycloalkyl-alkyl optionally having substituent(s), cycloalkenyl-alkyl optionally having substituent(s), aryl-alkyl optionally having substituent(s), cycloalkanedienyl optionally having substituent(s) and the like.

In the present specification, the term "alkyl optionally having substituent(s)" means $C_{1-6}$ alkyl optionally having 1 to 3 substituents selected from the following substituent group (hereinafter to be abbreviated as substituent group A).

Substituent Group A:
(1) a halogen atom;
(2) cyano;
(3) nitro;
(4) hydroxy;
(5) $C_{1-6}$ alkoxy optionally having 1 to 3 halogen atoms;
(6) $C_{2-6}$ alkenyloxy (e.g., ethenyloxy, propenyloxy, butenyloxy, pentenyloxy, hexenyloxy etc.) optionally having 1 to 3 halogen atoms;
(7) $C_{2-6}$ alkynyloxy (e.g., ethynyloxy, propynyloxy, butynyloxy, pentynyloxy, hexynyloxy etc.) optionally having 1 to 3 halogen atoms;
(8) $C_{3-6}$ cycloalkyloxy (e.g., cyclopropyloxy, cyclobutyloxy, cyclopentyloxy, cyclohexyloxy etc.) optionally having 1 to 3 halogen atoms;
(9) $C_{3-6}$ cycloalkenyloxy (e.g., cyclopropenyloxy, cyclobutenyloxy, cyclopentenyloxy, cyclohexenyloxy etc.) optionally having 1 to 3 halogen atoms;
(10) $C_{6-10}$ aryloxy (e.g., phenyloxy, 1-naphthyloxy, 2-naphthyloxy etc.) optionally having 1 to 3 substituents (excluding oxo) selected from substituent group B and substituent group C (mentioned later);
(11) $C_{3-6}$ cycloalkyl-$C_{1-6}$ alkoxy (e.g., cyclopropylmethyloxy, cyclopropylethyloxy, cyclobutylmethyloxy, cyclopentylmethyloxy, cyclohexylmethyloxy, cyclohexylethyloxy etc.) optionally having 1 to 3 halogen atoms;
(12) $C_{3-6}$ cycloalkenyl-$C_{1-6}$ alkoxy (e.g., cyclopentenylmethyloxy, cyclohexenylmethyloxy, cyclohexenylethyloxy, cyclohexenylpropyloxy etc.) optionally having 1 to 3 halogen atoms;
(13) $C_{6-10}$ aryl-$C_{1-6}$ alkoxy (e.g., phenylmethyloxy, phenylethyloxy etc.) optionally having 1 to 3 substituents (excluding oxo) selected from substituent group B and substituent group C (mentioned later);
(14) $C_{1-6}$ alkylsulfamoyl (e.g., methylsulfamoyl, ethylsulfamoyl, propylsulfamoyl etc.);
(15) di-$C_{1-6}$ alkylsulfamoyl (e.g., dimethylsulfamoyl, diethylsulfamoyl, dipropylsulfamoyl etc.);
(16) $C_{1-6}$ alkylamino-carbonyl (e.g., methylaminocarbonyl, ethylaminocarbonyl, propylaminocarbonyl etc.);
(17) di-$C_{1-6}$ alkylamino-carbonyl (e.g., dimethylaminocarbonyl, diethylaminocarbonyl, dipropylaminocarbonyl etc.);
(18) formyl;
(19) $C_{1-6}$ alkyl-carbonyl (e.g., acetyl, ethylcarbonyl, propylcarbonyl, isopropylcarbonyl etc.);
(20) $C_{2-6}$ alkenyl-carbonyl (e.g., ethenylcarbonyl, propenylcarbonyl, butenylcarbonyl, pentenylcarbonylz, hexenylcarbonyl etc.);
(21) $C_{2-6}$ alkynyl-carbonyl (e.g., ethynylcarbonyl, propynylcarbonyl, butynylcarbonyl, pentynylcarbonyl, hexynylcarbonyl etc.);
(22) $C_{3-6}$ cycloalkyl-carbonyl (e.g., cyclopropylcarbonyl, cyclobutylcarbonyl, cyclopentylcarbonyl, cyclohexylcarbonyl etc.);
(23) $C_{3-6}$ cycloalkenyl-carbonyl (e.g., cyclopropenylcarbonyl, cyclobutenylcarbonyl, cyclopentenylcarbonyl, cyclohexenylcarbonyl etc.);
(24) $C_{6-10}$ aryl-carbonyl (e.g., benzoyl, 1-naphthylcarbonyl, 2-naphthylcarbonyl etc.);
(25) $C_{3-6}$ cycloalkyl-$C_{1-6}$ alkyl-carbonyl (e.g., cyclopropylmethylcarbonyl, cyclopropylethylcarbonyl, cyclobutylmethylcarbonyl, cyclopentylmethylcarbonyl, cyclohexylmethylcarbonyl, cyclohexylethylcarbonyl etc.);
(26) $C_{3-6}$ cycloalkenyl-$C_{1-6}$ alkyl-carbonyl (e.g., cyclopentenylmethylcarbonyl, cyclohexenylmethylcarbonyl, cyclohexenylethylcarbonyl, cyclohexenyipropylcarbonyl etc.);
(27) $C_{6-10}$ aryl-$C_{1-6}$ alkyl-carbonyl (e.g., benzylcarbonyl, phenylethylcarbonyl etc.);
(28) 5- or 6-membered monocyclic aromatic heterocyclyl-carbonyl (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyridylcarbonyl, pyrazolylcarbonyl etc.);

(29) 8- to 12-membered fused aromatic heterocyclyl-carbonyl (e.g., benzofurylcarbonyl, isobenzofurylcarbonyl, benzothienylcarbonyl, isobenzothienylcarbonyl, indolylcarbonyl, isoindolylcarbonyl, 1H-indazolylcarbonyl, benzimidazolylcarbonyl, benzoxazolylcarbonyl etc.);

(30) 3- or 8-membered non-aromatic heterocyclyl-carbonyl (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidinylcarbonyl etc.);

(31) $C_{1-6}$ alkylsulfonyl (e.g., methylsulfonyl, ethylsulfonyl etc.);

(32) $C_{2-6}$ alkenylsulfonyl (e.g., ethenylsulfonyl, propenylsulfonyl etc.);

(33) $C_{2-6}$ alkynylsulfonyl (e.g., ethynylsulfonyl, propynylsulfonyl, butynylsulfonyl, pentynylsulfonyl, hexynylsulfonyl etc.);

(34) $C_{3-6}$ cycloalkylsulfonyl (e.g., cyclopropylsulfonyl, cyclobutylsulfonyl etc.);

(35) $C_{3-6}$ cycloalkenylsulfonyl (e.g., cyclopropenylsulfonyl, cyclobutenylsulfonyl etc.);

(36) $C_{6-10}$ arylsulfonyl (e.g., phenylsulfonyl etc.);

(37) $C_{3-6}$ cycloalkyl-$C_{1-6}$ alkyl-sulfonyl (e.g., cyclopropylmethylsulfonyl etc.);

(38) $C_{3-6}$ cycloalkenyl-$C_{1-6}$ alkyl-sulfonyl (e.g., cyclopentenylmethylsulfonyl etc.);

(39) $C_{6-10}$ aryl-$C_{1-6}$ alkyl-sulfonyl (e.g., benzylsulfonyl etc.);

(40) 5- or 6-membered monocyclic aromatic heterocyclyl-sulfonyl (e.g., furylsulfonyl, thienylsulfonyl, pyridylsulfonyl etc.);

(41) 8- to 12-membered fused aromatic heterocyclyl-sulfonyl (e.g., benzofurylsulfonyl, isobenzofurylsulfonyl etc.);

(42) 3- to 8-membered non-aromatic heterocyclyl-sulfonyl (e.g., oxiranylsulfonyl, azetidinylsulfonyl etc.);

(43) amino;

(44) mono-$C_{1-6}$ alkylamino (e.g., methylamino, ethylamino, propylamino, isopropylamino, butylamino, isobutylamino, tert-butylamino etc.) optionally having one substituent selected from
   (a) $C_{6-10}$ aryl, and
   (b) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.) optionally having one $C_{1-6}$ alkyl;

(45) di-$C_{1-6}$ alkylamino (e.g., dimethylamino, diethylamino, dipropylamino, diisopropylamino, dibutylamino, diisobutylamino, di-tert-butylamino etc.);

(46) $C_{1-6}$ alkyl-carbonylamino optionally having 1 to 3 substituents selected from
   (a) a halogen atom, and
   (b) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.);

(47) $C_{3-6}$ cycloalkyl-carbonylamino (e.g., cyclopropylcarbonylamino, cyclobutylcarbonylamino, cyclopentylcarbonylamino, cyclohexylcarbonylamino etc.);

(48) $C_{3-6}$ cycloalkenyl-carbonylamino (e.g., cyclopropenylcarbonylamino, cyclobutenylcarbonylamino, cyclopentenylcarbonylamino, cyclohexenylcarbonylamino etc.);

(49) $C_{6-10}$ aryl-carbonylamino (e.g., benzoylamino etc.) optionally having 1 to 3 substituents (excluding oxo) selected from substituent group B and substituent group C (mentioned later);

(50) mono(5- or 6-membered monocyclic aromatic heterocyclyl-carbonyl)amino (e.g., furylcarbonylamino, thienylcarbonylamino, pyrrolylcarbonylamino, oxazolylcarbonylamino, isoxazolylcarbonylamino, thiazolylcarbonylamino, isothiazolylcarbonylamino, imidazolylcarbonylamino, tetrazolylcarbonylamino, pyridylcarbonylamino, pyrazolylcarbonylamino etc.) optionally having 1 to 3 substituents (excluding oxo) selected from substituent group B and substituent group C (mentioned later);

(51) mono(8- to 12-membered fused aromatic heterocyclyl-carbonyl)amino (e.g., benzofurylcarbonylamino, isobenzofurylcarbonylamino, benzothienylcarbonylamino, isobenzothienylcarbonylamino, benzopyrazolylcarbonylamino etc.) optionally having 1 to 3 substituents (excluding oxo) selected from substituent group B and substituent group C (mentioned later);

(52) mono(3- to 8-membered non-aromatic heterocyclyl-carbonyl)amino (e.g., oxiranylcarbonylamino, azetidinylcarbonylamino, oxetanylcarbonylamino, thietanylcarbonylamino, pyrrolidinylcarbonylamino; tetrahydrofurylcarbonylamino, thioranylcarbonylamino, piperidinylcarbonylamino etc.) optionally having 1 to 3 substituents selected from substituent group B and substituent group C (mentioned later);

(53) mono-$C_{1-6}$ alkoxy-carbonylamino (e.g., methoxycarbonylamino, ethoxycarbonylamino, tert-butoxycarbonylamino etc.);

(54) mercapto;

(55) $C_{1-6}$ alkylsulfanyl (e.g., methylsulfanyl, ethylsulfanyl etc.);

(56) $C_{2-6}$ alkenylsulfanyl (e.g., ethenylsulfanyl, propenylsulfanyl etc.);

(57) $C_{2-6}$ alkynylsulfanyl (e.g., ethynylsulfanyl, propynylsulfanyl, butynylsulfanyl, pentynylsulfanyl, hexynylsulfanyl etc.);

(58) $C_{3-6}$ cycloalkylsulfanyl (e.g., cyclopropylsulfanyl, cyclobutylsulfanyl etc.);

(59) $C_{3-6}$ cycloalkenylsulfanyl (e.g., cyclopropenylsulfanyl, cyclobutenylsulfanyl etc.);

(60) $C_{6-10}$ arylsulfanyl (e.g., phenylsulfanyl etc.);

(61) $C_{3-6}$ cycloalkyl-$C_{1-6}$ alkylsulfanyl (e.g., cyclopropylmethylsulfanyl etc.);

(62) $C_{3-6}$ cycloalkenyl-$C_{1-6}$ alkylsulfanyl (e.g., cyclopentenylmethylsulfanyl etc.);

(63) 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.);

(64) 8- to 12-membered fused aromatic heterocyclic group (e.g., benzofuryl, isobenzofuryl, benzothienyl, isobenzothienyl, indolyl, isoindolyl, 1H-indazolyl, benzimidazolyl, benzoxazolyl etc.);

(65) 3- to 8-membered non-aromatic heterocyclic group (e.g., oxiranyl, azetidinyl, oxetanyl, thietanyl, pyrrolidinyl, tetrahydrofuryl, thiolanyl, piperidinyl etc.);

(66) 5- or 6-membered monocyclic aromatic heterocyclyl-oxy (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy etc.) optionally having 1 to 3 substituents (excluding oxo) selected from substituent group B and substituent group C (mentioned later);

(67) 8- to 12-membered fused aromatic heterocyclyl-oxy (e.g., benzofuryloxy, isobenzofuryloxy, benzothienyloxy, isobenzothienyloxy, indolyloxy, isoindolyloxy, 1H-indazolyloxy, benzimidazolyloxy, benzoxazolyloxy etc.) optionally having 1 to 3 substituents (excluding oxo) selected from substituent group B and substituent group C (mentioned later);

(68) 3- to 8-membered non-aromatic heterocyclyl-oxy (e.g., oxiranyloxy, azetidinyloxy, oxetanyloxy, thietanyloxy, pyrrolidinyloxy, tetrahydrofuryloxy, thiolanyloxy, piperidinyloxy etc.) optionally having 1 to 3 substituents selected from substituent group B and substituent group C (mentioned later);
(69) oxo;
(70) $C_{1-6}$ alkylsulfinyl (e.g., methylsulfinyl, ethylsulfinyl etc.);
(71) $C_{2-6}$ alkenylsulfinyl (e.g., ethenylsulfinyl, propenylsulfinyl etc.);
(72) $C_{2-6}$ alkynylsulfinyl (e.g., ethynylsulfinyl, propynylsulfinyl, butynylsulfinyl, pentynylsulfinyl, hexynylsulfinyl etc.);
(73) $C_{3-6}$ cycloalkylsulfinyl (e.g., cyclopropylsulfinyl, cyclobutylsulfinyl etc.);
(74) $C_{3-6}$ cycloalkenylsulfinyl (e.g., cyclopropenylsulfinyl, cyclobutenylsulfinyl etc.);
(75) $C_{6-10}$ arylsulfinyl (e.g., phenylsulfinyl etc.);
(76) $C_{3-6}$ cycloalkyl-$C_{1-6}$ alkyl-sulfinyl (e.g., cyclopropylmethylsulfinyl etc.);
(77) $C_{3-6}$ cycloalkenyl-$C_{1-6}$ alkyl-sulfinyl (e.g., cyclopentenylmethylsulfinyl etc.);
(78) $C_{1-6}$ alkylamino-thiocarbonyl (e.g., methylaminothiocarbonyl, ethylaminothiocarbonyl, propylaminothiocarbonyl etc.);
(79) di-$C_{1-6}$ alkyl-aminothiocarbonyl (e.g., dimethylaminothiocarbonyl, diethylaminothiocarbonyl, dipropylaminothiocarbonyl etc.);
(80) carboxy;
(81) $C_{1-6}$ alkoxycarbonyl (e.g., methoxycarbonyl, ethoxycarbonyl, propoxycarbonyl, isopropoxycarbonyl, butoxycarbonyl, isobutoxycarbonyl, tert-butoxycarbonyl etc.);
(82) $C_{2-6}$ alkenyloxy-carbonyl (e.g., ethenyloxycarbonyl, propenyloxycarbonyl, butenyloxycarbonyl, pentenyloxycarbonyl, hexenyloxycarbonyl etc.);
(83) $C_{2-6}$ alkynyloxy-carbonyl (e.g., ethynyloxycarbonyl, propynyloxycarbonyl, butynyloxycarbonyl, pentynyloxycarbonyl, hexynyloxycarbonyl etc.);
(84) $C_{3-6}$ cycloalkyl-oxy-carbonyl (e.g., cyclopropyloxycarbonyl, cyclobutyloxycarbonyl, cyclopentyloxycarbonyl, cyclohexyloxycarbonyl etc.);
(85) $C_{3-6}$ cycloalkenyloxy-carbonyl (e.g., cyclopropenyloxycarbonyl, cyclobutenyloxycarbonyl, cyclopentenyloxycarbonyl, cyclohexenyloxycarbonyl etc.);
(86) $C_{6-10}$ aryloxy-carbonyl (e.g., phenyloxycarbonyl, 1-naphthyloxycarbonyl, 2-naphthyloxycarbonyl etc.);
(87) $C_{3-6}$ cycloalkyl-$C_{1-6}$ alkoxy-carbonyl (e.g., cyclopropylmethyloxycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl etc.);
(88) $C_{3-6}$ cycloalkenyl-$C_{1-6}$ alkoxy-carbonyl (e.g., cyclopentenylmethyloxycarbonyl, cyclohexenylmethyloxycarbonyl, cyclohexenylethyloxycarbonyl, cyclohexenyipropyloxycarbonyl etc.);
(89) $C_{6-10}$ aryl-$C_{1-6}$ alkoxy-carbonyl (e.g., phenylmethyloxycarbonyl, phenylethyloxycarbonyl etc.);
(90) sulfamoyl;
(91) carbamoyl;
(92) mono($C_{6-10}$ aryl-$C_{1-6}$ alkyl-carbonyl)amino (e.g., phenylmethylcarbonylamino etc.) optionally having 1 to 3 substituents (excluding oxo) selected from substituent group B and substituent group C (mentioned later);
(93) mono(5- or 6-membered monocyclic aromatic heterocyclyl-$C_{1-6}$ alkyl-carbonyl)amino (e.g., furylmethylcarbonylamino, thienylmethylcarbonylamino, pyrrolylmethylcarbonylamino, oxazolylmethylcarbonylamino, isoxazolylmethylcarbonylamino, thiazolylmethylcarbonylamino, isothiazolylmethylcarbonylamino, imidazolylmethylcarbonylamino, tetrazolylmethylcarbonylamino, pyridylmethylcarbonylamino, pyrazolylmethylcarbonylamino etc.) optionally having 1 to 3 substituents (excluding oxo) selected from substituent group B and substituent group C (mentioned later);
(94) mono(8- to 12-membered fused aromatic heterocyclyl-$C_{1-6}$ alkyl-carbonyl)amino (e.g., benzofurylmethylcarbonylamino, isobenzofurylmethylcarbonylamino, benzothienylmethylcarbonylamino, isobenzothienylmethylcarbonylamino, benzopyrazolylmethylcarbonylamino etc.) optionally having 1 to 3 substituents (excluding oxo) selected from substituent group B and substituent group C (mentioned later);
(95) mono(3- to 8-membered non-aromatic heterocyclyl-$C_{1-6}$ alkyl-carbonyl)amino (e.g., oxiranylmethylcarbonylamino, azetidinylmethylcarbonylamino, oxetanylmethylcarbonylamino, thietanylmethylcarbonylamino, pyrrolidinylmethylcarbonylamino, tetrahydrofurylmethylcarbonylamino, thioranylmethylcarbonylamino, piperidinylmethylcarbonylamino etc.) optionally having 1 to 3 substituents selected from substituent group B and substituent group C (mentioned later);
(96) mono-$C_{6-10}$ aryl-ureido (e.g., phenylureido etc.) optionally having 1 to 3 substituents (excluding oxo) selected from substituent group B and substituent group C (mentioned later);
(97) mono-5- or 6-membered monocyclic aromatic heterocyclyl-ureido (e.g., furylureido, thienylureido, pyrrolylureido, oxazolylureido, isoxazolylureido, thiazolylureido, isothiazolylureido, imidazolylureido, tetrazolylureido, pyridylureido, pyrazolylureido etc.) optionally having 1 to 3 substituents (excluding oxo) selected from substituent group B and substituent group C (mentioned later);
(98) mono-8- to 12-membered fused aromatic heterocyclyl-ureido (e.g., benzofurylureido, isobenzofurylureido, benzothienylureido, isobenzothienylureido, benzopyrazolylureido etc.) optionally having 1 to 3 substituents (excluding oxo) selected from substituent group B and substituent group C (mentioned later);
(99) mono-3- to 8-membered non-aromatic heterocyclyl-ureido (e.g., oxiranylureido, azetidinylureido, oxetanylureido, thietanylureido, pyrrolidinylureido, tetrahydrofurylureido, thioranylureido, piperidinylureido etc.) optionally having 1 to 3 substituents selected from substituent group B and substituent group C (mentioned later);
(100) mono($C_{6-10}$ aryl-$C_{1-6}$ alkyl)ureido (e.g., phenylmethylureido etc.) optionally having 1 to 3 substituents (excluding oxo) selected from substituent group B and substituent group C (mentioned later);
(101) mono(5- or 6-membered monocyclic aromatic heterocyclyl-$C_{1-6}$ alkyl)ureido (e.g., furylmethylureido, thienylmethylureido, pyrrolylmethylureido, oxazolylmethylureido, isoxazolylmethylureido, thiazolylmethylureido, isothiazolylmethylureido, imidazolylmethylureido, tetrazolylmethylureido, pyridylmethylureido, pyrazolylmethylureido etc.) optionally having 1 to 3 substituents (excluding oxo) selected from substituent group B and substituent group C (mentioned later);
(102) mono(8- to 12-membered fused aromatic heterocyclyl-$C_{1-6}$ alkyl)ureido (e.g., benzofurylmethylureido, isobenzofurylmethylureido, benzothienylmethylureido, isobenzothienylmethylureido, benzopyrazolylmethylureido etc.) optionally having 1 to 3 substituents (excluding oxo) selected from substituent group B and substituent group C (mentioned later);
(103) mono(3- to 8-membered non-aromatic heterocyclyl-$C_{1-6}$ alkyl)ureido (e.g., oxiranylmethylureido, azetidinylmethylureido, oxetanylmethylureido, thietanylmethylureido, pyrrolidinylmethylureido, tetrahydrofurylmethylureido, thioranylmethylureido, piperidinylmethylureido etc.) optionally having 1 to 3 substituents selected from substituent group B and substituent group C (mentioned later);
(104) mono-$C_{6-10}$ aryl-aminocarbonyl optionally having 1 to 3 substituents (excluding oxo) selected from substituent group B and substituent group C (mentioned later);
(105) mono-5- or 6-membered monocyclic aromatic heterocyclyl-aminocarbonyl (e.g., furylaminocarbonyl, thienylaminocarbonyl, pyrrolylaminocarbonyl, oxazolylaminocarbonyl, isoxazolylaminocarbonyl, thiazolylaminocarbonyl, isothiazolylaminocarbonyl, imidazolylaminocarbonyl, tetrazolylaminocarbonyl, pyridylaminocarbonyl, pyrazolylaminocarbonyl etc.) optionally having 1 to 3 substituents (excluding oxo) selected from substituent group B and substituent group C (mentioned later);
(106) mono-8- to 12-membered fused aromatic heterocyclyl-aminocarbonyl (e.g., benzofurylaminocarbonyl, isobenzofurylaminocarbonyl, benzothienylaminocarbonyl, isobenzothienylaminocarbonyl, benzopyrazolylaminocarbonyl etc.) optionally having 1 to 3 substituents (excluding oxo) selected from substituent group B and substituent group C (mentioned later);
(107) mono-3- to 8-membered non-aromatic heterocyclyl-aminocarbonyl (e.g., oxiranylaminocarbonyl, azetidinylaminocarbonyl, oxetanylaminocarbonyl, thietanylaminocarbonyl, pyrrolidinylaminocarbonyl, tetrahydrofurylaminocarbonyl, thioranylaminocarbonyl, piperidinylaminocarbonyl etc.) optionally having 1 to 3 substituents selected from substituent group B and substituent group C (mentioned later);
(108) mono($C_{6-10}$ aryl-$C_{1-6}$ alkyl)aminocarbonyl (e.g., phenylmethylaminocarbonyl etc.) optionally having 1 to 3 substituents (excluding oxo) selected from substituent group B and substituent group C (mentioned later);
(109) mono(5- or 6-membered monocyclic aromatic heterocyclyl-$C_{1-6}$ alkyl)aminocarbonyl (e.g., furylmethylaminocarbonyl, thienylmethylaminocarbonyl, pyrrolylmethylaminocarbonyl, oxazolylmethylaminocarbonyl, isoxazolylmethylaminocarbonyl, thiazolylmethylaminocarbonyl, isothiazolylmethylaminocarbonyl, imidazolylmethylaminocarbonyl, tetrazolylmethylaminocarbonyl, pyridylmethylaminocarbonyl, pyrazolylmethylaminocarbonyl etc.) optionally having 1 to 3 substituents (excluding oxo) selected from substituent group B and substituent group C (mentioned later);
(110) mono(8- to 12-membered fused aromatic heterocyclyl-$C_{1-6}$ alkyl)aminocarbonyl (e.g., benzofurylmethylaminocarbonyl, isobenzofurylmethylaminocarbonyl, benzothienylmethylaminocarbonyl, isobenzothienylmethylaminocarbonyl, benzopyrazolylmethylaminocarbonyl etc.) optionally having 1 to 3 substituents (excluding oxo) selected from substituent group B and substituent group C (mentioned later);
(111) mono(3- to 8-membered non-aromatic heterocyclyl-$C_{1-6}$ alkyl)aminocarbonyl (e.g., oxiranylmethylaminocarbonyl, azetidinylmethylaminocarbonyl, oxetanylmethylaminocarbonyl, thietanylmethylaminocarbonyl, pyrrolidinylmethylaminocarbonyl, tetrahydrofurylmethylaminocarbonyl, thioranylmethylaminocarbonyl, piperidinylmethylaminocarbonyl etc.) optionally having 1 to 3 substituents selected from substituent group B and substituent group C (mentioned later);
(112) mono-5- or 6-membered monocyclic aromatic heterocyclyl-amino (e.g., furylamino, thienylamino, pyrrolylamino, oxazolylamino, isoxazolylamino, thiazolylamino, isothiazolylamino, imidazolylamino, tetrazolylamino, pyridylamino, pyrazolylamino etc.) optionally having 1 to 3 substituents (excluding oxo) selected from substituent group B and substituent group C (mentioned later);
(113) cyclic amino (e.g., pyrrolidino, piperidino, piperazino, morpholino, thiomorpholino etc.) fused with a benzene ring and optionally having one oxo;
(114) $C_{2-6}$ alkynyl-carbonylamino (e.g., ethynylcarbonylamino, propynylcarbonylamino, butynylcarbonylamino, pentynylcarbonylamino, hexynylcarbonylamino etc.) optionally having one $C_{6-10}$ aryl (e.g., phenyl etc.);
(115) $C_{6-10}$ aryl-sulfonylamino (e.g., phenylsulfonylamino, naphthylsulfonylamino etc.) optionally having one substituent selected from
(a) a halogen atom,
(b) $C_{1-6}$ alkyl optionally having 1 to 3 halogen atoms, and
(c) $C_{1-6}$ alkylsulfonyl (e.g., methylsulfonyl, ethylsulfonyl etc.);
(116) 5- or 6-membered monocyclic aromatic heterocyclyl-sulfonylamino (e.g., furylsulfonylamino, thienylsulfonylamino, pyrrolylsulfonylamino, oxazolylsulfonylamino, isoxazolylsulfonylamino, thiazolylsulfonylamino, isothiazolylsulfonylamino, imidazolylsulfonylamino, tetrazolylsulfonylamino, pyridylsulfonylamino, pyrazolylsulfonylamino etc.) optionally having one $C_{1-6}$ alkyl;
(117) ureido; and
(118) $C_{1-6}$ alkyl-ureido (e.g., methylureido, ethylureido, propylureido etc.).

Substituent Group B:
(1) a halogen atom;
(2) cyano;
(3) hydroxy;
(4) 3- to 8-membered non-aromatic heterocyclyl-oxy (e.g., oxiranyloxy, azetidinyloxy, oxetanyloxy, thietanyloxy, pyrrolidinyloxy, tetrahydrofuryloxy, thioranyloxy, piperidinyloxy etc.);
(5) amino;
(6) mono-$C_{1-6}$ alkyl-amino (e.g., methylamino, ethylamino, propylamino, isopropylamino, butylamino, isobutylamino, tert-butylamino etc.);
(7) di-$C_{1-6}$ alkyl-amino (e.g., dimethylamino, diethylamino, dipropylamino, diisopropylamino, dibutylamino, diisobutylamino, di-tert-butylamino, N-ethyl-N-methylamino, N-methyl-N-propylamino, N-ethyl-N-propylamino etc.);
(8) mono-$C_{3-6}$ cycloalkyl-amino (e.g., cyclopropylamino, cyclobutylamino, cyclopentylamino, cyclohexylamino etc.);
(9) mono($C_{1-6}$ alkyl-carbonyl)amino (e.g., acetylamino, ethylcarbonylamino, propylcarbonylamino, isobutylcarbonylamino, tert-butylcarbonylamino etc.);
(10) mono($C_{3-6}$ cycloalkyl-carbonyl)amino (e.g., cyclopropylcarbonylamino, cyclobutylcarbonylamino, cyclopentylcarbonylamino, cyclohexylcarbonylamino etc.);
(11) mercapto;
(12) $C_{1-6}$ alkyl-sulfanyl (e.g., methylsulfanyl, ethylsulfanyl etc.);
(13) $C_{3-6}$ cycloalkyl-sulfanyl (e.g., cyclopropylsulfanyl, cyclobutylsulfanyl etc.);
(14) 3- to 8-membered non-aromatic heterocyclyl-sulfanyl (e.g., oxiranylsulfanyl, azetidinylsulfanyl etc.);
(15) $C_{1-6}$ alkyl-sulfinyl (e.g., methylsulfinyl, ethylsulfinyl etc.);
(16) $C_{3-6}$ cycloalkyl-sulfinyl (e.g., cyclopropylsulfinyl, cyclobutylsulfinyl etc.);
(17) 3- to 8-membered non-aromatic heterocyclyl-sulfinyl (e.g., oxiranylsulfinyl, azetidinylsulfinyl etc.);
(18) $C_{1-6}$ alkyl-sulfonyl (e.g., methylsulfonyl, ethylsulfonyl etc.);
(19) $C_{3-6}$ cycloalkyl-sulfonyl (e.g., cyclopropylsulfonyl, cyclobutylsulfonyl etc.);

(20) 3- to 8-membered non-aromatic heterocyclyl-sulfonyl (e.g., oxiranylsulfonyl, azetidinylsulfonyl etc.);
(21) oxo;
(22) formyl;
(23) $C_{1-6}$ alkyl-carbonyl (e.g., acetyl, ethylcarbonyl, propylcarbonyl, isopropylcarbonyl etc.);
(24) $C_{3-6}$ cycloalkyl-carbonyl (e.g., cyclopropylcarbonyl, cyclobutylcarbonyl, cyclopentylcarbonyl, cyclohexylcarbonyl etc.);
(25) 3- to 8-membered non-aromatic heterocyclyl-carbonyl (e.g., oxiranylcarbonyl, azetidinylcarbonyl, oxetanylcarbonyl, thietanylcarbonyl, pyrrolidinylcarbonyl, tetrahydrofurylcarbonyl, thioranylcarbonyl, piperidinylcarbonyl etc.);
(26) carboxy;
(27) carbamoyl;
(28) mono($C_{1-6}$ alkyl-amino)carbonyl (e.g., methylaminocarbonyl, ethylaminocarbonyl, propylaminocarbonyl etc.);
(29) di-($C_{1-6}$ alkyl-amino)carbonyl (e.g., dimethylaminocarbonyl, diethylaminocarbonyl, dipropylaminocarbonyl etc.);
(30) sulfo;
(31) sulfamoyl;
(32) mono-$C_{1-6}$ alkylsulfamoyl (e.g., methylsulfamoyl, ethylsulfamoyl, propylsulfamoyl etc.);
(33) di-$C_{1-6}$ alkylsulfamoyl (e.g., dimethylsulfamoyl, diethylsulfamoyl, dipropylsulfamoyl etc.);
(34) a 3- to 8-membered nonaromatic heterocyclic group (e.g., oxiranyl, azetidinyl, oxetanyl, thietanyl, pyrrolidinyl, tetrahydrofuryl, thioranyl, piperidinyl etc.);
(35) $C_{1-4}$ alkylenedioxy (e.g., methylenedioxy, ethylenedioxy, trimethylendioxy etc.); and
(36) $C_{1-6}$ alkylsulfanyl (e.g., methylsulfanyl, ethylsulfanyl, propylsulfanyl etc.).

Substituent Group C:
(1) $C_{1-6}$ alkyl optionally having 1 to 3 substituents selected from substituent group B;
(2) $C_{1-6}$ alkoxy optionally having 1 to 3 substituents selected from substituent group B;
(3) $C_{3-6}$ cycloalkyl optionally having 1 to 3 substituents selected from substituent group B;
(4) $C_{3-6}$ cycloalkyloxy (e.g., cyclopropyloxy, cyclobutyloxy, cyclopentyloxy, cyclohexyloxy etc.) optionally having 1 to 3 substituents selected from substituent group B;
(5) $C_{3-6}$ cycloalkyl-$C_{1-6}$ alkyl (e.g., cyclopropylmethyl, cyclopropylethyl, cyclobutylmethyl, cyclopentylmethyl, cyclohexylmethyl, cyclohexylethyl etc.) optionally having 1 to 3 substituents selected from substituent group B;
(6) $C_{3-6}$ cycloalkyl-$C_{1-6}$ alkoxy (e.g., cyclopropylmethyloxy, cyclopropylethyloxy, cyclobutylmethyloxy, cyclopentylmethyloxy, cyclohexylmethyloxy, cyclohexylethyloxy etc.) optionally having 1 to 3 substituents selected from substituent group B;
(7) $C_{6-10}$ aryl optionally having 1 to 3 substituents (excluding oxo) selected from substituent group B;
(8) $C_{6-10}$ aryloxy (e.g., phenyloxy, 1-naphthyloxy, 2-naphthyloxy etc.) optionally having 1 to 3 substituents (excluding oxo) selected from substituent group B;
(9) $C_{6-10}$ aryl-$C_{1-6}$ alkyl (e.g., benzyl, phenylethyl etc.) optionally having 1 to 3 substituents (excluding oxo) selected from substituent group B;
(10) $C_{6-10}$ aryl-$C_{1-6}$ alkoxy (e.g., phenylmethyloxy, phenylethyloxy etc.) optionally having 1 to 3 substituents (excluding oxo) selected from substituent group B;
(11) 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.) optionally having 1 to 3 substituents (excluding oxo) selected from substituent group B;
(12) 5- or 6-membered monocyclic aromatic heterocyclyloxy (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy etc.) optionally having 1 to 3 substituents (excluding oxo) selected from substituent group B;
(13) 5- or 6-membered monocyclic aromatic heterocyclyl-$C_{1-6}$ alkyl (e.g., furylmethyl, thienylmethyl, pyrrolylmethyl, oxazolylmethyl, isoxazolylmethyl, thiazolylmethyl, isothiazolylmethyl, imidazolylmethyl, pyridylmethyl, pyrazolylmethyl etc.) optionally having 1 to 3 substituents (excluding oxo) selected from substituent group B; and
(14) 5- or 6-membered monocyclic aromatic heterocyclyl-$C_{1-6}$ alkoxy (e.g., furylmethyloxy, thienylmethyloxy, pyrrolylmethyloxy, oxazolylmethyloxy, isoxazolylmethyloxy, thiazolylmethyloxy, isothiazolylmethyloxy, imidazolylmethyloxy, pyridylmethyloxy, pyrazolylmethyloxy etc.) optionally having 1 to 3 substituents (excluding oxo) selected from substituent group B.

In the present specification, the term "alkenyl optionally having substituent(s)" means $C_{2-6}$ alkenyl (e.g., ethenyl, propenyl, butenyl, pentenyl, hexenyl, butadienyl etc.) optionally having 1 to 3 substituents selected from substituent group A.

In the present specification, the term "alkynyl optionally having substituent(s)" means $C_{2-6}$ alkynyl (e.g., ethynyl, propynyl, butynyl, pentynyl, hexynyl etc.) optionally having 1 to 3 substituents selected from substituent group A.

In the present specification, the term "cycloalkyl optionally having substituent(s)" means $C_{3-6}$ cycloalkyl optionally having 1 to 3 substituents selected from
(1) $C_{1-6}$ alkyl optionally having 1 to 3 halogen atoms, and
(2) substituent group A.

In the present specification, the term "cycloalkenyl optionally having substituent(s)" means $C_{3-6}$ cycloalkenyl (e.g., cyclopropenyl, cyclobutenyl, cyclopentenyl, cyclohexenyl etc.) optionally having 1 to 3 substituents selected from
(1) $C_{1-6}$ alkyl optionally having 1 to 3 halogen atoms, and
(2) substituent group A.

In the present specification, the term "aryl optionally having substituent(s)" means $C_{6-10}$ aryl optionally having 1 to 3 substituents selected from
(1) $C_{1-6}$ alkyl optionally having 1 to 3 halogen atoms, and
(2) substituent group A (excluding oxo).

In the present specification, the term "cycloalkyl-alkyl optionally having substituent(s)" means $C_{3-6}$ cycloalkyl-$C_{1-4}$ alkyl (e.g., cyclopropylmethyl, cyclopropylethyl, cyclobutylmethyl, cyclopentylmethyl, cyclohexylmethyl, cyclohexylethyl etc.) optionally having 1 to 3 substituents selected from
(1) $C_{1-6}$ alkyl optionally having 1 to 3 halogen atoms, and
(2) substituent group A.

In the present specification, the term "cycloalkenyl-alkyl optionally having substituent(s)" means $C_{3-6}$ cycloalkenyl-$C_{1-4}$ alkyl (e.g., cyclopentenylmethyl, cyclohexenylmethyl, cyclohexenylethyl, cyclohexenylpropyl etc.) optionally having 1 to 3 substituents selected from
(1) $C_{1-6}$ alkyl optionally having 1 to 3 halogen atoms, and
(2) substituent group A.

In the present specification, the term "aryl-alkyl optionally having substituent(s)" means $C_{6-10}$ aryl-$C_{1-4}$ alkyl (e.g., benzyl, phenylethyl etc.) optionally having 1 to 3 substituents selected from
(1) $C_{1-6}$ alkyl optionally having 1 to 3 halogen atoms, and
(2) substituent group A (excluding oxo).

In the present specification, the term "cycloalkanedienyl optionally having substituent(s)" means $C_{4-6}$ cycloalkanedienyl (e.g., 2,4-cyclopentadien-1-yl, 2,4-cyclohexadien-1-yl, 2,5-cyclohexadien-1-yl etc.) optionally having 1 to 3 substituents selected from
(1) $C_{1-6}$ alkyl optionally having 1 to 3 halogen atoms, and
(2) substituent group A.

In the present specification, the term "heterocyclic group bonded via a carbon atom and optionally having substituent(s)" means
(A) a monocyclic aromatic heterocyclic group or fused aromatic heterocyclic group bonded via a carbon atom and optionally having 1 to 3 substituents selected from (1) $C_{1-6}$ alkyl optionally having 1 to 3 halogen atoms, and
(2) substituent group A (excluding oxo), or
(B) a nonaromatic heterocyclic group bonded via a carbon atom and optionally having 1 to 3 substituents selected from
(1) $C_{1-6}$ alkyl optionally having 1 to 3 halogen atoms, and
(2) substituent group A.

The "bonded via a carbon atom monocyclic aromatic heterocyclic group" is, for example, a 5- to 7-membered (preferably, 5- or 6-membered) monocyclic aromatic heterocyclic group (having a bond at carbon atom) containing, as a ring constituting atom besides carbon atom, 1 to 4 hetero atoms selected from an oxygen atom, a sulfur atom (optionally oxidized) and a nitrogen atom, and the like. Examples thereof include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 2-pyrrolyl, 3-pyrrolyl), imidazolyl (e.g., 2-imidazolyl, 4-imidazolyl, 5-imidazolyl), pyrazolyl (e.g., 3-pyrazolyl, 4-pyrazolyl, 5-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-3-yl, 1,2,3-triazol-4-yl), tetrazolyl (e.g., tetrazol-5-yl), triazinyl (e.g., 1,3,5-triazin-2-yl) and the like.

The "fused aromatic heterocyclic group bonded via a carbon atom" is, for example, a 8- to 12-membered fused aromatic heterocyclic group (having a bond at carbon atom) wherein a 5- to 7-membered monocyclic aromatic heterocyclic group containing, as a ring constituting atom besides carbon atom, 1 to 4 hetero atoms selected from an oxygen atom, a sulfur atom (optionally oxidized) and a nitrogen atom, etc. and $C_{6-10}$ aryl and the like are fused; a 8- to 12-membered fused aromatic heterocyclic group (having a bond at carbon atom) wherein 5- to 7-membered monocyclic aromatic heterocyclic groups are fused, and the like. Examples thereof include quinolyl (e.g., 2-quinolyl, 3-quinolyl, 4-quinolyl), isoquinolyl (e.g., 1-isoquinolyl, 3-isoquinolyl, 4-isoquinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), isobenzofuryl (e.g., 1-isobenzofuryl, 3-isobenzofuryl), benzothienyl (e.g., 2-benzothienyl, 3-benzothienyl), isobenzothienyl (e.g., 1-isobenzothienyl, 3-isobenzothienyl), benzoxazolyl (e.g., 2-benzoxazolyl), benzothiazolyl (e.g., 2-benzothiazolyl, 5-benzothiazolyl, 6-benzothiazolyl), benzimidazolyl (e.g., benzimidazol-2-yl, benzimidazol-5-yl), indolyl (e.g., indol-2-yl, indol-3-yl, indol-4-yl, indol-5-yl, indol-6-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl), imidazopyrazinyl (e.g., 1H-imidazo[4,5-b]pyrazin-2-yl), benzisoxazolyl (e.g., benzisoxazol-3-yl), benzotriazolyl (e.g., 1H-1,2,3-benzotriazol-5-yl), benzopyrazolyl (e.g., benzopyrazol-5-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

Examples of the "nonaromatic heterocyclic group bonded via a carbon atom" include a 3- to 8-membered nonaromatic heterocyclic group (having a bond at carbon atom) containing, as a ring constituting atom besides carbon atom, 1 to 4 hetero atoms selected from an oxygen atom, a sulfur atom (optionally oxidized) and a nitrogen atom, and the like. Examples thereof include oxiranyl (e.g., 2-oxiranyl), azetidinyl (e.g., 2-azetidinyl, 3-azetidinyl), oxetanyl (e.g., 2-oxetanyl, 3-oxetanyl), thietanyl (e.g., 2-thietanyl, 3-thietanyl), pyrrolidinyl (e.g., 2-pyrrolidinyl, 3-pyrrolidinyl), tetrahydrofuryl (e.g., 2-tetrahydrofuryl, 3-tetrahydrofuryl), thioranyl (e.g., 2-thioranyl, 3-thioranyl), piperidinyl (e.g., 2-piperidinyl, 3-piperidinyl, 4-piperidinyl), tetrahydropyranyl (e.g., 2-tetrahydropyranyl, 3-tetrahydropyranyl, 4-tetrahydropyranyl), thianyl (e.g., 2-thianyl, 3-thianyl), morpholinyl (e.g., 2-morpholinyl, 3-morpholinyl), thiomorpholinyl (e.g., 2-thiomorpholinyl, 3-thiomorpholinyl), piperazinyl (e.g., 2-piperazinyl), azepanyl (e.g., 3-azepanyl), oxepanyl (e.g., 3-oxepanyl), thiepanyl (e.g., 3-thiepanyl), oxazepanyl (e.g., 1,4-oxazepane-5-yl), thiazepanyl (e.g., 1,4-thiazepane-5-yl), azocanyl (e.g., 4-azocanyl), oxocanyl (e.g., 4-oxocanyl), thiocanyl (e.g., 4-thiocanyl), oxazocanyl (e.g., 1,4-oxazocan-5-yl), thioazocanyl (e.g., 1,4-thioazocan5-yl), dioxinyl (e.g., 1,4-dioxin-2-yl), dihydropyrazolyl (e.g., 2,3-dihydropyrazol-3-yl, 2,3-dihydropyrazol-4-yl, 2,3-dihydropyrazol-5-yl), hexahydropyrimidinyl (e.g., hexahydropyrimidin-2-yl, hexahydropyrimidin-4-yl, hexahydropyrimidin-5-yl), tetrahydropyrimidinyl (e.g., 1,2,3,4-tetrahydropyrimidin-2-yl, 1,2,5,6-tetrahydropyrimidin-2-yl), dihydropyrimidinyl (e.g., 1,2-dihydropyrimidin-2-yl), tetrahydropyridyl (e.g., 1,2,3,4-tetrahydropyridin-2-yl, 1,2,5,6-tetrahydropyridin-2-yl), dihydropyridyl (e.g., 1,2-dihydropyridin-2-yl, 1,2-dihydropyridin-3-yl, 1,2-dihydropyridin-4-yl), tetrahydroimidazolyl (e.g., tetrahydroimidazol-2-yl, tetrahydroimidazol-4-yl), dihydroimidazolyl (e.g., 4,5-dihydroimidazol-2-yl, 4,5-dihydroimidazol-4-yl, 4,5-dihydroimidazol-5-yl) and the like.

In the present specification, the term "a group bonded via a nitrogen atom" means, for example,
(1) nitro,
(2) amino optionally having substituent(s),
(3) a heterocyclic group bonded via a nitrogen atom and optionally having substituent(s),
and the like.

In the present specification, the substituent of amino of the term "amino optionally having substituent(s)" includes, for example, a group bonded via a carbon atom, and the formula —$SO_2R^a$ ($R^a$ is a group bonded via a carbon atom) and the like, wherein the amino is optionally mono- or di-substituted. When it is di-substituted, the substituents may be the same or different.

The "heterocyclic group bonded via a nitrogen atom and optionally having substituent(s)" includes, for example,
(A) a monocyclic aromatic heterocyclic group or fused aromatic heterocyclic group, which is bonded via a nitrogen atom and optionally has 1 to 3 substituents selected from
(1) $C_{1-6}$ alkyl optionally having 1 to 3 halogen atoms, and
(2) substituent group A (excluding oxo), or
(B) a nonaromatic heterocyclic group, which is bonded via a nitrogen atom and optionally has 1 to 3 substituents selected from (1) $C_{1-6}$ alkyl optionally having 1 to 3 halogen atoms, and
(2) substituent group A.

The "monocyclic aromatic heterocyclic group bonded via a nitrogen atom" includes, for example, a 5- to 7-membered (preferably, 5- or 6-membered) monocyclic aromatic heterocyclic group (having a bond at nitrogen atom) optionally containing, as ring constituting atom besides carbon atom and one nitrogen atom, 1 to 4 hetero atoms selected from an oxygen atom, a sulfur atom (optionally oxidized), and a nitrogen atom, and the like. Examples thereof include pyrrolyl (e.g., 1-pyrrolyl), imidazolyl (e.g., 1-imidazolyl), pyrazolyl (e.g., 1-pyrazolyl), triazolyl (e.g., 1,2,4-triazol-1-yl), tetrazolyl (e.g., tetrazol-1-yl)) and the like.

The "fused aromatic heterocyclic group bonded via a nitrogen atom" is, for example, a 8- to 12-membered fused aromatic heterocyclic group (having a bond at nitrogen atom), wherein a 5- to 7-membered monocyclic aromatic heterocyclic group optionally containing, as ring constituting atom besides carbon atom and one nitrogen atom, 1 to 4 hetero atoms selected from an oxygen atom, a sulfur atom (optionally oxidized), and a nitrogen atom, etc. and $C_{6-10}$ aryl and the like are fused; a 8- to 12-membered fused aromatic heterocyclic group (having a bond at nitrogen atom) wherein 5- to 7-membered monocyclic aromatic heterocyclic groups are fused, and the like. Examples thereof include benzimidazolyl (e.g., benzimidazol-1-yl), indolyl (e.g., indol-1-yl) and the like.

Examples of the "nonaromatic heterocyclic group bonded via a nitrogen atom" include a 3- to 8-membered nonaromatic heterocyclic group (having a bond at nitrogen atom) optionally containing, as ring constituting atom besides carbon atom and one nitrogen atom, 1 to 4 hetero atoms selected from an oxygen atom, a sulfur atom (optionally oxidized), and a nitrogen atom, and the like. Examples thereof include azetidinyl (e.g., 1-azetidinyl), pyrrolidinyl (e.g., 1-pyrrolidinyl), piperidinyl (e.g., 1-piperidinyl), morpholinyl (e.g., 4-morpholinyl), thiomorpholinyl (e.g., 4-thiomorpholinyl), piperazinyl (e.g., 1-piperazinyl), azepanyl (e.g., 1-azepanyl), oxazepanyl (e.g., 1,4-oxazepan-4-yl), thiazepanyl (e.g., 1,4-thiazepane-4-yl), azocanyl (e.g., 1-azocanyl), dihydropyrazolyl (e.g., 2,3-dihydropyrazol-1-yl), hexahydropyrimidinyl (e.g., hexahydropyrimidin-1-yl), tetrahydropyrimidinyl (e.g., 1,2,3,4-tetrahydropyrimidin-1-yl), 1,2,5,6-tetrahydropyrimidin-1-yl), dihydropyrimidinyl (e.g., 1,2-dihydropyrimidin-1-yl), tetrahydropyridyl (e.g., 1,2,3,4-tetrahydropyridin-1-yl, 1,2,5,6-tetrahydropyridin-1-yl), dihydropyridyl (e.g., 1,2-dihydropyridin-1-yl), tetrahydroimidazolyl (e.g., tetrahydroimidazol-1-yl), dihydroimidazolyl (e.g., 4,5-dihydroimidazol-1-yl) and the like.

In the present specification, the "nitrogen-containing heterocyclic group" is a heterocyclic group containing one or more nitrogen atoms as ring constituting atom. Specific preferable examples include
(1) 5- to 7-membered (preferably, 5- or 6-membered) monocyclic nitrogen-containing aromatic heterocycle containing one or more nitrogen atoms as ring constituting atom, specifically, pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl, 5-pyrazolyl), triazolyl (e.g., 1,2,4-triazol-1-yl, 1,2,4-triazol-3-yl, 1,2,3-triazol-4-yl), tetrazolyl (e.g., tetrazol-1-yl, tetrazol-5-yl) and the like;
(2) a 3- to 8-membered nitrogen-containing nonaromatic heterocyclic group containing one or more nitrogen atoms as ring constituting atom, specifically, azetidinyl (e.g., 1-azetidinyl, 2-azetidinyl, 3-azetidinyl), pyrrolidinyl (e.g., 1-pyrrolidinyl, 2-pyrrolidinyl, 3-pyrrolidinyl), piperidinyl (e.g., 1-piperidinyl, 2-piperidinyl, 3-piperidinyl, 4-piperidinyl), morpholinyl (e.g., 2-morpholinyl, 3-morpholinyl, 4-morpholinyl), thiomorpholinyl (e.g., 2-thiomorpholinyl, 3-thiomorpholinyl, 4-thiomorpholinyl), piperazinyl (e.g., 1-piperazinyl, 2-piperazinyl), azepanyl (e.g., 1-azepanyl, 3-azepanyl), dihydropyrazolyl (e.g., 2,3-dihydropyrazol-1-yl, 2,3-dihydropyrazol-3-yl, 2,3-dihydropyrazol-4-yl, 2,3-dihydropyrazol-5-yl), hexahydropyrimidinyl (e.g., hexahydropyrimidin-1-yl, hexahydropyrimidin-2-yl, hexahydropyrimidin-4-yl, hexahydropyrimidin-5-yl), tetrahydropyrimidinyl (e.g., 1,2,3,4-tetrahydropyrimidin-1-yl, 1,2,3,4-tetrahydropyrimidin-2-yl, 1,2,5,6-tetrahydropyrimidin-1-yl, 1,2,5,6-tetrahydropyrimidin-2-yl), dihydropyrimidinyl (e.g., 1,2-dihydropyrimidin-1-yl, 1,2-dihydropyrimidin-2-yl), tetrahydropyridyl (e.g., 1,2,3,4-tetrahydropyridin-1-yl, 1,2,3,4-tetrahydropyridin-2-yl, 1,2,5,6-tetrahydropyridin-1-yl, 1,2,5,6-tetrahydropyridin-2-yl), dihydropyridyl (e.g., 1,2-dihydropyridin-1-yl, 1,2-dihydropyridin-2-yl, 1,2-dihydropyridin-3-yl, 1,2-dihydropyridin-4-yl), tetrahydroimidazolyl (e.g., tetrahydroimidazol-1-yl, tetrahydroimidazol-2-yl, tetrahydroimidazol-4-yl), dihydroimidazolyl (e.g., 4,5-dihydroimidazol-1-yl, 4,5-dihydroimidazol-2-yl, 4,5-dihydroimidazol-4-yl, 4,5-dihydroimidazol-5-yl) and the like;
and the like.

In the present specification, "N-oxide of the nitrogen-containing heterocyclic group" is the above-mentioned nitrogen-containing heterocyclic group wherein an oxygen atom is bonded to the nitrogen atom of the ring and, for example, N-oxidepyridyl (e.g., N-oxidepyridin-2-yl, N-oxidepyridin-3-yl, N-oxidepyridin-4-yl), N-oxidepyrazinyl (e.g., N-oxidepyrazin-2-yl), N-oxidepyrimidinyl (e.g., N-oxidepyrimidin-2-yl, N-oxidepyrimidin-4-yl, N-oxidepyrimidin-5-yl), N-oxidepyridazinyl (e.g., N-oxidepyridazin-3-yl, N-oxidepyridazin-4-yl) and the like can be mentioned.

In the present specification, the term "a group bonded via an oxygen atom" means, for example, hydroxy optionally having substituent(s). The substituent of the "hydroxy optionally having substituent(s)" is a group bonded via a carbon atom and the like.

In the present specification, the term "a group bonded via a sulfur atom" means, for example, mercapto, a group represented by the formula —S(O)$_n$R$^b$ wherein n is an integer of 0 to 2 and R$^b$ is a group bonded via a carbon atom or a group bonded via a nitrogen atom, and the like.

The compound (I) is explained in the following.
R$^1$ is
(1) a hydrogen atom,
(2) a halogen atom,
(3) a group bonded via a carbon atom,
(4) a group bonded via a nitrogen atom,
(5) a group bonded via an oxygen atom, or
(6) a group bonded via a sulfur atom.

R$^1$ is a hydrogen atom, a halogen atom (particularly, a fluorine atom), or a $C_{1-6}$ alkyl group (particularly, methyl) is preferable, and a hydrogen atom is more preferable.
R$^2$ is
(1) a hydrogen atom,
(2) a halogen atom,
(3) a group bonded via a carbon atom,
(4) a group bonded via a nitrogen atom,
(5) a group bonded via an oxygen atom, or
(6) a group bonded via a sulfur atom.

$R^2$ is preferably a hydrogen atom.

W is O or S.

As W, O is preferable.

X is $CR^3$ ($R^3$ is a hydrogen atom, a halogen atom or $C_{1-6}$ alkyl) or N.

X is preferably $CR^{3'}$ wherein $R^{3'}$ is a hydrogen atom, a halogen atom or methyl, or N. Particularly, CH, CF, CCl, $C(CH_3)$ or N is preferable, and CH, CF or N is more preferable.

Y is $CR^4$ ($R^4$ is a hydrogen atom, a halogen atom or $C_{1-6}$ alkyl) or N.

Y is preferably $CR^{4'}$ wherein $R^{4'}$ is a hydrogen atom, a halogen atom or methyl, or N. Particularly, CH, CF, CCl, $C(CH_3)$ or N is preferable, and CH, CF or N is more preferable.

$R^5$ is (1) $C_{3-6}$ cycloalkyl optionally having one $C_{6-10}$ aryl-aminocarbonyl optionally having 1 to 3 substituents selected from a halogen atom and $C_{1-6}$ alkyl, (2) $C_{1-6}$ alkyl-carbonylamino optionally having one $C_{6-10}$ aryl, (3) $C_{1-6}$ alkoxy optionally having one $C_{6-10}$ aryl, or (4) a nitrogen-containing heterocyclic group or an N-oxide thereof optionally having 1 to 4 substituents selected from (a) $C_{6-10}$ aryl optionally having 1 to 3 substituents selected from a halogen atom and $C_{1-6}$ alkyl, (b) $C_{1-6}$ alkyl optionally having 1 to 3 halogen atoms, and (c) oxo.

$R^5$ is preferably (1) cyclopropyl optionally having one phenylaminocarbonyl optionally having 1 to 3 substituents selected from a fluorine atom and methyl, (2) acetylamino optionally having one phenyl, (3) methoxy optionally having one phenyl, (4) tert-butoxy, or, (5) a nitrogen-containing heterocyclic group or an N-oxide thereof (particularly, pyrazolyl (e.g., 3-pyrazolyl, 5-pyrazolyl), dihydropyrazolyl (e.g., 2,3-dihydropyrazol-4-yl), dihydropyridyl (e.g., 1,2-dihydropyridin-3-yl), N-oxidepyridyl (e.g., N-oxidepyridin-2-yl), hexahydropyrimidinyl (e.g., hexahydropyrimidin-1-yl), tetrahydroimidazolyl (e.g., tetrahydroimidazol-1-yl)) optionally having 1 to 4 substituents selected from (a) phenyl optionally having 1 to 3 substituents selected from a fluorine atom, a chlorine atom, a bromine atom, methyl and isopropyl, (b) methyl optionally having 1 to 3 fluorine atoms, (c) ethyl optionally having 1 to 3 fluorine atoms, (d) isopropyl, and (e) oxo.

$R^6$ is a hydrogen atom.

$R^7$ is a hydrogen atom, a halogen atom or $C_{1-6}$ alkyl.

$R^7$ is preferably a hydrogen atom.

$R^8$ is a hydrogen atom, a halogen atom or $C_{1-6}$ alkyl.

$R^8$ is preferably a hydrogen atom.

As compound (I), the compounds described in Examples 1-38 are preferable, and the compounds described in Examples 1, 3-38 are more preferable.

As compound (I), the compounds described in Examples 39-85 are also preferable.

In compound (I), $Z_1$, $Z_2$, $Z_3$ and $Z_4$ are in the following combination.

$(Z_1, Z_2, Z_3, Z_4) = (CR^1, N, CR^2, C)$ $(N, N, CR^2, C)$, $(N, C, CR^2, N)$, $(S, C, CR^2, C)$ or $(S, C, N, C)$.

That is, compound (I) can be subdivided into the compounds represented by following formulas (Ia)-(Ie) (hereinafter sometimes to be abbreviated as compounds (Ia)-(Ie)).

The compounds (Ia)-(Ie) are explained in the following.

[Compound (Ia)]

imidazo[1,2-a]pyridine derivative: a compound represented by the formula wherein $R^{1a}$ and $R^{2a}$ are the same or different and each is
(1) a hydrogen atom,
(2) a halogen atom,
(3) a group bonded via a carbon atom,
(4) a group bonded via a nitrogen atom,
(5) a group bonded via an oxygen atom, or
(6) a group bonded via a sulfur atom;
$W^a$ is O or S;
$X^a$ is $CR^{3a}$ ($R^{3a}$ is a hydrogen atom, a halogen atom or $C_{1-6}$ alkyl), or N;
$Y^a$ is $CR^{3a}$ ($R^{4a}$ is a hydrogen atom, a halogen atom or $C_{1-6}$ alkyl), or N;
$R^{5a}$ is
(1) $C_{3-6}$ cycloalkyl optionally having one $C_{6-10}$ aryl-aminocarbonyl optionally having 1 to 3 substituents selected from a halogen atom and $C_{1-6}$ alkyl,
(2) $C_{1-6}$ alkyl-carbonylamino optionally having one $C_{6-10}$ aryl,
(3) $C_{1-6}$ alkoxy optionally having one $C_{6-10}$ aryl, or
(4) a nitrogen-containing heterocyclic group or an N-oxide thereof optionally having 1 to 4 substituents selected from
   (a) $C_{6-10}$ aryl optionally having 1 to 3 substituents selected from a halogen atom and $C_{1-6}$ alkyl,
   (b) $C_{1-6}$ alkyl optionally having 1 to 3 halogen atoms, and
   (c) oxo;
$R^{6a}$ is a hydrogen atom;
$R^{7a}$ is a hydrogen atom, a halogen atom or $C_{1-6}$ alkyl; and
$R^{8a}$ is a hydrogen atom, a halogen atom or $C_{1-6}$ alkyl,
or a salt thereof (compound (Ia)).

$R^{1a}$ is preferably a hydrogen atom, a halogen atom (particularly, a fluorine atom), or a $C_{1-6}$ alkyl group (particularly, methyl), and a hydrogen atom is more preferable.

$R^{2a}$ is preferably a hydrogen atom.

$W^a$ is preferably O.

$X^a$ is preferably $CR^{3a'}$ wherein $R^{3a'}$ is a hydrogen atom, a halogen atom or methyl, or N. Particularly, CH, CF, CCl, C(CH$_3$) or N is preferable, and CH, CF or N is more preferable.

$Y^a$ is preferably $CR^{4a'}$ wherein $R^{4a'}$ is a hydrogen atom, a halogen atom or methyl, or N. Particularly, CH, CF, CCl, C(CH$_3$) or N is preferable, and CH, CF or N is more preferable.

$R^{5a}$ is preferably
(1) cyclopropyl optionally having one phenylaminocarbonyl optionally having 1 to 3 substituents selected from a fluorine atom and methyl,
(2) acetylamino optionally having one phenyl,
(3) methoxy optionally having one phenyl,
(4) tert-butoxy, or
(5) a nitrogen-containing heterocyclic group or an N-oxide thereof (particularly, pyrazolyl (e.g., 3-pyrazolyl, 5-pyrazolyl), dihydropyrazolyl (e.g., 2,3-dihydropyrazol-4-yl), dihydropyridyl (e.g., 1,2-dihydropyridin-3-yl), N-oxidepyridyl (e.g., N-oxidepyridin-2-yl), hexahydropyrimidinyl (e.g., hexahydropyrimidin-1-yl), tetrahydroimidazolyl (e.g., tetrahydroimidazol-1-yl)) optionally having 1 to 4 substituents selected from
   (a) phenyl optionally having 1 to 3 substituents selected from a fluorine atom, a chlorine atom, a bromine atom, methyl and isopropyl,
   (b) methyl optionally having 1 to 3 fluorine atoms,
   (c) ethyl optionally having 1 to 3 fluorine atoms,
   (d) isopropyl, and
   (e) oxo.
$R^{7a}$ is preferably a hydrogen atom.
$R^{8a}$ is preferably a hydrogen atom.

Preferable specific examples of compound (Ia) include the following.
[Compound (Ia-A)]
In compound (Ia), a compound wherein
$R^{1a}$ is a hydrogen atom;
$R^{2a}$ is a hydrogen atom;
$W^a$ is O or S;
$X^a$ is $CR^{3a'}$ wherein $R^{3a'}$ is a hydrogen atom or a halogen atom;
$Y^a$ is $CR^{4a'}$ wherein $R^{4a'}$ is a hydrogen atom or a halogen atom;
$R^{5a}$ is
(1) cyclopropyl optionally having one phenylaminocarbonyl optionally having 1 to 3 substituents selected from a fluorine atom and methyl,
(2) acetylamino optionally having one phenyl,
(3) methoxy optionally having one phenyl,
(4) tert-butoxy, or
(5) a nitrogen-containing heterocyclic group or an N-oxide thereof (pyrazolyl (e.g., 3-pyrazolyl, 5-pyrazolyl), dihydropyrazolyl (e.g., 2,3-dihydropyrazol-4-yl), dihydropyridyl (e.g., 1,2-dihydropyridin-3-yl), N-oxidepyridyl (e.g., N-oxidepyridin-2-yl)) optionally having 1 to 4 substituents selected from
   (a) phenyl optionally having 1 to 3 substituents selected from a fluorine atom and methyl,
   (b) methyl optionally having 1 to 3 fluorine atoms,
   (c) ethyl optionally having 1 to 3 fluorine atoms, and
   (d) oxo;
$R^{6a}$ is a hydrogen atom;
$R^{7a}$ is a hydrogen atom; and
$R^{8a}$ is a hydrogen atom is preferable.
[Compound (Ia-A1)]
In compound (Ia-A), a compound wherein
$R^{1a}$ is a hydrogen atom;
$R^{2a}$ is a hydrogen atom;
$W^a$ is O;
$X^a$ is CH or CF;
$Y^a$ is CH or CF;
$R^{5a}$ is
(1) cyclopropyl optionally having one phenylaminocarbonyl optionally having 1 to 3 substituents selected from a fluorine atom and methyl,
(2) acetylamino optionally having one phenyl,
(3) methoxy optionally having one phenyl,
(4) tert-butoxy, or
(5) a nitrogen-containing heterocyclic group or an N-oxide thereof (particularly, pyrazolyl (e.g., 3-pyrazolyl, 5-pyrazolyl), dihydropyrazolyl (e.g., 2,3-dihydropyrazol-4-yl), dihydropyridyl (e.g., 1,2-dihydropyridin-3-yl), N-oxidepyridyl (e.g., N-oxidepyridin-2-yl)) optionally having 1 to 4 substituents selected from
   (a) phenyl optionally having 1 to 3 substituents selected from a fluorine atom and methyl,
   (b) methyl optionally having 1 to 3 fluorine atoms,
   (c) ethyl optionally having 1 to 3 fluorine atoms, and
   (d) oxo;
$R^{6a}$ is a hydrogen atom;
$R^{7a}$ is a hydrogen atom; and
$R^{8a}$ is a hydrogen atom is preferable.
[Compound (Ia-A2)]
The compounds of Examples 1-17, Examples 22-33 and Examples 35-38, particularly Examples 1, 3-17, Examples 22-33 and Examples 35-38.

[Compound (Ia-B)]
In compound (Ia), a compound wherein
$R^{1a}$ is a hydrogen atom, a halogen atom (particularly, a fluorine atom), or a $C_{1-6}$ alkyl group (particularly, methyl);
$R^{2a}$ is a hydrogen atom;
$W^a$ is O or S (particularly, O);
$X^a$ is $CR^{3a'}$ wherein $R^{3a'}$ is a hydrogen atom, a halogen atom or methyl, or N;
$Y^a$ is $CR^{4a'}$ wherein $R^{4a'}$ is a hydrogen atom, a halogen atom or methyl, or N;
$R^{5a}$ is
(1) cyclopropyl optionally having one phenylaminocarbonyl optionally having 1 to 3 substituents selected from a fluorine atom and methyl,
(2) acetylamino optionally having one phenyl,
(3) methoxy optionally having one phenyl,
(4) tert-butoxy, or
(5) a nitrogen-containing heterocyclic group or an N-oxide thereof (particularly, pyrazolyl (e.g., 3-pyrazolyl, 5-pyrazolyl), dihydropyrazolyl (e.g., 2,3-dihydropyrazol-4-yl), dihydropyridyl (e.g., 1,2-dihydropyridin-3-yl), N-oxidepyridyl (e.g., N-oxidepyridin-2-yl), hexahydropyrimidinyl (e.g., hexahydropyrimidin-1-yl), tetrahydroimidazolyl (e.g., tetrahydroimidazol-1-yl)) optionally having 1 to 4 substituents selected from
    (a) phenyl optionally having 1 to 3 substituents selected from a fluorine atom, a chlorine atom, a bromine atom, methyl and isopropyl,
    (b) methyl optionally having 1 to 3 fluorine atoms,
    (c) ethyl optionally having 1 to 3 fluorine atoms,
    (d) isopropyl, and
    (e) oxo;
$R^{6a}$ is a hydrogen atom;
$R^{7a}$ is a hydrogen atom; and
$R^{8a}$ is a hydrogen atom is preferable.

[Compound (Ia-B1)]
In compound (Ia-B), a compound wherein
$R^{1a}$ is a hydrogen atom, a fluorine atom or methyl;
$R^{2a}$ is a hydrogen atom;
$W^a$ is O;
$X^a$ is CH, CF, CCl, C(CH$_3$) or N;
$Y^a$ is CH, CF, CCl, C(CH$_3$) or N;
$R^{5a}$ is
(1) cyclopropyl optionally having one phenylaminocarbonyl optionally having 1 to 3 substituents selected from a fluorine atom and methyl,
(2) acetylamino optionally having one phenyl,
(3) methoxy optionally having one phenyl,
(4) tert-butoxy, or
(5) a nitrogen-containing heterocyclic group or an N-oxide thereof (particularly, pyrazolyl (e.g., 3-pyrazolyl, 5-pyrazolyl), dihydropyrazolyl (e.g., 2,3-dihydropyrazol-4-yl), dihydropyridyl (e.g., 1,2-dihydropyridin-3-yl), N-oxidepyridyl (e.g., N-oxidepyridin-2-yl), hexahydropyrimidinyl (e.g., hexahydropyrimidin-1-yl), tetrahydroimidazolyl (e.g., tetrahydroimidazol-1-yl)) optionally having 1 to 4 substituents selected from
    (a) phenyl optionally having 1 to 3 substituents selected from a fluorine atom, a chlorine atom, a bromine atom, methyl and isopropyl,
    (b) methyl optionally having 1 to 3 fluorine atoms,
    (c) ethyl optionally having 1 to 3 fluorine atoms,
    (d) isopropyl, and
    (e) oxo;
$R^{6a}$ is a hydrogen atom;
$R^{7a}$ is a hydrogen atom; and
$R^{8a}$ is a hydrogen atom is preferable.

[Compound (Ia-B2)]
The compounds of Examples 1-17, Examples 22-33, Examples 35-75 and Examples 77-85, particularly Examples 1, 3-17, Examples 22-33, Examples 35-75 and Examples 77-85.

[Compound (Ia-B3)]
The compounds of Examples 1-17, Examples 22-33, Examples 35-75 and Examples 77-94, particularly Examples 1, 3-17, Examples 22-33, Examples 35-75 and Examples 77-94.

[Compound (Ia-C)]
N-[4-({2-[(cyclopropylcarbonyl)amino]imidazo[1,2-a]pyridin-6-yl}oxy)-3-fluorophenyl]-N'-phenylcyclopropane-1,1-dicarboxamide or a salt thereof;
N-[4-({2-[(cyclopropylcarbonyl)amino]imidazo[1,2-a]pyridin-6-yl}oxy)-3-fluorophenyl]-6-methyl-2-oxo-1-phenyl-1,2-dihydropyridine-3-carboxamide or a salt thereof;
N-[4-({2-[(cyclopropylcarbonyl)amino]imidazo[1,2-a]pyridin-6-yl}oxy)-3-fluorophenyl]-1-(4-fluorophenyl)-6-methyl-2-oxo-1,2-dihydropyridine-3-carboxamide or a salt thereof; or
N-[5-({2-[(cyclopropylcarbonyl)amino]imidazo[1,2-a]pyridin-6-yl}oxy)pyridin-2-yl]-6-(4-fluorophenyl)-5-methylpyridine-2-carboxamide 1-oxide or a salt thereof.

[Compound (Ib)]
1,2,4-triazolo[1,5-a]pyridine derivative: a compound represented by the formula (Ib)

wherein $R^{2b}$ is
(1) a hydrogen atom,
(2) a halogen atom,
(3) a group bonded via a carbon atom,
(4) a group bonded via a nitrogen atom,
(5) a group bonded via an oxygen atom, or
(6) a group bonded via a sulfur atom;
$W^b$ is O or S;
$X^b$ is $CR^{3b}$ ($R^{3b}$ is a hydrogen atom, a halogen atom or $C_{1-6}$ alkyl), or N;
$Y^b$ is $CR^{4b}$ ($R^{4b}$ is a hydrogen atom, a halogen atom or $C_{1-6}$ alkyl), or N;
$R^{5b}$ is
(1) $C_{3-6}$ cycloalkyl optionally having one $C_{6-10}$ aryl-aminocarbonyl optionally having 1 to 3 substituents selected from a halogen atom and $C_{1-6}$ alkyl,
(2) $C_{1-6}$ alkyl-carbonylamino optionally having one $C_{6-10}$ aryl,
(3) $C_{1-6}$ alkoxy optionally having one $C_{6-10}$ aryl, or
(4) a nitrogen-containing heterocyclic group or an N-oxide thereof optionally having 1 to 4 substituents selected from
    (a) $C_{6-10}$ aryl optionally having 1 to 3 substituents selected from a halogen atom and $C_{1-6}$ alkyl,
    (b) $C_{1-6}$ alkyl optionally having 1 to 3 halogen atoms, and
    (c) oxo;
$R^{6b}$ is a hydrogen atom;
$R^{7b}$ is a hydrogen atom, a halogen atom or $C_{1-6}$ alkyl; and $R^{8b}$ is a hydrogen atom, a halogen atom or $C_{1-6}$ alkyl, or a salt thereof (compound (Ib)).

$R^{2b}$ is preferably a hydrogen atom.

$W^b$ is preferably O.

$X^b$ is preferably $CR^{3b'}$ wherein $R^{3b'}$ is a hydrogen atom or a halogen atom, and particularly, CF is preferable.

$Y^b$ is preferably $CR^{4b'}$ wherein $R^{4b'}$ is a hydrogen atom or a halogen atom, and particularly, CH is preferable.

$R^{5b}$ is preferably
(1) cyclopropyl optionally having one phenylaminocarbonyl optionally having 1 to 3 substituents selected from a fluorine atom and methyl,
(2) acetylamino optionally having one phenyl,
(3) methoxy optionally having one phenyl,
(4) tert-butoxy, or
(5) a nitrogen-containing heterocyclic group or an N-oxide thereof (particularly, pyrazolyl (e.g., 3-pyrazolyl, 5-pyrazolyl), dihydropyrazolyl (e.g., 2,3-dihydropyrazol-4-yl), dihydropyridyl (e.g., 1,2-dihydropyridin-3-yl), N-oxidepyridyl (e.g., N-oxidepyridin-2-yl)) optionally having 1 to 4 substituents selected from
　(a) phenyl optionally having 1 to 3 substituents selected from a fluorine atom and methyl,
　(b) methyl optionally having 1 to 3 fluorine atoms,
　(c) ethyl optionally having 1 to 3 fluorine atoms, and
　(d) oxo,
more preferably,
cyclopropyl optionally having one phenylaminocarbonyl optionally having 1 to 3 substituents selected from a fluorine atom and methyl.

$R^{7b}$ is preferably a hydrogen atom.

$R^{8b}$ is preferably a hydrogen atom.

Preferable specific examples of compound (Ib) include the following.

[Compound (Ib-A)]

In compound (Ib), a compound wherein
$R^{2b}$ is a hydrogen atom;
$W^b$ is O;
$X^b$ is $CR^{3b'}$ wherein $R^{3b'}$ is a hydrogen atom or a halogen atom;
$Y^b$ is $CR^{4b'}$ wherein $R^{4b'}$ is a hydrogen atom or a halogen atom;
$R^{5b}$ is
(1) cyclopropyl optionally having one phenylaminocarbonyl optionally having 1 to 3 substituents selected from a fluorine atom and methyl,
(2) acetylamino optionally having one phenyl,
(3) methoxy optionally having one phenyl,
(4) tert-butoxy, or
(5) a nitrogen-containing heterocyclic group or an N-oxide thereof (pyrazolyl, dihydropyrazolyl, dihydropyridyl, N-oxidepyridyl) optionally having 1 to 4 substituents selected from
　(a) phenyl optionally having 1 to 3 substituents selected from a fluorine atom and methyl,
　(b) methyl optionally having 1 to 3 fluorine atoms,
　(c) ethyl optionally having 1 to 3 fluorine atoms, and
　(d) oxo;
$R^{6b}$ is a hydrogen atom;
$R^{7b}$ is a hydrogen atom; and
$R^{8b}$ is a hydrogen atom is preferable.

Particularly, compound (Ib-A) wherein
$R^{2b}$ is a hydrogen atom;
$W^b$ is O;
$X^b$ is CF;
$Y^b$ is CH;
$R^{5b}$ is a cyclopropyl optionally having one phenylaminocarbonyl optionally having 1 to 3 substituents selected from a fluorine atom and methyl;
$R^{6b}$ is a hydrogen atom;
$R^{7b}$ is a hydrogen atom; and
$R^{8b}$ is a hydrogen atom is preferable.

Specifically, compound (Ib-A) is preferably the compound of Example 34.

[Compound (Ic)]

1,2,4-triazolo[1,5-a]pyridine derivative: a compound represented by the formula

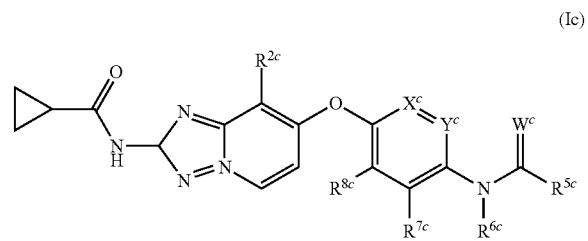

(Ic)

wherein $R^{2c}$ is
(1) a hydrogen atom,
(2) a halogen atom,
(3) a group bonded via a carbon atom,
(4) a group bonded via a nitrogen atom,
(5) a group bonded via an oxygen atom, or
(6) a group bonded via a sulfur atom;
$W^c$ is O or S;
$X^c$ is $CR^{3c}$ ($R^{3c}$ is a hydrogen atom, a halogen atom or $C_{1-6}$ alkyl), or N;
$Y^c$ is $CR^{4c}$ is a hydrogen atom, a halogen atom or $C_{1-6}$ alkyl), or N;
$R^{5c}$ is
(1) $C_{3-6}$ cycloalkyl optionally having one $C_{6-10}$ aryl-aminocarbonyl optionally having 1 to 3 substituents selected from a halogen atom and $C_{1-6}$ alkyl,
(2) $C_{1-6}$ alkyl-carbonylamino optionally having one $C_{6-10}$ aryl,
(3) $C_{1-6}$ alkoxy optionally having one $C_{6-10}$ aryl, or
(4) a nitrogen-containing heterocyclic group or an N-oxide thereof optionally having 1 to 4 substituents selected from
　(a) $C_{6-10}$ aryl optionally having 1 to 3 substituents selected from a halogen atom and $C_{1-6}$ alkyl,
　(b) $C_{1-6}$ alkyl optionally having 1 to 3 halogen atoms, and
　(c) oxo;
$R^{6c}$ is a hydrogen atom;
$R^{7c}$ is a hydrogen atom, a halogen atom or $C_{1-6}$ alkyl; and
$R^{8c}$ is a hydrogen atom, a halogen atom or $C_{1-6}$ alkyl,
or a salt thereof (compound (Ic)).

$R^{2c}$ is preferably a hydrogen atom.

$W^c$ is preferably O.

$X^c$ is preferably $CR^{3c'}$ wherein $R^{3c'}$ is a hydrogen atom or a halogen atom, and particularly preferably CF.

$Y^c$ is preferably $CR^{4c'}$ wherein $R^{4c'}$ is a hydrogen atom or a halogen atom is preferable, and particularly preferably CH.

$R^{5c}$ is preferably
(1) cyclopropyl optionally having one phenylaminocarbonyl optionally having 1 to 3 substituents selected from a fluorine atom and methyl,
(2) acetylamino optionally having one phenyl,
(3) methoxy optionally having one phenyl,
(4) tert-butoxy, or (5) a nitrogen-containing heterocyclic group or an N-oxide thereof (particularly, pyrazolyl (e.g., 3-pyrazolyl, 5-pyrazolyl), dihydropyrazolyl (e.g., 2,3-dihydropyrazol-4-yl), dihydropyridyl (e.g., 1,2-dihydropyridin-3-yl), N-oxidepyridyl (e.g., N-oxidepyridin-2-yl)) optionally having 1 to 4 substituents selected from
  (a) phenyl optionally having 1 to 3 substituents selected from a fluorine atom and methyl,
  (b) methyl optionally having 1 to 3 fluorine atoms,
  (c) ethyl optionally having 1 to 3 fluorine atoms, and
  (d) oxo,
and more preferably
a nitrogen-containing heterocyclic group (particularly, dihydropyridyl (e.g., 1,2-dihydropyridin-3-yl)) optionally having 1 to 4 substituents selected from
  (a) phenyl optionally having 1 to 3 substituents selected from a fluorine atom and methyl,
  (b) methyl optionally having 1 to 3 fluorine atoms,
  (c) ethyl optionally having 1 to 3 fluorine atoms, and
  (d) oxo.
$R^{7c}$ is preferably a hydrogen atom.
$R^{8c}$ is preferably a hydrogen atom.
Preferable specific examples of compound (Ic) include the following.
[Compound (Ic-A)]
In compound (Ic), a compound wherein
$R^{2c}$ is a hydrogen atom;
$W^c$ is O;
$X^c$ is $CR^{3c'}$ wherein $R^{3c'}$ is a hydrogen atom or a halogen atom;
$Y^c$ is $CR^{4c'}$ wherein $R^{3c'}$ is a hydrogen atom or a halogen atom;
$R^{5c}$ is
(1) cyclopropyl optionally having one phenylaminocarbonyl optionally having 1 to 3 substituents selected from a fluorine atom and methyl,
(2) acetylamino optionally having one phenyl,
(3) methoxy optionally having one phenyl,
(4) tert-butoxy, or
(5) a nitrogen-containing heterocyclic group or an N-oxide thereof (particularly, pyrazolyl (e.g., 3-pyrazolyl, 5-pyrazolyl), dihydropyrazolyl (e.g., 2,3-dihydropyrazol-4-yl), dihydropyridyl (e.g., 1,2-dihydropyridin-3-yl), N-oxidepyridyl (e.g., N-oxidepyridin-2-yl)) optionally having 1 to 4 substituents selected from
  (a) phenyl optionally having 1 to 3 substituents selected from a fluorine atom and methyl,
  (b) methyl optionally having 1 to 3 fluorine atoms,
  (c) ethyl optionally having 1 to 3 fluorine atoms, and
  (d) oxo;
$R^{6c}$ is a hydrogen atom;
$R^{7c}$ is a hydrogen atom; and
$R^{8c}$ is a hydrogen atom, is preferable.
Particularly, compound (Ic-A) wherein
$R^{2c}$ is a hydrogen atom;
$W^c$ is O;
$X^c$ is CF;
$Y^c$ is CH;
$R^{5c}$ is
a nitrogen-containing heterocyclic group (particularly, dihydropyridyl (e.g., 1,2-dihydropyridin-3-yl)) optionally having 1 to 4 substituents selected from
  (a) phenyl optionally having 1 to 3 substituents selected from a fluorine atom and methyl,
  (b) methyl optionally having 1 to 3 fluorine atoms,
  (c) ethyl optionally having 1 to 3 fluorine atoms, and
  (d) oxo;
$R^{6c}$ is a hydrogen atom;
$R^{7c}$ is a hydrogen atom; and
$R^{8c}$ is a hydrogen atom is preferable.
Specifically, compound (Ic-A) is preferably the compound of Example 76.
[Compound (Id)]
1,3-benzothiazole derivative: a compound represented by the formula

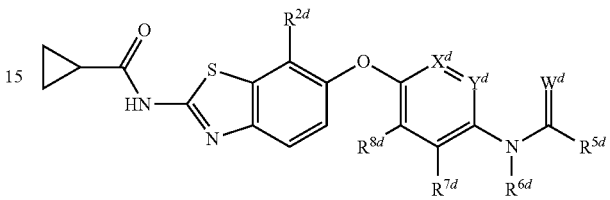

(Id)

wherein $R^{2d}$ is
(1) a hydrogen atom,
(2) a halogen atom,
(3) a group bonded via a carbon atom,
(4) a group bonded via a nitrogen atom,
(5) a group bonded via an oxygen atom, or
(6) a group bonded via a sulfur atom;
$W^d$ is O or S;
$X^d$ is $CR^{3d}$ ($R^{3d}$ is a hydrogen atom, a halogen atom or $C_{1-6}$ alkyl), or N;
$Y^d$ is $CR^{4d}$ ($R^{4d}$ is a hydrogen atom, a halogen atom or $C_{1-6}$ alkyl), or N;
$R^{5d}$ is
(1) $C_{3-6}$ cycloalkyl optionally having one $C_{6-10}$ aryl-aminocarbonyl optionally having 1 to 3 substituents selected from a halogen atom and $C_{1-6}$ alkyl,
(2) $C_{1-6}$ alkyl-carbonylamino optionally having one $C_{6-10}$ aryl,
(3) $C_{1-6}$ alkoxy optionally having one $C_{6-10}$ aryl, or
(4) a nitrogen-containing heterocyclic group or an N-oxide thereof optionally having 1 to 4 substituents selected from
  (a) $C_{6-10}$ aryl optionally having 1 to 3 substituents selected from a halogen atom and $C_{1-6}$ alkyl,
  (b) $C_{1-6}$ alkyl optionally having 1 to 3 halogen atoms, and
  (c) oxo;
$R^{6d}$ is a hydrogen atom;
$R^{7d}$ is a hydrogen atom, a halogen atom or $C_{1-6}$ alkyl; and
$R^{8d}$ is a hydrogen atom, a halogen atom or $C_{1-6}$ alkyl,
or a salt thereof (compound (Id)).
$R^{2d}$ is preferably a hydrogen atom.
$W^d$ is preferably O.
$X^d$ is preferably $CR^{3d'}$ wherein $R^{3d'}$ is a hydrogen atom or a halogen atom, and particularly preferably CF.
$Y^d$ is preferably $CR^{4d'}$ wherein $R^{4d'}$ is a hydrogen atom or a halogen atom, and particularly preferably CH.
$R^{5d}$ is preferably
(1) cyclopropyl optionally having one phenylaminocarbonyl optionally having 1 to 3 substituents selected from a fluorine atom and methyl,
(2) acetylamino optionally having one phenyl,
(3) methoxy optionally having one phenyl,
(4) tert-butoxy, or
(5) a nitrogen-containing heterocyclic group or an N-oxide thereof (particularly, pyrazolyl (e.g., 3-pyrazolyl, 5-pyrazolyl), dihydropyrazolyl (e.g., 2,3-dihydropyrazol-4-yl), dihydropyridyl (e.g., 1,2-dihydropyridin-3-yl), N-oxidepyridyl (e.g., N-oxidepyridin-2-yl)) optionally having 1 to 4 substituents selected from (a) phenyl optionally having 1 to 3 substituents selected from a fluorine atom and methyl,
(b) methyl optionally having 1 to 3 fluorine atoms,
(c) ethyl optionally having 1 to 3 fluorine atoms, and
(d) oxo, and more preferably
cyclopropyl optionally having one phenylaminocarbonyl optionally having 1 to 3 substituents selected from a fluorine atom and methyl.

$R^{7d}$ is preferably a hydrogen atom.

$R^{8d}$ is preferably a hydrogen atom.

Preferable specific examples of compound (Id) include the following.

[Compound (Id-A)]

In compound (Id), a compound wherein
$R^{2d}$ is a hydrogen atom;
$W^d$ is O;
$X^d$ is $CR^{3d'}$ wherein $R^{3d'}$ is a hydrogen atom or a halogen atom;
$Y^d$ is $CR^{4d'}$ wherein $R^{4d'}$ is a hydrogen atom or a halogen atom;
$R^{5d}$ is
(1) cyclopropyl optionally having one phenylaminocarbonyl optionally having 1 to 3 substituents selected from a fluorine atom and methyl,
(2) acetylamino optionally having one phenyl,
(3) methoxy optionally having one phenyl,
(4) tert-butoxy, or
(5) a nitrogen-containing heterocyclic group or an N-oxide thereof (particularly, pyrazolyl (e.g., 3-pyrazolyl, 5-pyrazolyl), dihydropyridyl (e.g., 1,2-dihydropyridin-3-yl), N-oxidepyridyl (e.g., N-oxidepyridin-2-yl)) optionally having 1 to 4 substituents selected from (a) phenyl optionally having 1 to 3 substituents selected from a fluorine atom and methyl,
(b) methyl optionally having 1 to 3 fluorine atoms,
(c) ethyl optionally having 1 to 3 fluorine atoms, and
(d) oxo;

$R^{6d}$ is a hydrogen atom;
$R^{7d}$ is a hydrogen atom; and
$R^{8d}$ is a hydrogen atom is preferable.

Particularly, in compound (Id-A), a compound wherein
$R^{2d}$ is a hydrogen atom;
$W^d$ is O;
$X^d$ is CF;
$Y^d$ is CH;
$R^{5d}$ is a cyclopropyl optionally having one phenylaminocarbonyl optionally having 1 to 3 substituents selected from a fluorine atom and methyl;
$R^{6d}$ is a hydrogen atom;
$R^{7d}$ is a hydrogen atom; and
$R^{8d}$ is a hydrogen atom is preferable.

Specifically, as compound (Id-A), the compound of Example 18 is preferable.

[Compound (Ie)]
1,3-thiazolo[5,4-b]pyridine derivative: a compound represented by the formula

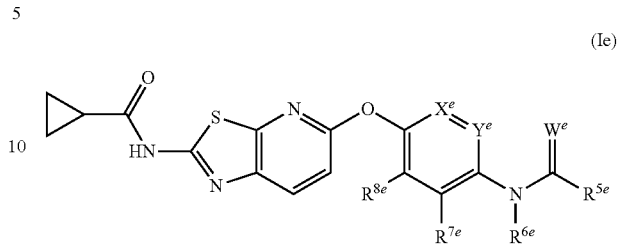

(Ie)

wherein
$W^e$ is O or S;
$X^e$ is $CR^{3e}$ ($R^{3e}$ is a hydrogen atom, a halogen atom or $C_{1-6}$ alkyl), or N;
$Y^e$ is $CR^{4e}$ ($R^{4e}$ is a hydrogen atom, a halogen atom or $C_{1-6}$ alkyl), or N;
$R^{5e}$ is
(1) $C_{3-6}$ cycloalkyl optionally having one $C_{6-10}$ aryl-aminocarbonyl optionally having 1 to 3 substituents selected from a halogen atom and $C_{1-6}$ alkyl,
(2) $C_{1-6}$ alkyl-carbonylamino optionally having one $C_{6-10}$ aryl,
(3) $C_{1-6}$ alkoxy optionally having one $C_{6-10}$ aryl, or
(4) a nitrogen-containing heterocyclic group or an N-oxide thereof optionally having 1 to 4 substituents selected from
(a) $C_{6-10}$ aryl optionally having 1 to 3 substituents selected from a halogen atom and $C_{1-6}$ alkyl,
(b) $C_{1-6}$ alkyl optionally having 1 to 3 halogen atoms, and
(c) oxo;
$R^{6e}$ is a hydrogen atom;
$R^{7e}$ is a hydrogen atom, a halogen atom or $C_{1-6}$ alkyl; and
$R^{8e}$ is a hydrogen atom, a halogen atom or $C_{1-6}$ alkyl,
or a salt thereof (compound (Ie)).

$W^e$ is preferably O.

$X^e$ is preferably $CR^{3e'}$ wherein $R^{3e'}$ is a hydrogen atom or a halogen atom, and particularly preferably CF.

$Y^e$ is preferably $CR^{4e'}$ wherein $R^{4e'}$ is a hydrogen atom or a halogen atom, and particularly preferably CH.

$R^{5e}$ is preferably
(1) cyclopropyl optionally having one phenylaminocarbonyl optionally having 1 to 3 fluorine atoms,
(2) acetylamino optionally having one phenyl,
(3) methoxy or tert-butoxy optionally having one phenyl, or
(4) a nitrogen-containing heterocyclic group or an N-oxide thereof (particularly, pyrazolyl (e.g., 3-pyrazolyl, 5-pyrazolyl), dihydropyridyl (e.g., 1,2-dihydropyridin-3-yl), N-oxidepyridyl (e.g., N-oxidepyridin-2-yl)) optionally having 1 to 3 substituents selected from (a) phenyl optionally having 1 to 3 fluorine atoms,
(b) methyl,
(c) ethyl, and
(d) oxo, and more preferably, a nitrogen-containing heterocyclic group (particularly, dihydropyridyl (e.g., 1,2-dihydropyridin-3-yl)) optionally having 1 to 3 substituents selected from (a) phenyl optionally having 1 to 3 fluorine atoms,
(b) methyl,
(c) ethyl, and
(d) oxo.

$R^{6e}$ is a hydrogen atom.

$R^{7e}$ is preferably a hydrogen atom.

$R^{8e}$ is preferably a hydrogen atom.

Preferable specific examples of compound (Ie) include the following.

[Compound (Ie-A)]

In compound (Ie), a compound wherein
$W^e$ is O;
$X^e$ is $CR^{3e'}$ wherein $R^{3e'}$ is a hydrogen atom or a halogen atom;
$Y^e$ is $CR^{4e'}$ wherein $R^{4e'}$ is a hydrogen atom or a halogen atom;
$R^{5e}$ is
(1) cyclopropyl optionally having one phenylaminocarbonyl optionally having 1 to 3 fluorine atoms,
(2) acetylamino optionally having one phenyl,
(3) methoxy or tert-butoxy optionally having one phenyl, or
(4) a nitrogen-containing heterocyclic group or an N-oxide thereof (particularly, pyrazolyl (e.g., 3-pyrazolyl, 5-pyrazolyl), dihydropyridyl (e.g., 1,2-dihydropyridin-3-yl), N-oxidepyridyl (e.g., N-oxidepyridin-2-yl)) optionally having 1 to 3 substituents selected from
   (a) phenyl optionally having 1 to 3 fluorine atoms,
   (b) methyl,
   (c) ethyl, and
   (d) oxo;
$R^{6e}$ is a hydrogen atom;
$R^{7e}$ is a hydrogen atom; and
$R^{8e}$ is a hydrogen atom is preferable.

Particularly, compound (Ie-A) wherein
$W^e$ is O;
$X^e$ is CF;
$Y^e$ is CH;
$R^{5e}$ is
(1) cyclopropyl optionally having one phenylaminocarbonyl optionally having 1 to 3 fluorine atoms,
(2) tert-butoxy optionally having one phenyl, or
(3) a nitrogen-containing heterocyclic group (particularly, dihydropyridyl (e.g., 1,2-dihydropyridin-3-yl)) optionally having 1 to 3 substituents selected from
   (a) phenyl optionally having 1 to 3 fluorine atoms,
   (b) methyl,
   (c) ethyl, and
   (d) oxo;
$R^{6e}$ is a hydrogen atom;
$R^{7e}$ is a hydrogen atom; and
$R^{8e}$ is a hydrogen atom is preferable.

Specifically, as compound (Ie-A), compounds of Examples 19-21 are preferable.

When compound (I) is a salt, examples of the salt include a metal salt, an ammonium salt, a salt with organic base, a salt with inorganic acid, a salt with organic acid, a salt with basic or acidic amino acid and the like. Preferable examples of the metal salt include alkali metal salt such as sodium salt, potassium salt and the like; alkaline earth metal salt such as calcium salt, magnesium salt, barium salt and the like; aluminum salt and the like. Preferable examples of the salt with the organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with the inorganic acid include a salt with hydrochloric acid, hydrobromic acid, nitric acid, sulfuric acid, phosphoric acid and the like. Preferable examples of the salt with the organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with the basic amino acid include a salt with arginine, lysine, ornithine and the like. Preferable examples of the salt with the acidic amino acid include a salt with aspartic acid, glutamic acid and the like.

Of these, pharmaceutically acceptable salt is preferable. For example, where the compound has an acidic functional group, inorganic salt such as alkali metal salt (e.g., sodium salt, potassium salt etc.), alkaline earth metal salt (e.g., calcium salt, magnesium salt etc.) and the like, ammonium salt and the like can be mentioned. Alternatively, where the compound has a basic functional group, for example, a salt with inorganic acid such as hydrochloric acid, hydrobromic acid, nitric acid, sulfuric acid, phosphoric acid and the like, or a salt with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like can be mentioned.

Hereinafter, the production methods of compound (I) of the present invention are explained.

The compound (I) of the present invention can be obtained, for example, according to the methods shown in the following Schemes or a method analogous thereto and the like.

Each compound in the following Schemes includes salts, and as such salts, for example, those similar to the salts of the compound (I) and the like can be used.

The compound obtained in each step can be used in the form of a reaction mixture or a crude product for the next reaction. In addition, the compound can be isolated from a reaction mixture according to a conventional method, and can be easily purified by a separation means such as recrystallization, distillation, chromatography and the like.

Schematic reaction formulas are shown in the following, wherein each symbol in the compounds is as defined above.

[Production Method 1]

In compound (Ia), compound (Ia-1) wherein $W^a$ is an oxygen atom can be produced, for example, by a method shown in Reaction scheme 1. The compound (Ia-1) is encompassed in compound (Ia).

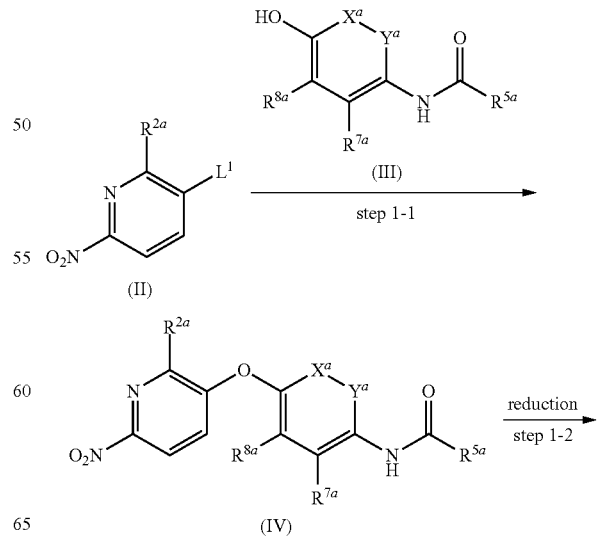

Reaction Scheme 1

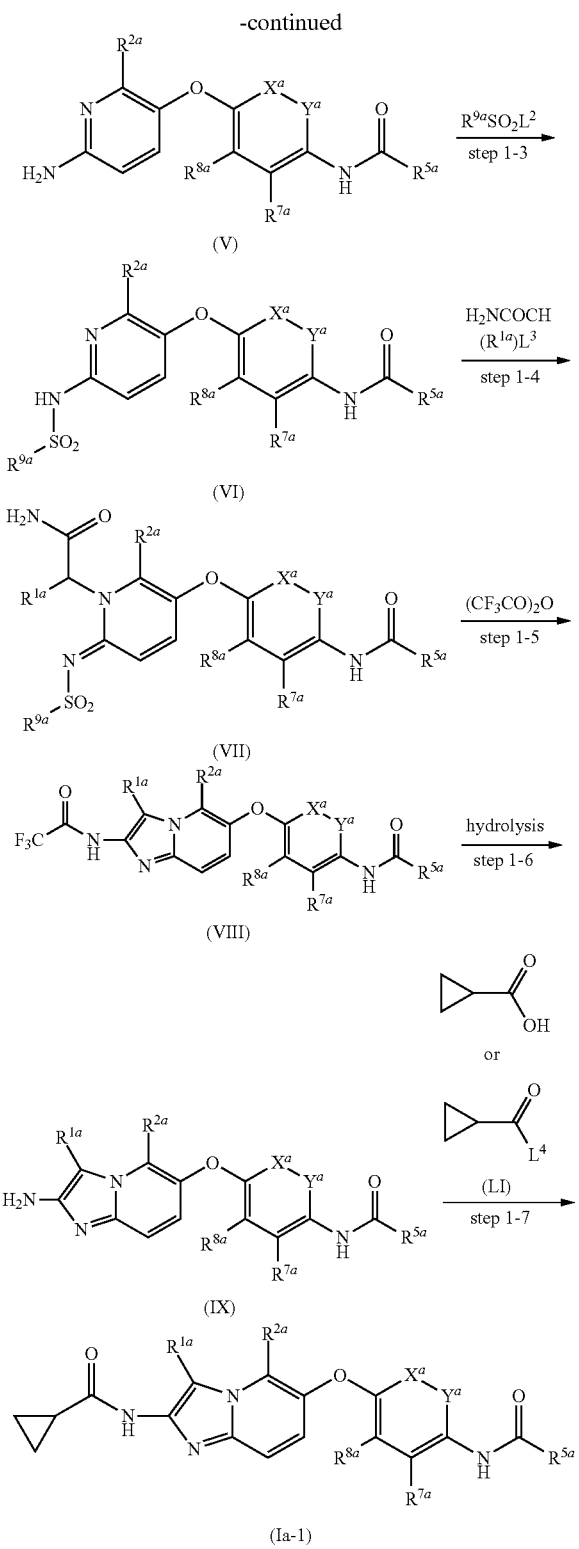

wherein $L^1$-$L^4$ are each a leaving group; $R^{9a}$ is (1) $C_{1-6}$ alkyl (e.g., methyl, ethyl) optionally having 1 to 3 substituents selected from (a) a halogen atom and (b) nitro, or (2) $C_{6-10}$ aryl (e.g., phenyl) optionally having 1 to 3 substituents selected from (a) a halogen atom, (b) nitro, and (c) $C_{1-6}$ alkyl (e.g., methyl, ethyl) optionally having 1 to 3 halogen atoms; and other symbols are as defined above.

Examples of the leaving group for $L^1$ include (1) a halogen atom, (2) $C_{1-6}$ alkylsulfonyloxy (e.g., methylsulfonyloxy, ethylsulfonyloxy) optionally having 1 to 3 substituents selected from (a) a halogen atom, (b) nitro, and (c) $C_{1-6}$ alkyl (e.g., methyl, ethyl) optionally having 1 to 3 halogen atoms, (3) $C_{6-10}$ arylsulfonyloxy (e.g., phenylsulfonyloxy) optionally having 1 to 3 substituents selected from (a) a halogen atom, (b) nitro, and (c) $C_{1-6}$ alkyl (e.g., methyl, ethyl) optionally having 1 to 3 halogen atoms, and the like.

Examples of the leaving group for $L^2$ include a halogen atom and the like.

Examples of the leaving group for $L^3$ include those similar to the leaving group for $L^1$.

Examples of the leaving group for $L^4$ include a halogen atom and the like.

(Step 1-1):

Compound (IV) can be produced by reacting compound (II) with compound (III).

Compound (III) is used in a proportion of about 0.1 mol to about 10 mol, preferably about 0.3 mol to about 3 mol, per 1 mol of compound (II).

In this reaction, a base may be added as necessary. As the base, an inorganic base, an organic base and the like are used. Specific examples include sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline, sodium methoxide, sodium ethoxide, potassium tert-butoxide, sodium hydride, sodium amide, lithiumdiisopropylamide and the like. The base is used in a proportion of about 1 mol to about 30 mol, preferably about 1 mol to about 10 mol, per 1 mol of compound (II).

This reaction is advantageously carried out using a solvent inert to the reaction. While the solvent is not particularly limited as long as the reaction proceeds, for example, alcohols such as methanol, ethanol, 2-propanol, 2-methyl-2-propanol and the like; ethers such as diethyl ether, tetrahydrofuran, 1,4-dioxane, 1,2-dimethoxyethane and the like; hydrocarbons such as benzene, toluene, cyclohexane, hexane and the like; esters such as ethyl acetate and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane, chlorobenzene, trifluoromethylbenzene and the like; nitriles such as acetonitrile and the like; sulfoxides such as dimethyl sulfoxide and the like; pyridine; acetic acid; water; and the like can be used alone or in a mixture.

While the reaction time varies depending on the kind of reagent and solvent to be used, it is generally about 10 min to about 100 hr, preferably about 30 min to about 50 hr.

The reaction temperature is generally about −78° C. to about 200° C., preferably about −20° C. to about 150° C.

This reaction may be performed in a microwave reactor.

(Step 1-2):

Compound (V) can be produced by reducing nitro of compound (IV). Nitro can be reduced according to a method known per se, for example, the methods described in "Advanced Organic Chemistry, 4th Ed." (Jerry March), "Comprehensive Organic Transformations, 2nd Ed." (Richard C. Larock), the fourth series of experimental chemistry, vol. 20, 279-280 and the like, or a method analogous thereto.

(Step 1-3):

Compound (VI) can be produced by reacting compound (V) with a compound represented by the formula $R^{9a}SO_2L^2$ in the presence of a base.

$R^{9a}SO_2L^2$ is used in a proportion of about 0.1 mol to about 10 mol, preferably about 0.3 mol to about 3 mol, per 1 mol of compound (V).

As the base, those similar to the bases of step 1-1 are used. The base is used in a proportion of about 0.1 mol to about 10 mol, preferably about 0.3 mol to about 3 mol, per 1 mol of compound (V).

This reaction is advantageously carried out using a solvent inert to the reaction. As the solvent, those similar to the solvents exemplified in step 1-1 are used. Alternatively, an excess amount of a base may be used as a solvent.

The reaction time is generally about 10 min to about 100 hr, preferably about 30 min to about 50 hr.

The reaction temperature is generally about −78° C. to about 200° C., preferably about −20° C. to about 150° C.

$R^{9a}SO_2L^2$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

(Step 1-4):

Compound (VII) can be produced by reacting compound (VI) with a compound represented by the formula $H_2NCOCH(R^{1a})L^3$ in the presence of a base.

$H_2NCOCH(R^{1a})L^3$ is used in a proportion of about 0.1 mol to about 10 mol, preferably about 0.3 mol to about 3 mol, per 1 mol of compound (VI).

As the base, those similar to the bases of step 1-1 are used. The base is used in a proportion of about 0.1 mol to 10 mol, preferably about 0.3 mol to about 3 mol, per 1 mol of compound (VI).

This reaction is advantageously carried out using a solvent inert to the reaction. As the solvent, those similar to the solvents exemplified in step 1-1 are used. Alternatively, an excess amount of a base may be used as a solvent.

The reaction time is generally about 10 min to about 100 hr, preferably about 30 min to about 50 hr.

The reaction temperature is generally about −78° C. to about 200° C., preferably about −20° C. to about 150° C.

$H_2NCOCH(R^{1a})L^3$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

(Step 1-5):

Compound (VIII) can be produced by reacting compound (VII) with trifluoroacetic acid anhydride.

Trifluoroacetic acid anhydride is used in a solvent amount for compound (VII).

This reaction is advantageously performed using an additional solvent inert to the reaction. As the solvent, those similar to the solvents exemplified in step 1-1 are used.

The reaction time is generally about 10 min to about 100 hr, preferably about 30 min to about 50 hr.

The reaction temperature is generally about −78° C. to about 200° C., preferably about −20° C. to about 150° C.

(Step 1-6):

Compound (IX) can be produced by alkalihydrolysis of compound (VIII). This reaction is performed in a water-containing solvent in the presence of a base.

Examples of the base include sodium hydroxide, potassium hydroxide, lithium hydroxide, barium hydroxide, calcium hydroxide, potassium carbonate, sodium carbonate, cesium carbonate, sodium methoxide and the like. The base is used in a proportion of about 1 mol to about 50 mol, preferably about 1 mol to about 10 mol, per 1 mol of compound (VIII).

Examples of the water-containing solvent include mixed solvent of one or more kinds of solvents selected from methanol, ethanol, tetrahydrofuran, 1,4-dioxane and the like and water, and the like.

The reaction time is generally about 10 min to about 100 hr, preferably about 30 min to about 50 hr.

The reaction temperature is generally about −78° C. to about 200° C., preferably about −20° C. to about 100° C.

(Step 1-7):

Compound (Ia-1) can be produced by reacting compound (IX) with cyclopropanecarboxylic acid in the presence of a condensation agent, or compound (IX) with compound (LI).

When compound (IX) is reacted with cyclopropanecarboxylic acid in the presence of a condensation agent, cyclopropanecarboxylic acid is used in a proportion of about 1 mol to about 10 mol, preferably about 1 mol to about 3 mol, per 1 mol of compound (IX).

Examples of the condensation agent include 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(7-azabenzotriazol-1-yl)-N,N,N',N'-tetramethyluronium hexafluorophosphate and the like. The condensation agent is used in a proportion of about 1 mol to about 10 mol, preferably about 1 mol to about 5 mol, per 1 mol of compound (IX).

Where necessary, a suitable condensation promoter (e.g., 1-hydroxybenzotriazole, N-hydroxysuccinimide and the like) can be used in this reaction.

Such condensation promoter is used in a proportion of about 0.1 mol to about 10 mol, preferably about 0.3 mol to about 3 mol, per 1 mol of compound (IX).

This reaction may proceed more smoothly by addition of a base (e.g., triethylamine, N,N-diisopropylethylamine, N-methylmorpholine, 1,8-diazabicyclo[5.4.0]undec-7-ene, 4-(dimethylamino)pyridine and the like). The base is used in a proportion of about 0.01 mol to about 10 mol, preferably about 0.03 mol to about 5 mol, per 1 mol of compound (IX).

This reaction is advantageously carried out using a solvent inert to the reaction. As the solvent, those similar to the solvents exemplified in step 1-1 are used.

The reaction time is generally about 10 min to about 100 hr, preferably about 30 min to about 50 hr.

The reaction temperature is generally about −78° C. to about 200° C., preferably about −20° C. to about 150° C.

When compound (IX) is reacted with compound (LI), compound (LI) is used in a proportion of about 0.1 mol to about 10 mol, preferably about 0.3 mol to about 3 mol, per 1 mol of compound (IX).

Generally, this reaction is preferably performed in the presence of a base. However, the presence of a base is not always essential. Examples of the base to be used include sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline and the like. The base is used in a proportion of about 0.01 mol to about 10 mol, preferably about 0.03 mol to about 5 mol, per 1 mol of compound (IX).

This reaction is advantageously carried out using a solvent inert to the reaction. As the solvent, those similar to the solvents exemplified in step 1-1 are used.

The reaction time is generally about 10 min to about 100 hr, preferably about 30 min to about 50 hr.

The reaction temperature is generally about −78° C. to about 200° C., preferably about −20° C. to about 150° C.

[Production Method 2]

In compound (Ia), compound (Ia-2) wherein $W^a$ is a sulfur atom and $R^{5a}$ is $C_{1-6}$ alkyl-carbonylamino optionally having one $C_{6-10}$ aryl can be produced, for example, by a method shown in Reaction scheme 2. The compound (Ia-2) is encompassed in compound (Ia). In addition, compound (Ia-1) can also be produced by a method shown in Reaction scheme 2.

Reaction Scheme 2

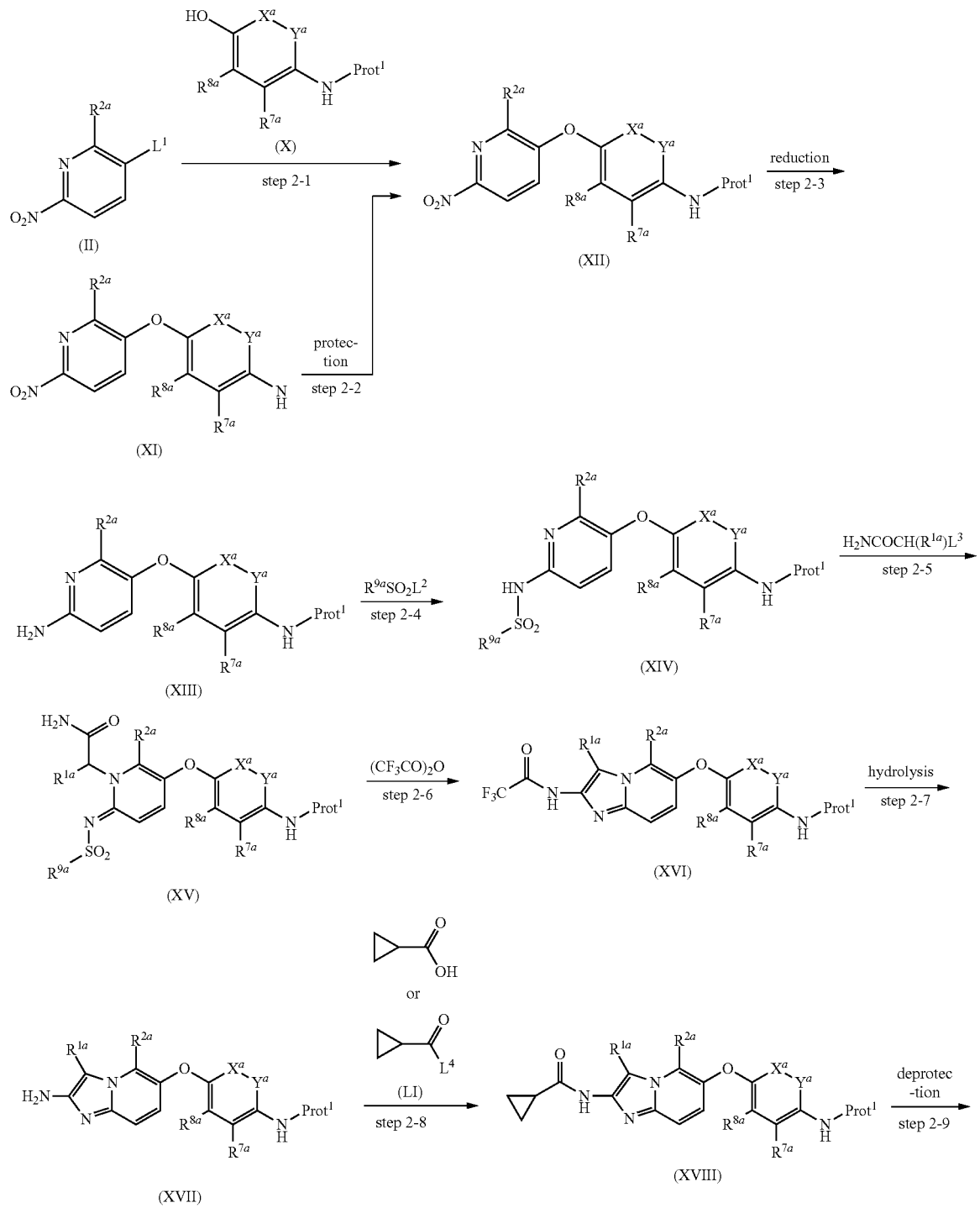

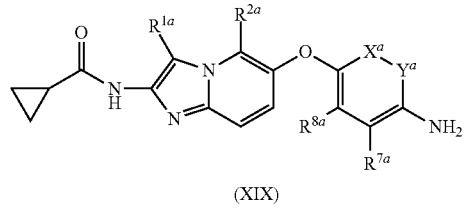
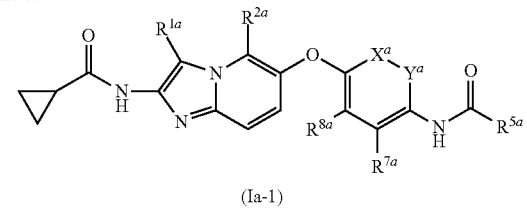

(XIX)　　(Ia-1)

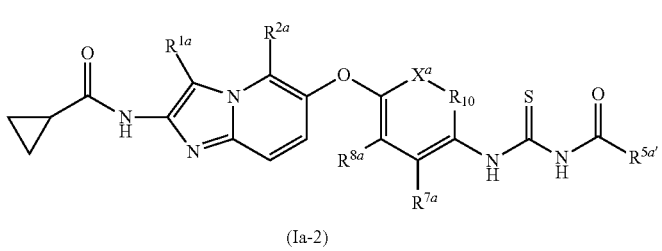

(Ia-2)

wherein Prot¹ is an amino-protecting group; $L^5$ is a leaving group; $R^{5a'}$ is $C_{1-6}$ alkyl optionally having one $C_{6-10}$ aryl; and other symbols are as defined above.

Examples of the amino-protecting group for Prot¹ include benzyloxycarbonyl, tert-butoxycarbonyl and the like.

Examples of the leaving group for $L^5$ include a halogen atom and the like.

The "$C_{1-6}$ alkyl optionally having one $C_{6-10}$ aryl" for $R^{5a}$ means a group bonded to carbonylamino to form "$C_{1-6}$ alkyl-carbonylamino optionally having one $C_{6-10}$ aryl" for the above-mentioned $R^5$.

(Step 2-1):

Compound (XII) can be produced by reacting compound (II) with compound (X) in the presence of a base.

Compound (X) is used in a proportion of about 0.1 mol to about 10 mol, preferably about 0.3 mol to about 3 mol, per 1 mol of compound (II).

As the base, those similar to the bases of step 1-1 are used. The base is used in a proportion of about 1 mol to about 30 mol, preferably about 1 mol to about 10 mol, per 1 mol of compound (II).

This reaction is advantageously carried out using a solvent inert to the reaction. As the solvent, those similar to the solvents exemplified in step 1-1 are used.

The reaction time is generally about 10 min to about 100 hr, preferably about 30 min to about 50 hr.

The reaction temperature is generally about −78° C. to about 200° C., preferably about −20° C. to about 150° C.

(Step 2-2):

Compound (XII) can also be produced by protecting amino of compound (XI). Amino can be protected according to a method known per se, for example, the methods described in "Protective Groups in Organic Synthesis, 3rd Ed." (Theodora W. Greene) and the like, or a method analogous thereto.

(Steps 2-3-2-8):

Compound (XIII), compound (XIV), compound (XV), compound (XVI), compound (XVII) and compound (XVIII) can be synthesized from compound (XII) in the same manner as in steps 1-2 to 1-7, respectively.

(Step 2-9):

Compound (XIX) can be produced by removing the amino-protecting group of compound (XVIII). The amino-protecting group can be removed according to a method known per se, for example, the methods described in "Protective Groups in Organic Synthesis, 3rd Ed." (Theodora W. Greene) and the like, or a method analogous thereto.

(Step 2-10):

Compound (Ia-1) can be produced by reacting compound (XIX) with carboxylic acid ($R^{5a}CO_2H$) in the presence of a condensation agent.

Carboxylic acid ($R^{5a}CO_2H$) is used in a proportion of about 1 mol to about 10 mol, preferably about 1 mol to about 3 mol, per 1 mol of compound (XIX).

Examples of the condensation agent include 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(benzotriazol-1-yl)-N,N,N',N'-tetramethyluronium hexafluorophosphate, O-(7-azabenzotriazol-1-yl)-N,N,N,N-tetramethyluronium hexafluorophosphate and the like. The condensation agent is used in a proportion of about 1 mol to about 10 mol, preferably about 1 mol to about 5 mol, per 1 mol of compound (XIX).

Where necessary, a suitable condensation promoter (e.g., 1-hydroxybenzotriazole, N-hydroxysuccinimide etc.) can be used in this reaction. Such condensation promoter is used in a proportion of about 0.1 mol to about 10 mol, preferably about 0.3 mol to about 3 mol, per 1 mol of compound (XIX).

This reaction may proceed more smoothly by addition of a base. As the base, those similar to the bases of step 1-1 are used. The base is used in a proportion of about 0.01 mol to about 10 mol, preferably about 0.03 mol to about 5 mol, per 1 mol of compound (XIX).

This reaction is advantageously carried out using a solvent inert to the reaction. As the solvent, those similar to the solvents exemplified in step 1-1 are used.

The reaction time is generally about 1 min to about 200 hr, preferably about 10 min to about 100 hr.

The reaction temperature is generally about −100° C. to about 250° C., preferably about −78° C. to about 200° C.

$R^{5a}CO_2H$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

Compound (Ia-1) can also be produced by reacting compound (XIX) with a reactive derivative ($R^{5a}COL^5$) of carboxylic acid in the presence of a base.

The reactive derivative ($R^{5a}COL^5$) of carboxylic acid is used in a proportion of about 1 mol to about 10 mol, preferably about 1 mol to about 3 mol, per 1 mol of compound (XIX).

The base may be used in a proportion of about 0.01 mol to about 10 mol, preferably about 0.03 mol to about 5 mol, per 1 mol of compound (XIX). As the base, those similar to the bases of step 1-1 are used.

This reaction is advantageously carried out using a solvent inert to the reaction. As the solvent, those similar to the solvents exemplified in step 1-1 are used.

The reaction time is generally about 1 min to about 200 hr, preferably about 10 min to about 100 hr.

The reaction temperature is generally about −100° C. to about 250° C., preferably about −78° C. to about 200° C.

$R^{5a}COL^5$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

(Step 2-11):

Compound (Ia-2) can be produced by reacting compound (XIX) with acylthiocyanate derivative (XX).

The acylthiocyanate derivative (XX) is used in a proportion of about 0.1 mol to 10 mol, preferably about 0.5 mol to about 5 mol, per 1 mol of compound (XIX).

This reaction is advantageously carried out using a solvent inert to the reaction. As the solvent, those similar to the solvents exemplified in step 1-1 are used.

The reaction time is generally about 1 min to about 200 hr, preferably about 10 min to about 100 hr.

The reaction temperature is generally about −100° C. to about 250° C., preferably about −78° C. to about 200° C.

[Production Method 3]

In compound (Ib), compound (Ib-1) wherein $W^b$ is an oxygen atom can be produced, for example, by the method shown in Reaction scheme 3. The compound (Ib-1) is encompassed in compound (Ib).

Reaction Scheme 3

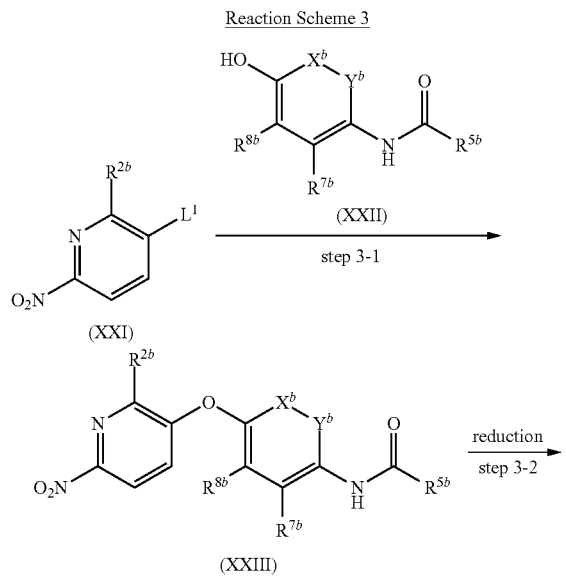

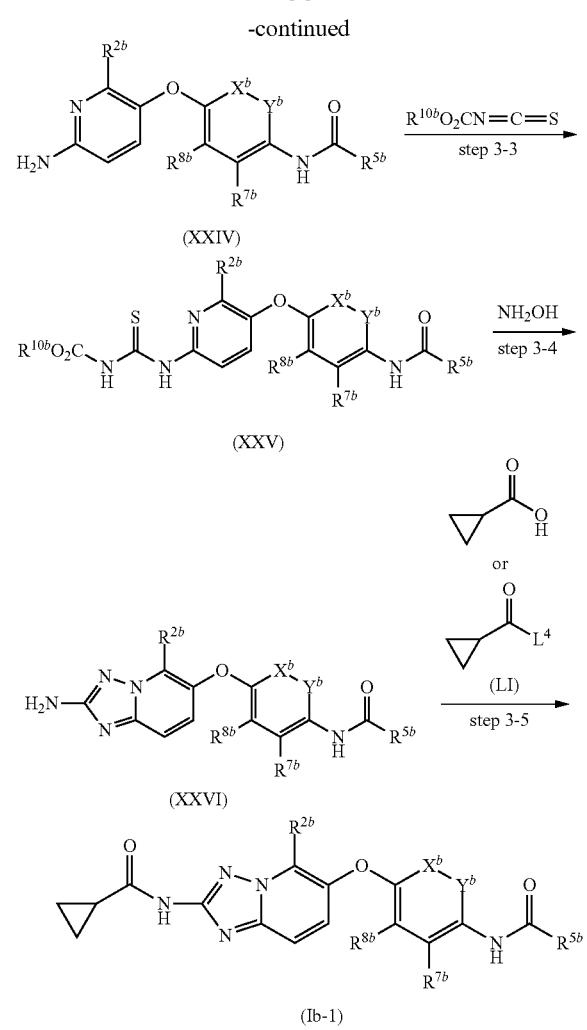

wherein $R^{10b}$ is $C_{1-6}$ alkyl optionally having 1 to 3 substituents selected from (a) a halogen atom and (b) nitro; and other symbols are as defined above.

(Step 3-1):

Compound (XXIII) can be produced by reacting compound (XXI) with compound (XXII).

Compound (XXII) is used in a proportion of about 0.1 mol to about 10 mol, preferably about 0.3 mol to about 3 mol, per 1 mol of compound (XXI).

In this reaction, a base may be added as necessary. As the base, an inorganic base, an organic base and the like are used. Specific examples include sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline, sodium methoxide, sodium ethoxide, potassium tert-butoxide, sodium hydride, sodium amide, lithiumdiisopropylamide and the like. The base is used in a proportion of about 1 mol to about 30 mol, preferably about 1 mol to about 10 mol, per 1 mol of compound (XXI).

This reaction is advantageously carried out using a solvent inert to the reaction. The solvent is not particularly limited as long as the reaction proceeds and, for example, alcohols such as methanol, ethanol, 2-propanol, 2-methyl-2-propanol and the like; ethers such as diethyl ether, tetrahydrofuran, 1,4-dioxane, 1,2-dimethoxyethane and the like; hydrocarbons such as benzene, toluene, cyclohexane, hexane and the like; esters such as ethyl acetate and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile and the like; sulfoxides such as dimethyl sulfoxide and the like; pyridine; acetic acid; water; and the like can be used alone or in a mixture.

While the reaction time varies depending on the kind of reagent and solvent to be used, it is generally about 10 min to about 100 hr, preferably about 30 min to about 50 hr.

The reaction temperature is generally about −78° C. to about 200° C., preferably about −20° C. to about 150° C.

This reaction may be performed in a microwave reactor.
(Step 3-2):
Compound (XXIV) can be produced by reducing nitro of compound (XXIII).

Nitro can be reduced according to a method known per se, for example, the methods described in "Advanced Organic Chemistry, 4th Ed." (Jerry March), "Comprehensive Organic Transformations, 2nd Ed." (Richard C. Larock), the fourth series of experimental chemistry, vol. 20, 279-280 and the like, or a method analogous thereto.
(Step 3-3):
Compound (XXV) can be produced by reacting compound (XXIV) with a compound represented by the formula $R^{10b}O_2C—N=C=S$.

$R^{10b}O_2C—N=C=S$ is used in a proportion of about 0.1 mol to about 10 mol, preferably about 0.3 mol to about 3 mol, per 1 mol of compound (XXIV).

This reaction is advantageously carried out using a solvent inert to the reaction. As the solvent, those similar to the solvents exemplified in step 3-1 are used.

The reaction time is generally about 10 min to about 100 hr, preferably about 30 min to about 50 hr.

The reaction temperature is generally about −78° C. to about 200° C., preferably about −20° C. to about 150° C.

$R^{10b}O_2C—N=C=S$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.
(Step 3-4):
Compound (XXVI) can be produced by reacting compound (XXV) with hydroxylamine in the presence of a base.

Hydroxylamine is used in a proportion of about 0.1 mol to about 100 mol, preferably about 0.3 mol to about 30 mol, per 1 mol of compound (XXV).

As the base, those similar to the bases exemplified in step 3-1 are used. The base is used in a proportion of about 0.1 mol to about 100 mol, preferably about 0.3 mol to about 30 mol, per 1 mol of compound (XXV).

This reaction is advantageously carried out using a solvent inert to the reaction. As the solvent, those similar to the solvents exemplified in step 3-1 are used.

The reaction time is generally about 10 min to about 100 hr, preferably about 30 min to about 50 hr.

The reaction temperature is generally about −78° C. to about 200° C., preferably about −20° C. to about 150° C.

(Step 3-5):
Compound (Ib-1) can be produced by reacting compound (XXVI) with cyclopropanecarboxylic acid in the presence of a condensation agent or compound (XXVI) with compound (LI).

When compound (XXVI) is reacted with cyclopropanecarboxylic acid in the presence of a condensation agent, cyclopropanecarboxylic acid is used in a proportion of about 1 mol to about 10 mol, preferably about 1 mol to about 3 mol, per 1 mol of compound (XXVI).

Examples of the condensation agent include 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(7-azabenzotriazol-1-yl)-N,N,N',N'-tetramethyluronium hexafluorophosphate and the like. The condensation agent is used in a proportion of about 1 mol to about 10 mol, preferably about 1 mol to about 5 mol, per 1 mol of compound (XXVI).

Where necessary, a suitable condensation promoter (e.g., 1-hydroxybenzotriazole, N-hydroxysuccinimide and the like) can be used in this reaction. Such condensation promoter is used in a proportion of about 0.1 mol to about 10 mol, preferably about 0.3 mol to about 3 mol, per 1 mol of compound (XXVI).

This reaction may proceed more smoothly by addition of a base (e.g., triethylamine, N,N-diisopropylethylamine, N-methylmorpholine, 1,8-diazabicyclo[5.4.0]undec-7-ene and the like). The base is used in a proportion of about 0.01 mol to about 10 mol, preferably about 0.03 mol to about 5 mol, per 1 mol of compound (XXVI).

This reaction is advantageously carried out using a solvent inert to the reaction. As the solvent, those similar to the solvents exemplified in step 3-1 are used.

The reaction time is generally about 10 min to about 100 hr, preferably about 30 min to about 50 hr.

The reaction temperature is generally about −78° C. to about 200° C., preferably about −20° C. to about 150° C.

When compound (XXVI) is reacted with compound (LI), compound (LI) is used in a proportion of about 0.1 mol to about 10 mol, preferably about 0.3 mol to about 3 mol, per 1 mol of compound (XXVI).

Generally, this reaction is preferably performed in the presence of a base. However, the presence of a base is not always essential. Examples of the base include sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline and the like. The base is used in a proportion of about 0.01 mol to about 10 mol, preferably about 0.03 mol to about 5 mol, per 1 mol of compound (XXVI).

This reaction is advantageously carried out using a solvent inert to the reaction. As the solvent, those similar to the solvents exemplified in step 3-1 are used.

The reaction time is generally about 10 min to about 100 hr, preferably about 30 min to about 50 hr.

The reaction temperature is generally about −78° C. to about 200° C., preferably about −20° C. to about 150° C.

[Production Method 4]
Compound (Ib-1) can also be produced, for example, by a method shown in Reaction scheme 4.

Reaction Scheme 4

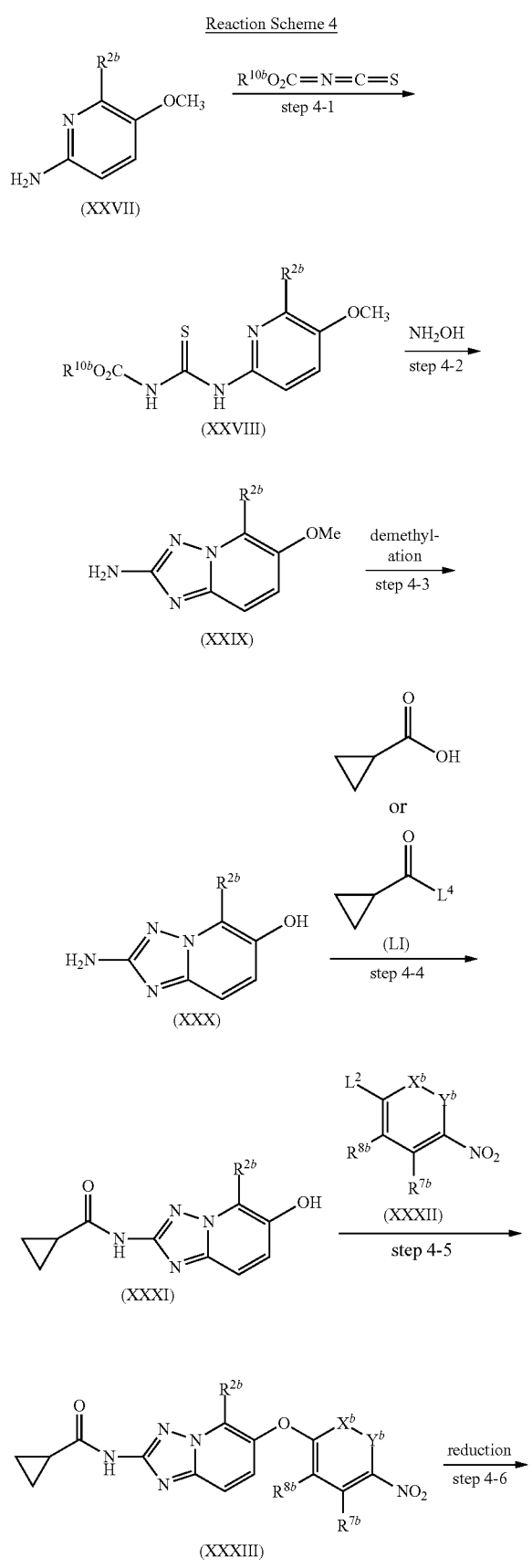

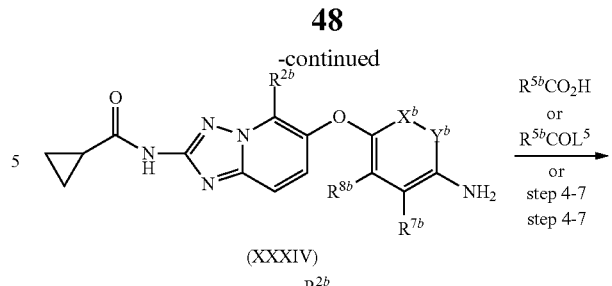

(XXXIV)

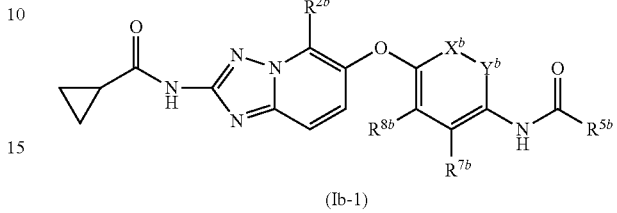

(Ib-1)

wherein the symbols are as defined above.

(Steps 4-1 and 4-2):

Compound (XXVIII) and compound (XXIX) can be synthesized from compound (XXVII) in the same manner as in steps 3-3 and 3-4, respectively.

(Step 4-3):

Compound (XXX) can be produced by demethylation of compound (XXIX).

Demethylation can be performed according to a method known per se, for example, the method described in "Protective Groups in Organic Synthesis, 3rd Ed." (Theodora W. Greene) and the like, or a method analogous thereto.

(Step 4-4):

Compound (XXXI) can be produced by reacting compound (XXX) with cyclopropanecarboxylic acid in the presence of a condensation agent, or by reacting compound (XXX) with compound (LI) in the same manner as in step 3-5.

(Step 4-5):

Compound (XXXIII) can be produced by reacting compound (XXXI) with compound (XXXII) in the presence of a base.

Compound (XXXII) is used in a proportion of about 0.1 mol to about 10 mol, preferably about 0.3 mol to about 3 mol, per 1 mol of compound (XXXI).

As the base, those similar to the bases exemplified in step 3-1 are used. The base is used in a proportion of about 1 mol to about 30 mol, preferably about 1 mol to about 10 mol, per 1 mol of compound (XXXI).

This reaction is advantageously carried out using a solvent inert to the reaction. As the solvent, those similar to the solvents exemplified in step 3-1 are used.

The reaction time is generally about 10 min to about 100 hr, preferably about 30 min to about 50 hr.

The reaction temperature is generally about −78° C. to about 200° C., preferably about −20° C. to about 150° C.

(Step 4-6):

Compound (XXXIV) can be produced by reducing nitro of compound (XXXIII) in the same manner as in step 3-2.

(Step 4-7):

Compound (Ib-1) can be produced by reacting compound (XXXIV) with carboxylic acid ($R^{5b}CO_2H$) in the presence of a condensation agent.

Carboxylic acid ($R^{5b}CO_2H$) is used in a proportion of about 1 mol to about 10 mol, preferably about 1 mol to about 3 mol, per 1 mol of compound (XXXIV).

Examples of the condensation agent include 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, 0-(benzotriazol-1-yl)-N,N,N',N'-tetramethyluronium hexafluorophosphate, O-(7-azabenzotriazol-1-yl)-N,N,N,N-tetramethyluronium hexafluorophosphate and the like. The condensation agent is used in a proportion of about 1 mol to about 10 mol, preferably about 1 mol to about 5 mol, per 1 mol of compound (XXXIV).

Where necessary, a suitable condensation promoter (e.g., 1-hydroxybenzotriazole, N-hydroxysuccinimide etc.) can be used in this reaction. Such condensation promoter is used in a proportion of about 0.1 mol to about 10 mol, preferably about 0.3 mol to about 3 mol, per 1 mol of compound (XXXIV).

This reaction may proceed more smoothly by the addition of a base. As the base, those similar to the bases exemplified in step 3-1 are used. The base is used in a proportion of about 0.01 mol to about 10 mol, preferably about 0.03 mol to about 5 mol, per 1 mol of compound (XXXIV).

This reaction is advantageously carried out using a solvent inert to the reaction. As the solvent, those similar to the solvents exemplified in step 3-1 are used.

The reaction time is generally about 1 min to about 200 hr, preferably about 10 min to about 100 hr.

The reaction temperature is generally about −100° C. to about 250° C., preferably about −78° C. to about 200° C.

$R^{5b}CO_2H$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

Compound (Ib-1) can also be produced by reacting compound (XXXIV) with a reactive derivative ($R^{5b}COL^5$) of carboxylic acid.

The reactive derivative ($R^{5b}COL^5$) of carboxylic acid is used in a proportion of about 1 mol to about 10 mol, preferably about 1 mol to about 3 mol, per 1 mol of compound (XXXIV).

This reaction may be performed in the presence of a base. As the base, those similar to the bases exemplified in step 3-1 are used. The base is used in a proportion of about 0.01 mol to about 10 mol, preferably about 0.03 mol to about 5 mol, per 1 mol of compound (XXXIV).

This reaction is advantageously carried out using a solvent inert to the reaction. As the solvent, those similar to the solvents exemplified in step 3-1 are used.

The reaction time is generally about 1 min to about 200 hr, preferably about 10 min to about 100 hr.

The reaction temperature is generally about −100° C. to about 250° C., preferably about −78° C. to about 200° C.

$R^{5b}COL^5$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

[Production Method 5]

In compound (Id), compound (Id-1) wherein $W^d$ is an oxygen atom can also be produced, for example, by a method shown in Reaction scheme 5. The compound (Id-1) is encompassed in compound (Id).

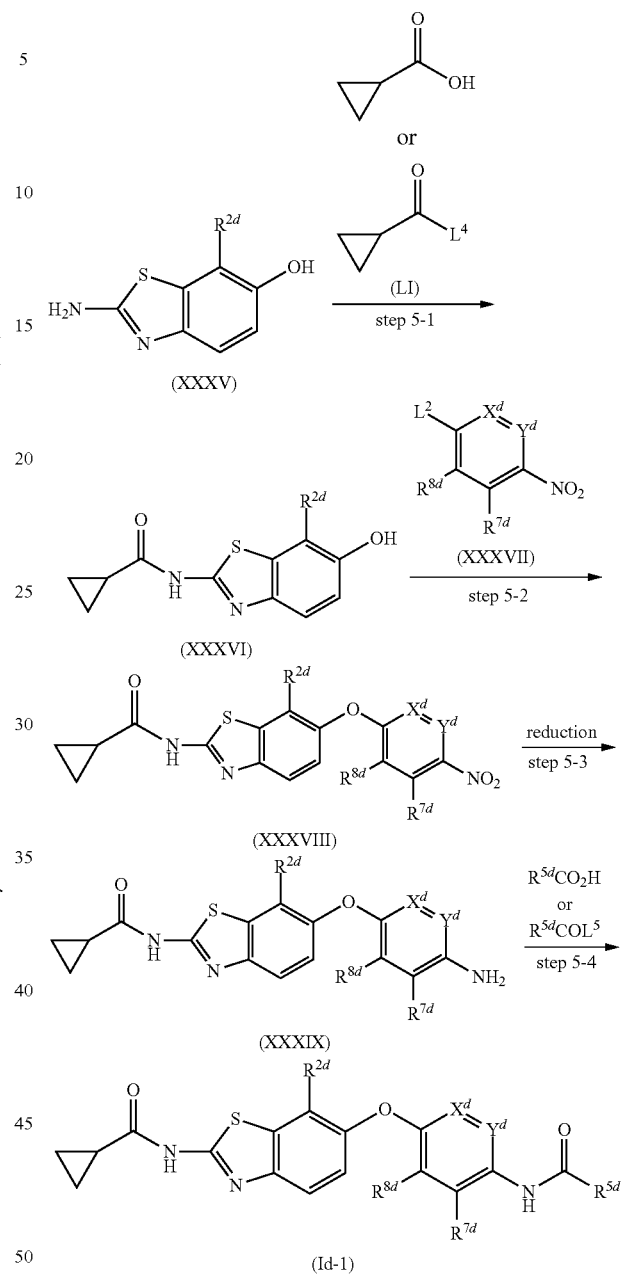

Reaction Scheme 5 wherein the symbols are as defined above.

(Step 5-1):

Compound (XXXVI) can be produced by reacting compound (XXXV) with cyclopropanecarboxylic acid in the presence of a condensation agent, or by reacting compound (XXXV) with compound (LI).

When compound (XXXV) is reacted with cyclopropanecarboxylic acid in the presence of a condensation agent, cyclopropanecarboxylic acid is used in a proportion of about 1 mol to about 10 mol, preferably about 1 mol to about 3 mol, per 1 mol of compound (XXXV).

Examples of the condensation agent include 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(7-azabenzotriazol-1-yl)-N,N,N',N'-tetramethyluronium hexafluorophosphate and the like. The condensation agent is used in a proportion of about 1 mol to about 10 mol, preferably about 1 mol to about 5 mol, per 1 mol of compound (XXXV).

Where necessary, a suitable condensation promoter (e.g., 1-hydroxybenzotriazole, N-hydroxysuccinimide and the like) can be used in this reaction. Such condensation promoter is used in a proportion of about 0.1 mol to about 10 mol, preferably about 0.3 mol to about 3 mol, per 1 mol of compound (XXXV).

This reaction may proceed more smoothly by the addition of a base (e.g., triethylamine, N,N-diisopropylethylamine, N-methylmorpholine, 1,8-diazabicyclo[5.4.0]undec-7-ene and the like). The base is used in a proportion of about 0.01 mol to about 10 mol, preferably about 0.03 mol to about 5 mol, per 1 mol of compound (XXXV).

This reaction is advantageously carried out using a solvent inert to the reaction. While the solvent is not particularly limited as long as the reaction proceeds, for example, alcohols such as methanol, ethanol, 2-propanol, 2-methyl-2-propanol and the like; ethers such as diethyl ether, tetrahydrofuran, 1,4-dioxane, 1,2-dimethoxyethane and the like; hydrocarbons such as benzene, toluene, cyclohexane, hexane and the like; esters such as ethyl acetate and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile and the like; sulfoxides such as dimethyl sulfoxide and the like; pyridine; acetic acid; water; and the like can be used alone or in a mixture.

While the reaction time varies depending on the kind of reagent and solvent to be used, it is generally about 10 min to about 100 hr, preferably about 30 min to about 50 hr.

The reaction temperature is generally about −78° C. to about 200° C., preferably about −20° C. to about 150° C.

This reaction may be performed in a microwave reactor.

When compound (XXXV) is reacted with compound (LI), compound (LI) is used in a proportion of about 0.1 mol to about 10 mol, preferably about 0.3 mol to about 3 mol, per 1 mol of compound (XXXV).

Generally, this reaction is preferably performed in the presence of a base. However, the presence of a base is not always essential. Examples of the base include sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline and the like. The base is used in a proportion of about 0.01 mol to about 10 mol, preferably about 0.03 mol to about 5 mol, per 1 mol of compound (XXXV).

This reaction is advantageously carried out using a solvent inert to the reaction. As the solvent, those similar to the aforementioned solvents are used.

The reaction time is generally about 10 min to about 100 hr, preferably about 30 min to about 50 hr.

The reaction temperature is generally about −78° C. to about 200° C., preferably about −20° C. to about 150° C.

This reaction may be performed in a microwave reactor.
(Step 5-2):

Compound (XXXVIII) can be produced by reacting compound (XXXVI) with compound (XXXVII).

Compound (XXXVII) is used in a proportion of about 0.1 mol to about 10 mol, preferably about 0.3 mol to about 3 mol, per 1 mol of compound (XXXVI).

In this reaction, a base may be added as necessary. As the base, an inorganic base, an organic base and the like are used. Specific examples include sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline, sodium methoxide, sodium ethoxide, potassium tert-butoxide, sodium hydride, sodium amide, lithiumdiisopropylamide and the like. The base is used in a proportion of about 1 mol to about 30 mol, preferably about 1 mol to about 10 mol, per 1 mol of compound (XXXVI).

This reaction is advantageously carried out using a solvent inert to the reaction. As the solvent, those similar to the solvents exemplified in step 5-1 are used.

While the reaction time varies depending on the reagent and solvent to be used, it is generally about 10 min to about 100 hr, preferably about 30 min to about 50 hr.

The reaction temperature is generally about −78° C. to about 200° C., preferably about −20° C. to about 150° C.

This reaction may be performed in a microwave reactor.
(Step 5-3):

Compound (XXXIX) can be produced by reducing nitro of compound (XXXVIII).

Nitro can be reduced according to a method known per se, for example, the methods described in "Advanced Organic Chemistry, 4th Ed." (Jerry March), "Comprehensive Organic Transformations, 2nd Ed." (Richard C. Larock), the fourth series of experimental chemistry, vol. 20, 279-280 and the like, or a method analogous thereto.
(Step 5-4):

Compound (Id-1) can be produced by reacting compound (XXXIX) with carboxylic acid ($R^{5d}CO_2H$) in the presence of a condensation agent, or by reacting compound (XXXIX) with a reactive derivative of carboxylic acid ($R^{5d}COL^5$).

When compound (XXXIX) is reacted with carboxylic acid ($R^{5d}CO_2H$) in the presence of a condensation agent, carboxylic acid is used in a proportion of about 1 mol to about 10 mol, preferably about 1 mol to about 3 mol, per 1 mol of compound (XXXIX).

Examples of the condensation agent include 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(7-azabenzotriazol-1-yl)-N,N,N',N'-tetramethyluronium hexafluorophosphate and the like. The condensation agent is used in a proportion of about 1 mol to about 10 mol, preferably about 1 mol to about 5 mol, per 1 mol of compound (XXXIX).

Where necessary, a suitable condensation promoter (e.g., 1-hydroxybenzotriazole, N-hydroxysuccinimide and the like) can be used in this reaction. Such condensation promoter is used in a proportion of about 0.1 mol to about 10 mol, preferably about 0.3 mol to about 3 mol, per 1 mol of compound (XXXIX).

This reaction may proceed more smoothly by the addition of a base (e.g., triethylamine, N,N-diisopropylethylamine, N-methylmorpholine, 1,8-diazabicyclo[5.4.0]undec-7-ene and the like). The base is used in a proportion of about 0.01 mol to about 10 mol, preferably about 0.03 mol to about 5 mol, per 1 mol of compound (XXXIX).

This reaction is advantageously carried out using a solvent inert to the reaction. As the solvent, those similar to the solvents exemplified in step 5-1 are used.

The reaction time is generally about 10 min to about 100 hr, preferably about 30 min to about 50 hr.

The reaction temperature is generally about −78° C. to about 200° C., preferably about −20° C. to about 150° C.

$R^{5d}CO_2H$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

When compound (XXXIX) is reacted with a reactive derivative of carboxylic acid ($R^{5d}COL^5$), the reactive derivative of carboxylic acid ($R^{5d}COL^5$) is used in a proportion of about 1 mol to about 10 mol, preferably about 1 mol to about 3 mol, per 1 mol of compound (XXXIX).

Generally, this reaction is preferably performed in the presence of a base. However, the presence of a base is not always essential. Examples of the base include sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline and the like. The base is used in a proportion of about 0.01 mol to about 10 mol, preferably about 0.03 mol to about 5 mol, per 1 mol of compound (XXXIX).

This reaction is advantageously carried out using a solvent inert to the reaction. As the solvent, those similar to the solvents exemplified in step 5-1 are used.

The reaction time is generally about 10 min to about 100 hr, preferably about 30 min to about 50 hr.

The reaction temperature is generally about −78° C. to about 200° C., preferably about −20° C. to about 150° C.

$R^{5d}COL^5$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

[Production Method 6]

In compound (Ie), compound (Ie-1) wherein $W^e$ is an oxygen atom can be produced, for example, by the method shown in Reaction scheme 6. The compound (Ie-1) is encompassed in compound (Ie).

Reaction Scheme 6

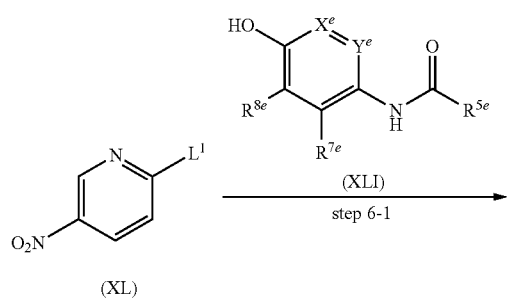

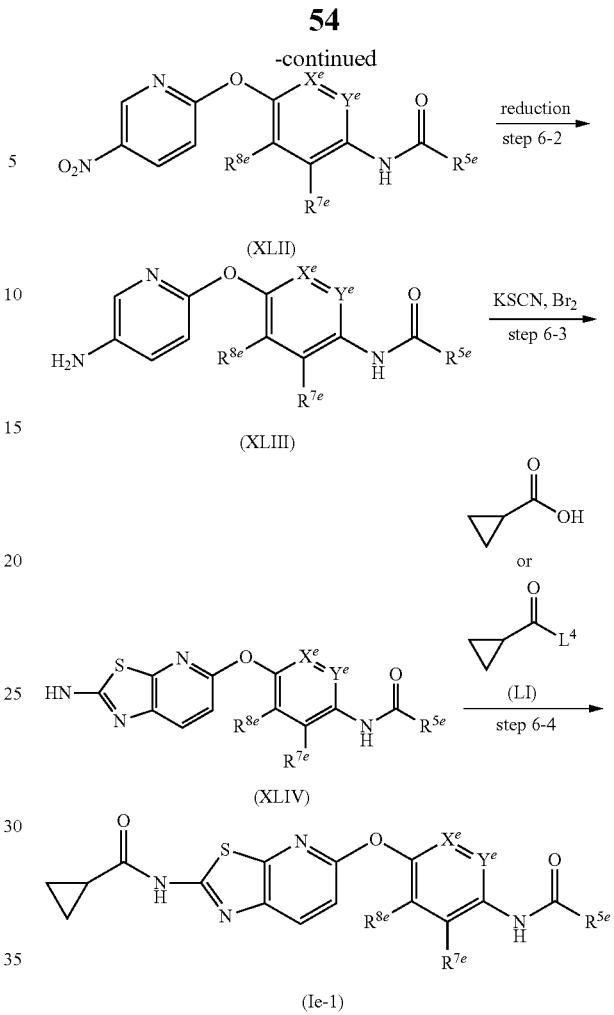

wherein the symbols are as defined above.

(Step 6-1):

Compound (XLII) can be produced by reacting compound (XL) with compound (XLI).

Compound (XLI) is used in a proportion of about 0.1 mol to about 10 mol, preferably about 0.3 mol to about 3 mol, per 1 mol of compound (XL).

Where necessary, a base may be added in this reaction. As the base, an inorganic base, an organic base and the like are used. Specific examples include sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline, sodium methoxide, sodium ethoxide, potassium tert-butoxide, sodium hydride, sodium amide, lithiumdiisopropylamide and the like. The base is used in a proportion of about 1 mol to about 30 mol, preferably about 1 mol to about 10 mol, per 1 mol of compound (XL).

This reaction is advantageously carried out using a solvent inert to the reaction. The solvent is not particularly limited as long as the reaction proceeds, and, for example, alcohols such as methanol, ethanol, 2-propanol, 2-methyl-2-propanol and the like; ethers such as diethyl ether, tetrahydrofuran, 1,4-dioxane, 1,2-dimethoxyethane and the like; hydrocarbons such as benzene, toluene, cyclohexane, hexane and the like; esters such as ethyl acetate and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile and the like; sulfoxides such as dimethyl sulfoxide and the like; pyridine; acetic acid; water; and the like can be used alone or in a mixture.

While the reaction time varies depending on the kind of reagent and solvent to be used, it is generally about 10 min to about 100 hr, preferably about 30 min to about 50 hr.

The reaction temperature is generally about −78° C. to about 200° C., preferably about −20° C. to about 150° C.

This reaction may be performed in a microwave reactor.
(Step 6-2):

Compound (XLIII) can be produced by reducing nitro of compound (XLII).

Nitro can be reduced according to a method known per se, for example, the methods described in "Advanced Organic Chemistry, 4th Ed." (Jerry March), "Comprehensive Organic Transformations, 2nd Ed." (Richard C. Larock), the fourth series of experimental chemistry, vol. 20, 279-280 and the like, or a method analogous thereto.
(Step 6-3):

Compound (XLIV) can be produced by reacting compound (XLIII) with potassium thiocyanate and bromine.

Potassium thiocyanate is used in a proportion of about 1 mol to about 100 mol, preferably about 1 mol to about 30 mol, per 1 mol of compound (XLIII).

Bromine is used in a proportion of about 1 mol to about 30 mol, preferably about 1 mol to about 10 mol, per 1 mol of compound (XLIII).

This reaction is advantageously carried out using a solvent inert to the reaction. Examples of the solvent include acetic acid and the like.

The reaction time is generally about 10 min to about 100 hr, preferably about 30 min to about 50 hr.

The reaction temperature is generally about −78° C. to about 200° C., preferably about −20° C. to about 150° C.
(Step 6-4):

Compound (Ie-1) can be produced by reacting compound (XLIV) with cyclopropanecarboxylic acid in the presence of a condensation agent, or by reacting compound (XLIV) with compound (LI).

When compound (XLIV) is reacted with cyclopropanecarboxylic acid in the presence of a condensation agent, cyclopropanecarboxylic acid is used in a proportion of about 1 mol to about 10 mol, preferably about 1 mol to about 3 mol, per 1 mol of compound (XLIV).

Examples of the condensation agent include 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(7-azabenzotriazol-1-yl)-N,N,N',N'-tetramethyluronium hexafluorophosphate and the like. The condensation agent is used in a proportion of about 1 mol to about 10 mol, preferably about 1 mol to about 5 mol, per 1 mol of compound (XLIV).

Where necessary, a suitable condensation promoter (e.g., 1-hydroxybenzotriazole, N-hydroxysuccinimide and the like) can be used in this reaction. Such condensation promoter is used in a proportion of about 0.1 mol to about 10 mol, preferably about 0.3 mol to about 3 mol, per 1 mol of compound (XLIV).

This reaction may proceed more smoothly by the addition of a base (e.g., triethylamine, N,N-diisopropylethylamine, N-methylmorpholine, 1,8-diazabicyclo[5.4.0]undec-7-ene and the like). The base is used in a proportion of about 0.01 mol to about 10 mol, preferably about 0.03 mol to about 5 mol, per 1 mol of compound (XLIV).

This reaction is advantageously carried out using a solvent inert to the reaction. As the solvent, those similar to the solvents exemplified in step 6-1 are used.

The reaction time is generally about 10 min to about 100 hr, preferably about 30 min to about 50 hr.

The reaction temperature is generally about −78° C. to about 200° C., preferably about −20° C. to about 150° C.

when compound (XLIV) is reacted with compound (LI), compound (LI) is used in a proportion of about 1 to about 10 mol, preferably about 1 to about 3 mol, per 1 mol of compound (XLIV).

Generally, this reaction is preferably performed in the presence of a base. However, the presence of a base is not always essential. Examples of the base include sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline and the like. The base is used in a proportion of about 0.01 mol to about 10 mol, preferably about 0.03 mol to about 5 mol, per 1 mol of compound (XLIV).

This reaction is advantageously carried out using a solvent inert to the reaction. As the solvent, those similar to the solvents exemplified in step 6-1 are used.

The reaction time is generally about 10 min to about 100 hr, preferably about 30 min to about 50 hr.

The reaction temperature is generally about −78° C. to about 200° C., preferably about −20° C. to about 150° C.

[Production Method 7]

Compound (Ie-1) can also be produced, for example, by the method shown in Reaction scheme 7.

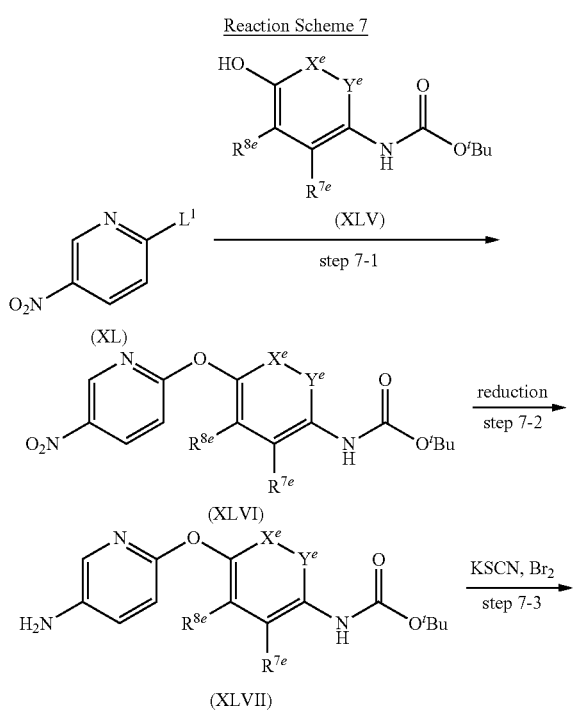

-continued

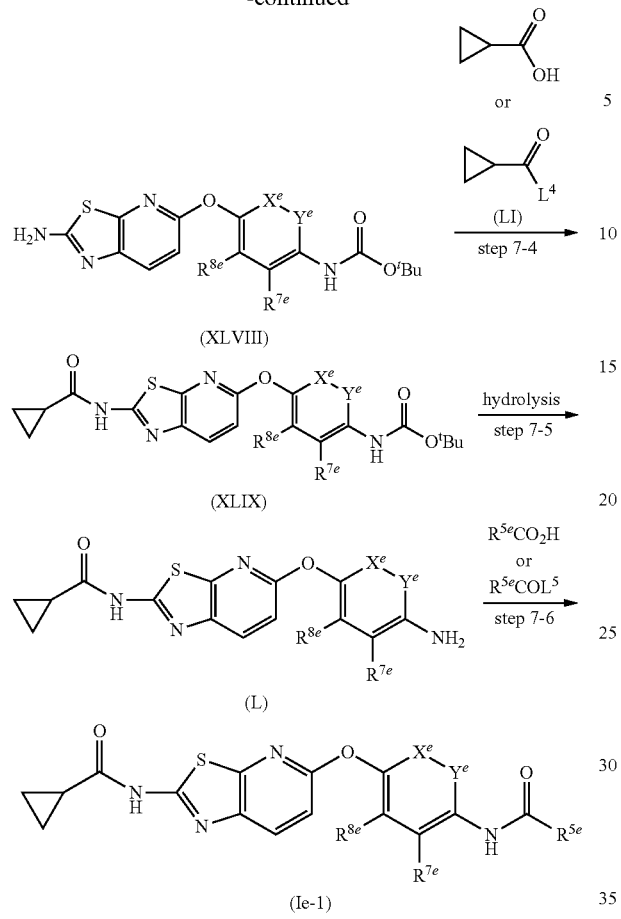

(XLVIII)

(XLIX)

(L)

(Ie-1)

wherein the symbols are as defined above.

(Steps 7-1 to 7-4):

compound (XLVI), compound (XLVII), compound (XLVIII) and compound (XLIX) can be synthesized from compound (XL) and compound (XLV) in the same manner as in steps 6-1 to 6-4, respectively.

(Step 7-5):

Compound (L) can be produced by removing the amino-protecting group from compound (XLIX).

The amino-protecting group can be removed according to a method known per se, for example, the methods described in "Protective Groups in Organic Synthesis, 3rd Ed." (Theodora W. Greene) and the like, or a method analogous thereto.

(Step 7-6):

Compound (Ie-1) can be produced by reacting compound (L) with carboxylic acid ($R^{5e}CO_2H$) in the presence of a condensation agent in the same manner as in step 6-4, or by reacting compound (L) with a reactive derivative ($R^{5e}COL^5$) of carboxylic acid.

$R^{5e}CO_2H$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

$R^{5e}COL^5$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

[Production Method 8]

Compound (Ia-1) can also be produced, for example, by the method shown in Reaction scheme 8.

Reaction Scheme 8

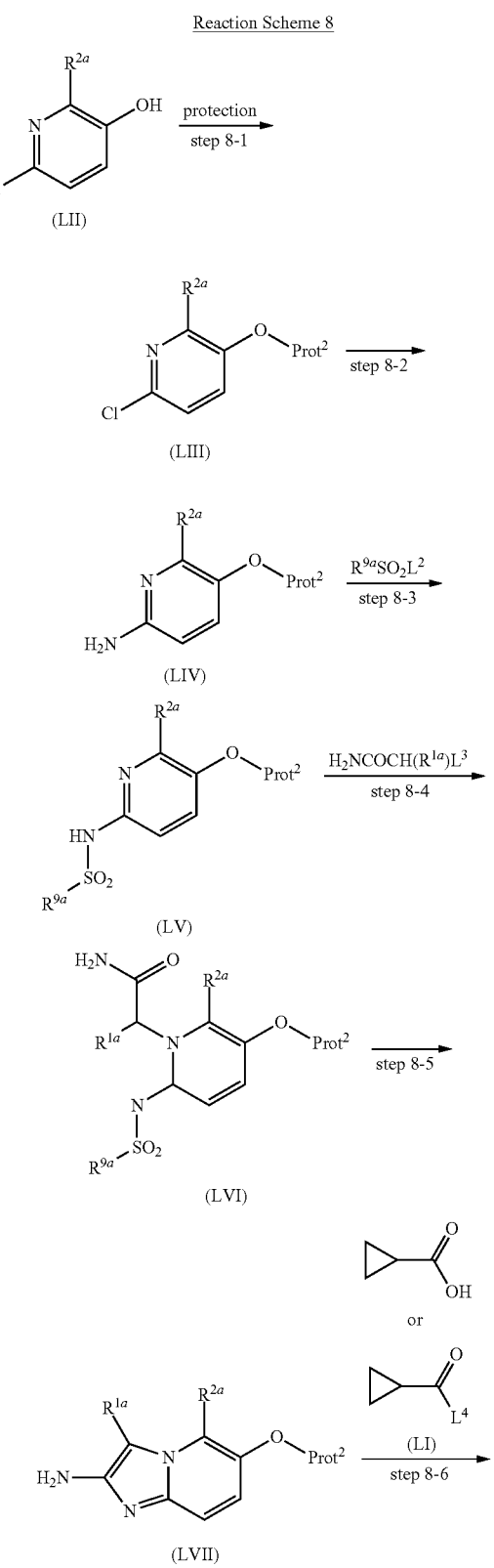

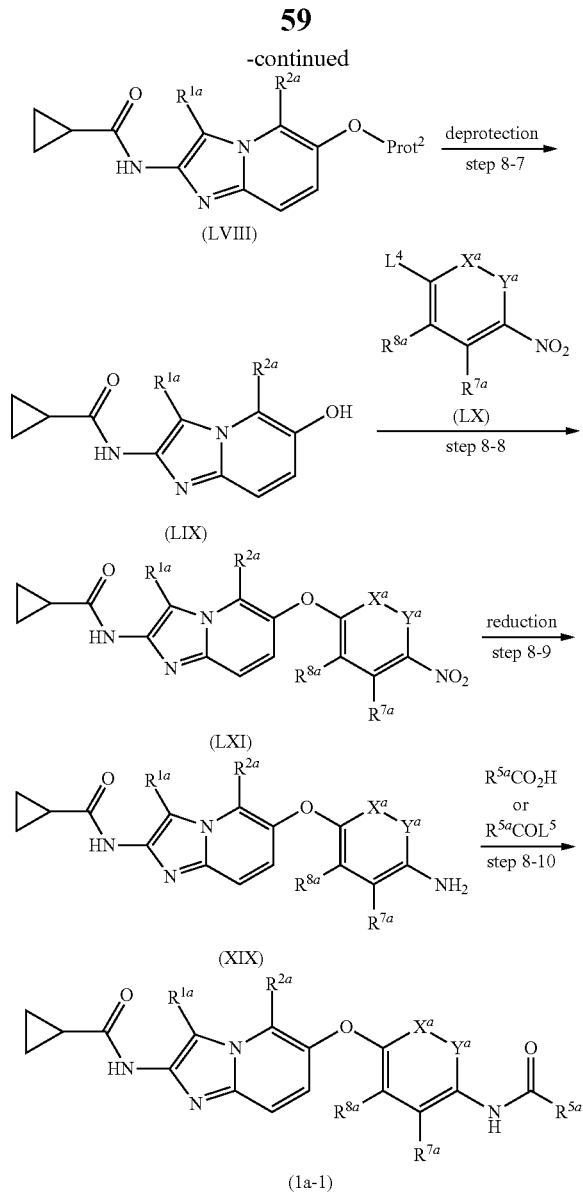

wherein Prot² is a phenolic hydroxyl-protecting group; and other symbols are as defined above.

As the phenolic hydroxyl-protecting group for Prot², benzyl, 4-methoxybenzyl, 2,4-dimethoxybenzyl and the like are used.

(Step 8-1):

Compound (LIII) can be produced by protecting the phenolic hydroxyl group of compound (LII).

The phenolic hydroxyl group can be protected according to a method known per se, for example, the methods described in "Protective Groups in Organic Synthesis, 3rd Ed." (Theodora W. Greene) and the like, or a method analogous thereto.

(Step 8-2):

Compound (LIV) can be produced using compound (LIII) according to the method described in "ORGANIC LETTERS, 2001, Vol. 3, No. 21, 3417-3419" (Xiaohua Huang), or a method analogous thereto a method.

(Steps 8-3 to 8-4):

Compound (LV) and compound (LVI) can be produced from compound (LIV) by steps 8-3 and 8-4 in the same manner as in steps 2-4 and 2-5, respectively.

(Step 8-5):

Compound (LVII) can be produced by reacting compound (LVI) with trifluoroacetic acid anhydride and then subjecting the obtained compound to alkalihydrolysis in the presence of a base.

Trifluoroacetic acid anhydride is used in a proportion of about 1 mol to about 30 mol, preferably about 1 mol to about 10 mol, per 1 mol of compound (LVI).

This reaction is advantageously performed by further using a solvent inert to the reaction. The solvent is not particularly limited as long as the reaction proceeds and, for example, alcohols such as methanol, ethanol, 2-propanol, 2-methyl-2-propanol and the like; ethers such as diethyl ether, tetrahydrofuran, 1,4-dioxane, 1,2-dimethoxyethane and the like; hydrocarbons such as benzene, toluene, cyclohexane, hexane and the like; esters such as ethyl acetate and the like; amides such as N,N-dimethylformamide, N,N-dimethylacetamide, 1-methyl-2-pyrrolidone and the like; nitriles such as acetonitrile and the like; sulfoxides such as dimethyl sulfoxide and the like; and the like can be used alone or in a mixture.

While the reaction time varies depending on the reagent and solvent to be used, it is generally about 10 min to about 100 hr, preferably about 30 min to about 50 hr.

The reaction temperature is generally about −78° C. to about 200° C., preferably about −20° C. to about 150° C.

This reaction may be performed in a microwave reactor.

Examples of the base to be used for the subsequent alkalihydrolysis include aqueous sodium hydroxide solution, aqueous potassium hydroxide solution, aqueous barium hydroxide solution, aqueous calcium hydroxide solution, aqueous potassium carbonate solution, aqueous sodium carbonate solution, aqueous cesium carbonate solution and the like.

While the reaction time varies depending on the reagent and solvent to be used, it is generally about 10 min to about 100 hr, preferably about 30 min to about 50 hr.

The reaction temperature is generally about −78° C. to about 200° C., preferably about −20° C. to about 150° C.

This reaction may be performed in a microwave reactor.

(Step 8-6):

Compound (LVIII) can be produced from compound (LVII) in the same manner as in step 2-8.

(Step 8-7):

Compound (LIX) can be produced by removing the phenolic hydroxyl-protecting group of compound (LVIII).

The phenolic hydroxyl-protecting group can be removed according to a method known per se, for example, the methods described in "Protective Groups in Organic Synthesis, 3rd Ed." (Theodora W. Greene) and the like, or a method analogous thereto.

(Step 8-8):

Compound (LXI) can be produced by reacting compound (LIX) with compound (LX) in the presence of a base.

Compound (LX) is used in a proportion of about 0.1 mol to about 30 mol, preferably about 0.3 mol to about 3 mol, per 1 mol of compound (LIX).

As the base, inorganic base or organic base and the like are used. Specifically, for example, sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline, sodium methoxide, sodium ethoxide, potassium tert-butoxide, sodium hydride, sodium amide, lithium diisopropylamide and the like can be mentioned. The base is used in a proportion of about 1 mol to about 30 mol, preferably about 1 mol to about 10 mol, per 1 mol of compound (LIX).

This reaction is advantageously carried out using a solvent inert to the reaction. The solvent is not particularly limited as long as the reaction proceeds and, for example, ethers such as diethyl ether, tetrahydrofuran, 1,4-dioxane, 1,2-dimethoxyethane and the like; hydrocarbons such as benzene, toluene, cyclohexane, hexane and the like; esters such as ethyl acetate and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane, chlorobenzene, trifluoromethylbenzene and the like; nitriles such as acetonitrile and the like; sulfoxides such as dimethyl sulfoxide and the like; and the like can be used alone or in a mixture.

While the reaction time varies depending on the reagent and solvent to be used, it is generally about 10 min to about 100 hr, preferably about 30 min to about 50 hr.

The reaction temperature is generally about −78° C. to about 200° C., preferably about −20° C. to about 150° C.

This reaction may be performed in a microwave reactor.
(Step 8-9):

Compound (XIX) can be produced by reducing nitro of compound (LXI). Nitro can be reduced according to a method known per se, for example, the methods described in "Advanced Organic Chemistry, 4th Ed." (Jerry March), "Comprehensive Organic Transformations, 2nd Ed." (Richard C. Larock), the fourth series of experimental chemistry, vol. 20, 279-280 and the like, or a method analogous thereto.
(Step 8-10):

Compound (Ia-1) can be synthesized from compound (XIX) in the same manner as in step 2-10.

[Production Method 9]

In compound (Ic), compound (Ic-1) wherein $W^c$ is an oxygen atom can be produced, for example, by the method shown in Reaction scheme 9. The compound (Ic-1) is encompassed in compound (Ic).

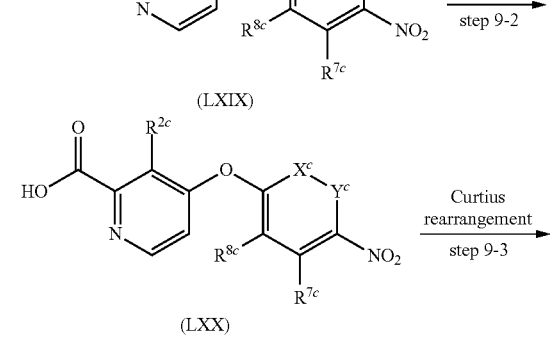

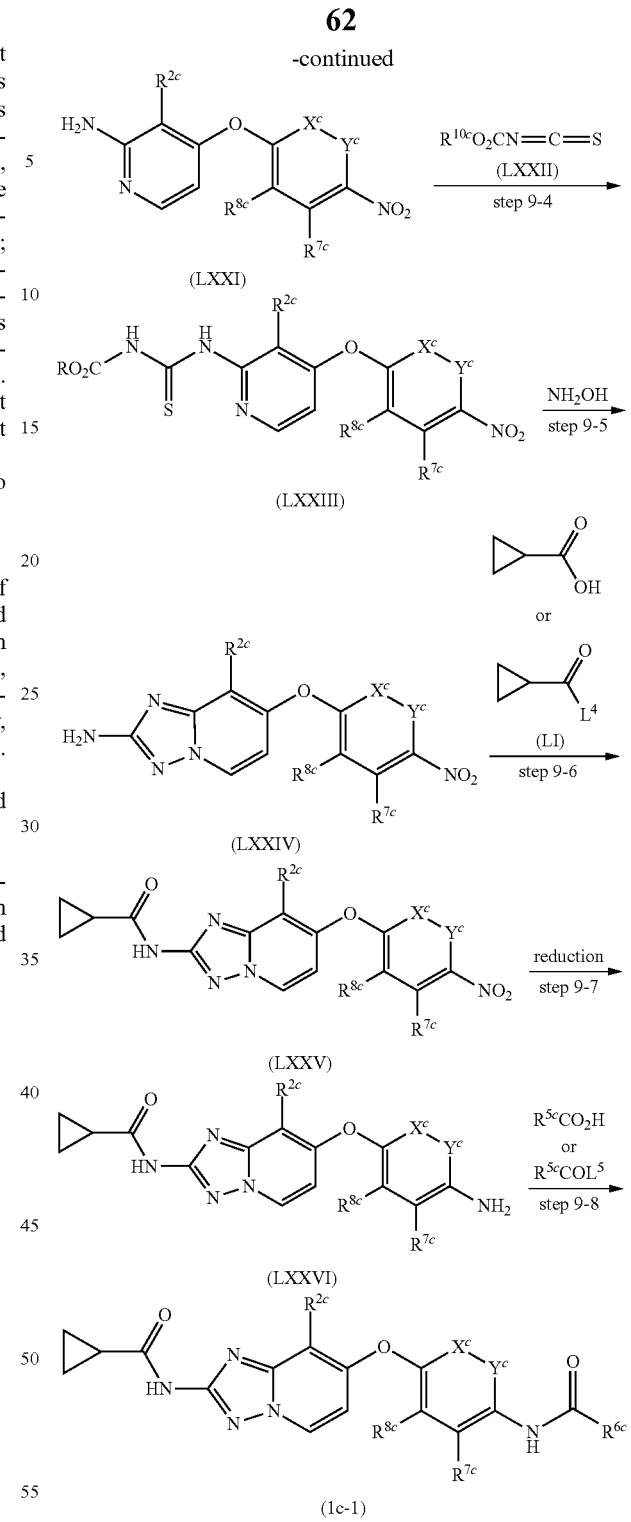

wherein $R^{10c}$ is $C_{1-6}$ alkyl optionally having 1 to 3 substituents selected from (a) a halogen atom and (b) nitro; and other symbols are as defined above.

(Step 9-1):

Compound (LXIX) can be produced by reacting compound (LXVII) with compound (LXVIII).

Compound (LXVIII) is used in a proportion of about 0.1 mol to about 30 mol, preferably about 0.3 mol to about 3 mol, per 1 mol of compound (LXVII).

This reaction is advantageously carried out using a solvent inert to the reaction. The solvent is not particularly limited as long as the reaction proceeds and, for example, ethers such as diethyl ether, tetrahydrofuran, 1,4-dioxane, 1,2-dimethoxyethane and the like; hydrocarbons such as benzene, toluene, cyclohexane, hexane and the like; esters such as ethyl acetate and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane, chlorobenzene, trifluoromethylbenzene and the like; nitriles such as acetonitrile and the like; sulfoxides such as dimethyl sulfoxide and the like; and the like can be used alone or in a mixture.

Where necessary, a base may be used in this reaction. Examples of the base include triethylamine, N,N-diisopropylethylamine, N-methylmorpholine, 1,8-diazabicyclo[5.4.0]undec-7-ene, pyridine, 4-(dimethylamino)pyridine, N,N-dimethylaniline, potassium tert-butoxide, sodium hydride and the like. The base is used in a proportion of about 1 mol to about 30 mol, preferably about 1 mol to about 20 mol, per 1 mol of compound (LXVII).

While the reaction time varies depending on the reagent and solvent to be used, it is generally about 10 min to about 100 hr, preferably about 30 min to about 50 hr.

The reaction temperature is generally about −78° C. to about 200° C., preferably about −20° C. to about 150° C.

This reaction may be performed in a microwave reactor.
(Step 9-2):

Compound (LXX) can be produced by alkalihydrolysis of compound (LXIX).

This reaction is performed in a water-containing solvent in the presence of a base. Examples of the base include sodium hydroxide, potassium hydroxide, lithium hydroxide, barium hydroxide, calcium hydroxide, potassium carbonate, sodium carbonate, cesium carbonate, sodium methoxide and the like. The base is used in a proportion of about 1 mol to about 50 mol, preferably about 1 mol to about 10 mol, per 1 mol of compound (LXIX). Examples of the water-containing solvent include a mixed solvent of one or more kinds of solvents selected from methanol, ethanol, tetrahydrofuran, 1,4-dioxane, 1,2-dimethoxyethane and the like, and water, and the like.

The reaction time is generally about 10 min to about 100 hr, preferably about 30 min to about 50 hr.

The reaction temperature is generally about −78° C. to about 200° C., preferably about 0° C. to about 150° C.
(Step 9-3):

Compound (LXXI) can be produced by converting carboxyl of compound (LXX) to amino by a method such as Curtius rearrangement and the like.

Carboxyl can be converted to amino according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.
(Step 9-4):

Compound (LXXIII) can be produced by reacting compound (LXXI) with compound (LXXII).

Compound (LXXII) is used in a proportion of about 0.1 mol to about 10 mol, preferably about 0.3 mol to about 3 mol, per 1 mol of compound (LXXI).

This reaction is advantageously carried out using a solvent inert to the reaction. As the solvent, those similar to the solvents exemplified in step 9-1 are used.

The reaction time is generally about 10 min to about 100 hr, preferably about 30 min to about 50 hr.

The reaction temperature is generally about −78° C. to about 200° C., preferably about −20° C. to about 150° C.
(Step 9-5):

Compound (LXXIV) can be produced by reacting compound (LXXIII) with hydroxylamine in the presence of a base.

Hydroxylamine is used in a proportion of about 0.1 mol to about 100 mol, preferably about 0.3 mol to about 30 mol, per 1 mol of compound (LXXIII).

Examples of the base include triethylamine, N,N-diisopropylethylamine, N-methylmorpholine, 1,8-diazabicyclo[5.4.0]undec-7-ene, pyridine, 4-(dimethylamino)pyridine, N,N-dimethylaniline and the like. The base is used in a proportion of about 0.1 mol to about 100 mol, preferably about 0.3 mol to about 30 mol, per 1 mol of compound (LXXIII).

This reaction is advantageously carried out using a solvent inert to the reaction. As the solvent, those similar to the solvents exemplified in step 9-1 are used.

The reaction time is generally about 10 min to about 100 hr, preferably about 30 min to about 50 hr.

The reaction temperature is generally about −78° C. to about 200° C., preferably about −20° C. to about 150° C.
(Step 9-6):

Compound (LXXV) can be produced by reacting compound (LXXIV) with cyclopropanecarboxylic acid in the presence of a condensation agent, or reacting compound (LXXIV) with compound (LI) in the same manner as in step 2-8.
(Step 9-7):

Compound (LXXVI) can be produced by reducing nitro of compound (LXXV).

Nitro can be reduced according to a method known per se, for example, the methods described in "Advanced Organic Chemistry, 4th Ed." (Jerry March), "Comprehensive Organic Transformations, 2nd Ed." (Richard C. Larock), the fourth series of experimental chemistry, vol. 20, 279-280 and the like, or a method analogous thereto.
(Step 9-8):

Compound (1c-1) can be produced by reacting compound (LXXVI) with $R^{5c}CO_2H$ in the presence of a condensation agent, or reacting compound (LXXVI) with $R^{5c}COL^5$ in the same manner as in step 2-10.

[Production Method 10]

In compound (Ia), compound (Ia-3) wherein $W^a$ is an oxygen atom; and $R^{5a}$ is (1) $C_{1-6}$ alkyl-carbonylamino optionally having one $C_{6-10}$ aryl, or (2) a nitrogen-containing heterocyclic group (having a bond on nitrogen atom) optionally having 1 to 4 substituents selected from (a) $C_{6-10}$ aryl optionally having 1 to 3 substituents selected from a halogen atom and $C_{1-6}$ alkyl, (b) $C_{1-6}$ alkyl optionally having 1 to 3 halogen atoms, and (c) oxo can also be produced, for example, by the method shown in Reaction scheme 10. The compound (Ia-3) is encompassed in compound (Ia).

Reaction Scheme 10

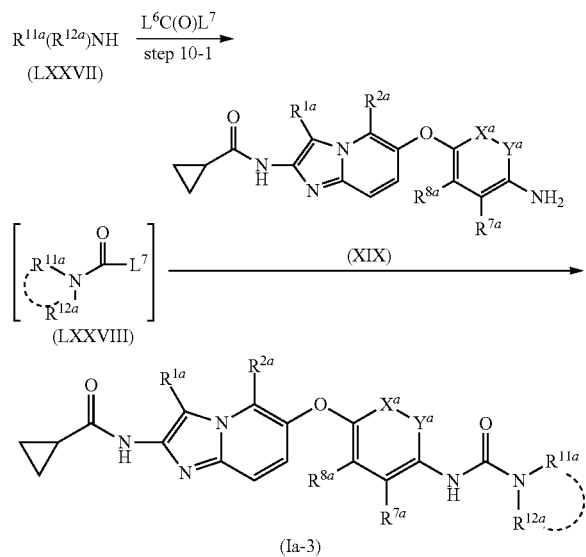

wherein $R^{11a}$ is a hydrogen atom, $R^{12a}$ is $C_{1-6}$ alkyl-carbonyl optionally having one $C_{6-10}$ aryl, or $R^{11a}$ and $R^{12a}$ may form, together with the adjacent nitrogen atom, a nitrogen-containing heterocyclic group (having a bond on nitrogen atom) optionally having 1 to 4 substituents selected from (a) $C_{6-10}$ aryl optionally having 1 to 3 substituents selected from a halogen atom and $C_{1-6}$ alkyl, (b) $C_{1-6}$ alkyl optionally having 1 to 3 halogen atoms, and (c) oxo; $L^6$ and $L^7$ are each a leaving group; and other symbols are as defined above.

The leaving groups for $L^6$ and $L^7$ are the same or different and each is, for example, (1) a halogen atom, (2) alkoxy optionally having 1 to 3 substituents selected from a halogen atom and $C_{1-6}$ alkyl, (3) aryloxy optionally having 1 to 3 substituents selected from a halogen atom, $C_{1-6}$ alkyl and nitro, and the like.
(Step 10-1):

Compound (Ia-3) can be produced by first reacting compound (LXXVII) with a compound represented by the formula $L^6C(O)L^7$ to give compound (LXXVIII), and then reacting compound (LXXVIII) with compound (XIX).

$L^6C(O)L^7$ is used in a proportion of 0.1 to 10 mol, preferably 0.3 to 3 mol, per 1 mol of compound (LXXVII).

The reaction may be performed in the presence of a base. As the base, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline and the like can be mentioned. The base is used in a proportion of about 0.1 mol to about 30 mol, preferably about 0.3 mol to about 10 mol, per 1 mol of compound (LXXVII).

This reaction is advantageously carried out using a solvent inert to the reaction. The solvent is not particularly limited as long as the reaction proceeds and, for example, ethers such as diethyl ether, tetrahydrofuran, 1,4-dioxane, 1,2-dimethoxyethane and the like; hydrocarbons such as benzene, toluene, cyclohexane, hexane and the like; esters such as ethyl acetate and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane, chlorobenzene, trifluoromethylbenzene and the like; nitriles such as acetonitrile and the like; sulfoxides such as dimethyl sulfoxide and the like; pyridine; and the like can be used alone or in a mixture.

While the reaction time varies depending on the reagent and solvent to be used, it is generally about 10 min to about 100 hr, preferably about 30 min to about 50 hr.

The reaction temperature is generally about −78° C. to about 200° C., preferably about −20° C. to about 150° C.

This reaction may be performed in a microwave reactor.

A compound represented by the formula $L^6C(O)L^7$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

The obtained $R^{11a}(R^{12a})NC(O)L^7$ [compound (LXXVIII)] can be used for the next reaction in the form of a reaction mixture or a crude product. It may be isolated and purified from the reaction mixture according to a conventional method and used for the next reaction.

Compound (XIX) is used in a proportion of 0.1 to 10 mol, preferably 0.3 to 3 mol, per 1 mol of compound (LXXVIII).

This reaction may be performed in the presence of a base. As the base, those similar to the bases exemplified above can be used. The base is used in a proportion of 0.1 to 10 mol, preferably 0.3 to 3 mol, per 1 mol of compound (LXXVIII).

This reaction is advantageously carried out using a solvent inert to the reaction. As the solvent, those similar to the solvents exemplified above are used.

The reaction time is generally about 1 min to about 200 hr, preferably about 10 min to about 100 hr.

The reaction temperature is generally about −100° C. to about 250° C., preferably about −78° C. to about 200° C.

In the aforementioned reactions, compounds (II), (III), (X), (XI), (XX), (XXI), (XXII), (XXVII), (XXXII), (XXXV), (XXXVII), (XL), (XLI), (XLV), (LI), (LII), (LX), (LXVII), (LXVIII), (LXXII) and (LXXVII) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

In each of the above-mentioned reactions, when a starting material compound has amino, carboxyl or hydroxyl as a substituent, these groups may be protected by a protecting group generally used for peptide chemistry and the like. In this case, the object compound can be obtained by removing the protecting group after reaction, as necessary. The introduction and removal of these protecting groups can be performed according to a method known per se, for example, the methods described in Wiley-Interscience, 1999, "Protective Groups in Organic Synthesis, 3rd Ed." (Theodora W. Greene, Peter G. M. Wuts) and the like.

Examples of the amino-protecting group include formyl group, $C_{1-6}$ alkyl-carbonyl group, $C_{1-6}$ alkoxy-carbonyl group, benzoyl group, $C_{7-10}$ aralkyl-carbonyl group (e.g., benzylcarbonyl), $C_{7-14}$ aralkyloxy-carbonyl group (e.g., benzyloxycarbonyl, 9-fluorenylmethoxycarbonyl), trityl group, phthaloyl group, N,N-dimethylaminomethylene group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxyl-protecting group include $C_{1-6}$ alkyl group, $C_{7-11}$ aralkyl group (e.g., benzyl), phenyl group, trityl group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like.

Examples of the hydroxyl-protecting group include $C_{1-6}$ alkyl group, phenyl group, trityl group, $C_{7-10}$ aralkyl group (e.g., benzyl), formyl group, $C_{1-6}$ alkyl-carbonyl group, benzoyl group, $C_{7-10}$ aralkyl-carbonyl group (e.g., benzylcarbonyl), 2-tetrahydropyranyl group, 2-tetrahydrofuranyl group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group and a nitro group.

When desired, the above-mentioned reaction may be combined with any one or two or more of known hydrolysis, deprotection, acylation reaction, alkylation reaction, oxidation reaction, cyclization reaction, carbon chain extension reaction, and substituent change reaction, whereby compound (I) can also be produced.

Compound (I) can be isolated and purified by a means known per se, such as phase transfer, concentration, solvent extraction, fractionation, liquid conversion, crystallization, recrystallization, chromatography and the like. When compound (I) is obtained as free compounds, they can be converted to desired salts by a method known per se or a modification thereof; conversely, when the compounds are obtained as salts, they can be converted to free forms or other desired salts by a method known per se or a modification thereof.

Compound (I) may be used as a prodrug. A prodrug of compound (I) and the like means a compound which is converted to compound (I) and the like by a reaction due to an enzyme, a gastric acid, etc. under the physiological condition in the living body, that is, a compound which is converted to compound (I) and the like by oxidation, reduction, hydrolysis, etc. due to an enzyme; a compound which is converted to compound (I) and the like by hydrolysis etc. due to gastric acid, and the like.

A prodrug of compound (I) may be a compound obtained by subjecting an amino in compound (I) to an acylation, alkylation or phosphorylation (e.g., a compound obtained by subjecting an amino in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation, etc.); a compound obtained by subjecting a hydroxy in compound (I) to an acylation, alkylation, phosphorylation or boration (e.g., a compound obtained by subjecting an hydroxy in compound (I) to an acetylation, palmitoylation, propanoylation, pivaloylation, succinylation, fumarylation, alanylation or dimethylaminomethylcarbonylation, etc.); a compound obtained by subjecting a carboxy in compound (I) to an esterification or amidation (e.g., a compound obtained by subjecting a carboxy in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, etc.); and the like. Any one of these compounds can be produced from compound (I) by a method known per se.

A prodrug of compound (I) may also be one which is converted into compound (I) under a physiological condition, such as those described in *IYAKUHIN no KAIHATSU* (Development of Pharmaceuticals), Vol. 7, Design of Molecules, p. 163-198, Published by HIROKAWA SHOTEN (1990).

When compound (I) has isomers such as optical isomer, stereoisomer, positional isomer, rotational isomer and the like, any isomers and mixtures are encompassed in compound (I). For example, when compound (I) has an optical isomer, an optical isomer separated from a racemate is also encompassed in compound (I). These isomers can be obtained as independent products by a synthesis means or a separation means (concentration, solvent extraction, column chromatography, recrystallization and the like) known per se.

The compound (I) may be a crystal, and both a single crystal and crystal mixtures are encompassed in compound (I). Crystals can be produced by crystallization according to crystallization methods known per se.

Compound (I) encompasses hydrate, non-hydrate, solvate and non-solvate within the scope thereof.

A compound labeled with an isotope (e.g., $^3H$, $^{14}C$, $^{35}S$, $^{125}I$ etc.) and the like is also encompassed in compound (I).

Furthermore, compound (I) may be a deuterated compound wherein $^1H$ is converted to $^2H(D)$.

Compound (I) of the present invention and a prodrug thereof (hereinafter sometimes to be abbreviated as the compound of the present invention) have, for example, phosphorylation-inhibitory activity against a kinase having such phosphorylating action. As used herein, kinase encompasses not only a substance having a phosphorylating action by itself as a whole, but also a substance a part of which has a phosphorylating action. The phosphorylating action possessed by kinases encompasses both a phosphorylating action on its own and that on other substances.

Examples of kinase include vascular endothelial growth factor receptor (VEGFR), platelet-derived growth factor receptor (PDGFR), Raf, hepatocyte growth factor receptor (c-Met), angiopoietin receptor, FLT3 and the like.

Examples of vascular endothelial growth factor receptor (VEGFR) include vascular endothelial growth factor receptor 1 (VEGFR1, Flt-1), vascular endothelial growth factor receptor 2 (VEGFR2, KDR, Flk-1), vascular endothelial growth factor receptor 3 (VEGFR3, Flt-4) and the like. Of these, vascular endothelial growth factor receptor 2 (VEGFR2) is preferable.

Examples of platelet-derived growth factor receptor (PDGFR) include platelet-derived growth factor receptor α (PDGFRα), platelet-derived growth factor receptor β (PDGFRβ) and the like.

Examples of Raf include A-Raf, B-Raf, C-Raf and the like.

Examples of angiopoietin receptor include Tyrosine Kinase with Immunoglobulin and Epidermal Growth homology domain 1 (TIE1), TIE2 and the like.

Particularly, as kinase, vascular endothelial growth factor receptor 2 (VEGFR2), platelet-derived growth factor receptor (PDGFR), Raf, hepatocyte growth factor receptor (c-Met), TIE2 and FLT3 are preferable.

Besides these, as kinase, fibroblast growth factor receptor 1 (FGFR1), fibroblast growth factor receptor 2 (FGFR2), fibroblast growth factor receptor 3 (FGFR3), fibroblast growth factor receptor 4 (FGFR4), stem cell factor receptor (c-Kit), Aurora A, Aurora B, Axl, CDK, MEK1, MEK2, Akt, ERK, MAPK, Src, epithelial cell growth factor receptor (EGFR), human epithelial growth factor receptor 2 (HER2), human epithelial growth factor receptor 4 (HER4), Abl, Fgr, Fms, Ron, Ret, Eph, TrkA and the like can also be used.

For example, the vascular endothelial growth factor receptor 2 (VEGFR2) inhibitory activity of the compound of the present invention can be determined according to Test Example 1, the vascular endothelial cell proliferation inhibitory activity can be determined according to Test Example 2, the hepatocyte growth factor receptor (c-Met) inhibitory activity can be determined according to Test Example 3, the human gastric cancer cell line MKN-45 growth inhibitory activity can be determined according to Test Example 4, the human gastric cancer cell line MKN-45 antitumor activity and human blood cell cancer cell line MV-4-11 antitumor activity can be determined according to Test Example 5, the FLT3 inhibitory activity can be determined according to Test Example 6, the TIE2 inhibitory activity can be determined according to Test Example 7, and the human blood cell cancer cell line MV-4-11 growth inhibitory activity can be determined according to Test Example 8.

The compound of the present invention particularly shows potent inhibitory activity for vascular endothelial growth factor receptor (VEGFR), and specifically high selectivity for vascular endothelial growth factor receptor 2 (VEGFR2, KDR, Flk-1) and potent kinase inhibitory activity for VEGFR1 and PDGFR. In addition, the compound of the present invention shows potent inhibitory action on hepatocyte growth factor receptor (c-Met). The compound of the present invention also shows potent inhibitory action on TIE2. Moreover, the compound of the present invention shows potent inhibitory action on FLT3. Furthermore, since the compound of the present invention is also superior in the efficacy, pharmacokinetics (absorption, distribution, metabolism, excretion etc.), solubility (water-solubility etc.), interaction with other pharmaceutical products, safety (acute toxicity, chronic toxicity, genetic toxicity, reproductive toxicity, cardiotoxicity, carcinogenicity etc.) and stability (chemical stability, stability to enzyme etc.), it is useful as a pharmaceutical agent.

The compound of the present invention is useful as a kinase inhibitor, preferably a vascular endothelial growth factor receptor (VEGFR) inhibitor [preferably a vascular endothelial growth factor receptor 2 (VEGFR2, KDR, Flk-1) inhibitor], a platelet-derived growth factor receptor (PDGFR) inhibitor, hepatocyte growth factor receptor (c-Met) inhibitor, TIE2 inhibitor, FLT3 inhibitor for a mammal (e.g., mouse, rat, hamster, rabbit, cat, dog, bovine, sheep, monkey, human etc.).

Therefore, the compound of the present invention is useful as an angiogenesis inhibitor, a vascular endothelial cell proliferation inhibitor, cancer cell proliferation inhibitor and the like.

The compound of the present invention is used as a pharmaceutical agent such as an agent for the prophylaxis or treatment of diseases possibly affected by a vascular endothelial growth factor, platelet-derived growth factor, hepatocyte growth factor, angiopoietin, for example, cancer [e.g., colorectal cancer (e.g., familial colorectal cancer, hereditary nonpolyposis colorectal cancer, gastrointestinal stromal tumor etc.), lung cancer (e.g., non-small cell lung cancer, small cell lung cancer, malignant mesothelioma, etc.), mesothelioma, pancreatic cancer (e.g., pancreatic duct cancer, etc.), gastric cancer (e.g., scirrhous gastric cancer, papillary glandular cancer, mucinous glandular cancer, adenosquamous cancer, etc.), breast cancer (e.g., invasive ductal carcinoma, ductal cancer in situ, inflammatory breast cancer, etc.), ovary cancer (e.g., ovarian epithelial cancer, extragonadal germ cell tumor, ovarian germ cell tumor, ovarian low malignant potential tumor etc.), prostate cancer (e.g., hormone-dependent prostate cancer, non-hormone dependent prostate cancer, etc.), liver cancer (e.g., primary liver cancer, extrahepatic bile duct cancer, etc.), thyroid cancer (e.g., medullary thyroid cancer, etc.), head and neck cancer (laryngeal cancer), kidney cancer (e.g., renal cell carcinoma, renal pelvis and ureter transitional cell cancer, etc.), esophagus cancer, testis cancer, uterus cancer, pancreatic endocrine tumor, brain tumor (e.g., pineal astrocytoma, pilocytic astrocytoma, diffuse astrocytoma, anaplastic astrocytoma, etc.), melanoma, sarcoma, urinary bladder cancer, blood cancer including multiple myeloma (e.g., acute myelocytic leukemia, myelodysplastic syndrome) etc.], diabetic retinopathy, rheumatoid arthritis, psoriasis, atherosclerosis, Kaposi's sarcoma, COPD, pain, asthma, endometriosis, nephritis, osteoarthritis, inflammation such as age-related macular degeneration and the like and hypertension; the above-mentioned cancer growth inhibitor; the above-mentioned cancer metastasis suppressor; an apoptosis promoter; and the like.

Of these, it is effective as an agent for the prophylaxis or treatment of colorectal cancer, lung cancer, pancreatic cancer, gastric cancer, breast cancer, ovary cancer, prostate cancer, liver cancer, thyroid cancer, kidney cancer, brain tumor melanoma, urinary bladder cancer and blood cancer. Particularly, the compound of the present invention is effective as an agent for the prophylaxis or treatment of lung cancer, gastric cancer, colorectal cancer, ovary cancer, prostate cancer, kidney cancer or blood cancer.

In addition, based on the strong hepatocyte growth factor receptor (c-Met) inhibitory action, the compound of the present invention is useful as an agent for suppressing invasion and/or metastasis of cancer (e.g., colorectal cancer, gastric cancer, lung cancer, kidney cancer, breast cancer, ovary cancer, prostate cancer, brain tumor). Based on the strong Fms Like Tyrosine Kinase 3 (FLT3) inhibitory action, moreover, the compound of the present invention is effective as an agent for the prophylaxis or treatment of leukemia (e.g., acute myelocytic leukemia, acute lymphatic leukemia).

The compound of the present invention can be administered orally or parenterally as it is or in a mixture with a pharmacologically acceptable carrier.

The dosage form of the compound of the present invention for oral administration is, for example, tablet (including sugar-coated tablet, film-coated tablet), pill, granule, powder, capsule (including soft capsule, microcapsule), syrup, emulsion, suspension and the like, and the dosage form for parenteral administration is, for example, injection, injecting agent, instillation, suppository and the like. In addition, it is effective to make a sustained release preparation by combining the compound with a suitable base (e.g., polymer of butyric acid, polymer of glycolic acid, copolymer of butyric acid-glycolic acid, a mixture of a polymer of butyric acid and a polymer of glycolic acid, polyglycerol fatty acid ester etc.).

As a method to produce the compound of the present invention in the above-mentioned dosage form, a known production method generally used in the pertinent field can be employed. When the above-mentioned dosage form is produced, suitable amounts of additives such as excipient, binder, disintegrant, lubricant, sweetening agent, surfactant, suspending agent, emulsifier and the like, generally used in the pertinent field, are appropriately added as necessary for production.

When the compound of the present invention is prepared into a tablet, for example, it can be produced by adding an excipient, a binder, a disintegrant, a lubricant and the like, and when a pill or a granule is to be prepared, it can be produced by adding an excipient, a binder, a disintegrant and the like. When a powder or a capsule is to be prepared, it can be produced by adding an excipient and the like, when a syrup is to be prepared, it can be produced by adding a sweetener and the like, and when an emulsion or a suspension is to be prepared, it can be produced by adding a suspending agent, a surfactant, an emulsifier and the like.

Examples of the excipient include lactose, sucrose, glucose, starch, sucrose, crystalline cellulose, powdered glycyrrhiza, mannitol, sodium hydrogen carbonate, calcium phosphate, calcium sulfate and the like.

Examples of the binder include 5-10 wt % starch liquid paste, 10-20 wt % gum arabic solution or gelatin solution, 1-5 wt % tragacanth solution, carboxymethyl cellulose solution, sodium alginate solution, glycerin and the like.

Examples of the disintegrant include starch, calcium carbonate and the like.

Examples of the lubricant include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, sodium carboxymethyl cellulose, methyl cellulose, bentonite and the like.

Examples of the emulsifier include gum arabic, tragacanth, gelatin, polysorbate 80 and the like.

Furthermore, when the compound of the present invention is produced in the above-mentioned dosage form, a suitable amount of a colorant, a preservative, an aromatic, a corrigent, a stabilizer, a thickening agent and the like typically used in the field of preparation can be added on demand.

As the injection, intravenous injection as well as subcutaneous injection, intracutaneous injection, intramuscular injection, instillation and the like are mentioned, and as the sustained release preparation, an iontophoresis transdermal agent and the like are mentioned.

Such injections are prepared by methods known per se, or by dissolving, suspending or emulsifying the compound of the present invention in a sterilized aqueous or oily liquid. As an aqueous liquid for injection, physiological saline, isotonic solutions containing glucose or other auxiliary drugs (e.g., D-sorbitol, D-mannitol, sodium chloride and the like) and the like can be mentioned, and they can be used in combination with suitable solubilizing agents, such as alcohols (e.g., ethanol), polyalcohols (e.g., propylene glycol, polyethylene glycol), nonionic surfactants (e.g., polysorbate 80, HCO-50) and the like. As an oily liquid, sesame oil, soybean oil and the like can be mentioned, which may be used in combination with solubilizing agents such as benzyl benzoate, benzyl alcohol and the like. In addition, buffers (e.g., phosphate buffer, sodium acetate buffer), soothing agents (e.g., benzalkonium chloride, procaine hydrochloride and the like), stabilizers (e.g., human serum albumin, polyethylene glycol and the like), preservatives (e.g., benzyl alcohol, phenol and the like) and the like can be mentioned. A prepared injection is generally filled in an ampoule.

While the content of the compound of the present invention in the pharmaceutical agent of the present invention varies depending on the form of the pharmaceutical preparation, it is generally about 0.01 to 100 wt %, preferably about 2 to 85 wt %, more preferably about 5 to 70 wt %, relative to the entire preparation.

While the content of the additive in the pharmaceutical agent of the present invention varies depending on the form of the pharmaceutical preparation, it is generally about 1 to 99.9 wt %, preferably about 10 to 90 wt %, relative to the entire preparation.

The compound of the present invention is stable and low toxic, and can be used safely. While the daily dose varies depending on the condition and body weight of patients, the kind of compound, administration route and the like, in the case of, for example, oral administration to patients for the treatment of cancer, the daily dose to an adult (body weight about 60 kg) is about 0.1 to 1000 mg, preferably about 0.3 to 300 mg, more preferably about 1 to 200 mg, as an active ingredient (the compound of the present invention), which can be given in a single administration or administered in 2 or 3 portions a day.

When the compound of the present invention is administered parenterally, it is generally administered in the form of a liquid (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, in the form of an injection, relative to 1 kg body weight, which is preferably given by intravenous injection.

The compound of the present invention can be used concurrently with other drugs. To be specific, the compound of the present invention can be used together with medicaments such as hormonal therapeutic agents, chemotherapeutic agents, immunotherapeutic agents, pharmaceutical agents inhibiting the action of cell growth factors or cell growth factor receptors and the like. In the following, the drugs that can be used in combination with the compound of the present invention are abbreviated as concomitant drugs.

Examples of the "hormonal therapeutic agents" include fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate, and the like), pill preparations, mepitiostane, testrolactone, aminoglutethimide, LH-RH agonists (e.g., goserelin acetate, buserelin, leuprorelin, and the like), droloxifene, epitiostanol, ethinylestradiol sulfonate, aromatase inhibitors (e.g., fadrozole hydrochloride, anastrozole, retrozole, exemestane, vorozole, formestane, and the like), anti-androgens (e.g., flutamide, bicartamide, nilutamide, and the like), 5α-reductase inhibitors (e.g., finasteride, episteride, and the like), adrenal cortex hormone drugs (e.g., dexamethasone, prednisolone, betamethasone, triamcinolone, and the like), androgen synthesis inhibitors (e.g., abiraterone, and the like), retinoid and drugs that retard retinoid metabolism (e.g., liarozole, and the like), thyroid gland hormone, and DDS (Drug Delivery System) preparations therefor and the like.

Examples of the "chemotherapeutic agents" include alkylating agents, antimetabolites, anticancer antibiotics, plant-derived anticancer agents, and the like.

Examples of the "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, DDS (Drug Delivery System) preparations thereof, and the like.

Examples of the "antimetabolites" include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, gallocitabine, emmitefur, capecitabine, and the like), aminopterine, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine, bendamustine, DDS preparations thereof, and the like.

Examples of the "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, DDS preparations thereof, and the like.

Examples of the "plant-derived anticancer agents" include etoposide, etoposide phosphate, vinblastine sulfate, vincristine sulfate, vindesine sulfate, teniposide, paclitaxel, docetaxel, vinorelbine, DDS preparations thereof, and the like.

Examples of the "immunotherapeutic agents (BRM)" include picibanil, krestin, sizofuran, lentinan, ubenimex, interferons, interleukins, macrophage colony-stimulating factor, granulocyte colony-stimulating factor, erythropoietin, lymphotoxin, BCG vaccine, *corynebacterium parvum*, levamisole, polysaccharide K, procodazole, anti-CTLA4 antibody, and the like.

Example of the "cell growth factor" in the "pharmaceutical agents inhibiting the action of cell growth factors or cell growth factor receptors" include any substances that promote cell proliferation, which are normally peptides having not more than 20,000 molecular weight that are capable of exhibiting their activity at low concentrations by binding to a receptor including (1) EGF (epidermal growth factor) or substances possessing substantially the same activity as EGF [e.g., $TGF_\alpha$, and the like], (2) insulin or substances possessing substantially the same activity as insulin [e.g., insulin, IGF (insulin-like growth factor)-1, IGF-2, and the like], (3) FGF (fibroblast growth factor) or substances possessing substantially the same activity as FGF [e.g., acidic FGF, basic FGF, KGF (keratinocyte growth factor), FGF-10, and the like], (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, angiopoietin, and the like].

Examples of the "cell growth factor receptors" include any receptors capable of binding to the aforementioned growth factors, including EGF receptor heregulin receptor (HER3, etc.), insulin receptor IGF receptor-1, IGF receptor-2, FGF receptor-1 or FGF receptor-2, VEGF receptor angiopoietin receptor (Tie2 etc.), PDGF receptor HGF receptor (c-Met), NGF receptor (TrkA) and the like.

As the "pharmaceutical agents inhibiting the action of cell growth factors or cell growth factor receptors", EGF inhibitor, TGFα inhibitor, haregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGF inhibitor, HGF inhibitor, VEGF inhibitor, angiopoietin inhibitor, EGF receptor inhibitor, HER2 inhibitor, HER4 inhibitor, insulin receptor inhibitor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Trk inhibitor, Ret inhibitor, mTOR inhibitor, Aurora inhibitor, PLK inhibitor, MEK (MEK1/2) inhibitor, c-MET inhibitor, CDK inhibitor, Akt inhibitor, ERK inhibitor, TrkA inhibitor and the like are used. More specifically, anti-VEGF antibody (Bevacizumab etc.), anti-HER2 antibody (Trastuzumab, Pertuzumab etc.), anti-EGFR antibody (Cetuximab, Panitumumab, Matuzumab, Nimotuzumab etc.), anti-VEGFR antibody, anti-HGF antibody, Imatinib, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl)propoxy]quinazoline (AZD-2171), Lestaurtinib, Pazopanib, Canertinib, Tandutinib, 3-(4-bromo-2,6-difluorobenzyloxy)-5-[(3-(4-(1-pyrrolidinyl)butyl]ureido]isothiazole-4-carboxamide (CP-547632), Axitinib, N-(3,3-dimethyl-2,3-dihydro-1H-indol-6-yl)-2-(pyridin-4-ylmethylamino)pyridine-3-carboxamide (AMG-706), Nilotinib, 6-[4-(4-ethylpiperazin-1-ylmethyl)phenyl]-N-[1 (R)-phenylethyl]-7H-pyrrolo[2,3-d]pyrimidin-4-amine (AEE-788), Vandetanib, Temsirolimus, Everolimus, Enzastaurin, N-[4-[4-(4-methylpiperazin-1-yl)-6-(3-methyl-1H-pyrazol-5-ylamino)pyrimidin-2-ylsulfanyl]phenyl]cyclopropanecarboxamide (VX-680), phosphoric acid 2-[N-[3-[4-[5-[N-(3-fluorophenyl)carbamoylmethyl]-1H-pyrazol-3-ylamino]quinazolin-7-yloxy]propyl]-N-ethylamino]ethyl ester (AZD-1152), 4-[9-chloro-7-(2,6-difluorophenyl)-5H-pyrimido[5,4-d][2]benzazepin-2-ylamino]benzoic acid (MLN-8054), N-(2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 5-(4-bromo-2-chlorophenylamino)-4-fluoro-1-methyl-1H-benzimidazole-6-carbohydroxamic acid 2-hydroxyethyl ester (AZD-6244), N-[2(R), 3-dihydroxypropoxy]-3,4-difluoro-2-(2-fluoro-4-iodophenylamino)benzamide (PD-0325901) and the like are used.

In addition to the aforementioned drugs, L-asparaginase, aceglatone, procarbazine hydrochloride, protoporphyrin-cobalt complex salt, mercuric hematoporphyrin-sodium, topoisomerase I inhibitors (e.g., irinotecan, topotecan, and the like), topoisomerase II inhibitors (e.g., sobuzoxane, and the like), differentiation inducers (e.g., retinoid, vitamin D, and the like), other angiogenesis inhibitors (e.g., humagillin, shark extract, COX-2 inhibitor and the like), α-blockers (e.g., tamsulosin hydrochloride, and the like), bisphosphonic acids (e.g., pamidronate, zoledronate), thalidomide, 5 azacytidine, decitabine, proteasome inhibitor (e.g., bortezomib), antitumor antibody such as anti-CD20 antibody and the like, toxin labeled antibody and the like can also be used.

By combining the compound of the present invention and a concomitant drug, a superior effect such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer, (4) a sustained treatment effect can be designed, (5) a synergistic effect can be afforded by a combined use of the compound of the present invention and a concomitant drug, and the like, can be achieved.

In the present specification, the compound of the present invention and a concomitant drug used in combination are referred to as the "combination agent of the present invention".

For use of the combination agent of the present invention, the administration time of the compound of the present invention and the concomitant drug is not restricted, and the compound of the present invention and the concomitant drug can be administered to an administration subject simultaneously, or may be administered at different times. The dosage of the concomitant drug may be determined according to the dose clinically set, and can be appropriately selected depending on the administration subject, administration route, disease, combination and the like.

Examples of the administration mode of the combined use of the compound of the present invention and the concomitant drug include the following methods:
(1) The compound of the present invention and the concomitant drug are simultaneously produced to give a single preparation, which is then administered. (2) The compound of the present invention and the concomitant drug are separately produced to give two kinds of preparations which are administered simultaneously by the same administration route. (3) The compound of the present invention and the concomitant drug are separately produced to give two kinds of preparations which are administered by the same administration route at different times. (4) The compound of the present invention and the concomitant drug are separately produced to give two kinds of preparations which are administered simultaneously by different administration routes. (5) The compound of the present invention and the concomitant drug are separately produced to give two kinds of preparations which are administered by different administration routes at different times (e.g., the compound of the present invention and the concomitant drug are administered in this order, or in the reverse order). The dose of the concomitant drug is determined in accordance with its clinical dose, and the ratio of the compound of the present invention and the concomitant drug is determined depending on the subject, administration route, disease, symptom, combination, and the like. For example, when the subject is human, the concomitant drug is used in 0.01 to 100 (w/w), relative to the compound of the present invention.

The combination agent of the present invention has low toxicity and, for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules (including soft capsule), solutions, injections, suppositories, sustained release agents and the like, which can be safely administered orally or parenterally (e.g., local, rectum, venous, and the like). An injection can be administered directly to the lesion or administered by intravenous, intramuscular, subcutaneous or intra-tissue administration.

As a pharmacologically acceptable carrier which may be used for preparing a preparation of the combination agent of the present invention, those similar to the aforementioned pharmacologically acceptable carriers, that can be used for the production of the pharmaceutical agent of the present invention, can be mentioned. Where necessary, the aforementioned additives that can be used for the production of the pharmaceutical agent of the present invention, such as preservatives, antioxidants, colorants, sweetening agents, adsorbents, wetting agents and the like can also be used in appropriate amounts.

The compounding ratio of the compound of the present invention to the concomitant drug in the combination agent of the present invention can be appropriately set depending on the administration subject, administration route, diseases and the like.

For example, the content of the compound of the present invention in the combination agent of the present invention varies depending on the dosage form, and is usually from about 0.01 to 100% by weight, preferably from about 0.1 to 50% by weight, further preferably from about 0.5 to 20% by weight, based on the preparation.

The content of the concomitant drug in the combination agent of the present invention varies depending on the dosage form, and is usually from about 0.01 to 90% by weight, preferably from about 0.1 to 50% by weight, further preferably from about 0.5 to 20% by weight, based on the preparation.

The content of additives in the combination agent of the present invention varies depending on the dosage form, and is usually from about 1 to 99.99% by weight, preferably from about 10 to 90% by weight, based on the preparation.

When the compound of the present invention and the concomitant drug are separately prepared, the same content may be adopted.

These preparations can be produced by a method known per se, which is generally employed in the preparation process.

For example, the compound of the present invention and the concomitant drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH adjuster (e.g., hydrochloric acid, sodium hydroxide and the like), a preservative (e.g., ethyl parahydroxybenzoate, benzoic acid, methylparaben, propylparaben, benzyl alcohol and the like), a dissolving agent (e.g., conc. glycerin, meglumine and the like), a solubilizing agent (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a solubilizing agent such as propylene glycol and the like and prepared into an oily injection, whereby an injection is afforded.

In addition, an excipient (e.g., lactose, sucrose, starch and the like), a disintegrating agent (e.g., starch, calcium carbonate and the like), a binder (e.g., starch, gum arabic, carboxymethylcellulose, polyvinylpyrrolidone, hydroxypropylcellulose and the like), a lubricant (e.g., talc, magnesium stearate, polyethylene glycol 6000 and the like) and the like may be added to the compound of the present invention or the concomitant drug according to a method known per se, and the mixture can be compression-molded, then if desirable, the molded product can be coated by a method known per se for the purpose of masking of taste, enteric property or durability, to give a preparation for oral administration. As the coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid•acrylic acid copolymer, manufactured by Rohm, Germany), pigment (e.g., iron oxide red, titanium dioxide, etc.) and the like can be used. The preparation for oral administration may be any of an immediate-release preparation and a sustained release preparation.

Moreover, the compound of the present invention and the concomitant drug can be made into an oily or aqueous solid, semisolid or liquid suppository according to a method known per se, by mixing them with an oily substrate, aqueous substrate or aqueous gel substrate. As the above-mentioned oily substrate, for example, glycerides of higher fatty acids [e.g., cacao butter, Witepsols (manufactured by Dynamit Nobel, Germany), etc.], glycerides of medium chain fatty acid [e.g., Miglyols (manufactured by Dynamit Nobel, Germany), etc.], or vegetable oils (e.g., sesame oil, soybean oil, cotton seed oil and the like), and the like are mentioned. Furthermore, as the aqueous substrate, for example, polyethylene glycol, propylene glycol and the like are mentioned, and as the aqueous gel substrate, for example, natural gums, cellulose derivatives, vinyl polymers, acrylic acid polymers and the like are mentioned.

As the above-mentioned sustained release preparation, sustained release microcapsules and the like are mentioned. The sustained release microcapsule can be produced by a method known per se.

The compound of the present invention is preferably molded into a preparation for oral administration such as a solid preparation (e.g., powder, granule, tablet, capsule) and the like, or molded into a preparation for rectal administration such as a suppository and the like. Particularly, a preparation for oral administration is preferable.

The concomitant drug can be made into the above-mentioned drug form depending on the kind of the drug.

The dosage of a combination agent of the present invention differs depending on the kind of a compound of the present invention, age, body weight, condition, drug form, administration method, administration period and the like, and for example, for one cancer patient (adult, body weight: about 60 kg), the combination agent is administered intravenously, at a dose of about 0.01 to about 1000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or several times in division a day. Of course, since the dose as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity of the symptom, age, sex, body weight, sensitivity difference of the subject, administration period, interval, and nature, pharmacy, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg of a mammal and this is usually administered once to 4-times in division a day.

In administration of a combination agent of the present invention, the compound of the present invention may be administered after administration of the concomitant drug or the concomitant drug may be administered after administration of the compound of the present invention, though they may be administered simultaneously. When administered at a time interval, the interval differs depending on the effective ingredient to be administered, drug form and administration method, and for example, when the concomitant drug is administered first, a method in which the compound of the present invention is administered within time range of from 1 min to 3 days, preferably from 10 min to 1 day, more preferably from 15 min to 1 hr after administration of the concomitant drug is exemplified. When the compound of the present invention is administered first, a method in which the concomitant drug is administered within time range of from 1 min to 1 day, preferably from 10 min to 6 hrs, more preferably from 15 min to 1 hr after administration of the compound of the present invention is exemplified.

In a preferable administration method, for example, the concomitant drug which has been molded into an oral administration preparation is administered orally at a daily dose of about 0.001 to 200 mg/kg, and about 15 min later, the compound of the present invention which has been molded into an oral administration preparation is administered orally at a daily dose of about 0.005 to 100 mg/kg.

Furthermore, the compound of the present invention or the combination agent of the present invention can be used concurrently with a non-drug therapy. To be precise, the compound of the present invention and the combination agent of the present invention can be combined with a non-drug therapy such as (1) surgery, (2) hypertensive chemotherapy using angiotensin II etc., (3) gene therapy, (4) thermotherapy, (5) cryotherapy, (6) laser cauterization, (7) radiotherapy, and the like.

For example, by using the compound of the present invention or the combination agent of the present invention before or after an surgery and the like, or before or after a combined treatment of two or three kinds thereof, effects such as prevention of emergence of resistance, prolongation of Disease-Free Survival, suppression of cancer metastasis or recurrence, prolongation of life and the like can be afforded.

In addition, it is possible to combine a treatment with the compound of the present invention or the combination agent of the present invention with a supportive therapy [(i) administration of antibiotic (e.g., (β-lactam type such as pansporin and the like, macrolide type such as clarithromycin and the like etc.) for the complication with various infectious diseases, (ii) administration of total parenteral nutrition, amino acid preparation or general vitamin preparation for the improvement of malnutrition, (iii) administration of morphine for pain mitigation, (iv) administration of a pharmaceutical agent for ameliorating side effects such as nausea, vomiting, anorexia, diarrhea, leucopenia, thrombocytopenia, decreased hemoglobin concentration, hair loss, hepatopathy, renopathy, DIC, fever and the like and (v) administration of a pharmaceutical agent for suppressing multiple drug resistance of cancer and the like].

Preferably, the compound of the present invention or the combination agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administering the compound of the present invention or the combination agent of the present invention before the surgery, etc., for example, it can be administrated 1-time about 30 min to 24 hrs before the surgery, etc., or in 1 to 3 cycles about 3 months to 6 months before the surgery, etc. In this way, the surgery, etc. can be conducted easily because, for example, a cancer tissue would be reduced by administering the compound of the present invention or the combination agent of the present invention before the surgery, and the like.

As a period for administering the compound of the present invention or the combination agent of the present invention after the surgery, etc., for example, it can be administrated repeatedly per a few weeks to 3 months, about 30 min to 24 hrs after the surgery, and the like. In this way, it enhances the effect of the surgery, etc. by administering the compound of the present invention or the combination agent of the present invention after the surgery, and the like.

EXAMPLES

The present invention is specifically explained in the following by way of Reference Examples, Examples, Formulation Examples, Experimental Examples and Test Examples, which are not to be construed as limitative.

In the Examples, preparative HPLC was performed as in the following.

Preparative HPLC tools: Gilson, Inc. High-Throughput purification system column: YMC Combiprep ODS-A S-5 5 µm, 50×20 mm detection method: UV 220 nm Unless otherwise specified, the elution by column chromatography was performed under observation by TLC (thin layer chromatography) in Reference Examples and Examples. For TLC observation, 60F254 manufactured by Merck, or NH TLC plate manufactured by Fuji Silysia Chemical Ltd. was used as a TLC plate, and the solvent used as an elution solvent in column chromatography was used as a eluent. For detection, moreover, a UV detector was employed. As the silica gel for column chromatography, silica gel 60 (70-230 mesh) manufactured by Merck, silica gel manufactured by Fuji Silysia Chemical Ltd. or NH silica gel manufactured by Fuji Silysia Chemical Ltd. and the like were used. The room temperature generally means from about 10° C. to 35° C. For drying the extract, anhydrous sodium sulfate or anhydrous magnesium sulfate was used.

In Formulation Examples, the Japanese Pharmacopoeia 15th Edition (hereinafter to be referred to as The Japanese Pharmacopoeia) or Japanese Pharmaceutical Excipients 2003 compatible products were used as the preparation additives (e.g., lactose, cornstarch, magnesium stearate, crystalline cellulose).

Abbreviations in the Examples and Reference Examples mean the following.

NMR: nuclear magnetic resonance spectra

Hz: hertz

J: coupling constant m: multiplet q: quartet t: triplet d: doublet s: singlet br: broad dt: double triplet brs: broad singlet wt %: weight percent DMSO: dimethyl sulfoxide HATU: O-(7-azabenzotriazol-1-yl)-N,N,N',N'-tetramethyluronium hexafluorophosphate Reference Example 1

Production of benzyl (4-hydroxyphenyl)carbamate

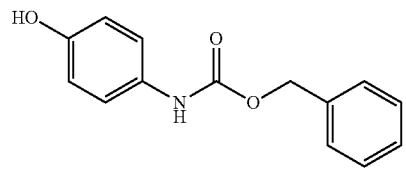 [SMILES: O=C(Nc1ccc(O)cc1)OCc1ccccc1]

To a suspension of p-aminophenol (7.0 g, 63.9 mmol) in tetrahydrofuran (105 mL) was added saturated aqueous sodium hydrogen carbonate (70 mL), and benzyl chloroformate (12.0 g, 70.3 mmol) was added dropwise at 0° C. After stirring at room temperature for 16 hr, the reaction mixture was extracted with ethyl acetate (200 mL). The organic layer was washed with saturated brine (100 mL) and dried over anhydrous magnesium sulfate. The solvent was evaporated under reduced pressure. The residue was washed with hexane/ethyl acetate (=4/1) and collected by filtration to give the title compound (8.2 g, 53%).

$^1$H-NMR (CDCl$_3$, 300 MHz) δ 4.78 (1H, s), 5.19 (2H, s), 6.52 (1H, br s), 6.77 (2H, d, J=9.2 Hz), 7.22-7.26 (2H, d, J=8.1 Hz), 7.30-7.42 (5H, m).

Reference Example 2

Production of benzyl {4-[(6-nitropyridin-3-yl)oxy]phenyl}carbamate

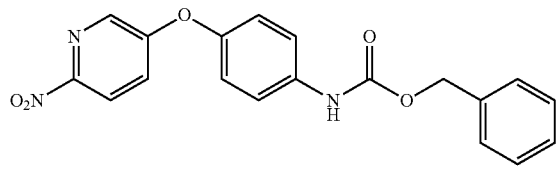 [SMILES: O=C(Nc1ccc(Oc2ccc([N+](=O)[O-])nc2)cc1)OCc1ccccc1]

To a solution of benzyl (4-hydroxyphenyl)carbamate (1.44 g, 5.91 mmol) in N,N-dimethylformamide (10 mL) were added cesium carbonate (2.41 g, 7.39 mmol) and 5-bromo-2-nitropyridine (1.0 g, 4.93 mmol), and the mixture was stirred at room temperature for 16 hr. Water (40 mL) was added to the reaction mixture, and the mixture was extracted with ethyl acetate/tetrahydrofuran (=2/1, 120 mL). The organic layer was washed with saturated brine, and dried over anhydrous magnesium sulfate. The solvent was evaporated under reduced pressure, and the residue was purified by silica gel chromatography (NH silica gel, hexane/ethyl acetate=3/1→1/3) to give the title compound (1.01 g, 56%).

¹H-NMR (CDCl₃, 300 MHz) δ 5.22 (2H, s), 6.90 (1H, s), 7.07 (2H, d, J=8.9 Hz), 7.34-7.43 (6H, m), 7.50 (2H, d, J=8.9 Hz), 8.22 (1H, d, J=8.7 Hz), 8.31 (1H, d, J=2.7 Hz).

Reference Example 3

Production of benzyl {4-[(6-aminopyridin-3-yl)oxy]phenyl}carbamate

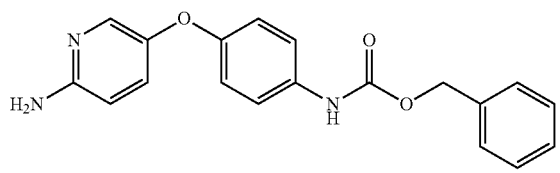

To a solution of benzyl {4-[(6-nitropyridin-3-yl)oxy]phenyl}carbamate (5.99 g, 16.4 mmol) in ethanol (80 mL)/water (16 mL) were added reduced iron (5.8 g, 98.4 mmol) and calcium chloride (1.42 g, 11.5 mmol), and the mixture was heated under reflux for 16 hr. The reaction mixture was cooled to room temperature, filtered through celite, and washed with ethanol. The solvent was evaporated under reduced pressure, saturated aqueous sodium hydrogen carbonate (50 mL) was added to the residue, and the mixture was extracted with ethyl acetate (150 mL). The organic layer was washed with water and saturated brine in this order, and dried over anhydrous magnesium sulfate. The solvent was evaporated under reduced pressure, a solid was precipitated with hexane/ethyl acetate (=2/1, 30 mL) and collected by filtration to give the title compound (4.43 g, 81%). The solvent of the filtrate was evaporated under reduced pressure, and the residue was purified by silica gel chromatography (NH silica, hexane/ethyl acetate=3/1→1/3) to give the title compound (0.43 mg, 8%).

¹H-NMR (DMSO-d₆, 300 MHz) δ 5.13 (2H, s), 5.82 (2H, s), 6.47 (1H, d, J=8.9 Hz), 6.85 (2H, ddd, J=10.3, 3.4, 2.2 Hz), 7.15 (1H, dd, J=8.9, 2.8 Hz), 7.27-7.50 (7H, m), 7.71 (1H, d, J=2.8 Hz), 9.67 (1H, br s).

Reference Example 4

Production of benzyl {4-[(6-{[(4-methylphenyl)sulfonyl]amino}pyridin-3-yl)oxy]phenyl}carbamate

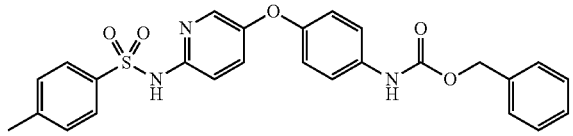 [SMILES: Cc1ccc(S(=O)(=O)Nc2ccc(Oc3ccc(NC(=O)OCc4ccccc4)cc3)cn2)cc1]

To a solution of benzyl {4-[(6-aminopyridin-3-yl)oxy]phenyl}carbamate (20.0 g, 59.6 mmol) in pyridine (100 mL) was added p-toluenesulfonyl chloride (13.6 g, 71.6 mmol), and the mixture was stirred at room temperature for 16 hr. Water was added to the reaction mixture, and the mixture was extracted with ethyl acetate. The organic layer was washed with 0.5N hydrochloric acid, water and saturated brine in this order, dried over anhydrous magnesium sulfate and filtered. The solvent was evaporated under reduced pressure, and the residue was washed with hexane/ethyl acetate and collected by filtration to give the title compound (23.8 g, 82%).

¹H-NMR (DMSO-d₆, 300 MHz) δ 2.35 (3H, s), 5.14 (2H, s), 6.94 (2H, d, J=9.0 Hz), 7.09 (1H, d, J=9.0 Hz), 7.32-7.47 (10H, m), 7.76 (2H, d, J=8.4 Hz), 7.91 (1H, d, J=2.4 Hz), 9.76 (1H, s), 10.96 (1H, br s).

Reference Example 5

Production of benzyl (4-{[1-(2-amino-2-oxoethyl)-6-{[(4-methylphenyl)sulfonyl]imino}-1,6-dihydropyridin-3-yl]oxy}phenyl)carbamate

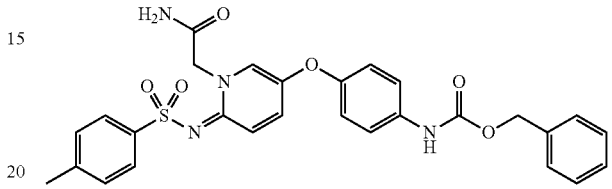

To a solution of benzyl {4-[(6-{[(4-methylphenyl)sulfonyl]amino}pyridin-3-yl)oxy]phenyl}carbamate (23.8 g, 48.6 mmol) in N,N-dimethylformamide (238 mL) were added N,N-diisopropylethylamine (11.0 mL, 63.2 mmol) and iodoacetamide (11.7 g, 63.2 mmol), and the mixture was stirred at room temperature for 24 hr. Water was added to the reaction mixture, and the mixture was extracted twice with ethyl acetate/tetrahydrofuran. The combined organic layer was washed with water and saturated brine, dried over anhydrous magnesium sulfate and filtered. The solvent was evaporated under reduced pressure, and the residue was washed with hexane/ethyl acetate and collected by filtration to give the title compound (20.6 g, 78%).

¹H-NMR (DMSO-d₆, 300 MHz) δ 2.34 (3H, s), 4.81 (2H, s), 5.14 (2H, s), 6.97 (2H, d, J=9.0 Hz), 7.27 (2H, d, J=8.1 Hz), 7.31-7.48 (9H, m), 7.63-7.68 (3H, m), 7.74 (1H, br s), 7.99 (1H, d, J=3.0 Hz), 9.76 (1H, br s).

Reference Example 6

Production of benzyl {4-[(2-aminoimidazo[1,2-a]pyridin-6-yl)oxy]phenyl}carbamate

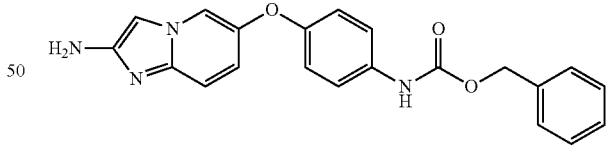

To a solution of benzyl (4-{[1-(2-amino-2-oxoethyl)-6-{([(4-methylphenyl)sulfonyl]imino}-1,6-dihydropyridin-3-yl]oxy}phenyl)carbamate (20.6 g, 37.7 mmol) in tetrahydrofuran (206 mL) was added trifluoroacetic acid anhydride (144 mL), and the mixture was stirred at room temperature for 48 hr. The solvent was evaporated under reduced pressure, ethyl acetate/tetrahydrofuran was added to the residue, washed with saturated aqueous sodium hydrogen carbonate and saturated brine in this order, dried over anhydrous magnesium sulfate and filtered. The solvent was evaporated under reduced pressure, ethanol (200 mL) and 4N aqueous sodium hydroxide solution (50 mL) were added to the residue, and the mixture was stirred at 45° C. for 10 hr. The solvent was concentrated to about half under reduced pressure, water was added to the residue, and the mixture was extracted with ethyl acetate/tetrahydrofuran. The organic layer was washed with saturated brine, dried over anhydrous magnesium sulfate and filtered. The solvent was evaporated under reduced pressure, and the residue was purified by silica gel column chromatography (ethyl acetate→ethyl acetate/methanol=10/1) to give the title compound (9.0 g, 64%).

¹H-NMR (DMSO-d₆, 300 MHz) δ 5.14 (2H, s), 5.28 (2H, br s), 6.84 (1H, dd, J=9.5, 2.3 Hz), 6.93-7.01 (3H, m), 7.19 (1H, d, J=9.5 Hz), 7.30-7.49 (7H, m), 8.19 (1H, d, J=2.3 Hz), 9.73 (1H, s).

Reference Example 7

Production of N-[6-(4-aminophenoxy)imidazo[1,2-a]pyridin-2-yl]cyclopropanecarboxamide

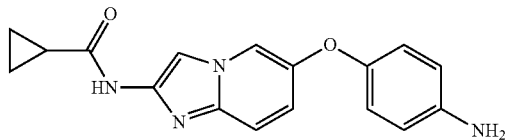 [SMILES: Nc1ccc(Oc2ccc3nc(NC(=O)C4CC4)cn3c2)cc1]

To a solution of benzyl [4-({2[(cyclopropylcarbonyl)amino]imidazo[1,2-a]pyridin-6-yl}oxy)phenyl]carbamate (500 mg, 1.13 mmol) in 1,2-dimethoxyethane (15 mL) was added 0.15 mol/L aqueous barium hydroxide solution (10 mL), and the mixture was stirred at 90° C. for 36 hr. After cooling to room temperature, the reaction mixture was adjusted to pH about 5 with citric acid, and to pH about 10 with saturated aqueous sodium hydrogen carbonate. The mixture was extracted with ethyl acetate/tetrahydrofuran, and the organic layer was washed with saturated brine, dried over anhydrous magnesium sulfate and filtered. The solvent was evaporated under reduced pressure, and the residue was purified by silica gel column chromatography (hexane/ethyl acetate=50/50→0/100) to give the title compound (223 g, 64%).

¹H-NMR (DMSO-d₆, 300 MHz) δ 0.76-0.82 (4H, m), 1.85-1.96 (1H, m), 4.95 (2H, m), 6.57 (2H, d, J=8.7 Hz), 6.79 (2H, d, J=8.7 Hz), 6.96-7.11 (1H, m), 7.38 (1H, d, J=9.6 Hz), 7.99 (1H, s), 8.25 (1H, d, J=1.8 Hz), 10.89 (1H, s).

Reference Example 8

Production of benzyl (3-fluoro-4-hydroxyphenyl)carbamate

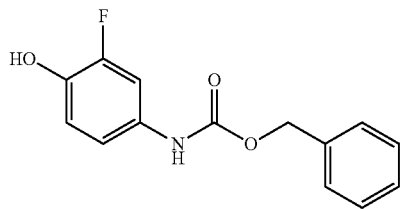 [SMILES: O=C(Nc1ccc(O)c(F)c1)OCc1ccccc1]

To a suspension of 4-amino-2-fluorophenol (60 g, 472 mmol) in tetrahydrofuran/water (=1/1, 600 mL) was added sodium hydrogen carbonate (43.6 g, 519 mmol), and benzyl chloroformate (74.1 mL, 519 mmol) was added dropwise at 0° C. The mixture was stirred at room temperature for 16 hr, 2N hydrochloric acid (150 mL) was added to the reaction mixture, and the mixture was extracted with ethyl acetate. The organic layer was washed with water, dried over anhydrous magnesium sulfate and filtered. The solvent was evaporated under reduced pressure, the residue was washed with hexane/diethyl ether (=1/1) and collected by filtration to give the title compound (82.5 g, 67%). The solvent of the filtrate was evaporated under reduced pressure, and the residue was washed with hexane/diethyl ether (=1/1) and collected by filtration to give the title compound (17.7 g, 14%).

¹H-NMR (DMSO-d₆, 300 MHz) δ 5.12 (2H, s), 6.85 (1H, t, J=9.3 Hz), 6.97-7.04 (1H, m), 7.25-7.45 (6H, m), 9.48 (1H, br s), 9.64 (1H, br s).

Reference Example 9

Production of benzyl {3-fluoro-4-[(6-nitropyridin-3-yl)oxy]phenyl}carbamate

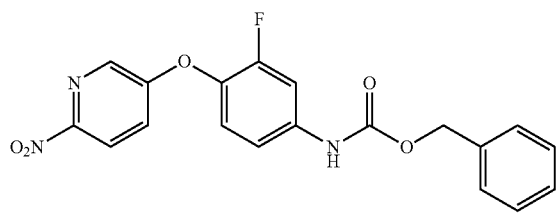 [SMILES: O=C(Nc1ccc(Oc2ccc([N+](=O)[O-])nc2)c(F)c1)OCc1ccccc1]

To a solution of benzyl (3-fluoro-4-hydroxyphenyl)carbamate (80 g, 252 mmol) in dimethyl sulfoxide (600 mL) were added cesium carbonate (123 g, 378 mmol) and 5-chloro-2-nitropyridine (40 g, 252 mmol), and the mixture was stirred at room temperature for 3 hr. Saturated aqueous sodium hydrogen carbonate (1000 mL) and water (1000 mL) were added to the reaction mixture, and the mixture was extracted twice with ethyl acetate. The combined organic layer was washed with saturated brine, dried over anhydrous magnesium sulfate and filtered. The solvent was evaporated under reduced pressure, and the residue was washed with hexane/ethyl acetate (=3/1) and collected by filtration to give the title compound (79.8 g, 83%).

¹H-NMR (CDCl₃, 300 MHz) δ 5.23 (2H, s), 6.82 (1H, s), 7.05-7.19 (2H, m), 7.31-7.44 (6H, m), 7.59 (1H, dd, J=12.3, 2.4 Hz), 8.24 (1H, d, J=9.0 Hz), 8.32 (1H, d, J=2.7 Hz).

Reference Example 10

Production of benzyl {4-[(6-aminopyridin-3-yl)oxy]-3-fluorophenyl}carbamate

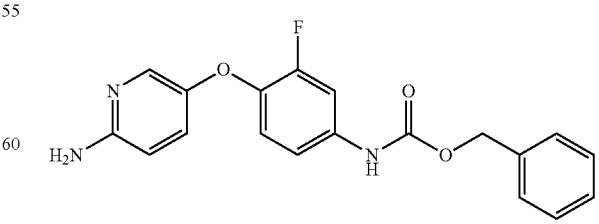

To a solution of benzyl {4-[(6-nitropyridin-3-yl)oxy]phenyl}carbamate (40 g, 104 mmol) in ethanol (1020 mL)/water (180 mL) were added reduced iron (29.1 g, 522 mmol)

and calcium chloride (5.8 g, 52 mmol), and the mixture was heated under reflux for 8 hr. The reaction mixture was cooled to room temperature, filtered through celite, and washed with ethanol. The solvent was evaporated under reduced pressure, water (200 mL) was added to the residue, and the mixture was extracted with ethyl-acetate (800 mL). The organic layer was washed with water and saturated brine in this order, and dried over anhydrous magnesium sulfate. The solvent was evaporated under reduced pressure, and a solid was precipitated with hexane/ethyl acetate (=3/1) and collected by filtration to give the title compound (28.2 g, 76%).

$^1$H-NMR (DMSO-$d_6$, 300 MHz) δ 5.15 (2H, s), 5.82 (2H, s), 6.45 (1H, d, J=8.7 Hz), 6.96 (1H, t, J=9.0 Hz), 7.11-7.19 (2H, m), 7.30-7.53 (6H, m), 7.70 (1H, d, J=2.7 Hz), 9.94 (1H, s).

Reference Example 11

Production of benzyl {3-fluoro-4-[(6-{[(4-methylphenyl)sulfonyl]amino}pyridin-3-yl)oxy]phenyl}carbamate

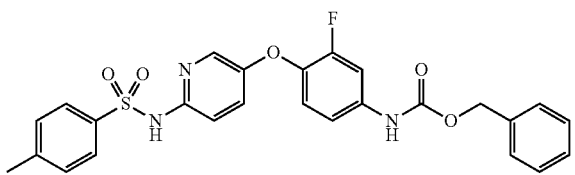 [SMILES: Cc1ccc(S(=O)(=O)Nc2ccc(Oc3ccc(NC(=O)OCc4ccccc4)cc3F)cn2)cc1]

To a solution of benzyl {4-[(6-aminopyridin-3-yl)oxy]-3-fluorophenyl}carbamate (28.2 g, 79.8 mmol) in pyridine (141 mL) was added p-toluenesulfonyl chloride (18.3 g, 98.5 mmol), and the mixture was stirred at room temperature for 16 hr. Water was added to the reaction mixture, and the mixture was extracted with ethyl acetate. The organic layer was washed with 0.5N hydrochloric acid, water and saturated brine in this order, dried over anhydrous magnesium sulfate and filtered. The solvent was evaporated under reduced pressure, and the residue was washed with hexane/ethyl acetate and collected by filtration to give the title compound (29.2 g, 72%).

$^1$H-NMR (DMSO-$d_6$, 300 MHz) δ 2.35 (3H, s), 5.16 (2H, s), 7.05-7.24 (2H, m), 7.28-7.46 (9H, m), 7.50-7.58 (1H, m), 7.75 (2H, d, J=8.4 Hz), 7.91 (1H, d, J=2.7 Hz), 10.03 (1H, s), 10.95 (1H, br s).

Reference Example 12

Production of benzyl (4-{[(6Z)-1-(2-amino-2-oxoethyl)-6-{[(4-methylphenyl)sulfonyl]imino}-1,6-dihydropyridin-3-yl]oxy}-3-fluorophenyl)carbamate

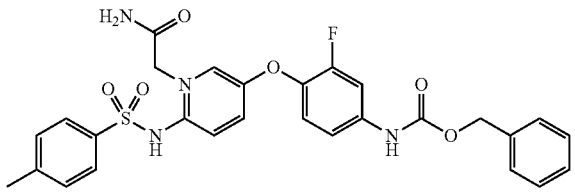

To a solution of benzyl {3-fluoro-4-[(6-{[(4-methylphenyl)sulfonyl]amino}pyridin-3-yl)oxy]phenyl}carbamate (35.0 g, 69.0 mmol) in N,N-dimethylformamide (350 mL) were added N,N-diisopropylethylamine (15.6 mL, 89.6 mmol) and iodoacetamide (16.6 g, 89.6 mmol), and the mixture was stirred at room temperature for 24 hr. Water was added to the reaction mixture, and the mixture was extracted twice with ethyl acetate/tetrahydrofuran. The combined organic layer was washed with water and saturated brine, dried over anhydrous magnesium sulfate and filtered. The solvent was evaporated under reduced pressure, and the residue was washed with hexane/ethyl acetate and collected by filtration to give the title compound (28.0 g, 72%).

$^1$H-NMR (DMSO-$d_6$, 300 MHz) δ 2.34 (3H, s), 4.80 (2H, s), 5.16 (2H, s), 7.08-7.46 (12H, m), 7.50-7.58 (1H, m), 7.64-7.74 (3H, m), 7.95 (1H, d, J=3.0 Hz), 10.03 (1H, s).

Reference Example 13

Production of benzyl {4-[(2-aminoimidazo[1,2-a]pyridin-6-yl)oxy]-3-fluorophenyl}carbamate

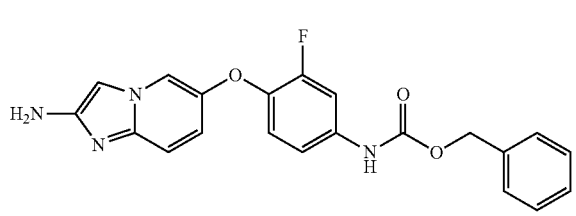 [SMILES: Nc1cn2cc(Oc3ccc(NC(=O)OCc4ccccc4)cc3F)ccc2n1]

To a solution of benzyl (4-{[1-(2-amino-2-oxoethyl)-6-{[(4-methylphenyl)sulfonyl]imino}-1,6-dihydropyridin-3-yl]oxy}-3-fluorophenyl)carbamate (28.0 g, 49.6 mmol) in tetrahydrofuran (280 mL) was added trifluoroacetic acid anhydride (196 mL), and the mixture was stirred at room temperature for 3 hr. The solvent was evaporated under reduced pressure, ethyl acetate/tetrahydrofuran was added to the residue, and the mixture was washed with saturated aqueous sodium hydrogen carbonate and saturated brine in this order, dried over anhydrous magnesium sulfate and filtered. The solvent was evaporated under reduced pressure, ethanol (140 mL) and 4N aqueous sodium hydroxide solution (40 mL) were added to the residue, and the mixture was stirred at room temperature for 4 hr. The solvent was concentrated under reduced pressure to about 1/3, water was added to the residue, and the mixture was extracted with ethyl acetate/tetrahydrofuran. The organic layer was washed with saturated brine, dried over anhydrous magnesium sulfate and filtered. The solvent was evaporated under reduced pressure, and the residue was purified by silica gel column chromatography (ethyl acetate/methanol=10/0→9/1) to give the title compound (10.0 g, 51%).

$^1$H-NMR (DMSO-$d_6$, 300 MHz) δ 5.03 (2H, s), 5.16 (2H, s), 6.85 (1H, dd, J=9.5, 2.3 Hz), 6.97 (1H, s), 7.08-7.23 (3H, m), 7.32-7.45 (5H, m), 7.54 (1H, dd, J=13.5, 2.4 Hz), 8.14 (1H, d, J=1.8 Hz), 9.99 (1H, s).

Reference Example 14

Production of N-[6-(4-amino-2-fluorophenoxy)imidazo[1,2-a]pyridin-2-yl]cyclopropanecarboxamide

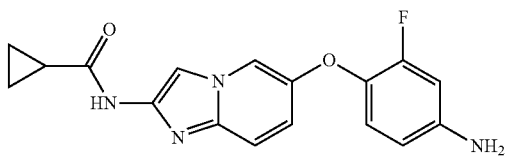

To a suspension of benzyl [4-({2-[(cyclopropylcarbonyl)amino]imidazo[1,2-a]pyridin-6-yl}oxy)-3-fluorophenyl]carbamate (18.0 g, 39.1 mmol) in 1,2-dimethoxyethane (360 mL) was added 0.15 mol/L aqueous barium hydroxide solution (240 mL), and the mixture was stirred at 90° C. for 16 hr. After cooling to room temperature, the reaction mixture was adjusted to about pH 8 with 2N hydrochloric acid, and the mixture was extracted with ethyl acetate/tetrahydrofuran. The organic layer was washed with saturated brine, dried over anhydrous magnesium sulfate and filtered. The solvent was evaporated under reduced pressure, and the residue was washed with ethyl acetate and collected by filtration to give the title compound (9.1 g, 71%).

$^1$H-NMR (DMSO-$d_6$, 300 MHz) δ 0.74-0.81 (4H, m), 1.85-1.94 (1H, m), 5.34 (2H, s), 6.38 (1H, dd, J=8.7 1.2 Hz), 6.49 (1H, dd, J=13.5, 2.4 Hz), 6.90-7.05 (2H, m), 7.38 (1H, d, J=9.6 Hz), 8.00 (1H, s), 8.22 (1H, d, J=2.1 Hz), 10.88 (1H, s).

Reference Example 15

Production of benzyl (2-fluoro-4-hydroxyphenyl)carbamate

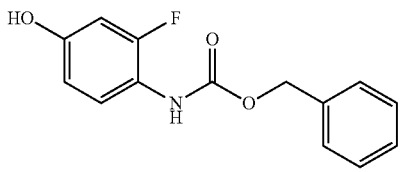 [SMILES: O=C(Nc1ccc(O)cc1F)OCc1ccccc1]

To a suspension of 4-amino-3-fluorophenol (50 g, 39.3 mmol) in tetrahydrofuran/water (=1/1, 500 mL) was added sodium hydrogen carbonate (36.3 g, 39.3 mmol), and benzyl chloroformate (62 mL, 43.3 mmol) was added dropwise at room temperature. The mixture was stirred at room temperature for 16 hr, and extracted with ethyl acetate (1000 mL). The organic layer was washed with saturated brine, dried over anhydrous magnesium sulfate and filtered. The solvent was evaporated under reduced pressure, and the residue was washed with hexane/diethyl ether (=1/1) and collected by filtration to give the title compound (94.5 g, 92%).

$^1$H-NMR (DMSO-$d_6$, 300 MHz) δ 5.10 (2H, s), 6.53-6.64 (2H, m), 7.10-7.26 (1H, m), 7.30-7.43 (5H, m), 9.02 (1H, br s), 9.76 (1H, s).

Reference Example 16

Production of benzyl {2-fluoro-4-[(6-nitropyridin-3-yl)oxy]phenyl}carbamate

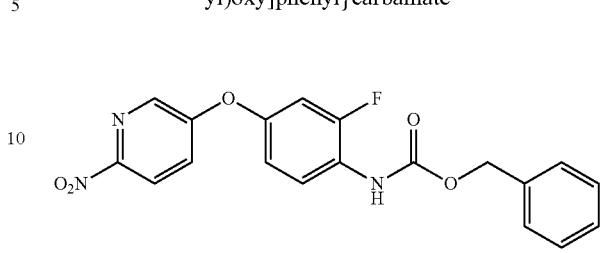

To a solution of benzyl (2-fluoro-4-hydroxyphenyl)carbamate (79 g, 303 mmol) in dimethyl sulfoxide (480 mL) were added cesium carbonate (123 g, 378 mmol) and 5-chloro-2-nitropyridine (40 g, 252 mmol), and the mixture was stirred at room temperature for 6 hr. Water (1000 mL) was added to the reaction mixture, and the mixture was extracted with ethyl acetate/tetrahydrofuran. The organic layer was washed with saturated brine, dried over anhydrous magnesium sulfate and filtered. The solvent was evaporated under reduced pressure, and the residue was washed with hexane/ethyl acetate (=3/1) and collected by filtration to give the title compound (74 g, 77%).

$^1$H-NMR (DMSO-$d_6$, 300 MHz) δ 5.17 (2H, s), 7.05-7.12 (1H, m), 7.27-7.46 (6H, m), 7.66-7.78 (2H, m), 8.34 (1H, d, J=8.6 Hz), 8.46 (1H, d, J=2.9 Hz), 9.57 (1H, s).

Reference Example 17

Production of benzyl {4-[(6-aminopyridin-3-yl)oxy]-2-fluorophenyl}carbamate

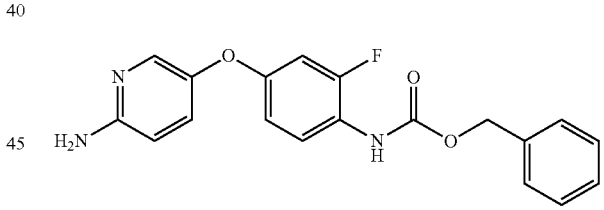

To a solution of benzyl {2-fluoro-4-[(6-nitropyridin-3-yl)oxy]phenyl}carbamate (40 g, 104.3 mmol) in ethanol (1020 mL)/water (180 mL) were added reduced iron (29.1 g, 521.7 mmol) and calcium chloride (5.8 g, 52.2 mmol), and the mixture was heated under reflux for 8 hr. The reaction mixture was cooled to room temperature, filtered through celite, and washed with ethanol. The solvent was evaporated under reduced pressure, water (200 mL) was added to the residue, and the mixture was extracted with ethyl acetate (800 mL). The organic layer was washed with water and saturated brine in this order, and dried over anhydrous magnesium sulfate. The solvent was evaporated under reduced pressure, hexane/ethyl acetate (=3/1) was added, and the precipitate was collected by filtration to give the title compound (28.2 g, 76%).

$^1$H-NMR (DMSO-$d_6$, 300 MHz) δ 5.13 (2H, s), 5.92 (2H, s), 6.49 (1H, d, J=9.0 Hz), 6.63-6.68 (1H, m), 6.81 (1H, dd,

J=11.9, 2.9 Hz), 7.22 (1H, dd, J=8.7, 2.9 Hz), 7.30-7.48 (6H, m), 7.76 (1H, d, J=2.9 Hz), 9.28 (1H, br s).

Reference Example 18

Production of benzyl {2-fluoro-4-[(6-{[(4-methylphenyl)sulfonyl]amino}pyridin-3-yl)oxy]phenyl}carbamate

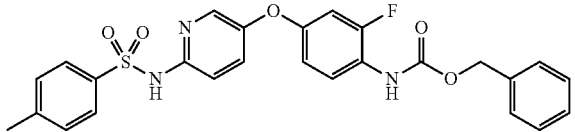 [SMILES: Cc1ccc(S(=O)(=O)Nc2ccc(Oc3ccc(NC(=O)OCc4ccccc4)c(F)c3)cn2)cc1]

To a solution of benzyl {4-[(6-aminopyridin-3-yl)oxy]-2-fluorophenyl}carbamate (32 g, 90.6 mmol) in pyridine (141 mL) was added p-toluenesulfonyl chloride (18.3 g, 108.7 mmol), and the mixture was stirred at 80° C. for 3 hr. After cooling to room temperature, pyridine was evaporated under reduced pressure, water was added to the residue, and the mixture was extracted with ethyl acetate/tetrahydrofuran. The organic layer was washed with saturated brine, dried over anhydrous magnesium sulfate and filtered. The solvent was evaporated under reduced pressure, and the residue was washed with hexane/ethyl acetate and collected by filtration to give the title compound (32.0 g, 70%).

$^1$H-NMR (DMSO-$d_6$, 300 MHz) δ 2.36 (3H, s), 5.13 (2H, s), 6.73-6.79 (1H, m), 6.95 (1H, dd, J=11.6, 2.9 Hz), 7.12 (1H, d, J=9.0 Hz), 7.30-7.56 (9H, m), 7.78 (2H, d, J=8.4 Hz), 8.00 (1H, d, J=2.7 Hz), 9.37 (1H, s), 11.04 (1H, br s).

Reference Example 19

Production of benzyl (4-{[(6Z)-1-(2-amino-2-oxoethyl)-6-{[(4-methylphenyl)sulfonyl]imino}-1,6-dihydropyridin-3-yl]oxy}-2-fluorophenyl)carbamate

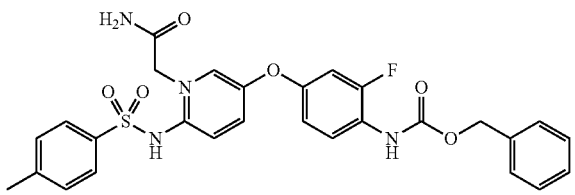

To a solution of benzyl {2-fluoro-4-[(6-{[(4-methylphenyl)sulfonyl]amino}pyridin-3-yl)oxy]phenyl}carbamate (32.0 g, 63.1 mmol) in N,N-dimethylformamide (320 mL) were added N,N-diisopropylethylamine (14.3 mL, 82.0 mmol) and iodoacetamide (15.2 g, 82.0 mmol), and the mixture was stirred at room temperature for 24 hr. Water was added to the reaction mixture, and the mixture was extracted twice with ethyl acetate/tetrahydrofuran. The combined organic layer was washed with water and saturated brine, dried over anhydrous magnesium sulfate and filtered. The solvent was evaporated under reduced pressure, and the residue was washed with hexane/ethyl acetate and collected by filtration to give the title compound (34.2 g, 96%).

$^1$H-NMR (DMSO-$d_6$, 300 MHz) δ 2.34 (3H, s), 4.81 (2H, s), 5.13 (2H, s), 6.79-6.87 (1H, m), 7.02 (1H, dd, J=11.7, 2.9 Hz), 7.28 (1H, d, J=7.8 Hz), 7.30-7.43 (8H, m), 7.53-7.59 (1H, m), 7.65-7.75 (4H, m), 8.12 (1H, d, J=3.0 Hz), 9.38 (1H, br s).

Reference Example 20

Production of benzyl {4-[(2-aminoimidazo[1,2-a]pyridin-6-yl)oxy]-2-fluorophenyl}carbamate

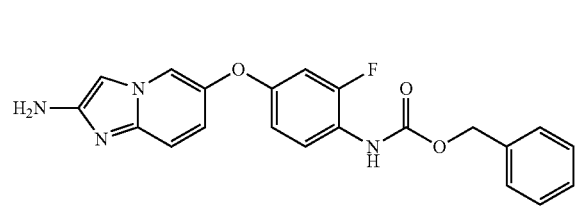 [SMILES: Nc1cn2cc(Oc3ccc(NC(=O)OCc4ccccc4)c(F)c3)ccc2n1]

To a solution of benzyl (4-{[1-(2-amino-2-oxoethyl)-6-{[(4-methylphenyl)sulfonyl]imino}-1,6-dihydropyridin-3-yl]oxy}-2-fluorophenyl)carbamate (28.0 g) in tetrahydrofuran (280 mL) was added trifluoroacetic acid anhydride (196 mL), and the mixture was stirred at room temperature for 3 hr. The solvent was evaporated under reduced pressure, ethyl acetate/tetrahydrofuran was added to the residue, and the mixture was washed with saturated aqueous sodium hydrogen carbonate and saturated brine in this order, dried over anhydrous magnesium sulfate and filtered. The solvent was evaporated under reduced pressure, ethanol (140 mL) and 4N aqueous sodium hydroxide solution (40 mL) were added to the residue, and the mixture was stirred at room temperature for 4 hr. The solvent was concentrated under reduced pressure to 1/3, water was added to the residue, and the mixture was extracted with ethyl acetate/tetrahydrofuran. The organic layer was washed with saturated brine, dried over anhydrous magnesium sulfate and filtered. The solvent was evaporated under reduced pressure, and the residue was purified by silica gel column chromatography (ethyl acetate/methanol=10/1→9/1) to give the title compound (12.1 g, 51%).

$^1$H-NMR (DMSO-$d_6$, 300 MHz) δ 5.13 (4H, s), 6.76-6.82 (1H, m), 6.87 (1H, dd, J=9.5, 2.3 Hz), 6.91-6.96 (1H, m), 7.00 (1H, s), 7.20 (1H, d, J=9.3 Hz), 7.33-7.44 (6H, m), 7.46-7.55 (1H, m), 8.32 (1H, d, J=1.8 Hz), 9.34 (1H, br s).

Reference Example 21

Production of N-[6-(4-amino-3-fluorophenoxy)imidazo[1,2-a]pyridin-2-yl]cyclopropanecarboxamide

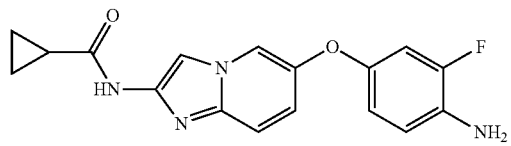 [SMILES: Nc1ccc(Oc2ccc3nc(NC(=O)C4CC4)cn3c2)cc1F]

To a suspension of benzyl [4-({2-[(cyclopropylcarbonyl)amino]imidazo[1,2-a]pyridin-6-yl}oxy)-2-fluorophenyl]carbamate (9.7 g, 21.1 mmol) in 1,2-dimethoxyethane (291 mL) was added 0.15 mol/L aqueous barium hydroxide solution (194 mL), and the mixture was stirred at 90° C. for 16 hr. After cooling to room temperature, the reaction mixture was adjusted to about pH 8 with 2N hydrochloric acid, and extracted with ethyl acetate/tetrahydrofuran. The organic layer was washed with saturated brine, dried over anhydrous sodium sulfate and filtered. The solvent was evaporated under reduced pressure, and the residue was washed with ethyl acetate and collected by filtration to give the title compound (4.3 g, 63%).

$^1$H-NMR (DMSO-d$_6$, 300 MHz) δ 0.78-0.82 (4H, m), 1.86-1.94 (1H, m), 4.98 (2H, s), 6.64-6.90 (3H, m), 7.02 (1H, dd, J=9.6, 52.4 Hz), 7.40 (1H, d, J=9.9 Hz), 8.01 (1H, s), 8.34 (1H, d, J=1.5 Hz), 10.92 (1H, s).

Reference Example 22

Production of N-(6-hydroxy-1,3-benzothiazol-2-yl) cyclopropanecarboxamide

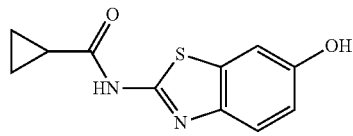 [SMILES: O=C(Nc1nc2ccc(O)cc2s1)C1CC1]

To a solution of 2-amino-1,3-benzothiazol-6-ol (4.99 g, 30.0 mmol) in N,N-dimethylacetamide (20 mL) was added cyclopropanecarbonyl chloride (4.08 mL, 45.0 mmol) at 0° C., and the mixture was stirred at room temperature for 18 hr. Water was added to the reaction mixture, and the mixture was extracted with ethyl acetate. The organic layer was washed 3 times with water, dried over anhydrous sodium sulfate and filtered. The solvent was evaporated under reduced pressure, and the residue was washed with ethyl acetate/diisopropyl ether and collected by filtration to give the title compound (3.22 g, 13.7 mmol) as a white solid.

$^1$H-NMR (DMSO-d$_6$, 300 MHz) δ 0.87-0.97 (4H, m), 1.92-2.01 (1H, m), 6.87 (1H, dd, J=8.7, 2.3 Hz), 7.25 (1H, d, J=2.3 Hz), 7.52 (1H, d, J=8.7 Hz), 9.53 (1H, br s), 12.41 (1H, br s).

Reference Example 23

Production of N-[6-(2-fluoro-4-nitrophenoxy)-1,3-benzothiazol-2-yl]cyclopropanecarboxamide

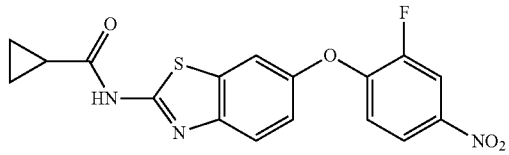 [SMILES: O=C(Nc1nc2ccc(Oc3ccc([N+](=O)[O-])cc3F)cc2s1)C1CC1]

A suspension of N-(6-hydroxy-1,3-benzothiazol-2-yl)cyclopropanecarboxamide (1.17 g, 5.00 mmol), 1,2-difluoro-4-nitrobenzene (0.96 g, 6.00 mmol) and cesium carbonate (3.26 g, 10.0 mmol) in dimethyl sulfoxide (10 mL) was stirred at 50° C. for 5 hr. After cooling to room temperature, water was added to the reaction mixture, and the mixture was extracted 3 times with ethyl acetate/tetrahydrofuran. The organic layer was washed with water, dried over anhydrous sodium sulfate and filtered. The solvent was evaporated under reduced pressure, and the residue was washed with ethyl acetate and collected by filtration to give the title compound (1.22 g, 65%) as a pale-yellow solid.

$^1$H-NMR (DMSO-d$_6$, 300 MHz) δ 0.92-0.99 (4H, m), 1.96-2.03 (1H, m), 7.10-7.17 (1H, m), 7.30 (1H, dd, J=8.9, 2.6 Hz), 7.82 (1H, d, J=8.9 Hz), 7.90 (1H, d, J=2.6 Hz), 8.04-8.09 (1H, m), 8.36 (1H, dd, J=10.8, 2.7 Hz), 12.71 (1H, br s).

Reference Example 24

Production of N-[6-(4-amino-2-fluorophenoxy)-1,3-benzothiazol-2-yl]cyclopropanecarboxamide

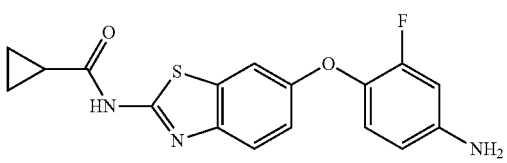

To a suspension of N-[6-(2-fluoro-4-nitrophenoxy)-1,3-benzothiazol-2-yl]cyclopropanecarboxamide (1.15 g, 3.07 mmol) in ethanol (50 mL)/water (10 mL) were added ammonium chloride (1.64 g, 30.7 mmol) and reduced iron (856 g, 15.3 mmol), and the mixture was heated under reflux for 4 hr. The reaction mixture was cooled to room temperature, filtered through celite, and washed with a mixed solution of ethanol/water. The solvent was evaporated under reduced pressure, 1N aqueous sodium hydroxide solution was added to the residue, and the mixture was extracted 3 times with ethyl acetate/tetrahydrofuran. The combined organic layer was dried over anhydrous sodium sulfate and filtered. The solvent was evaporated under reduced pressure, and the residue was washed with ethyl acetate/diisopropyl ether and collected by filtration to give the title compound (644 mg, 61%) as a pale-yellow solid.

$^1$H-NMR (DMSO-d$_6$, 300 MHz) δ 0.89-0.95 (4H, m), 1.92-2.02 (1H, m), 5.35 (2H, s), 6.35-6.43 (1H, m), 6.49 (1H, dd, J=13.2, 2.7 Hz), 6.90-7.02 (2H, m), 7.40 (1H, d, J=2.6 Hz), 7.65 (1H, d, J=8.7 Hz), 12.54 (1H, br s).

Reference Example 25

Production of tert-butyl {3-fluoro-4-[(5-nitropyridin-2-yl)oxy]phenyl}carbamate

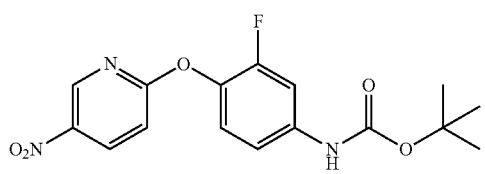

To a solution of tert-butyl (3-fluoro-4-hydroxyphenyl)carbamate (17.2 g, 75.7 mmol) in dimethyl sulfoxide (100 mL) were added 2-chloro-5-nitropyridine (10 g, 63.1 mmol) and cesium carbonate (30.8 g, 94.6 mmol), and the mixture was stirred at room temperature for 4 hr. Water was added to the reaction mixture, and the mixture was extracted twice with ethyl acetate. The combined organic layer was washed with saturated brine, dried over anhydrous sodium sulfate and filtered. The solvent was evaporated under reduced pressure, and the residue was washed with hexane/ethyl acetate (=5/1) and collected by filtration to give the title compound (17.0 g, 77%).

¹H-NMR (CDCl₃, 300 MHz) δ 1.53 (9H, s), 6.57 (1H, s), 7.00-7.16, (3H, m), 7.52 (1H, dd, J=12.3, 2.1 Hz), 8.49 (1H, dd, J=9.0, 2.9 Hz), 9.00 (1H, d, J=2.9 Hz).

Reference Example 26

Production of tert-butyl {4-[(5-aminopyridin-2-yl)oxy]-3-fluorophenyl}carbamate

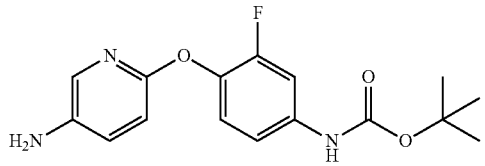 [SMILES: CC(C)(C)OC(=O)Nc1ccc(Oc2ccc([N+](=O)[O-])cn2)c(F)c1]

To a suspension of tert-butyl {3-fluoro-4-[(5-nitropyridin-2-yl)oxy]phenyl}carbamate (15 g, 42.9 mmol) in methanol (300 mL) was added 5 wt % palladium/carbon (3.0 g), and the mixture was stirred at room temperature for 8 hr under a hydrogen atmosphere. After nitrogen substitution, insoluble material was collected by filtration and washed with methanol. The solvent of the filtrate was evaporated under reduced pressure, water was added to the residue, and the mixture was extracted with ethyl acetate/tetrahydrofuran. The organic layer was washed with saturated brine, dried over anhydrous magnesium sulfate and filtered. The solvent was evaporated under reduced pressure to give the title compound (12.3 g, 90%).

¹H-NMR (DMSO-d₆, 300 MHz) δ 1.48 (9H, s), 4.98 (2H, s), 6.76 (1H, d, J=9.0 Hz), 7.04-7.10 (2H, m), 7.13-7.19 (1H, m), 7.40-7.47 (2H, m), 9.51 (1H, s).

Reference Example 27

Production of tert-butyl {4-[(2-amino[1,3]thiazolo[5,4-b]pyridin-5-yl)oxy]-3-fluorophenyl}carbamate

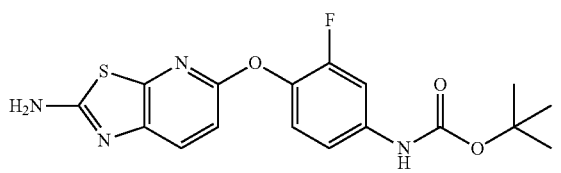 [SMILES: CC(C)(C)OC(=O)Nc1ccc(Oc2ccc3nc(N)sc3n2)c(F)c1]

To a solution of potassium thiocyanate (6.1 g, 62.6 mmol) in acetic acid (60 mL) was added a solution of tert-butyl {4-[(5-aminopyridin-2-yl)oxy]-3-fluorophenyl}carbamate (5.0 g, 15.7 mmol) in acetic acid (40 mL) at 0° C. A solution of bromine (3.25 g, 20.4 mmol) in acetic acid (20 mL) was added at 0° C., and the mixture was stirred at room temperature for 6 hr. Acetic acid was evaporated under reduced pressure, saturated aqueous sodium hydrogen carbonate was added to the residue, and the mixture was extracted with ethyl acetate. The organic layer was washed with saturated brine, dried over anhydrous sodium sulfate and filtered. The solvent was evaporated under reduced pressure, and the residue was purified by silica gel column chromatography (ethyl acetate alone) to give the title compound (2.07 g, 35%).

¹H-NMR (DMSO-d₆, 300 MHz) δ 1.49 (9H, s), 6.92 (1H, d, J=8.7 Hz), 7.17-7.23 (2H, m), 7.46-7.53 (1H, m), 7.57 (2H, s), 7.70 (1H, d, J=8.7 Hz), 9.59 (1H, s).

Reference Example 28

Production of N-[5-(4-amino-2-fluorophenoxy)[1,3]thiazolo[5,4-b]pyridin-2-yl]cyclopropanecarboxamide

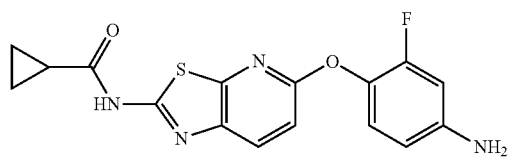

To a solution of tert-butyl [4-({2-[(cyclopropylcarbonyl)amino][1,3]thiazolo[5,4-b]pyridin-5-yl}oxy)-3-fluorophenyl]carbamate (0.50 g, 1.12 mmol) in trifluoroacetic acid (10 mL) was added anisole (0.5 mL), and the mixture was stirred at 0° C. for 2 hr. Trifluoroacetic acid was evaporated under reduced pressure, ethyl acetate was added to the residue, and the mixture was washed with saturated aqueous sodium hydrogen carbonate and saturated brine in this order, dried over anhydrous magnesium sulfate and filtered. The solvent was evaporated under reduced pressure, and the residue was purified by silica gel column chromatography (hexane/ethyl acetate=1/1→1/9) to give the title compound (294 mg, 76%) as a white solid.

¹H-NMR (DMSO-d₆, 300 MHz) δ 0.90-0.99 (4H, m), 1.95-2.05 (1H, m), 5.34 (2H, s), 6.36-6.51 (2H, m), 6.97 (1H, t, J=8.7 Hz), 7.06 (1H, d, J=8.7 Hz), 8.11 (1H, d, J=8.7 Hz), 12.64 (1H, br s).

Reference Example 29

Production of 2-cyano-N-(4-fluoro-2-methylphenyl)acetamide

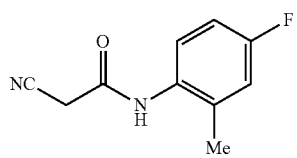 [SMILES: Cc1cc(F)ccc1NC(=O)CC#N]

4-Fluoro-2-methylaniline (3.9 g, 31 mmol) was added to ethyl cyanoacetate (5.3 g, 46 mmol) and the mixture was stirred at 150° C. for 4 hr. After cooling to room temperature, hexane-ethyl acetate was added to the reaction mixture, and the precipitate was collected by filtration to give the title compound (4.0 g, 67%) as a pale-yellow solid.

¹H-NMR (DMSO-d₆, 300 MHz) δ 2.20 (3H, s), 3.91 (2H, d, J=10.2 Hz), 7.02 (1H, td, J=8.6, 2.9 Hz), 7.11 (1H, dd, J=9.7, 2.9 Hz), 7.36 (1H, dd, J=8.8, 5.6 Hz), 9.69 (1H, s).

Reference Example 30

Production of 1-(4-fluoro-2-methylphenyl)-6-methyl-2-oxo-1,2-dihydropyridine-3-carbonitrile

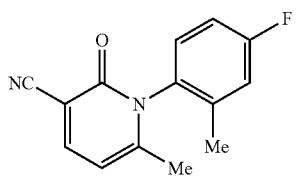

2-Cyano-N-(4-fluoro-2-methylphenyl)acetamide (2.0 g, 10 mmol) and 4-methoxybut-3-en-2-one (1.4 mL, 13 mmol) were suspended in 2-(2-methoxyethoxy)ethanol (20 mL), and 1,4-diazabicyclo[2.2.2]octane (1.2 g, 10 mmol) was added. The mixture was stirred at 120° C. for 6 hr, and cooled to room temperature. The mixture was diluted with ethyl acetate (40 mL), and washed with saturated aqueous sodium hydrogen carbonate solution. Then the organic layer was dried over anhydrous sodium sulfate, and the solvent was evaporated under reduced pressure. Hexane-ethyl acetate was added to the residue, and the resulting precipitate was collected by filtration to give the title compound (630 mg, 25%) as a yellow solid.

¹H-NMR (DMSO-d₆, 300 MHz) δ 1.97 (3H, s), 1.98 (3H, s), 6.53 (1H, d, J=7.6 Hz), 7.17-7.28 (1H, m), 7.29-7.40 (2H, m), 8.19 (1H, d, J=7.4 Hz).

Reference Example 31

Production of 1-(4-fluoro-2-methylphenyl)-6-methyl-2-oxo-1,2-dihydropyridine-3-carboxylic acid

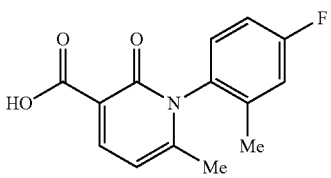 [SMILES: Cc1cc(F)ccc1-n1c(C)ccc(C(=O)O)c1=O]

1-(4-fluoro-2-methylphenyl)-6-methyl-2-oxo-1,2-dihydropyridine-3-carbonitrile (590 mg, 2.9 mmol) was suspended in water (3.0 mL), conc. sulfuric acid (3.0 mL) was slowly added dropwise. The mixture was stirred overnight at 100° C., and allowed to cool to room temperature. The reaction system was basified with aqueous sodium hydroxide solution (8N) and washed with ethyl acetate. The aqueous layer was acidified with hydrochloric acid (1N), and extracted twice with ethyl acetate. The mixed organic layer was dried over anhydrous sodium sulfate, and the solvent was evaporated under reduced pressure. Hexane-ethyl acetate was added to the residue, and the resulting precipitate was collected by filtration to give the title compound (480 mg, 75%) as a white solid.

¹H-NMR (DMSO-d₆, 300 MHz) δ 1.99 (3H, s), 2.06 (3H, s), 6.84 (1H, d, J=7.6 Hz), 7.22-7.32 (1H, m), 7.38 (1H, dd, J=9.6, 3.0 Hz), 7.44 (1H, dd, J=8.7, 5.5 Hz), 8.44 (1H, d, J=7.6 Hz), 14.14 (1H, s).

Reference Example 32

Production of 1-[(4-fluoro-2-methylphenyl)carbamoyl]cyclopropanecarboxylic acid

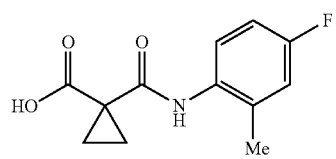 [SMILES: Cc1cc(F)ccc1NC(=O)C1(C(=O)O)CC1]

Cyclopropane-1,1-dicarboxylic acid (1.0 g, 8.0 mmol) was suspended in tetrahydrofuran (20 mL), and triethylamine (1.1 mL, 8.0 mmol) was added. After stirring at room temperature for 1 hr, the mixture was cooled in an ice bath. Under ice-cooling, thionyl chloride (0.58 mL, 8.0 mmol) was added dropwise, and the mixture was stirred as it was for 30 min. To this mixture was dropwise added a solution of 4-fluoro-2-methylaniline (3.9 g, 31 mmol) in tetrahydrofuran (2.0 mL) under ice-cooling, and the reaction mixture was warmed to room temperature and stirred overnight. An aqueous sodium hydroxide solution (1N, 50 mL) was added, and the mixture was washed twice with ethyl acetate. The aqueous layer was acidified with hydrochloric acid (1N), and the mixture was extracted twice with ethyl acetate. The mixed organic layer was dried over anhydrous magnesium sulfate, and the solvent was evaporated under reduced pressure. Hexane-ethyl acetate was added to the residue, and the precipitate was collected by filtration to give the title compound (1.1 g, 60%) as a white solid.

¹H-NMR (DMSO-d₆, 300 MHz) δ 1.52 (4H, s), 2.27 (3H, s), 6.99 (1H, td, J=8.7, 3.0 Hz), 7.10 (1H, dd, J=9.7, 2.9 Hz), 7.77 (1H, dd, J=8.9, 5.7 Hz), 10.66 (1H, s), 13.35 (1H, br s).

Reference Example 33

Production of methyl 6-phenylpyridine-2-carboxylate 1-oxide

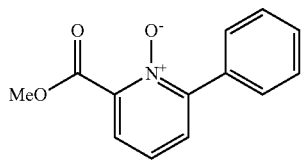 [SMILES: COC(=O)c1cccc(-c2ccccc2)[n+]1[O-]]

To a solution of methyl 6-phenylpyridine-2-carboxylate (509 mg, 6.24 mmol) in dichloromethane (5 mL) was added m-chloroperbenzoic acid (purity: 69-75%, 2.87 g, 12.5 mmol), and the mixture was stirred at room temperature for 3 days. Saturated sodium thiosulfate aqueous solution was added to the reaction mixture, and the mixture was extracted 3 times with ethyl acetate. The combined organic layer was washed with saturated brine, dried over anhydrous magnesium sulfate and filtered. The solvent was evaporated under reduced pressure. The obtained residue was purified by silica gel column chromatography (NH silica gel, ethyl acetate/hexane=1/2→1/1) to give the title compound (142 mg, 10%) as a colorless oil.

$^1$H-NMR (DMSO-$d_6$, 300 MHz) δ 3.88 (3H, s), 7.45-7.55 (4H, m), 7.69 (1H, dd, J=7.8, 2.1 Hz), 7.76 (1H, dd, J=7.8, 2.1 Hz), 7.78-7.84 (2H, m).

Reference Example 34

Production of 6-phenylpyridine-2-carboxylic acid 1-oxide

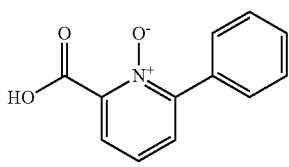 [SMILES: O=C(O)c1cccc(-c2ccccc2)[n+]1[O-]]

To a solution of methyl 6-phenylpyridine-2-carboxylate 1-oxide in methanol (2 mL) was added 1N aqueous sodium hydroxide solution (1 mL), and the mixture was stirred at room temperature for 3 hr. The reaction mixture was concentrated, 1N hydrochloric acid was added, the precipitate was collected by filtration, and washed with water to give the title compound (120 mg, 90%) as white crystals.

$^1$H-NMR (300 MHz, DMSO-$d_6$) δ 7.52-7.63 (3H, m), 7.76-7.85 (2H, m), 7.91-8.09 (2H, m), 8.35 (1H, dd, J=7.7, 2.3 Hz).

Reference Example 35

Production of 6-ethyl-2-oxo-1-phenyl-1,2-dihydropyridine-3-carbonitrile

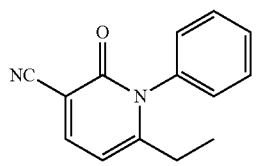 [SMILES: CCc1ccc(C#N)c(=O)n1-c1ccccc1]

A solution of 2-cyano-N-phenylacetamide (1.08 g, 6.73 mmol), (1E)-1-methoxypent-1-en-3-one (1.0 g, 8.76 mmol) and 1,4-diazabicyclo[2.2.2]octane (755 mg, 6.73 mmol) in 2-(2-methoxyethoxy)ethanol (10 mL) was stirred with heating at 120° C. for 7 hr. 1N Hydrochloric acid was added to the reaction mixture, and the mixture was extracted with ethyl acetate. The organic layer was washed with saturated brine, dried over anhydrous magnesium sulfate and filtered, and the solvent was evaporated under reduced pressure. The obtained residue was purified by silica gel column chromatography (NH silica gel, ethyl acetate/hexane=2/1→4/1) to give the title compound (412 mg, 27%) as a pale-brown solid.

$^1$H-NMR (DMSO-$d_6$, 300 MHz) δ 1.00 (3H, t, J=7.5 Hz), 2.24 (2H, q, J=7.5 Hz), 6.44 (1H, d, J=7.7 Hz), 7.31-7.39 (2H, m), 7.43-7.62 (3H, m), 8.20 (1H, d, J=7.7 Hz).

Reference Example 36

Production of 6-ethyl-2-oxo-1-phenyl-1,2-dihydropyridine-3-carboxylic acid

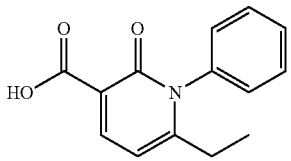 [SMILES: CCc1ccc(C(=O)O)c(=O)n1-c1ccccc1]

6-Ethyl-2-oxo-1-phenyl-1,2-dihydropyridine-3-carbonitrile (395 mg, 1.76 mmol) was dissolved in conc. sulfuric acid (0.4 mL) and water (0.4 mL), and the mixture was stirred with heating at 120° C. for 7 hr. 1N Aqueous sodium hydroxide solution was added to the reaction solution, and the mixture was washed with ethyl acetate. 1N Hydrochloric acid was added to the aqueous layer, and the mixture was extracted 3 times with ethyl acetate. The combined organic layer was washed with saturated brine, dried over anhydrous magnesium sulfate and filtered, and the solvent was evaporated under reduced pressure. The residue was washed with ethyl acetate to give the title compound (310 mg, 72%) as a colorless solid.

$^1$H-NMR (DMSO-$d_6$, 300 MHz) δ 1.04 (3H, t, J=7.5 Hz), 2.32 (2H, q, J=7.5 Hz), 6.77 (1H, d, J=7.7 Hz), 7.38-7.49 (2H, m), 7.51-7.67 (3H, m), 8.46 (1H, d, J=7.7 Hz), 14.28 (1H, s).

Reference Example 37

Production of 1-(4-fluorophenyl)-6-methyl-2-oxo-1,2-dihydropyridine-3-carbonitrile

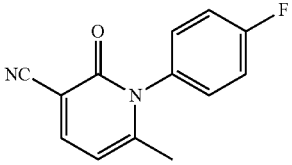 [SMILES: Cc1ccc(C#N)c(=O)n1-c1ccc(F)cc1]

A solution of 2-cyano-N-(4-fluorophenyl)acetamide (15 g, 84.2 mmol), 4-methoxybut-3-en-2-one (12.6 g, 125.9 mmol) and 1,4-diazabicyclo[2.2.2]octane (9.4 g, 84.2 mmol) in 2-(2-methoxyethoxy)ethanol (150 mL) was stirred with heating at 120° C. for 5 hr. (3E)-4-Methoxybut-3-en-2-one (4.2 g, 41.9 mmol) and 1,4-diazabicyclo[2,2,2]octane (4.7 g, 41.9 mmol) were further added to the reaction mixture, and the mixture was stirred with heating at 120° C. for 1 hr. 2N Hydrochloric acid was added to the reaction mixture, and the mixture was extracted with ethyl acetate. The organic layer was washed with saturated brine, dried over anhydrous magnesium sulfate and filtered, and the solvent was evaporated under reduced pressure. The obtained solid was washed with ethyl acetate to give the title compound (6 g, 31%) as a pale-brown solid.

¹H-NMR (DMSO-d$_6$, 300 MHz) δ 2.01 (3H, s), 6.45-6.52 (1H, m), 7.35-7.48 (4H, m), 8.15 (1H, d, J=7.4 Hz).

Reference Example 38

Production of 1-(4-fluorophenyl)-6-methyl-2-oxo-1,2-dihydropyridine-3-carboxylic acid

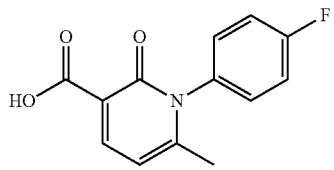 [SMILES: Cc1ccc(C(=O)O)c(=O)n1-c1ccc(F)cc1]

1-(4-Fluorophenyl)-6-methyl-2-oxo-1,2-dihydropyridine-3-carbonitrile (3 g, 13.1 mmol) was dissolved in conc. sulfuric acid (6.0 mL) and water (6.0 mL), and the mixture was stirred with heating at 120° C. for 20 hr. 8N Aqueous sodium hydroxide solution was added to the reaction solution, and the mixture was washed with ethyl acetate. 2N hydrochloric acid was added to the aqueous layer, and the mixture was extracted twice with ethyl acetate. The combined organic layer was washed with saturated brine, dried over anhydrous magnesium sulfate and filtered, and the solvent was evaporated under reduced pressure. The residue was washed with diethyl ether and collected by filtration to give the title compound (2.41 g, 74%) as a pale-brown solid.

¹H-NMR (DMSO-d$_6$, 300 MHz) δ 2.10 (3H, s), 6.80 (1H, d, J=7.9 Hz), 7.37-7.58 (4H, m), 8.41 (1H, d, J=7.9 Hz), 14.21 (1H, s).

Reference Example 39

Production of 5-methyl-6-phenylpyridine-2-carbonitrile 1-oxide

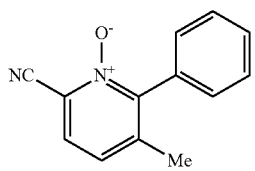 [SMILES: Cc1ccc(C#N)[n+]([O-])c1-c1ccccc1]

A solution of 6-(4-fluorophenyl)-5-methylpyridine-2-carbonitrile (750 mg, 3.86 mmol) and m-chloroperbenzoic acid (purity 69%, 2.4 g, 96.5 mmol) in tetrahydrofuran (8 mL) was stirred with heating at 50° C. for 3 days. Saturated aqueous sodium thiosulfate solution was added to the reaction mixture, and the mixture was extracted 3 times with ethyl acetate. The combined organic layer was washed with saturated aqueous sodium hydrogen carbonate solution and saturated brine, dried over anhydrous magnesium sulfate and filtered, and the solvent was evaporated under reduced pressure. The obtained residue was purified by silica gel column chromatography (ethyl acetate/hexane=1/3→1/2) to give the title compound (74.8 mg, 9%) as white crystals.

¹H-NMR (DMSO-d$_6$, 300 MHz) δ 2.10 (3H, s), 7.32-7.41 (2H, m), 7.45-7.59 (4H, m), 8.03 (1H, d, J=8.3 Hz).

Reference Example 40

Production of 5-methyl-6-phenylpyridine-2-carboxylic acid 1-oxide

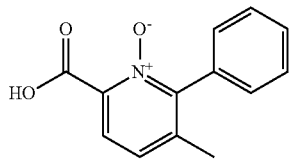 [SMILES: Cc1ccc(C(=O)O)[n+]([O-])c1-c1ccccc1]

In the same manner as in Reference Example 38 and using 5-methyl-6-phenylpyridine-2-carbonitrile 1-oxide (74.8 mg, 0.356 mmol), conc. sulfuric acid (0.3 mL) and water (0.3 mL), the title compound (83.1 mg, 99%) was obtained as colorless crystals.

¹H-NMR (DMSO-d$_6$, 300 MHz) δ 2.16 (3H, s), 7.43-7.49 (2H, m), 7.51-7.62 (3H, m), 7.92 (1H, d, J=8.5 Hz), 8.28 (1H, d, J=8.5 Hz).

Reference Example 41

Production of 2-(4-fluorophenyl)-3-methylpyridine 1-oxide

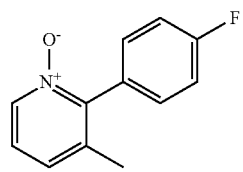

A solution of 2-(4-fluorophenyl)-3-methylpyridine (26.8 g, 0.143 mol) and m-chloroperbenzoic acid (purity 69%, 39 g, 0.157 mol) in tetrahydrofuran (100 mL) was stirred with heating at 50° C. for 5 hr. The solvent was evaporated under reduced pressure, and the obtained residue was purified 3 times by silica gel column chromatography (NH silica gel, ethyl acetate) to give a white solid. The obtained solid was washed with ethyl acetate to give the title compound (24.7 g, 85%) as a white solid.

¹H-NMR (DMSO-d$_6$, 300 MHz) δ 2.04 (3H, s), 7.21-7.46 (6H, m), 8.16-8.24 (1H, m).

Reference Example 42

Production of 6-(4-fluorophenyl)-5-methylpyridine-2-carbonitrile

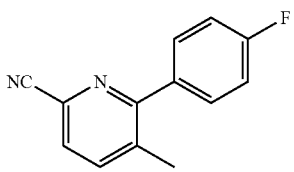 [SMILES: Cc1ccc(C#N)nc1-c1ccc(F)cc1]

To a solution of 2-(4-fluorophenyl)-3-methylpyridine 1-oxide (24 g, 0.118 mol) in tetrahydrofuran (200 mL) were added trimethylsilyl cyanide (19.2 mL, 0.153 mol) and dimethylcarbamoyl chloride (14.1 mL, 0.153 mmol), and the mixture was heated under reflux for 2 hr. Ethyl acetate and saturated aqueous sodium hydrogen carbonate solution were added to the reaction mixture, and the mixture was extracted 3 times with ethyl acetate. The combined organic layer was washed with saturated brine, dried over anhydrous magnesium sulfate and filtered, and the solvent was evaporated under reduced pressure. The obtained residue was washed with diethyl ether and collected by filtration to give the title compound (16.7 g, 67%) as a white solid. Under reduced pressure, the filtrate was concentrated, and the obtained residue was purified by silica gel column chromatography (ethyl acetate/hexane=1/9) to give the title compound (3.0 g, 12%) as a white solid.

$^1$H-NMR (DMSO-$d_6$, 300 MHz) δ 2.41 (3H, s), 7.07-7.43 (2H, m), 7.53-7.76 (2H, m), 7.90-8.07 (2H, m).

Reference Example 43

Production of 6-(4-fluorophenyl)-5-methylpyridine-2-carbonitrile 1-oxide

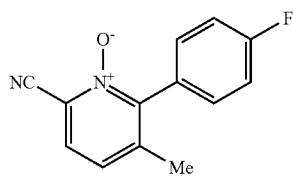 [SMILES: Cc1ccc(C#N)[n+]([O-])c1-c1ccc(F)cc1]

To a solution of 6-(4-fluorophenyl)-5-methylpyridine-2-carbonitrile (16.76 g, 79 mmol) and sodium percarbonate (24.8 g, 158 mmol) in acetonitrile (200 mL) was added dropwise trifluoromethanesulfonic acid anhydride (66.8 g, 237 mmol) at 0° C., and the mixture was stirred at 0° C. for 1 hr and further at room temperature overnight. Saturated aqueous sodium hydrogen carbonate solution was added to the reaction mixture, and the mixture was extracted 3 times with ethyl acetate. The combined organic layer was washed with saturated brine, dried over anhydrous magnesium sulfate and filtered, and the solvent was evaporated under reduced pressure. The residue was purified by silica gel column chromatography (ethyl acetate/hexane=1/2→1/1) to give the title compound (6.2 g, 40%) as a white solid.

$^1$H-NMR (DMSO-$d_6$, 300 MHz) δ 2.11 (3H, s), 7.30-7.42 (2H, m), 7.42-7.53 (3H, m), 8.03 (1H, d, J=8.3 Hz).

Reference Example 44

Production of 6-(4-fluorophenyl)-5-methylpyridine-2-carboxylic acid 1-oxide

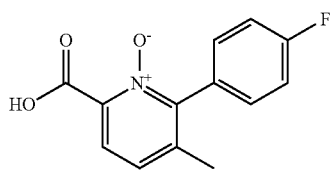 [SMILES: Cc1ccc(C(=O)O)[n+]([O-])c1-c1ccc(F)cc1]

In the same manner as in Reference Example 38 and using 6-(4-fluorophenyl)-5-methylpyridine-2-carbonitrile 1-oxide (6.07 g, 26.6 mmol), conc. sulfuric acid (18 mL) and water (18 mL), the title compound (5.72 g, 87%) was obtained as a white solid.

$^1$H-NMR (DMSO-$d_6$, 300 MHz) δ 2.18 (3H, s), 7.35-7.47 (2H, m), 7.50-7.62 (2H, m), 7.93 (1H, d, J=8.9 Hz), 8.30 (1H, d, J=8.1 Hz).

Reference Example 45

Production of ethyl [(5-methoxypyridin-2-yl)carbamothioyl]carbamate

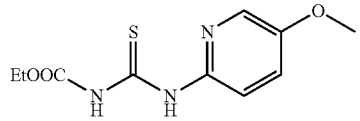 [SMILES: CCOC(=O)NC(=S)Nc1ccc(OC)cn1]

To a solution of 5-methoxypyridin-2-amine (1.05 g, 8.43 mmol) in dimethyl sulfoxide (5 mL) was added ethyl isothiocyanatoformate (1.44 g, 11.0 mmol), and the mixture was stirred for 15 hr. The reaction mixture was diluted with water, and extracted with ethyl acetate (×3). The combined organic layer was washed with saturated brine, dried over anhydrous magnesium sulfate and filtered. The filtrate was concentrated under reduced pressure, and the residue was dried to give the title compound (1.34 g, 62%) as a white solid.

$^1$H-NMR (DMSO-$d_6$, 300 MHz) δ 1.26 (3H, t, J=7.2 Hz), 3.84 (3H, s), 4.22 (2H, q, J=7.2 Hz), 7.51 (1H, dd, J=9.0, 3.0 Hz), 8.12 (1H, d, J=3.0 Hz), 8.54 (1H, br s), 11.38 (1H, br s), 12.04 (1H, br s).

Reference Example 46

Production of 6-methoxy[1,2,4]triazolo[1,5-a]pyridin-2-amine

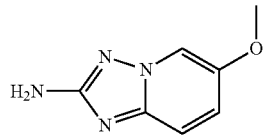

A mixture of ethyl [(5-methoxypyridin-2-yl)carbamothioyl]carbamate (1.34 g, 5.25 mmol), hydroxylammonium chloride (2.55 g, 36.7 mmol), N,N-diisopropylethylamine (4.57 mL, 26.2 mmol), ethanol (15 mL) and methanol (15 mL) was stirred at 80° C. for 8 hr. The reaction mixture was diluted with water, and extracted with ethyl acetate (×3). The combined organic layer was washed with saturated brine, dried over anhydrous magnesium sulfate and filtered. The filtrate was concentrated under reduced pressure, and the residue was collected by filtration, and washed with ethyl acetate-hexane to give the title compound (790 mg, 92%) as a yellow oil.

$^1$H-NMR (DMSO-$d_6$, 300 MHz) δ 3.78 (3H, s), 5.79 (2H, br s), 7.18 (1H, dd, J=9.6, 2.4 Hz), 7.27 (1H, d, J=9.6 Hz), 8.28 (1H, d, J=2.4 Hz).

Reference Example 47

Production of 2-amino[1,2,4]triazolo[1,5-a]pyridin-6-ol hydrobromide

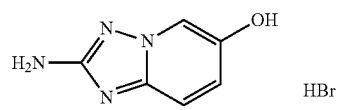

HBr

A mixture of 6-methoxy[1,2,4]triazolo[1,5-a]pyridin-2-amine (780 mg, 4.75 mmol), 48% hydrobromic acid (3 mL) was stirred under refluxing conditions for 7 hr. 48% Hydrobromic acid (2 mL) was further added and the mixture was stirred under refluxing conditions for 3 hr. The mixture was concentrated under reduced pressure, and diisopropyl ether (2 mL) and ethanol (1 mL) were added to the residue. The precipitate was collected by filtration, and washed with diisopropyl ether to give the title compound (984 mg, 89%) as a brown solid.

$^1$H-NMR (DMSO-$d_6$, 300 MHz) δ 7.53-7.61 (2H, m), 8.34 (1H, dd, J=1.8, 0.9 Hz), 10.57 (1H, br s).

Reference Example 48

Production of N-(6-hydroxy[1,2,4]triazolo[1,5-a]pyridin-2-yl)cyclopropanecarboxamide

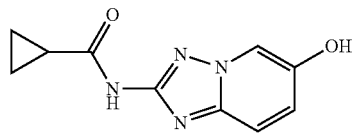 [SMILES: O=C(Nc1nc2ccc(O)cn2n1)C1CC1]

To a solution of 2-amino[1,2,4]triazolo[1,5-a]pyridin-6-ol hydrobromide (1.50 g, 4.22 mmol) in N,N-dimethylacetamide (5 mL) was added cyclopropanecarbonyl chloride (1.15 mL, 12.7 mmol) with stirring under ice-cooling, and the mixture was stirred at room temperature for 2 hr. The reaction mixture was diluted with water, and extracted with ethyl acetate. The organic layer was washed with water and saturated brine, dried over anhydrous magnesium sulfate and filtered. The filtrate was concentrated under reduced pressure, and the residue was collected by filtration, and washed with ethyl acetate-hexane to give the title compound (1.59 g, 89%) as a white solid.

$^1$H-NMR (DMSO-$d_6$, 300 MHz) δ 0.79-0.82 (4H, m), 1.96-2.05 (1H, m), 7.28 (1H, dd, J=9.4, 2.4 Hz), 7.52 (1H, d, J=9.4 Hz), 8.20 (1H, d, J=2.4 Hz), 10.01 (1H, br s), 10.82 (1H, s).

Reference Example 49

Production of N-[6-(2-fluoro-4-nitrophenoxy)[1,2,4]triazolo[1,5-a]pyridin-2-yl]cyclopropanecarboxamide

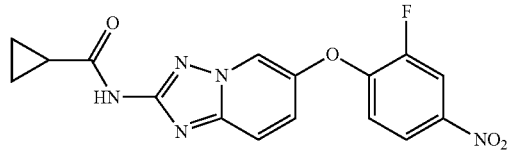

To a solution of N-(6-hydroxy[1,2,4]triazolo[1,5-a]pyridin-2-yl)cyclopropanecarboxamide (2 g, 9.16 mmol) and 1,2-difluoro-4-nitrobenzene (1.46 g, 9.16 mmol) in dimethyl sulfoxide (20 mL) was added cesium carbonate (4.48 g, 13.7 mmol), and the mixture was stirred at room temperature for 17 hr. The reaction mixture was filtered through celite, and the filtrate was diluted with water and ethyl acetate, and extracted twice with ethyl acetate. The combined organic layer was washed with saturated brine, dried over anhydrous magnesium sulfate and filtered, and the solvent was evaporated under reduced pressure. The obtained residue was washed with ethyl acetate to give the title compound (1.5 g, 46%) as a white solid.

$^1$H-NMR (300 MHz, DMSO-$d_6$) δ 0.77-0.87 (4H, m), 2.04 (1H, br s), 7.23-7.35 (1H, m), 7.64-7.73 (1H, m), 7.78-7.84 (1H, m), 8.05 (1H, dd, J=9.1, 1.1 Hz), 8.35 (1H, d, J=10.8 Hz), 9.17 (1H, s), 11.10 (1H, br s).

Reference Example 50

Production of N-[6-(4-amino-2-fluorophenoxy)[1,2,4]triazolo[1,5-a]pyridin-2-yl]cyclopropanecarboxamide

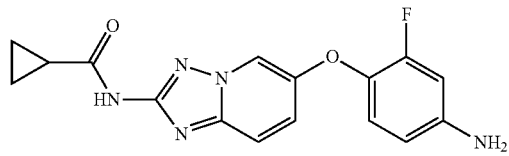 [SMILES: O=C(Nc1nc2ccc(Oc3ccc([N+](=O)[O-])cc3F)cn2n1)C1CC1]

A solution of N-[6-(2-fluoro-4-nitrophenoxy)[1,2,4]triazolo[1,5-a]pyridin-2-yl]cyclopropanecarboxamide (400 mg, 1.12 mmol), reduced iron (312 mg, 5.59 mmol) and ammonium chloride (600 mg, 11.2 mmol) in ethanol (8 mL) and water (2 mL) was heated under reflux for 1.5 hr. The reaction mixture was filtered through celite, and the filtrate was diluted with water and ethyl acetate and extracted 3 times with ethyl acetate. The combined organic layer was washed with saturated brine, dried over anhydrous magnesium sulfate and filtered, and the solvent was evaporated under reduced pressure. The residue was purified by silica gel column chromatography (ethyl acetate/hexane=1/2→ethyl acetate/methanol=9/1) to give the title compound (125 mg, 34%) as a white solid.

¹H-NMR (300 MHz, DMSO-d₆) δ 0.72-0.90 (4H, m), 1.93-2.13 (1H, m), 5.41 (2H, s), 6.33-6.44 (1H, m), 6.50 (1H, dd, J=13.4, 2.5 Hz), 6.92-7.05 (1H, m), 7.44 (1H, dd, J=9.6, 2.5 Hz), 7.66 (1H, dd, J=9.6, 0.8 Hz), 8.45 (1H, d, J=1.9 Hz), 10.98 (1H, s).

Reference Example 51

Production of methyl 1-(2-methylphenyl)-2-oxo-1,2-dihydropyridine-3-carboxylate

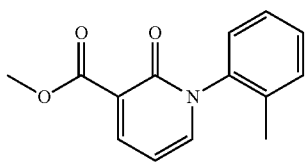 [SMILES: COC(=O)c1cccn(-c2ccccc2C)c1=O]

To a solution of methyl 2-oxo-2H-pyran-3-carboxylate (3 g, 19.5 mmol) in tetrahydrofuran (30 mL) and N,N-dimethylformamide (10 mL) was added 2-methylaniline (2.09 g, 19.5 mmol), and the mixture was stirred at room temperature for 7 hr. 4-Dimethylaminopyridine (119 mg, 0.974 mmol) and 1-ethyl-3-(3-dimethylaminopropyl)carbodiimide hydrochloride (4.48 g, 23.4 mmol) were added to the reaction mixture, and the mixture was further stirred at room temperature for 17 hr. 1N Hydrochloric acid was added to the reaction solution, and the mixture was extracted 3 times with ethyl acetate. The combined organic layer was washed with saturated brine, dried over anhydrous magnesium sulfate and filtered, and the solvent was evaporated under reduced pressure. The obtained residue was purified by silica gel column chromatography (NH silica gel, ethyl acetate/hexane=1/1) to give the title compound (882 mg, 19%) as yellow crystals.

¹H-NMR (300 MHz, DMSO-d₆) δ 2.04 (3H, s), 3.75 (3H, s), 6.36-6.47 (1H, m), 7.17-7.45 (4H, m), 7.86 (1H, dd, J=6.6, 2.3 Hz), 8.16 (1H, dd, J=7.2, 2.3 Hz).

Reference Example 52

Production of 1-(2-methylphenyl)-2-oxo-1,2-dihydropyridine-3-carboxylic acid

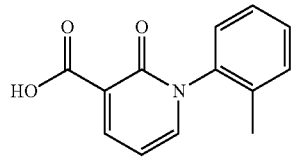 [SMILES: Cc1ccccc1-n1cccc(C(=O)O)c1=O]

To a solution (9 mL) of methyl 1-(2-methylphenyl)-2-oxo-1,2-dihydropyridine-3-carboxylate (880 mg, 3.62 mmol) in methanol was added 1N aqueous sodium hydroxide solution (5 mL), and the mixture was stirred at room temperature for 4 hr. The reaction mixture was adjusted to pH<7 with 1N hydrochloric acid and concentrated under reduced pressure. The precipitate was collected by filtration and washed with water to give the title compound (704 mg, 85%) as yellow crystals.

¹H-NMR (300 MHz, DMSO-d₆) δ 2.07 (3H, s), 6.74-6.88 (1H, m), 7.35-7.51 (4H, m), 8.14 (1H, dd, J=6.6, 2.1 Hz), 8.52 (1H, dd, J=7.4, 2.1 Hz), 14.25 (1H, br s).

Reference Example 53

Production of 1-(2,6-dimethylphenyl)-2-oxo-1,2-dihydropyridine-3-carboxylic acid

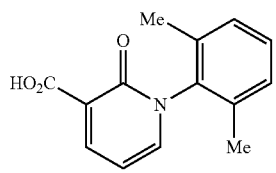 [SMILES: Cc1cccc(C)c1-n1cccc(C(=O)O)c1=O]

Dimethyl [(3-methoxyprop-2-en-1-ylidene)propanedionate (1.1 g, 5.6 mmol) and 2,6-dimethylaniline (0.69 mL, 5.6 mmol) were dissolved in N,N-dimethylacetamide (1.2 mL), and the mixture was stirred at 130° C. overnight. After cooling to room temperature, the reaction system was diluted with ethyl acetate and washed with saturated sodium hydrogen carbonate. The organic layer was dried over sodium sulfate, and the solvent was evaporated under reduced pressure. The residue was dissolved in methanol (15 mL), 60% sodium hydride (1.1 g, 28 mmol) was slowly added with stirring, and the mixture was further stirred at room temperature for 3 hr. Distilled water (10 mL) was added, and the mixture was further stirred at room temperature for 1 hr. 1N Aqueous sodium hydroxide solution (10 mL) was added to the reaction system and the mixture was washed with ethyl acetate. The aqueous layer was acidified with 1N hydrochloric acid (20 mL) and extracted twice with ethyl acetate. The collected organic layer was dried over magnesium sulfate, and the solvent was evaporated under reduced pressure. Hexane/ethyl acetate (=2/1) was added, and the resulting precipitate was collected by filtration to give the title compound (220 mg, 16%) as a white solid.

¹H-NMR (DMSO-d₆, 300 MHz) δ 2.00 (6H, s), 6.88 (1H, d, J=7.2 Hz), 7.26-7.41 (3H, m), 8.10 (1H, dd, J=6.6, 2.1 Hz), 8.56 (1H, dd, J=7.2, 2.1 Hz), 14.20 (1H, s).

Reference Example 54

Production of 1-[2-(1-methylethyl)phenyl]-2-oxo-1,2-dihydropyridine-3-carboxylic acid

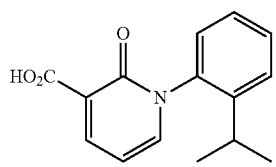 [SMILES: CC(C)c1ccccc1-n1cccc(C(=O)O)c1=O]

Methyl 2-oxo-2H-pyran-3-carboxylate (3.0 g, 19 mmol) was dissolved in a mixed solvent of tetrahydrofuran (40 mL) and N,N-dimethylformamide (10 mL), and 2-(1-methylethyl)aniline (2.7 mL, 19 mmol) was added. After stirring overnight at room temperature, 1-ethyl-3-(3-dimethylaminopropyl)carbodiimide hydrochloride (4.5 g, 23 mmol) and 4-(N,N-dimethylamino)pyridine (120 mg, 1.0 mmol) were added, and the mixture was further stirred overnight at room temperature. The reaction system was diluted with ethyl acetate and washed with saturated aqueous sodium hydrogen carbonate solution, and the organic layer was dried over sodium sulfate. The solvent was evaporated under reduced pressure, and the residue was purified by silica gel column chromatography (ethyl acetate/hexane=40/60→60/40) to give methyl 1-[2-(1-methylethyl)phenyl]-2-oxo-1,2-dihydropyridine-3-carboxylate (800 mg). Methyl 1-[2-(1-methylethyl)phenyl]-2-oxo-1,2-dihydropyridine-3-carboxylate (800 mg) was dissolved in a mixed solvent of tetrahydrofuran (5 mL) and methanol (5 mL), 1N aqueous sodium hydroxide solution (5 mL) was added, and the mixture was stirred at room temperature for 2 hr. The mixture was diluted with distilled water (20 mL) and washed with ethyl acetate. The aqueous layer was acidified with 1N hydrochloric acid (7 mL) and extracted twice with ethyl acetate. The collected organic layer was dried over sodium sulfate, and the solvent was evaporated under reduced pressure. A small amount of hexane/ethyl acetate was added to the residue, and the resulting precipitate was collected by filtration to give 1-[2-(1-methylethyl)phenyl]-2-oxo-1,2-dihydropyridine-3-carboxylic acid (760 mg, 15%) as a white solid.

$^1$H-NMR (DMSO-d$_6$, 300 MHz) δ 1.07-1.18 (6H, m), 2.51-2.57 (1H, m), 6.76-6.87 (1H, m), 7.32-7.43 (2H, m), 7.50-7.62 (2H, m), 8.19 (1H, dd, J=6.6, 2.1 Hz), 8.53 (1H, dd, J=7.2, 2.1 Hz), 14.25 (1H, s).

Reference Example 55

Production of
N-(2-chloro-4-fluorophenyl)--cyanoacetamide

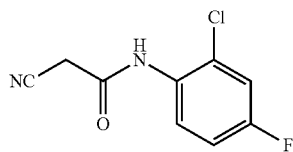 [SMILES: N#CCC(=O)Nc1ccc(F)cc1Cl]

A mixture of 2-chloro-4-fluoroaniline (3.55 g, 24.3 mmol), cyanoacetic acid (2.48 g, 29.2 mmol), N-[3-(dimethylamino)propyl]-N'-ethylcarbodiimide•hydrochloride (7.01 g, 36.5 mmol), 1H-1,2,3-benzotriazol-1-ol (4.94 g, 36.5 mmol), triethylamine (5.10 mL, 36.5 mmol) and N,N-dimethylformamide (50 mL) was stirred at room temperature for 16 hr. The mixture was diluted with ethyl acetate, washed with water, saturated aqueous sodium hydrogen carbonate solution and saturated brine, dried over anhydrous magnesium sulfate, and filtered through a basic silica gel pad. The solvent was evaporated under reduced pressure, and the obtained residue was washed with hexane and collected by filtration to give the title compound (2.84 g, 54%) as a white solid.

$^1$H-NMR (DMSO-d$_6$, 300 MHz) δ 3.98 (2H, s), 7.21-7.30 (1H, m), 7.49-7.58 (1H, m), 7.61-7.71 (1H, m), 10.00 (1H, s).

Reference Example 56

Production of 1-(2-chloro-4-fluorophenyl)-6-methyl-2-oxo-1,2-dihydropyridine-3-carbonitrile

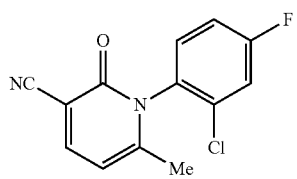 [SMILES: Cc1ccc(C#N)c(=O)n1-c1ccc(F)cc1Cl]

A mixture of N-(2-chloro-4-fluorophenyl)-2-cyanoacetamide (2.00 g, 9.40 mmol), (3E)-4-methoxybut-3-en-2-one (1.13 g, 11.2 mmol), 1,4-diazabicyclo[2.2.2]octane (1.05 g, 9.40 mmol) and 2-(2-methoxyethoxy)ethanol (20 mL) was stirred at 130° C. for 3 hr. After cooling to room temperature, the mixture was diluted with ethyl acetate, washed with 1N hydrochloric acid, water (×2) and saturated brine, dried over anhydrous magnesium sulfate, and filtered through a silica gel pad. The solvent was evaporated under reduced pressure, and the obtained residue was purified by silica gel column chromatography (100 g, ethyl acetate/hexane=2/98→50/50). The obtained residue was washed with ethyl acetate/hexane and collected by filtration to give the title compound (0.75 g, 30%) as a pale-yellow solid.

$^1$H-NMR (DMSO-d$_6$, 300 MHz) δ 2.01 (3H, s), 6.51-6.61 (1H, m), 7.42-7.55 (1H, m), 7.63-7.73 (1H, m), 7.77-7.85 (1H, m), 8.18-8.27 (1H, m).

Reference Example 57

Production of 1-(2-chloro-4-fluorophenyl)-6-methyl-2-oxo-1,2-dihydropyridine-3-carboxylic acid

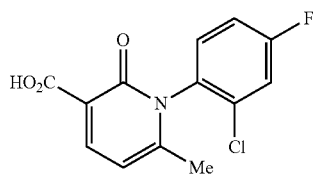 [SMILES: Cc1ccc(C(=O)O)c(=O)n1-c1ccc(F)cc1Cl]

To a mixture of 1-(2-chloro-4-fluorophenyl)-6-methyl-2-oxo-1,2-dihydropyridine-3-carbonitrile, 1-(2-chloro-4-fluorophenyl)-4-methyl-2-oxo-1,2-dihydropyridine-3-carbonitrile (0.75 g, 3.80 mmol) and water (5 mL) was added conc. sulfuric acid (5 mL) at 0° C., and the mixture was stirred at 100° C. for 18 hr. After cooling to 0° C., the mixture was basified (pH 11) with 8N aqueous sodium hydroxide solution and washed with ethyl acetate. The aqueous layer was acidified (pH 4) with 5N hydrochloric acid and extracted with ethyl acetate. The organic layer was dried over anhydrous magnesium sulfate and filtered, and the solvent was evaporated under reduced pressure. The obtained residue was washed with diethyl ether and collected by filtration to give the title compound (588 mg, 55%) as a white solid.

$^1$H-NMR (DMSO-d$_6$, 300 MHz) δ 2.09 (3H, s), 6.85 (1H, d, J=7.5 Hz), 7.48-7.57 (1H, m), 7.72-7.89 (2H, m), 8.46 (1H, d, J=7.5 Hz), 13.84 (1H, br s).

Reference Example 58

Production of
N-(2-bromo-4-fluorophenyl)-2-cyanoacetamide

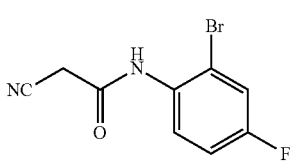 [SMILES: N#CCC(=O)Nc1ccc(F)cc1Br]

A mixture of 2-bromo-4-fluoroaniline (10.0 g, 52.6 mmol), cyanoacetic acid (5.36 g, 63.1 mmol), N-[3-(dimethylamino)propyl]-N'-ethylcarbodiimide•hydrochloride (15.1 g, 78.9 mmol), 1H-1,2,3-benzotriazol-1-ol (10.6 g, 78.9 mmol), triethylamine (10.9 mL, 78.9 mmol) and N,N-dimethylformamide (150 mL) was stirred at room temperature for 16 hr. The mixture was diluted with ethyl acetate, washed with water, saturated aqueous sodium hydrogen carbonate solution and saturated brine, dried over anhydrous magnesium sulfate, and filtered through a pad packed with NH silica gel. The solvent was evaporated under reduced pressure, and the obtained residue was washed with hexane and collected by filtration to give the title compound (8.04 g, 59%) as a white solid.

$^1$H-NMR (DMSO-d$_6$, 300 MHz) δ 3.96 (2H, s), 7.26-7.34 (1H, m), 7.54-7.61 (1H, m), 7.64-7.70 (1H, m), 9.97 (1H, s).

Reference Example 59

Production of 1-(2-bromo-4-fluorophenyl)-6-methyl-2-oxo-1,2-dihydropyridine-3-carbonitrile

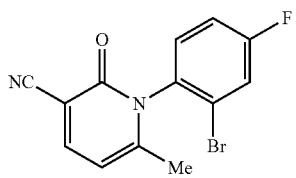 [SMILES: Cc1ccc(C#N)c(=O)n1-c1ccc(F)cc1Br]

A mixture of N-(2-bromo-4-fluorophenyl)-2-cyanoacetamide (5.00 g, 19.4 mmol), (3E)-4-methoxybut-3-en-2-one (2.33 g, 23.3 mmol), 1,4-diazabicyclo[2.2.2]octane (2.18 g, 19.4 mmol) and 2-(2-methoxyethoxy)ethanol (50 mL) was stirred at 130° C. for 5 hr. After cooling to room temperature, the mixture was diluted with ethyl acetate, washed with 1N hydrochloric acid, water (×2) and saturated brine, dried over anhydrous magnesium sulfate, and filtered through a silica gel pad. The solvent was evaporated under reduced pressure, and the obtained residue was purified by silica gel column chromatography (100 g, ethyl acetate/hexane=2/98→50/50), washed with ethyl acetate-hexane and collected by filtration to give the title compound (1.78 g, 29%) as a pale-brown powder.

$^1$H-NMR (DMSO-d$_6$, 300 MHz) δ 1.99 (3H, s), 6.51-6.59 (1H, m), 7.46-7.56 (1H, m), 7.63-7.70 (1H, m), 7.87-7.95 (1H, m), 8.21-8.26 (1H, m).

Reference Example 60

Production of 1-(2-bromo-4-fluorophenyl)-6-methyl-2-oxo-1,2-dihydropyridine-3-carboxylic acid

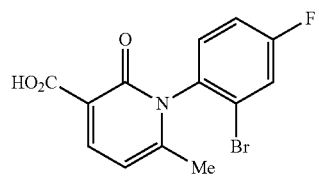 [SMILES: Cc1ccc(C(=O)O)c(=O)n1-c1ccc(F)cc1Br]

To a mixture of 1-(2-bromo-4-fluorophenyl)-6-methyl-2-oxo-1,2-dihydropyridine-3-carbonitrile, 1-(2-bromo-4-fluorophenyl)-4-methyl-2-oxo-1,2-dihydropyridine-3-carbonitrile (2.00 g, 6.51 mmol) and water (10 mL) was added conc. sulfuric acid (10 mL) at 0° C., and the mixture was stirred at 100° C. for 16 hr. After cooling to 0° C., the mixture was basified (pH 11) with 8N aqueous sodium hydroxide solution and washed with ethyl acetate. The aqueous layer was acidified (pH 4) with 5N hydrochloric acid and extracted with ethyl acetate. The organic layer was dried over anhydrous magnesium sulfate and filtered, and the solvent was evaporated under reduced pressure. The obtained residue was washed with diethyl ether and collected by filtration to give the title compound (1.12 g, 53%) as a white powder.

$^1$H-NMR (DMSO-d$_6$, 300 MHz) δ 2.08 (3H, s), 6.85 (1H, d, J=7.6 Hz), 7.52-7.60 (1H, m), 7.71-7.78 (1H, m), 7.91-7.98 (1H, m), 8.46 (1H, d, J=7.6 Hz), 13.87 (1H, br s).

Reference Example 61

Production of 1-(4-fluorophenyl)-6-(1-methylethyl)-2-oxo-1,2-dihydropyridine-3-carbonitrile

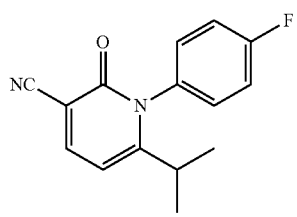 [SMILES: CC(C)c1ccc(C#N)c(=O)n1-c1ccc(F)cc1]

A mixture of (1E)-1-methoxy-4-methylpenta-1-en-3-one (508 mg, 3.96 mmol), 2-cyano-N-(4-fluorophenyl)acetamide (847 mg, 4.75 mmol), 1,4-diazabicyclo[2.2.2]octane (444 mg, 3.96 mmol) and 2-(2-methoxyethoxy)ethanol (10 mL) was stirred at 130° C. for 6 hr. After cooling to room temperature, the mixture was diluted with ethyl acetate, washed with 1N hydrochloric acid, water (×2) and saturated brine, dried over anhydrous magnesium sulfate and filtered. The solvent was evaporated under reduced pressure, and the obtained residue was purified by silica gel column chromatography (ethyl acetate/hexane=0/100→60/40) and silica gel column chromatography (NH silica gel, ethyl acetate/hexane=0/100→60/40) to give the title compound (604 mg, 59%) as a yellow solid.

$^1$H-NMR (DMSO-d$_6$, 300 MHz) δ 1.08 (6H, d, J=6.8 Hz), 2.34-2.45 (1H, m), 6.52 (1H, d, J=7.7 Hz), 7.34-7.57 (4H, m), 8.21 (1H, d, J=7.7 Hz).

Reference Example 62

Production of 1-(4-fluorophenyl)-6-(1-methylethyl)-2-oxo-1,2-dihydropyridine-3-carboxylic acid

To a mixture of 1-(4-fluorophenyl)-6-(1-methylethyl)-2-oxo-1,2-dihydropyridine-3-carbonitrile (604 mg, 2.35 mmol) and water (5 mL) was added conc. sulfuric acid (5 mL) at 0° C., and the mixture was stirred at 100° C. for 14 hr. After cooling to 0° C., the mixture was basified (pH 11) with 8N aqueous sodium hydroxide solution and washed with ethyl acetate. The aqueous layer was acidified (pH 4) with 5N hydrochloric acid and extracted with ethyl acetate. The organic layer was dried over anhydrous magnesium sulfate and filtered, and the solvent was evaporated under reduced pressure to give the title compound (425 mg, 65%) as a pale-yellow solid.

$^1$H-NMR (DMSO-$d_6$, 300 MHz) δ 1.12 (6H, d, J=6.8 Hz), 2.42-2.53 (1H, m), 6.85 (1H, d, J=7.7 Hz), 7.40-7.49 (2H, m), 7.53-7.61 (2H, m), 8.46 (1H, d, J=7.7 Hz), 14.22 (1H, s).

Reference Example 63

Production of ethyl 2-(4-fluorophenyl)-3-oxo-2,3-dihydro-1H-pyrazole-4-carboxylate

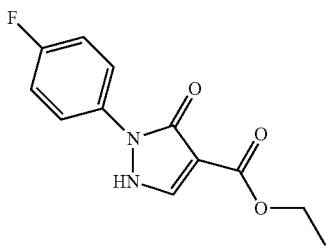 [SMILES: CCOC(=O)c1c[nH]n(-c2ccc(F)cc2)c1=O]

To a suspension of (4-fluorophenyl)hydrazine•hydrochloride (3 g, 18 mmol) and water (75 mL) were added potassium carbonate (5.6 g, 40 mmol) and diethyl ethoxymethylenemalonate (4.8 g, 22 mmol), and the mixture was heated under reflux for 7 hr. After cooling to room temperature, the mixture was washed with ethyl acetate. 6N Aqueous hydrochloric acid solution was added to the separated aqueous layer under ice-cooling. The precipitated solid was collected by filtration, washed with water and ethyl acetate/hexane (1/10), and dried under reduced pressure to give the title compound (2.2 g, 48%) as a yellow solid.

$^1$H-NMR (DMSO-$d_6$, 300 MHz) δ 1.28 (3H, t, J=6.5 Hz), 4.10-4.34 (2H, m), 7.25-7.44 (2H, m), 7.71 (2H, br s), 7.82 (1H, br s), 12.31 (1H, br s).

Reference Example 64

Production of ethyl 2-(4-fluorophenyl)-1-methyl-3-oxo-2,3-dihydro-1H-pyrazole-4-carboxylate

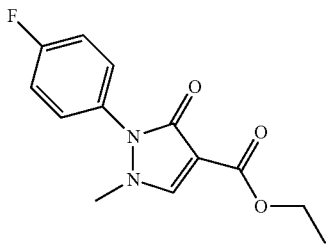 [SMILES: CCOC(=O)c1cn(C)n(-c2ccc(F)cc2)c1=O]

A mixture of ethyl 2-(4-fluorophenyl)-3-oxo-2,3-dihydro-1H-pyrazole-4-carboxylate (2.2 g, 8.9 mmol) and methyl trifluoromethanesulfonate (3 mL) was stirred at 80° C. for 40 min. The mixture was purified by silica gel column chromatography (NH silica gel, ethyl acetate/hexane=70/30→100/0) to give the title compound (1.6 g, 67%) as a pale-yellow solid.

$^1$H-NMR (DMSO-$d_6$, 300 MHz) δ 1.23 (3H, t, J=7.1 Hz), 3.39 (3H, s), 4.15 (2H, q, J=7.2 Hz), 7.34-7.47 (4H, m), 8.51 (1H, s).

Reference Example 65

Production of 2-(4-fluorophenyl)-1-methyl-3-oxo-2,3-dihydro-1H-pyrazole-4-carboxylic acid

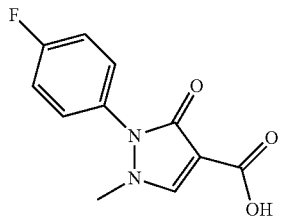 [SMILES: Cn1cc(C(=O)O)c(=O)n1-c1ccc(F)cc1]

To a solution of ethyl 2-(4-fluorophenyl)-1-methyl-3-oxo-2,3-dihydro-1H-pyrazole-4-carboxylate (1.6 g, 5.9 mmol) in tetrahydrofuran (6 mL)/methanol (5 mL) was added 4N aqueous sodium hydroxide solution (9 mL), and the mixture was stirred at 60° C. for 1 hr. Tetrahydrofuran and methanol were evaporated under reduced pressure. 6N Aqueous hydrochloric acid solution was added to the residue with stirring, and the precipitated solid was collected by filtration. The filtrate was washed with water and ethyl acetate/hexane (1/5), and dried under reduced pressure to give the title compound (1.1 g, 79%) as a white solid.

$^1$H-NMR (DMSO-$d_6$, 300 MHz) δ 3.41 (3H, s), 7.35-7.54 (4H, m), 8.52 (1H, s), 11.85 (1H, br s).

Reference Example 66

Production of ethyl 2-(2-methylphenyl)-3-oxo-2,3-dihydro-1H-pyrazole-4-carboxylate

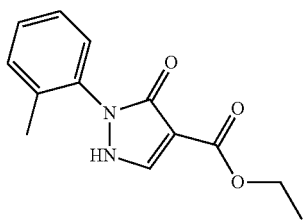 [SMILES: CCOC(=O)c1c[nH]n(-c2ccccc2C)c1=O]

In the same manner as in Reference Example 63 and using (2-methylphenyl)hydrazine•hydrochloride (5 g, 32 mmol), water (100 mL), potassium carbonate (9.7 g, 70 mmol) and diethyl ethoxymethylenemalonate (8.3 g, 38 mmol) as starting materials, the title compound (6.8 g, 87%) was obtained as a brown solid.

$^1$H-NMR (DMSO-$d_6$, 300 MHz) δ 1.28 (3H, t, J=7.2 Hz), 2.07 (3H, s), 4.22 (2H, q, J=7.2 Hz), 7.23-7.43 (4H, m), 7.79 (1H, s).

Reference Example 67

Production of ethyl 1-methyl-2-(2-methylphenyl)-3-oxo-2,3-dihydro-1H-pyrazole-4-carboxlate

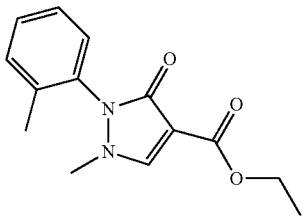 [SMILES: CCOC(=O)c1cn(C)n(-c2ccccc2C)c1=O]

In the same manner as in Reference Example 64 and using ethyl 2-(2-methylphenyl)-3-oxo-2,3-dihydro-1H-pyrazole-4-carboxylate (3.1 g, 12 mmol) and methyl trifluoromethanesulfonate (2.5 mL) as starting materials, the title compound (2.1 g, 66%) was obtained as a pale-yellow solid.

$^1$H-NMR (DMSO-$d_6$, 300 MHz) δ 1.23 (3H, t, J=7.1 Hz), 2.10 (3H, s), 3.29 (3H, s), 4.09-4.20 (2H, m), 7.27 (1H, d, J=7.6 Hz), 7.33-7.46 (3H, m), 8.49 (1H, s).

Reference Example 68

Production of 1-methyl-2-(2-methylphenyl)-3-oxo-2,3-dihydro-1H-pyrazole-4-carboxylic acid

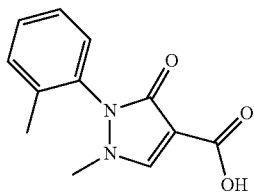 [SMILES: Cc1ccccc1-n1c(=O)c(C(=O)O)cn1C]

In the same manner as in Reference Example 65 and using ethyl 1-methyl-2-(2-methylphenyl)-3-oxo-2,3-dihydro-1H-pyrazole-4-carboxylate (2.1 g, 8.2 mmol), tetrahydrofuran (6 mL), methanol (4 mL) and 4N aqueous sodium hydroxide solution (9 mL) as starting materials, the title compound (750 mg, 40%) was obtained as a white solid.

$^1$H-NMR (DMSO-$d_6$, 300 MHz) δ 2.11 (3H, s), 3.29 (3H, s), 7.26-7.48 (4H, m), 8.42 (1H, s).

Reference Example 69

Production of ethyl 2-(2-chlorophenyl)-3-oxo-2,3-dihydro-1H-pyrazole-4-carboxylate

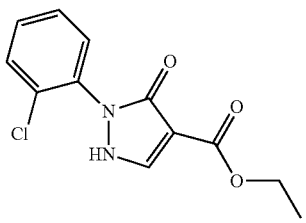 [SMILES: CCOC(=O)c1c[nH]n(-c2ccccc2Cl)c1=O]

In the same manner as in Reference Example 63 and using (2-chlorophenyl)hydrazine·hydrochloride (5 g, 28 mmol), water (100 mL), potassium carbonate (8.5 g, 62 mmol) and diethyl ethoxymethylenemalonate (7.3 g, 34 mmol) as starting materials, the title compound (5.8 g, 78%) was obtained as a white solid.

$^1$H-NMR (DMSO-$d_6$, 300 MHz) δ 1.28 (3H, t, J=7.0 Hz), 4.22 (2H, q, J=7.0 Hz), 7.48-7.60 (3H, m), 7.65-7.70 (1H, m), 7.81 (1H, s), 12.13 (1H, br s).

Reference Example 70

Production of ethyl 2-(2-chlorophenyl)-1-methyl-3-oxo-2,3-dihydro-1H-pyrazole-4-carboxylate

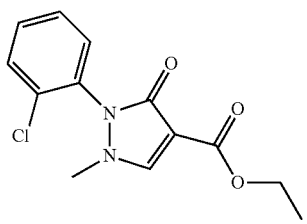 [SMILES: CCOC(=O)c1cn(C)n(-c2ccccc2Cl)c1=O]

In the same manner as in Reference Example 64 and using ethyl 2-(2-chlorophenyl)-3-oxo-2,3-dihydro-1H-pyrazole-4-carboxylate (3.4 g, 12 mmol) and methyl trifluoromethanesulfonate (3 mL) as starting materials, the title compound (2.8 g, 81%) was obtained as a white solid.

$^1$H-NMR (DMSO-$d_6$, 300 MHz) δ 1.23 (3H, t, J=7.1 Hz), 3.32 (3H, s), 4.15 (2H, q, J=7.1 Hz), 7.51-7.66 (3H, m), 7.70-7.75 (1H, m), 8.53 (1H, s).

Reference Example 71

Production of 2-(2-chlorophenyl)-1-methyl-3-oxo-2,3-dihydro-1H-pyrazole-4-carboxylic acid

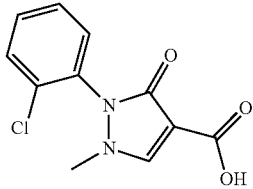 [SMILES: Cn1cc(C(=O)O)c(=O)n1-c1ccccc1Cl]

In the same manner as in Reference Example 65 and using ethyl 2-(2-chlorophenyl)-1-methyl-3-oxo-2,3-dihydro-1H-pyrazole-4-carboxylate (2.8 g, 9.9 mmol), tetrahydrofuran (6 mL), methanol (5 mL) and 4N aqueous sodium hydroxide solution (8 mL) as starting materials, the title compound (2.3 g, 91%) was obtained as a white solid.

$^1$H-NMR (DMSO-d$_6$, 300 MHz) δ 3.34 (3H, s), 7.52-7.68 (3H, m), 7.72-7.77 (1H, m), 8.53 (1H, s), 11.75 (1H, s).

Reference Example 72

Production of ethyl 2-(2,4-difluorophenyl)-3-oxo-2,3-dihydro-1H-pyrazole-4-carboxylate

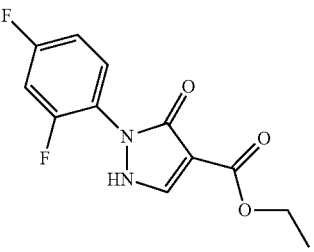 [SMILES: CCOC(=O)c1c[nH]n(-c2ccc(F)cc2F)c1=O]

In the same manner as in Reference Example 63 and using (2,4-difluorophenyl)hydrazine·hydrochloride (5.1 g, 28 mmol), water (100 mL), potassium carbonate (8.6 g, 62 mmol) and diethyl ethoxymethylenemalonate (7.4 g, 34 mmol) as starting materials, the title compound (5.0 g, 66%) was obtained as a pale-yellow solid.

$^1$H-NMR (DMSO-d$_6$, 300 MHz) δ 1.27 (3H, t, J=7.0 Hz), 4.22 (2H, q, J=7.0 Hz), 7.22-7.31 (1H, m), 7.49-7.66 (2H, m), 7.83 (1H, s), 12.26 (1H, br s).

Reference Example 73

Production of ethyl 2-(2,4-difluorophenyl)-1-methyl-3-oxo-2,3-dihydro-1H-pyrazole-4-carboxylate

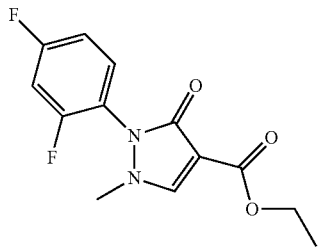 [SMILES: CCOC(=O)c1cn(C)n(-c2ccc(F)cc2F)c1=O]

In the same manner as in Reference Example 64 and using ethyl 2-(2,4-difluorophenyl)-3-oxo-2,3-dihydro-1H-pyrazole-4-carboxylate (3.6 g, 13 mmol) and methyl trifluoromethanesulfonate (3 mL) as starting materials, the title compound (2.4 g, 65%) was obtained as a white solid.

$^1$H-NMR (DMSO-d$_6$, 300 MHz) δ 1.23 (3H, t, J=7.1 Hz), 3.38 (3H, s), 4.09-4.20 (2H, m), 7.26-7.35 (1H, m), 7.54-7.70 (2H, m), 8.54 (1H, s).

Reference Example 74

Production of 2-(2,4-difluorophenyl)-1-methyl-3-oxo-2,3-dihydro-1H-pyrazole-4-carboxylic acid

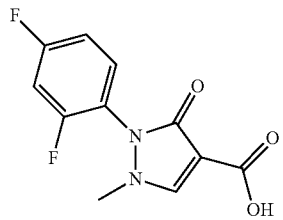

In the same manner as in Reference Example 65 and using ethyl 2-(2,4-difluorophenyl)-1-methyl-3-oxo-2,3-dihydro-1H-pyrazole-4-carboxylate (2.4 g, 8.7 mmol), tetrahydrofuran (6 mL), methanol (5 mL) and 4N aqueous sodium hydroxide solution (8 mL) as starting materials, the title compound (1.8 g, 83%) was obtained as a white solid.

$^1$H-NMR (DMSO-d$_6$, 300 MHz) δ 3.38 (3H, s), 7.26-7.37 (1H, m), 7.54-7.74 (2H, m), 8.53 (1H, s), 11.77 (1H, br s).

Reference Example 75

Production of ethyl 2-(2-methoxyphenyl)-3-oxo-2,3-dihydro-1H-pyrazole-4-carboxylate

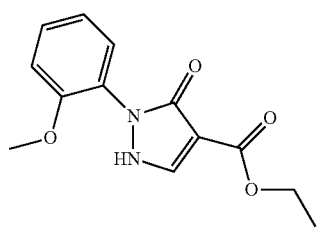 [SMILES: CCOC(=O)c1c[nH]n(-c2ccccc2OC)c1=O]

In the same manner as in Reference Example 63 and using (2-methoxyphenyl)hydrazine•hydrochloride (5.3 g, 30 mmol), water (100 mL), potassium carbonate (9.1 g, 66 mmol) and diethyl ethoxymethylenemalonate (7.8 g, 36 mmol) as starting materials, the title compound (6.1 g, 78%) was obtained as a white solid.

$^1$H-NMR (DMSO-$d_6$, 300 MHz) δ 1.27 (3H, t, J=7.0 Hz), 3.75 (3H, s), 4.21 (2H, q, J=7.0 Hz), 7.02-7.09 (1H, m), 7.20 (1H, dd, J=8.3, 1.1 Hz), 7.29 (1H, dd, J=7.7, 1.7 Hz), 7.44-7.52 (1H, m), 7.74 (1H, s), 11.56 (1H, br s).

Reference Example 76

Production of ethyl 2-(2-methoxyphenyl)-1-methyl-3-oxo-2,3-dihydro-1H-pyrazole-4-carboxylate

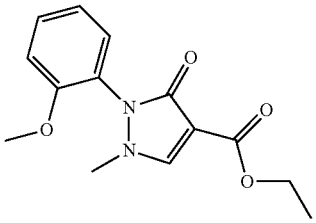 [SMILES: CCOC(=O)c1cn(C)n(-c2ccccc2OC)c1=O]

In the same manner as in Reference Example 64 and using ethyl 2-(2-methoxyphenyl)-3-oxo-2,3-dihydro-1H-pyrazole-4-carboxylate (3.6 g, 14 mmol) and methyl trifluoromethanesulfonate (3 mL) as starting materials, the title compound (2.5 g, 66%) was obtained as a pale-yellow solid.

$^1$H-NMR (DMSO-$d_6$, 300 MHz) δ 1.22 (3H, t, J=7.1 Hz), 3.28 (3H, s), 3.77 (3H, s), 4.08-4.18 (2H, m), 7.06-7.15 (1H, m), 7.23 (1H, dd, J=8.4, 1.0 Hz), 7.34 (1H, dd, J=7.7, 1.7 Hz), 7.49-7.58 (1H, m), 8.41 (1H, s).

Reference Example 77

Production of 2-(2-methoxyphenyl)-1-methyl-3-oxo-2,3-dihydro-1H-pyrazole-4-carboxylic acid

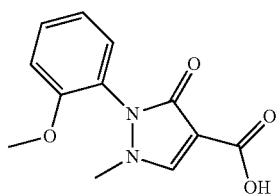 [SMILES: COc1ccccc1-n1c(=O)c(C(=O)O)cn1C]

In the same manner as in Reference Example 65 and using ethyl 2-(2-methoxyphenyl)-1-methyl-3-oxo-2,3-dihydro-1H-pyrazole-4-carboxylate (2.5 g, 9.2 mmol), tetrahydrofuran (6 mL), methanol (5 mL) and 4N aqueous sodium hydroxide solution (8 mL) as starting materials, the title compound (1.9 g, 85%) was obtained as a white solid.

$^1$H-NMR (DMSO-$d_6$, 300 MHz) δ 3.33 (3H, s), 3.79 (3H, s), 7.08-7.16 (1H, m), 7.26 (1H, dd, J=8.4, 1.0 Hz), 7.41 (1H, dd, J=7.7, 1.7 Hz), 7.53-7.62 (1H, m), 8.47 (1H, s), 11.79 (1H, s).

Reference Example 78

Production of ethyl 2-(2,6-dichlorophenyl)-3-oxo-2,3-dihydro-1H-pyrazole-4-carboxylate

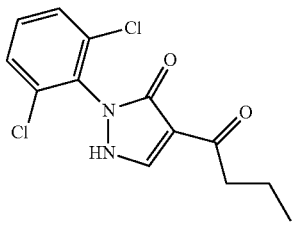 [SMILES: CCCC(=O)c1c[nH]n(-c2c(Cl)cccc2Cl)c1=O]

In the same manner as in Reference Example 63 and using (2,6-dichlorophenyl)hydrazine•hydrochloride (4.8 g, 23 mmol), water (100 mL), potassium carbonate (6.9 g, 50 mmol) and diethyl ethoxymethylenemalonate (5.9 g, 27 mmol) as starting materials, the title compound (5.0 g, 73%) was obtained as a pale-yellow solid.

$^1$H-NMR (DMSO-$d_6$, 300 MHz) δ 1.28 (3H, t, J=7.0 Hz), 4.22 (2H, q, J=7.0 Hz), 7.57-7.63 (1H, m), 7.68-7.73 (2H, m), 7.87 (1H, s), 12.37 (1H, br s).

Reference Example 79

Production of ethyl 2-(2,6-dichlorophenyl)-1-methyl-3-oxo-2,3-dihydro-1H-pyrazole-4-carboxylate

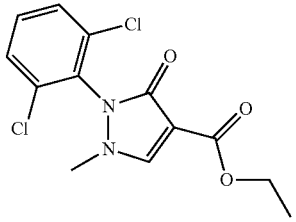 [SMILES: CCOC(=O)c1cn(C)n(-c2c(Cl)cccc2Cl)c1=O]

In the same manner as in Reference Example 64 and using ethyl 2-(2,6-dichlorophenyl)-3-oxo-2,3-dihydro-1H-pyrazole-4-carboxylate (3.7 g, 12 mmol) and methyl trifluoromethanesulfonate (3 mL) as starting materials, the title compound (3.4 g, 87%) was obtained as a pale-yellow solid.

$^1$H-NMR (DMSO-$d_6$, 300 MHz) δ 1.24 (3H, t, J=7.2 Hz), 3.35 (3H, s), 4.15 (2H, q, J=7.2 Hz), 7.63-7.70 (1H, m), 7.74-7.78 (2H, m), 8.59 (1H, s).

Reference Example 80

Production of 2-(2,6-dichlorophenyl)-1-methyl-3-oxo-2,3-dihydro-1H-pyrazole-4-carboxylic acid

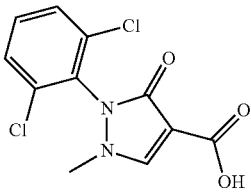 [SMILES: Cn1cc(C(=O)O)c(=O)n1-c1c(Cl)cccc1Cl]

In the same manner as in Reference Example 65 and using ethyl 2-(2,6-dichlorophenyl)-1-methyl-3-oxo-2,3-dihydro-1H-pyrazole-4-carboxylate (3.4 g, 11 mmol), tetrahydrofuran (6 mL), methanol (5 mL) and 4N aqueous sodium hydroxide solution (8 mL) as starting materials, the title compound (2.8 g, 90%) was obtained as a white solid.

$^1$H-NMR (DMSO-$d_6$, 300 MHz) δ 3.35 (3H, s), 7.63-7.71 (1H, m), 7.74-7.80 (2H, m), 8.57 (1H, s), 11.79 (1H, br s).

Reference Example 81

Production of ethyl 5-ethyl-2-(4-fluorophenyl)-3-oxo-2,3-dihydro-1H-pyrazole-4-carboxylate

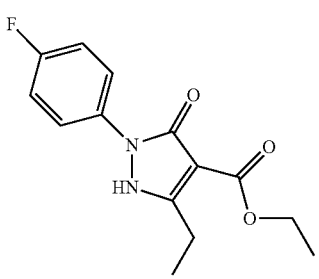 [SMILES: CCOC(=O)c1c(CC)[nH]n(-c2ccc(F)cc2)c1=O]

To a solution of (4-fluorophenyl)hydrazine (5.5 g, 43 mmol) in acetic acid (70 mL) was added diethylpropanoylpropanedionate (11 g, 52 mmol), and the mixture was stirred at 60° C. for 3.5 hr. The solvent was evaporated under reduced pressure, and hexane was added to the residue. The mixture was filtered to remove insoluble materials. The filtrate was concentrated under reduced pressure, and the residue was purified by silica gel column chromatography (ethyl acetate/hexane=10/90→50/50) to give the title compound (3.7 g, 31%) as a pale-yellow solid.

$^1$H-NMR (DMSO-$d_6$, 300 MHz) δ 1.19 (3H, t, J=7.6 Hz), 1.29 (3H, t, J=7.2 Hz), 2.74 (2H, q, J=7.6 Hz), 4.24 (2H, q, J=7.2 Hz), 7.26-7.40 (2H, m), 7.64-7.75 (2H, m).

Reference Example 82

Production of ethyl 5-ethyl-2-(4-fluorophenyl)-1-methyl-3-oxo-2,3-dihydro-1H-pyrazole-4-carboxylate

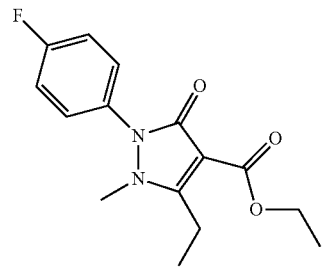 [SMILES: CCOC(=O)c1c(CC)n(C)n(-c2ccc(F)cc2)c1=O]

In the same manner as in Reference Example 64 and using ethyl 5-ethyl-2-(4-fluorophenyl)-3-oxo-2,3-dihydro-1H-pyrazole-4-carboxylate (3.1 g, 11 mmol) and methyl trifluoromethanesulfonate (3.7 mL) as starting materials, the title compound (1.9 g, 57%) was obtained as a pale-yellow solid.

$^1$H-NMR (DMSO-$d_6$, 300 MHz) δ 1.14-1.26 (6H, m), 2.99 (2H, q, J=7.6 Hz), 3.31 (3H, s), 4.15 (2H, q, J=7.1 Hz), 7.38 (4H, d, J=6.8 Hz).

Reference Example 83

Production of 5-ethyl-2-(4-fluorophenyl)-1-methyl-3-oxo-2,3-dihydro-1H-pyrazole-4-carboxylic acid

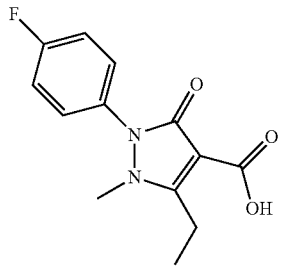 [SMILES: CCc1c(C(=O)O)c(=O)n(-c2ccc(F)cc2)n1C]

In the same manner as in Reference Example 65 and using ethyl 5-ethyl-2-(4-fluorophenyl)-1-methyl-3-oxo-2,3-dihydro-1H-pyrazole-4-carboxylate (1.9 g, 6.4 mmol), tetrahydrofuran (4 mL), methanol (4 mL) and 4N aqueous sodium hydroxide solution (5 mL) as starting materials, the title compound (1.5 g, 92%) was obtained as a white solid.

$^1$H-NMR (DMSO-$d_6$, 300 MHz) δ 1.20 (3H, t, J=7.6 Hz), 3.02 (2H, q, J=7.6 Hz), 3.39 (3H, s), 7.37-7.49 (2H, m), 7.49-7.59 (2H, m), 12.23 (1H, br s).

Reference Example 84

Production of 1-(3-bromobutyl)-3-(4-fluorophenyl)urea

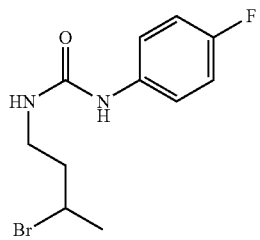 [SMILES: CC(Br)CCNC(=O)Nc1ccc(F)cc1]

To a solution of 3-bromobutane-1-aminehydrobromide (2270 mg, 9.7 mmol) in pyridine (18 mL) was slowly added 1-fluoro-4-isocyanatobenzene (1600 mg, 12 mmol) under ice-cooling, and the mixture was stirred at room temperature for 2 hr. The solvent was evaporated under reduced pressure, ethyl acetate/tetrahydrofuran and 0.5N aqueous hydrochloric acid solution were added to the residue, and the aqueous layer was extracted with ethyl acetate/tetrahydrofuran (×3). The combined organic layer was washed with saturated brine, dried over anhydrous magnesium sulfate and filtered. The filtrate was concentrated under reduced pressure, and the residue was washed with ethyl acetate/hexane (=1/1) to give the title compound (1750 mg, 62%) as a white solid.

$^1$H-NMR (DMSO-$d_6$, 300 MHz) δ 1.70 (3H, d, J=6.6 Hz), 1.89-2.01 (2H, m), 3.06-3.19 (1H, m), 3.22-3.32 (1H, m), 4.25-4.37 (1H, m), 6.23 (1H, t, J=5.8 Hz), 7.00-7.08 (2H, m), 7.35-7.42 (2H, m), 8.47 (1H, s).

Reference Example 85

Production of 1-(4-fluorophenyl)-6-methyltetrahydropyrimidin-2(1H)-one

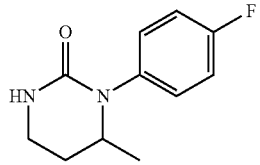

To a solution of 1-(3-bromobutyl)-3-(4-fluorophenyl)urea (1750 mg, 6.1 mmol) in N,N-dimethylformamide (30 mL) was added potassium tert-butoxide (920 mg, 7.0 mmol), and the mixture was stirred at 50° C. for 6 hr. The solvent was evaporated under reduced pressure, and ethyl acetate/tetrahydrofuran and 6N aqueous hydrochloric acid solution were added to the residue. The aqueous layer was extracted with ethyl acetate/tetrahydrofuran (×3). The combined organic layer was washed with water and saturated brine, dried over anhydrous magnesium sulfate and filtered. The filtrate was concentrated under reduced pressure, and the residue was purified by silica gel column chromatography (NH silica gel, ethyl acetate/hexane=50/50→100/0) to give the title compound (490 mg, 39%) as a white solid.

$^1$H-NMR (DMSO-$d_6$, 300 MHz) δ 1.02 (3H, d, J=6.4 Hz), 1.66-1.81 (1H, m), 1.96-2.13 (1H, m), 3.14-3.31 (2H, m), 3.85-3.96 (1H, m), 6.57 (1H, br s), 7.10-7.26 (4H, m).

Reference Example 86

Production of 2-(4-fluorophenyl)-N-(3-oxobutyl)acetamide

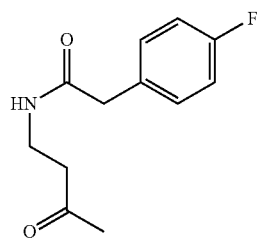

To a solution of 4-aminobutan-2-one hydrochloride (2.95 g, 24 mmol) in N,N-dimethylacetamide (50 mL) was slowly added (4-fluorophenyl)acetylchloride (4.90 g, 29 mmol) under ice-cooling, and the mixture was stirred at room temperature for 2 hr. Triethylamine (4.80 g, 48 mmol) was added to the mixture, and the mixture was stirred at room temperature for 17 hr. Ethyl acetate/tetrahydrofuran and saturated aqueous sodium hydrogen carbonate solution were added to the mixture, and the aqueous layer was extracted with ethyl acetate/tetrahydrofuran (×3). The combined organic layer was washed with water and saturated brine, dried over anhydrous magnesium sulfate and filtered. The filtrate was concentrated under reduced pressure, and the residue was purified by silica gel column chromatography (ethyl acetate/hexane=50/50→100/0) to give the title compound (2.10 g, 39%) as a white solid.

$^1$H-NMR (DMSO-$d_6$, 300 MHz) δ 2.07 (3H, s), 2.58 (2H, t, J=6.7 Hz), 3.17-3.25 (2H, m), 3.36 (2H, s), 7.05-7.16 (2H, m), 7.21-7.30 (2H, m), 8.04 (1H, br. s.).

Reference Example 87

Production of 3-(4-fluorophenyl)-4-methyl-5,6-dihydropyridin-2(1H)-one

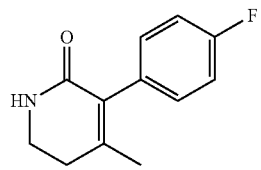

To a solution of 2-(4-fluorophenyl)-N-(3-oxobutyl)acetamide (1.95 g, 8.7 mmol) in ethanol (120 mL) was added 20 wt % sodium ethoxide/ethanol solution (6.54 g, 19 mmol), and the mixture was stirred at 80° C. for 8 hr. The solvent was evaporated under reduced pressure, ethyl acetate/tetrahydrofuran and 1N aqueous hydrochloric acid solution were added to the residue, and the aqueous layer was extracted with ethyl acetate/tetrahydrofuran (×3). The combined organic layer was washed with saturated brine, dried over anhydrous magnesium sulfate and filtered. The filtrate was concentrated under reduced pressure, and the residue was washed with ethyl acetate/hexane (1/10) to give the title compound (1.36 g, 76%) as a brown solid.

¹H-NMR (DMSO-d$_6$, 300 MHz) δ 1.73 (3H, s), 2.39 (2H, t, J=7.0 Hz), 3.28 (2H, td, J=7.0, 2.7 Hz), 7.14 (4H, d, J=7.6 Hz), 7.45 (1H, br s).

Reference Example 88

Production of 2-chloro-5-[(4-methoxybenzyl)oxy]pyridine

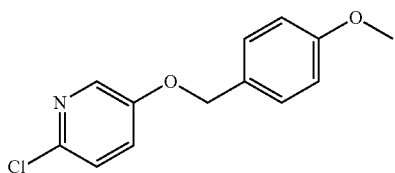 [SMILES: COc1ccc(COc2ccc(Cl)nc2)cc1]

To a solution of 2-chloro-5-hydroxypyridine (50 g, 0.386 mol) and potassium carbonate (80 g, 0.579 mol) in N,N-dimethylformamide (300 mL) was added p-methoxybenzyl chloride (66.5 g, 0.425 mol), and the mixture was stirred at 80° C. for 4 hr. Ethyl acetate and water were added to the reaction mixture, and the mixture was extracted 3 times with ethyl acetate. The organic layer was washed with water and saturated brine, dried over anhydrous magnesium sulfate and filtered. The solvent was evaporated under reduced pressure, and the obtained residue was washed with methanol to give the title compound (61.3 g, 64%) as a white solid.

¹H-NMR (DMSO-d$_6$, 300 MHz) δ 3.76 (3H, s), 5.10 (2H, s), 6.82-7.06 (2H, m), 7.34-7.46 (3H, m), 7.50-7.59 (1H, m), 8.17 (1H, d, J=2.6 Hz).

Reference Example 89

Production of 5-[(4-methoxybenzyl)oxy]pyridin-2-amine

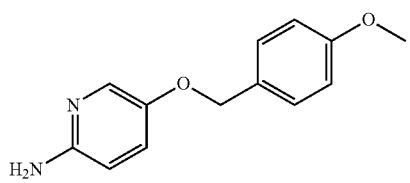

To a solution of 2-chloro-5-[(4-methoxybenzyl)oxy]pyridine (45 g, 180 mmol), tris(dibenzylideneacetone)dipalladium(0) (5 g, 5.46 mmol) and (2-biphenyl)dicyclohexylphosphine (5.1 g, 14.56 mmol) in tetrahydrofuran (500 mL) was added dropwise bis(trimethylsilyl)amidelithium (1.6 mol/L tetrahydrofuran solution, 170 mL, 273.2 mmol) at room temperature, and the mixture was stirred at 80° C. for 4 hr under a nitrogen atmosphere. 2N Hydrochloric acid (300 mL, 600 mmol) was added to the reaction mixture, and the mixture was stirred at room temperature for 1 hr. Ethyl acetate and saturated aqueous sodium hydrogen carbonate solution were added to the reaction mixture, and the mixture was extracted 3 times with ethyl acetate. The organic layer was washed with water and twice with saturated brine, dried over anhydrous magnesium sulfate and filtered. The solvent was evaporated under reduced pressure, and the obtained residue was washed with methanol to give the title compound (34.4 g, 82%) as a yellow solid.

¹H-NMR (DMSO-d$_6$, 300 MHz) δ 3.75 (3H, s), 4.90 (2H, s), 5.45 (2H, s), 6.40 (1H, d, J=8.9 Hz), 6.86-6.98 (2H, m), 7.14 (1H, dd, J=8.9, 3.0 Hz), 7.28-7.38 (2H, m), 7.67 (1H, d, J=2.6 Hz).

Reference Example 90

Production of N-{5-[(4-methoxybenzyl)oxy]pyridin-2-yl}-4-methylbenzenesulfonamide

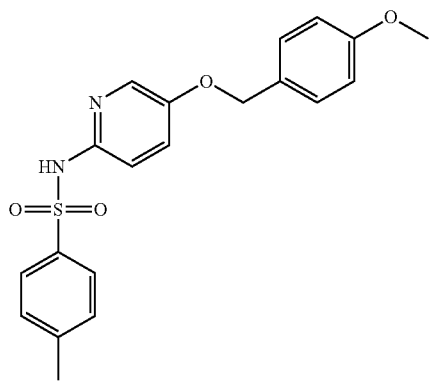 [SMILES: COc1ccc(COc2ccc(NS(=O)(=O)c3ccc(C)cc3)nc2)cc1]

To a solution of 5-[(4-methoxybenzyl)oxy]pyridin-2-amine (24 g, 104 mmol) in pyridine (210 mL) was added 4-methylbenzenesulfonyl chloride (20.9 g, 110 mmol) at 0° C., and the mixture was stirred at room temperature for 4 hr. The reaction mixture was concentrated, the residue was washed with saturated aqueous sodium hydrogen carbonate solution and ethyl acetate to give the title compound (37 g, 93%) as a pale-red solid.

¹H-NMR (DMSO-d$_6$, 300 MHz) δ 2.34 (3H, s), 3.75 (3H, s), 4.98 (2H, s), 6.82-7.00 (2H, m), 7.07 (1H, d, J=8.9 Hz), 7.26-7.46 (5H, m), 7.66-7.77 (2H, m), 7.91 (1H, d, J=2.6 Hz), 10.74 (1H, br s).

Reference Example 91

Production of 2-[5-[(4-methoxybenzyl)oxy]-2-{[(4-methylphenyl)sulfonyl]imino}pyridin-1(2H)-yl]acetamide

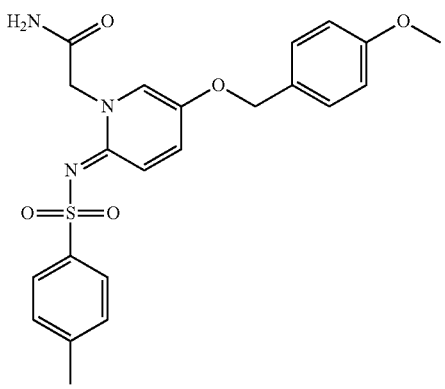 [SMILES: COc1ccc(COc2cc/c(=N\S(=O)(=O)c3ccc(C)cc3)n(CC(N)=O)c2)cc1]

To a suspension of N-{5-[(4-methoxybenzyl)oxy]pyridin-2-yl}-4-methylbenzenesulfonamide (10.0 g, 26.0 mmol) in N,N-dimethylformamide (85 mL) were added N,N-diisopropylethylamine (6.8 mL, 39.0 mmol) and iodoacetamide (5.77 g, 31.0 mmol), and the mixture was stirred at 60° C. for 5 hr. After cooling to room temperature, ethyl acetate and water were added, and the mixture was extracted 3 times with a mixed solution of ethyl acetate and tetrahydrofuran. The organic layer was washed with water and saturated brine, dried over anhydrous magnesium sulfate and filtered. The solvent was evaporated under reduced pressure. The obtained residue was washed with ethyl acetate and collected by filtration to give the title compound (34.4 g, 75%) as a white solid.

$^1$H-NMR (DMSO-$d_6$, 300 MHz) δ 2.33 (3H, s), 3.75 (3H, s), 4.82 (2H, s), 4.89 (2H, s), 6.81-7.03 (2H, m), 7.20-7.41 (6H, m), 7.60-7.69 (3H, m), 7.76 (1H, d), 7.92 (1H, d, J=3.0 Hz).

Reference Example 92

Production of 6-[(4-methoxybenzyl)oxy]imidazo[1,2-a]pyridin-2-amine

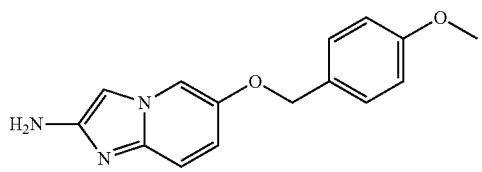 [SMILES: COc1ccc(COc2ccc3nc(N)cn3c2)cc1]

To a suspension of 2-[5-[(4-methoxybenzyl)oxy]-2-{[(4-methylphenyl)sulfonyl]imino}pyridin-1(2H)-yl]acetamide (20.8 g, 47.1 mmol) in tetrahydrofuran (200 mL) was added trifluoroacetic acid anhydride (49.5 g, 235.5 mmol) at 0° C., and the mixture was stirred for 1 hr. Methanol (100 mL) was added to the reaction mixture, 8N aqueous sodium hydroxide solution was added until pH reached 12 to 13, and the mixture was stirred at room temperature for 3 hr. Water and ethyl acetate were added to the reaction mixture, and the mixture was extracted 4 times with ethyl acetate. The organic layer was washed with saturated brine, dried over anhydrous magnesium sulfate and filtered. The solvent was evaporated under reduced pressure. The obtained residue was washed with ethyl acetate and collected by filtration to give the title compound (8.6 g, 68%) as a brown solid.

$^1$H-NMR (DMSO-$d_6$, 300 MHz) δ 3.76 (3H, s), 4.90 (2H, s), 4.93 (2H, s), 6.81 (1H, dd, J=9.5, 2.4 Hz), 6.88-7.00 (3H, m), 7.08 (1H, d, J=9.6 Hz), 7.32-7.44 (2H, m), 8.12 (1H, d, J=1.7 Hz).

Reference Example 93

Production of N-{6-[(4-methoxybenzyl)oxy]imidazo[1,2-a]pyridin-2-yl}cyclopropanecarboxamide

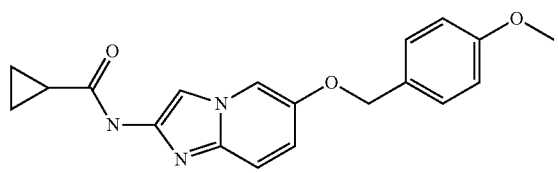 [SMILES: COc1ccc(COc2ccc3nc(NC(=O)C4CC4)cn3c2)cc1]

To a solution of 6-[(4-methoxybenzyl)oxy]imidazo[1,2-a]pyridin-2-amine (8.5 g, 31.6 mmol) in N,N-dimethylacetamide (80 mL) was added a solution of cyclopropanecarbonyl chloride (3.43 mL, 37.9 mmol) in N,N-dimethylacetamide (20 mL) at 0° C., and the mixture was stirred at 0° C. for 3 hr. The reaction mixture was diluted with water, and the precipitate was collected by filtration and washed with water and ethyl acetate to give the title compound (8.9 g, 83%) as a gray solid.

$^1$H-NMR (DMSO-$d_6$, 300 MHz) δ 0.62-0.89 (4H, m), 1.87-1.96 (1H, m), 3.76 (3H, s), 4.96 (2H, s), 6.89-6.99 (2H, m), 7.02 (1H, dd, J=9.6, 2.3 Hz), 7.32 (1H, d, J=9.6 Hz), 7.37-7.45 (2H, m), 7.96 (1H, s), 8.36 (1H, d, J=1.7 Hz), 10.88 (1H, s).

Reference Example 94

Production of N-(6-hydroxyimidazo[1,2-a]pyridin-2-yl)cyclopropanecarboxamide

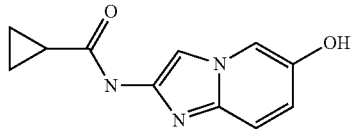 [SMILES: O=C(Nc1cn2cc(O)ccc2n1)C1CC1]

To a solution of N-{6-[(4-methoxybenzyl)oxy]imidazo[1,2-a]pyridin-2-yl}cyclopropanecarboxamide (10.1 g, 29.9 mmol) and anisole (25.97 mL, 239.2 mmol) in trifluoromethylbenzene (200 mL) was added trifluoroacetic acid (40.4 mL), and the mixture was stirred at room temperature for 3 hr. Saturated aqueous sodium hydrogen carbonate solution was added to the reaction mixture, and the mixture was extracted 5 times with ethyl acetate. The organic layer was washed with saturated brine, dried over anhydrous magnesium sulfate and filtered. The solvent was evaporated under reduced pressure. The obtained residue was washed with ethyl acetate and collected by filtration to give the title compound (5.7 g, 88%) as a pale-brown solid.

$^1$H-NMR (DMSO-$d_6$, 300 MHz) δ 0.67-0.86 (4H, m), 1.83-1.97 (1H, m), 6.89 (1H, dd, J=9.6, 2.3 Hz), 7.25 (1H, d, J=9.4 Hz), 7.91 (1H, s), 7.96-8.00 (1H, m), 9.43 (1H, br s), 10.81 (1H, s).

Reference Example 95

Production of 2-[5-[(4-methoxybenzyl)oxy]-2-{[(4-methylphenyl)sulfonyl]imino}pyridin-1(2H)-yl]propanamide

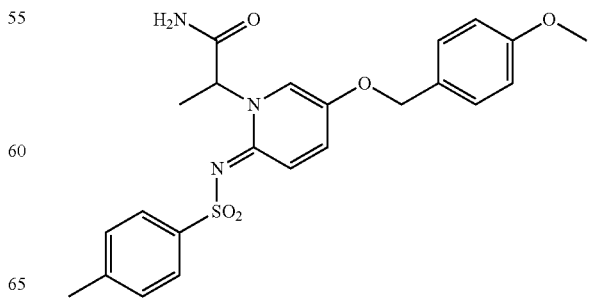

To a solution of N-{5-[(4-methoxybenzyl)oxy]pyridin-2-yl}-4-methylbenzenesulfonamide (3 g, 7.80 mmol) in N,N-dimethylformamide (30 mL) were added 2-bromopropanamide (2.82 g, 18.4 mmol) and N,N-diisopropylethylamine (4.04 mL, 23.4 mmol), and the mixture was stirred at room temperature for 2 days. Ethyl acetate and water were added to the reaction mixture, and the mixture was extracted 3 times with ethyl acetate. The organic layer was washed with saturated brine, dried over anhydrous magnesium sulfate and filtered. The solvent was evaporated under reduced pressure. The obtained residue was purified by silica gel column chromatography (ethyl acetate/hexane=3/1→ethyl acetate alone) to give the title compound (2.64 g, 74%) as a colorless oil.

$^1$H-NMR (DMSO-d$_6$, 300 MHz) δ 1.65 (3H, d, J=7.4 Hz), 2.33 (3H, s), 3.75 (3H, s), 4.83-5.12 (2H, m), 5.80 (1H, q, J=7.2 Hz), 6.86-6.98 (2H, m), 7.19-7.47 (6H, m), 7.59-7.83 (5H, m).

Reference Example 96

Production of 6-[(4-methoxybenzyl)oxy]-3-methylimidazo[1,2-a]pyridin-2-amine

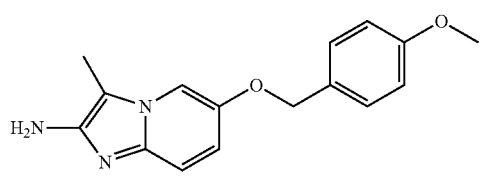 [SMILES: COc1ccc(COc2ccc3nc(N)c(C)n3c2)cc1]

To a suspension of 2-[5-[(4-methoxybenzyl)oxy]-2-{[(4-methylphenyl)sulfonyl]imino}pyridin-1(2H)-yl]propanamide (2.6 g, 5.71 mmol) in tetrahydrofuran (25 mL) was added trifluoroacetic acid anhydride (2.35 mL, 17.1 mmol) at 0° C., and the mixture was stirred at room temperature for 1 hr. 8N Aqueous sodium hydroxide solution was added to the reaction mixture until it reached pH 12 to 13, and the mixture was stirred at 50° C. for 5 hr. Water and ethyl acetate were added to the reaction mixture, and the mixture was extracted 3 times with ethyl acetate. The organic layer was washed with saturated brine, dried over anhydrous magnesium sulfate and filtered. The solvent was evaporated under reduced pressure. The obtained residue was washed with ethyl acetate and collected by filtration to give the title compound (1.0 g, 68%) as a white solid.

$^1$H-NMR (DMSO-d$_6$, 300 MHz) δ 2.26 (3H, s), 3.76 (3H, s), 4.81 (2H, s), 5.01 (2H, s), 6.80 (1H, dd, J=9.4, 2.3 Hz), 6.91-6.99 (2H, m), 7.09 (1H, d, J=9.4 Hz), 7.31-7.48 (2H, m), 7.67 (1H, d, J=2.1 Hz).

Reference Example 97

Production of N-{6-[(4-methoxybenzyl)oxy]-3-methylimidazo[1,2-a]pyridin-2-yl}cyclopropanecarboxamide

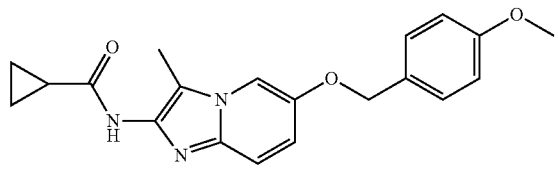 [SMILES: COc1ccc(COc2ccc3nc(NC(=O)C4CC4)c(C)n3c2)cc1]

To a solution of 6-[(4-methoxybenzyl)oxy]-3-methylimidazo[1,2-a]pyridin-2-amine (1.0 g, 3.53 mmol) in N,N-dimethylacetamide (10 mL) was added cyclopropanecarbonyl chloride (352 µL, 3.88 mmol), and the mixture was stirred at 0° C. for 2 hr. Ethyl acetate and saturated aqueous sodium hydrogen carbonate solution were added to the reaction mixture, and the mixture was extracted 3 times with ethyl acetate. The organic layer was washed with saturated brine, dried over anhydrous magnesium sulfate and filtered. The solvent was evaporated under reduced pressure. The obtained residue was washed with ethyl acetate and collected by filtration to give the title compound (750 mg, 60%) as a slightly-yellow solid.

$^1$H-NMR (DMSO-d$_6$, 300 MHz) δ 0.64-0.93 (4H, m), 1.80-1.89 (1H, m), 2.28 (3H, s), 3.76 (3H, s), 5.06 (2H, s), 6.91-7.08 (3H, m), 7.34-7.48 (3H, m), 7.91 (1H, d, J=1.9 Hz), 10.12 (1H, s).

Reference Example 98

Production of N-(6-hydroxy-3-methylimidazo[1,2-a]pyridin-2-yl)cyclopropanecarboxamide

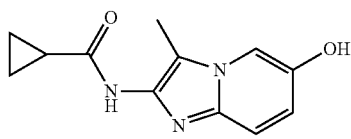 [SMILES: Cc1c(NC(=O)C2CC2)nc2ccc(O)cn12]

To a solution of N-{6-[(4-methoxybenzyl)oxy]-3-methylimidazo[1,2-a]pyridin-2-yl}cyclopropanecarboxamide (700 mg, 1.99 mmol) and anisole (1.73 mL, 15.9 mmol) in trifluoromethylbenzene (7 mL) was added trifluoroacetic acid (1.4 mL), and the mixture was stirred at room temperature for 2 hr. Saturated aqueous sodium hydrogen carbonate solution was added to the reaction mixture, and the mixture was extracted 4 times with ethyl acetate. The organic layer was washed with saturated brine, dried over anhydrous magnesium sulfate and filtered. The solvent was evaporated under reduced pressure. The obtained residue was washed with ethyl acetate to give the title compound (65 mg, 14%) as a slightly-yellow solid.

$^1$H-NMR (DMSO-d$_6$, 300 MHz) δ 0.70-0.82 (4H, m), 1.73-1.90 (1H, m), 2.21 (3H, s), 6.87-6.98 (1H, m), 7.32 (1H, d, J=9.6 Hz), 7.58 (1H, d, J=1.9 Hz), 9.51 (1H, br s), 10.06 (1H, s).

Reference Example 99

Production of N-[6-(2-fluoro-4-nitrophenoxy)-3-methylimidazo[1,2-a]pyridin-2-yl]cyclopropanecarboxamide

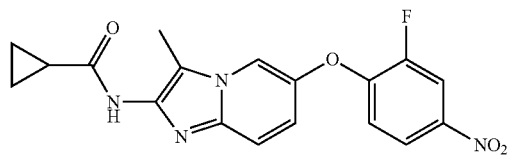

To a solution of N-(6-hydroxy-3-methylimidazo[1,2-a]pyridin-2-yl)cyclopropanecarboxamide (65 mg, 0.281 mmol) and 1,2-difluoro-4-nitrobenzene (37 μL, 0.337 mmol) in dimethyl sulfoxide (1 mL) was added cesium carbonate (137 mg, 0.422 mmol), and the mixture was stirred overnight at room temperature. Ethyl acetate and saturated aqueous ammonium chloride solution were added to the reaction mixture, and the mixture was extracted 3 times with ethyl acetate. The organic layer was washed with saturated brine, dried over anhydrous magnesium sulfate and filtered. The solvent was evaporated under reduced pressure. The obtained residue was purified by silica gel column chromatography (ethyl acetate/hexane=1/1→ethyl acetate alone) to give the title compound (80 mg, 77%) as a white solid.

$^1$H-NMR (DMSO-$d_6$, 300 MHz) δ 0.68-0.91 (4H, m), 1.76-1.92 (1H, m), 2.29 (3H, s), 7.12-7.28 (2H, m), 7.60 (1H, d, J=9.4 Hz), 7.96-8.11 (1H, m), 8.37 (1H, dd, J=10.9, 2.7 Hz), 8.53 (1H, d, J=1.9 Hz), 10.27 (1H, br s).

Reference Example 100

Production of N-[6-(4-amino-2-fluorophenoxy)-3-methylimidazo[1,2-a]pyridin-2-yl]cyclopropanecarboxamide

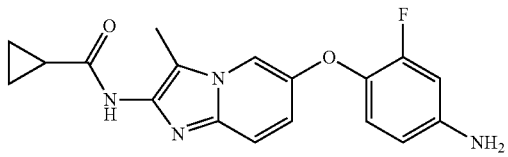 [SMILES: Cc1c(NC(=O)C2CC2)nc2ccc(Oc3ccc([N+](=O)[O-])cc3F)cn12]

A mixed solution of N-[6-(2-fluoro-4-nitrophenoxy)-3-methylimidazo[1,2-a]pyridin-2-yl]cyclopropanecarboxamide (80 mg, 0.216 mmol), reduced iron (64 mg, 1.08 mmol) and ammonium chloride (116 mg, 2.16 mmol) in ethanol (2 mL)/water (0.5 mL) was stirred at 80° C. for 3 hr. The reaction mixture was diluted with ethyl acetate and filtered through celite. Water was added to the filtrate, and the mixture was extracted 3 times with ethyl acetate. The organic layer was washed with saturated brine, dried over anhydrous magnesium sulfate and filtered. The solvent was evaporated under reduced pressure to give the title compound (60 mg, 82%) as a slightly yellow solid.

$^1$H-NMR (DMSO-$d_6$, 300 MHz) δ 0.77 (4H, d, J=5.9 Hz), 1.80-1.91 (1H, m), 2.22 (3H, s), 5.33 (2H, s), 6.33-6.42 (1H, m), 6.49 (1H, dd, J=13.4, 2.6 Hz), 6.88-7.04 (2H, m), 7.45 (1H, d, J=9.8 Hz), 7.85 (1H, d, J=2.1 Hz), 10.17 (1H, br s).

Reference Example 101

Production of N-[6-(3-methyl-4-nitrophenoxy)imidazo[1,2-a]pyridin-2-yl]cyclopropanecarboxamide

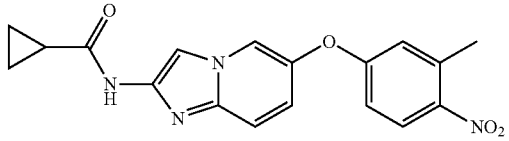 [SMILES: Cc1cc(Oc2ccc3nc(NC(=O)C4CC4)cn3c2)ccc1[N+](=O)[O-]]

To a solution of N-(6-hydroxyimidazo[1,2-a]pyridin-2-yl)cyclopropanecarboxamide (200 mg, 0.92 mmol) and 4-fluoro-2-methyl-1-nitrobenzene (171.3 mg, 1.1 mmol) in dimethyl sulfoxide (2 mL) was added cesium carbonate (450 mg, 1.38 mmol), and the mixture was stirred at room temperature for 6 hr. Ethyl acetate and saturated aqueous ammonium chloride solution were added to the reaction mixture, and the mixture was extracted 3 times with ethyl acetate. The organic layer was washed with saturated brine, dried over anhydrous magnesium sulfate and filtered. The solvent was evaporated under reduced pressure. The residue was washed with ethyl acetate and collected by filtration to give the title compound (232 mg, 72%) as a brown solid.

$^1$H-NMR (DMSO-$d_6$, 300 MHz) δ 0.74-0.88 (4H, m), 1.88-1.97 (1H, m), 2.52 (3H, s), 7.03 (1H, dd, J=9.1, 2.8 Hz), 7.09-7.18 (2H, m), 7.52 (1H, d, J=9.4 Hz), 7.99-8.16 (2H, m), 8.68 (1H, dd, J=2.5, 0.8 Hz), 11.02 (1H, s).

Reference Example 102

Production of N-[6-(4-amino-2-chlorophenoxy)imidazo[1,2-a]pyridin-2-yl]cyclopropanecarboxamide

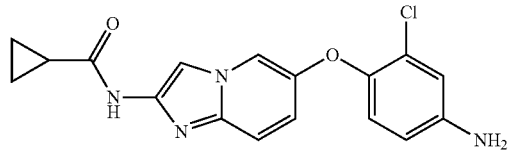 [SMILES: Nc1ccc(Oc2ccc3nc(NC(=O)C4CC4)cn3c2)c(Cl)c1]

To a solution of N-(6-hydroxyimidazo[1,2-a]pyridin-2-yl)cyclopropanecarboxamide (200 mg, 0.921 mmol) and 4-fluoro-3-chloro-1-nitrobenzene (193 mg, 1.11 mmol) in dimethyl sulfoxide (2 mL) was added cesium carbonate (450 mg, 1.38 mmol), and the mixture was stirred at room temperature for 6 hr. Ethyl acetate and saturated aqueous ammonium chloride solution were added to the reaction mixture, and the mixture was extracted 3 times with ethyl acetate. The organic layer was washed with saturated brine, and the solvent was evaporated under reduced pressure. A mixed solution of the obtained residue, reduced iron (271 mg, 4.61 mmol) and ammonium chloride (493 mg, 9.21 mmol) in ethanol (2 mL)/tetrahydrofuran (2 mL)/water (1 mL) was stirred at 80° C. for 7 hr. The reaction mixture was diluted with ethyl acetate and tetrahydrofuran, and filtered through celite. Water was added to the filtrate, and the mixture was extracted twice with ethyl acetate. The organic layer was washed with saturated brine, dried over anhydrous magnesium sulfate and filtered. The solvent was evaporated under reduced pressure. The obtained residue was purified by silica gel column chromatography (ethyl acetate/hexane=2/1→ethyl acetate alone) to give the title compound (177.5 mg, 56%) as a white solid.

$^1$H-NMR (DMSO-$d_6$, 300 MHz) δ 0.67-0.89 (4H, m), 1.82-1.96 (1H, m), 5.33 (2H, s), 6.54 (1H, dd, J=8.7, 2.6 Hz), 6.72 (1H, d, J=2.6 Hz), 6.93 (1H, d, J=8.7 Hz), 6.99 (1H, dd, J=9.6, 2.5 Hz), 7.38 (1H, d, J=9.6 Hz), 8.00 (1H, s), 8.17 (1H, d, J=1.9 Hz), 10.89 (1H, s).

Reference Example 103

Production of N-{6-[(5-nitropyridin-2-yl)oxy]imidazo[1,2-a]pyridin-2-yl}cyclopropanecarboxamide

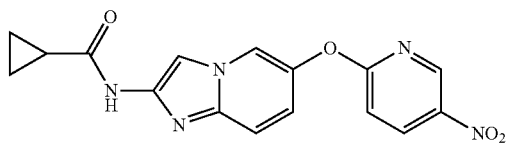 [SMILES: O=C(Nc1cn2cc(Oc3ccc([N+](=O)[O-])cn3)ccc2n1)C1CC1]

To a solution of N-(6-hydroxyimidazo[1,2-a]pyridin-2-yl)cyclopropanecarboxamide (200 mg, 0.921 mmol) and 2-chloro-5-nitropyridine (175 mg, 1.1 mmol) in dimethyl sulfoxide (3 mL) was added cesium carbonate (450 mg, 1.38 mmol), and the mixture was stirred at room temperature for 3 hr. Ethyl acetate, tetrahydrofuran and water were added to the reaction mixture, and the mixture was extracted 3 times with ethyl acetate. The organic layer was washed with saturated brine, dried over anhydrous magnesium sulfate and filtered. The solvent was evaporated under reduced pressure. The obtained residue was washed with ethyl acetate and collected by filtration to give the title compound (111 mg, 36%) as a brown solid.

$^1$H-NMR (DMSO-$d_6$, 300 MHz) δ 0.67-0.91 (4H, m), 1.90-1.98 (1H, m), 7.19 (1H, dd, J=9.6, 2.3 Hz), 7.37 (1H, d, J=9.1 Hz), 7.50 (1H, d, J=9.6 Hz), 8.08 (1H, s), 8.65 (1H, dd, J=9.1, 2.8 Hz), 8.69-8.74 (1H, m), 9.05 (1H, d, J=2.3 Hz), 11.02 (1H, s).

Reference Example 104

Production of N-{6-[(6-nitropyridin-3-yl)oxy]imidazo[1,2-a]pyridin-2-yl}cyclopropanecarboxamide

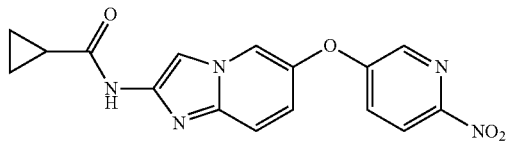 [SMILES: O=C(Nc1cn2cc(Oc3ccc([N+](=O)[O-])nc3)ccc2n1)C1CC1]

Using N-(6-hydroxyimidazo[1,2-a]pyridin-2-yl)cyclopropanecarboxamide (200 mg, 0.921 mmol), 5-chloro-2-nitropyridine (218.8 mg, 1.38 mmol), dimethyl sulfoxide (5 mL) and cesium carbonate (450 mg, 1.38 mmol), and in the same manner as in the production method of N-[6-(3-methyl-4-nitrophenoxy)imidazo[1,2-a]pyridin-2-yl]cyclopropanecarboxamide (Reference Example 101), the title compound (190 mg, 61%) was obtained as a yellow solid.

$^1$H-NMR (DMSO-$d_6$, 300 MHz) δ 0.70-0.88 (4H, m), 1.88-1.98 (1H, m), 7.22 (1H, dd, J=9.6, 2.3 Hz), 7.55 (1H, d, J=9.6 Hz), 7.74 (1H, dd, J=9.0, 2.9 Hz), 8.09 (1H, s), 8.33 (1H, d, J=9.4 Hz), 8.50 (1H, d, J=2.5 Hz), 8.76 (1H, dd, J=2.5, 0.8 Hz), 11.02 (1H, s).

Reference Example 105

Production of N-{6-[(6-aminopyridin-3-yl)oxy]imidazo[1,2-a]pyridin-2-yl}cyclopropanecarboxamide

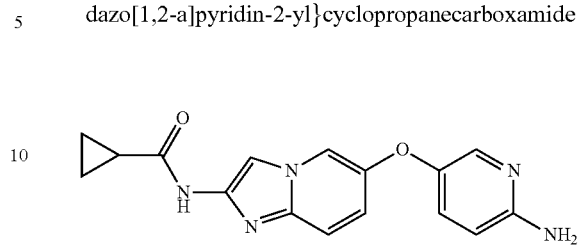

A mixed solution of N-{6-[(6-nitropyridin-3-yl)oxy]imidazo[1,2-a]pyridin-2-yl}cyclopropanecarboxamide (184 mg, 0.542 mmol), reduced iron (173 mg, 2.95 mmol) and ammonium chloride (315 mg, 5.89 mmol) in ethanol (2 mL) and water (0.5 mL) was stirred at 80° C. for 1 hr. The reaction mixture was diluted with ethyl acetate, and filtered through celite. Water was added to the filtrate, and the mixture was extracted twice with ethyl acetate. The organic layer was washed with saturated brine, dried over anhydrous magnesium sulfate and filtered. The solvent was evaporated under reduced pressure. The obtained residue was purified by silica gel column chromatography (ethyl acetate→ethyl acetate/methanol=95/5) to give the title compound (75 mg, 45%) as a yellow solid.

$^1$H-NMR (DMSO-$d_6$, 300 MHz) δ 0.70-0.87 (4H, m), 1.84-1.94 (1H, m), 5.87 (2H, s), 6.48 (1H, d, J=8.9 Hz), 7.04 (1H, dd, J=9.6, 2.5 Hz), 7.24 (1H, dd, J=8.9, 3.0 Hz), 7.39 (1H, d, J=9.6 Hz), 7.79 (1H, d, J=2.5 Hz), 8.00 (1H, s), 8.29 (1H, dd, J=2.5, 0.8 Hz), 10.91 (1H, s).

Reference Example 106

N-[6-(4-amino-2-methylphenoxy)imidazo[1,2-a]pyridin-2-yl]cyclopropanecarboxamide

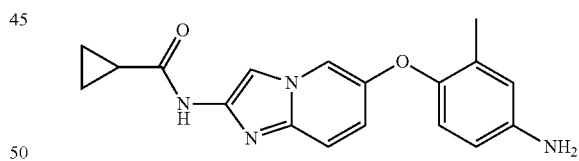

To a solution of N-(6-hydroxyimidazo[1,2-a]pyridin-2-yl)cyclopropanecarboxamide (300 mg, 1.38 mmol) and 4-fluoro-3-methyl-1-nitrobenzene (279 mg, 1.80 mmol) in dimethyl sulfoxide (3 mL) was added cesium carbonate (67.4 mg, 2.07 mmol), and the mixture was stirred at room temperature for 24 hr. Ethyl acetate, tetrahydrofuran and water were added to the reaction mixture, and the mixture was extracted 3 times with ethyl acetate. The organic layer was washed with saturated brine, and the solvent was evaporated under reduced pressure. The obtained residue was washed with ethyl acetate and collected by filtration. A mixed solution of the obtained solid, reduced iron (406 mg, 6.9 mmol) and ammonium chloride (738 mg, 13.8 mmol) in ethanol (5 mL)/tetrahydrofuran (3 mL)/water (2 mL) was stirred at 80° C. for 6 hr. The reaction mixture was diluted with ethyl acetate and tetrahydrofuran, and filtered through celite. Water was added to the filtrate, and the mixture was extracted twice with ethyl acetate. The organic layer was washed with saturated brine, dried over anhydrous magnesium sulfate and filtered. The solvent was evaporated under reduced pressure. The obtained residue was purified by silica gel column chromatography (ethyl acetate/hexane=2/1→ethyl acetate alone) to give the title compound (190 mg, 43%) as a white solid.

$^1$H-NMR (DMSO-d$_6$, 300 MHz) δ 0.60-0.92 (4H, m), 1.79-1.93 (1H, m), 2.06 (3H, s), 4.93 (2H, s), 6.35-6.44 (1H, m), 6.48 (1H, d, J=2.3 Hz), 6.69 (1H, d, J=8.5 Hz), 6.97 (1H, dd, J=9.6, 2.3 Hz), 7.36 (1H, d, J=9.6 Hz), 7.97 (1H, s), 8.03-8.06 (1H, m), 10.87 (1H, s).

Reference Example 107

Production of N-[6-(3-chloro-4-nitrophenoxy)imidazo[1,2-a]pyridin-2-yl]cyclopropanecarboxamide

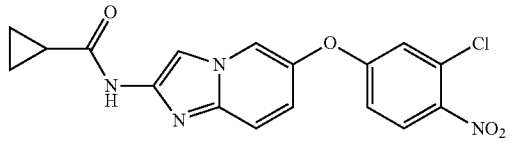

Using N-(6-hydroxyimidazo[1,2-a]pyridin-2-yl)cyclopropanecarboxamide (200 mg, 0.92 mmol), 4-fluoro-2-chloro-1-nitrobenzene (315 mg, 1.79 mmol), dimethyl sulfoxide (4 mL) and cesium carbonate (675 mg, 2.07 mmol), and in the same manner as in Reference Example 101, the title compound (382 mg, 74%) was obtained as a yellow solid.

$^1$H-NMR (DMSO-d$_6$, 300 MHz) δ 0.68-0.92 (4H, m), 1.88-1.97 (1H, m), 7.13-7.24 (2H, m), 7.44 (1H, d, J=2.6 Hz), 7.53 (1H, d), 8.04-8.20 (2H, m), 8.64-8.81 (1H, m), 11.02 (1H, s).

Reference Example 108

Production of N-[6-(4-amino-3-chlorophenoxy)imidazo[1,2-a]pyridin-2-yl]cyclopropanecarboxamide

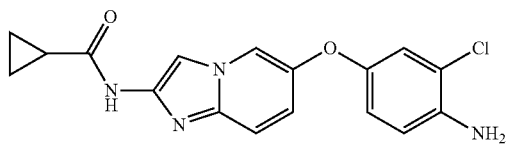

Using N-[6-(3-chloro-4-nitrophenoxy)imidazo[1,2-a]pyridin-2-yl]cyclopropanecarboxamide (300 mg, 0.805 mmol), reduced iron (237 mg, 4.02 mmol), ammonium chloride (430 mg, 8.05 mmol), ethanol (2 mL), tetrahydrofuran (2 mL) and water (0.5 mL), and in the same manner as in Reference Example 105, the title compound (166 mg, 60%) was obtained as a white solid.

$^1$H-NMR (DMSO-d$_6$, 300 MHz) δ 0.58-0.94 (4H, m), 1.85-1.97 (1H, m), 5.20 (2H, s), 6.73-6.91 (2H, m), 6.96-7.06 (2H, m), 7.40 (1H, d, J=9.6 Hz), 8.01 (1H, s), 8.34 (1H, d, J=1.5 Hz), 10.91 (1H, s).

Reference Example 109

Production of ethyl 1-(4-fluorophenyl)-5-methyl-2-oxo-1,2-dihydropyridine-3-carboxylate

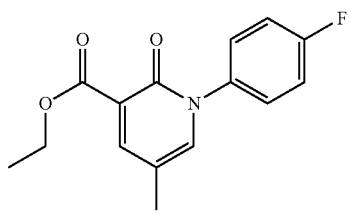 [SMILES: CCOC(=O)c1cc(C)cn(-c2ccc(F)cc2)c1=O]

To a solution (30 mL) of diethyl [(2E)-3-ethoxy-2-methylprop-2-en-1-ylidene]propanedionate (160 mg, 0.467 mmol) and piperidine (0.2 mL) in ethanol was added 4-fluoroaniline (1.12 mL, 11.7 mmol) was added, and the mixture was stirred at 80° C. for 17 hr. The reaction mixture was concentrated, and the obtained residue was purified by silica gel column chromatography (ethyl acetate/hexane=1/2-31/1) to give a brown solid. The brown solid was washed with diethyl ether and collected by filtration to give the title compound (1.2 g, 37%) as a white solid.

$^1$H-NMR (DMSO-d$_6$, 300 MHz) δ 1.25 (3H, t, J=7.1 Hz), 2.09 (3H, s), 4.21 (2H, q, J=7.2 Hz), 7.26-7.41 (2H, m), 7.43-7.54 (2H, m), 7.76 (1H, dd, J=2.6, 0.9 Hz), 7.98 (1H, d, J=2.6 Hz).

Reference Example 110

Production of 1-(4-fluorophenyl)-5-methyl-2-oxo-1,2-dihydropyridine-3-carboxylic acid

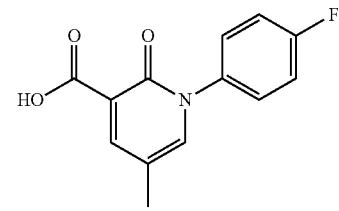 [SMILES: Cc1cc(C(=O)O)c(=O)n(-c2ccc(F)cc2)c1]

To a solution of ethyl 1-(4-fluorophenyl)-5-methyl-2-oxo-1,2-dihydropyridine-3-carboxylate (1.2 g, 4.36 mmol) in methanol (12 mL) was added 1N aqueous sodium hydroxide solution (10 mL, 10 mmol), and the mixture was stirred at room temperature for 2 hr. The reaction mixture was concentrated, and the obtained residue was diluted with ethyl acetate and water and extracted with water. The aqueous layer was treated with 1N hydrochloric acid (20 mL, 20 mmol), and the precipitate was collected by filtration to give a white solid. The white solid was washed with water to give the title compound (730 mg, 68%).

$^1$H-NMR (DMSO-$d_6$, 300 MHz) δ 2.20 (3H, s), 7.31-7.52 (2H, m), 7.55-7.67 (2H, m), 8.07 (1H, dd, J=2.6, 0.9 Hz), 8.39 (1H, d, J=2.5 Hz), 14.48 (1H, br s).

Reference Example 111

Production of 1-(2,4-difluorophenyl)-6-methyl-2-oxo-1,2-dihydropyridine-3-carbonitrile

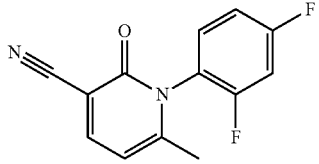 [SMILES: Cc1ccc(C#N)c(=O)n1-c1ccc(F)cc1F]

To a solution of 2-cyano-N-(2,4-difluorophenyl)acetamide (5.5 g, 28 mmol) and (3E)-4-methoxybut-3-en-2-one (3.65 g, 36.5 mmol) in dimethyleneglycol monomethylether (50 mL) was added 1,4-diazabicyclo[2.2.2]octane (3.14 g, 28 mmol), and the mixture was stirred at 120° C. for 12 hr. The reaction mixture was diluted with 2N hydrochloric acid, tetrahydrofuran and ethyl acetate, and extracted 3 times with ethyl acetate. The organic layer was washed with saturated brine, dried over anhydrous magnesium sulfate and filtered. The solvent was evaporated under reduced pressure. The obtained residue was washed with ethyl acetate to give a slightly yellow solid. The slightly yellow solid was suspended in tetrahydrofuran at 80° C., and the suspension was stirred for 30 min. The suspension was filtrated, and the obtained solid was washed with tetrahydrofuran to give the title compound (650 mg, 9.4%) as a white solid.

$^1$H-NMR (DMSO-$d_6$, 300 MHz) δ 2.07 (3H, s), 6.38-6.75 (1H, m), 7.17-7.39 (1H, m), 7.53-7.74 (2H, m), 8.05-8.39 (1H, m).

Reference Example 112

Production of 1-(2,4-difluorophenyl)-6-methyl-2-oxo-1,2-dihydropyridine-3-carboxylic acid

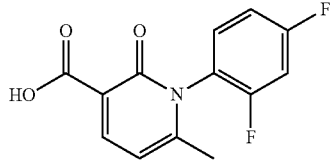 [SMILES: Cc1ccc(C(=O)O)c(=O)n1-c1ccc(F)cc1F]

A solution of 1-(2,4-difluorophenyl)-6-methyl-2-oxo-1,2-dihydropyridine-3-carbonitrile (600 mg, 2.44 mmol) in conc. sulfuric acid (3 mL)/water (3 mL) was stirred at 120° C. for 17 hr. The reaction solution was allowed to cool to room temperature, and alkalified with 8N aqueous sodium hydroxide solution. The aqueous layer was washed with ethyl acetate. The aqueous layer was acidified with 2N hydrochloric acid and the precipitate was collected by filtration and washed with water to give the title compound (600 mg, 93%) as a white solid.

$^1$H-NMR (DMSO-$d_6$, 300 MHz) δ 2.15 (3H, s), 6.83 (1H, d, J=8.1 Hz), 7.28-7.43 (1H, m), 7.56-7.82 (2H, m), 8.44 (1H, d, J=7.6 Hz), 13.74 (1H, br s).

Reference Example 113

Production of 1-(4-fluorophenyl)-2-oxo-6-(trifluoromethyl)-1,2-dihydropyridine-3-carbonitrile

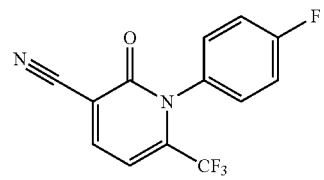 [SMILES: N#Cc1ccc(C(F)(F)F)n(-c2ccc(F)cc2)c1=O]

To a solution of 2-cyano-N-(4-fluorophenyl)acetamide (2 g, 11.2 mmol) and (3E)-4-ethoxy-1,1,1-trifluorobut-3-en-2-one (2.26 g, 13.4 mmol) in dimethyleneglycol monomethylether (20 mL) was added 1,4-diazabicyclo[2.2.2]octane (1.26 g, 11.2 mmol), and the mixture was stirred at 120° C. for 6 hr. The reaction mixture was diluted with 1N hydrochloric acid and ethyl acetate, and the mixture was extracted 3 times with ethyl acetate. The organic layer was washed with saturated brine, dried over anhydrous magnesium sulfate and filtered. The solvent was evaporated under reduced pressure. The obtained residue was purified by silica gel column chromatography (NH silica gel, ethyl acetate/hexane=1/2→1/1) to give a white solid. The white solid was washed with ethyl acetate and collected by filtration to give the title compound (230 mg, 7.2%) as a white solid.

$^1$H-NMR (DMSO-$d_6$, 300 MHz) δ 7.13 (1H, d, J=7.6 Hz), 7.32-7.46 (2H, m), 7.49-7.60 (2H, m), 8.44 (1H, d, J=7.4 Hz).

Reference Example 114

Production of 1-(4-fluorophenyl)-2-oxo-6-(trifluoromethyl)-1,2-dihydropyridine-3-carboxylic acid

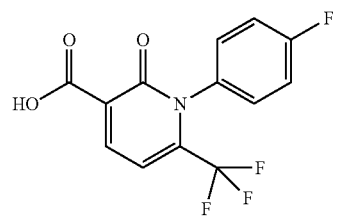 [SMILES: O=C(O)c1ccc(C(F)(F)F)n(-c2ccc(F)cc2)c1=O]

A solution of 1-(4-fluorophenyl)-2-oxo-6-(trifluoromethyl)-1,2-dihydropyridine-3-carbonitrile (200 mg, 0.709 mmol) in conc. sulfuric acid (1.5 mL)/water (1.5 mL) was stirred at 120° C. for 17 hr. The reaction solution was allowed to cool to room temperature, 6N aqueous sodium hydroxide solution was added, and the aqueous layer was washed with ethyl acetate. 1N Hydrochloric acid was added to the aqueous layer, and the precipitate was filtered and washed with water to give the title compound (160 mg, 75%) as a white solid.

¹H-NMR (DMSO-d₆, 300 MHz) δ 7.24 (1H, d, J=7.6 Hz), 7.35-7.48 (2H, m), 7.51-7.65 (2H, m), 8.40 (1H, d, J=7.6 Hz), 13.62 (1H, br s).

Reference Example 115

Production of 6-ethyl-1-(4-fluorophenyl)-2-oxo-1,2-dihydropyridine-3-carbonitrile

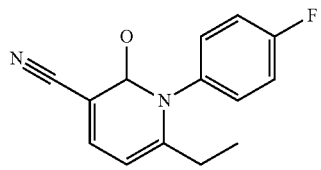 [SMILES: CCC1=CC=C(C#N)C(O)N1c1ccc(F)cc1]

To a solution of 2-cyano-N-(4-fluorophenyl)acetamide (1.7 g, 10.6 mmol) in dimethyleneglycol monomethylether (20 mL) were added 1,4-diazabicyclo[2.2.2]octane (1.2 g, 10.6 mmol) and (1E)-1-methoxypent-1-en-3-one (1.82 g, 15.9 mmol), and the mixture was stirred at 120° C. for 12 hr. The reaction mixture was diluted with 1N hydrochloric acid and ethyl acetate, and extracted 3 times with ethyl acetate. The organic layer was washed with saturated brine, dried over anhydrous magnesium sulfate and filtered. The solvent was evaporated under reduced pressure. The obtained residue was purified by silica gel column chromatography (NH silica gel, ethyl acetate/hexane=50/50→100/0) to give a white solid. The white solid was washed with ethyl acetate to give the title compound (410 mg, 16%) as a white solid.

¹H-NMR (DMSO-d₆, 300 MHz) δ 1.00 (3H, t, J=7.4 Hz), 2.25 (2H, q, J=7.4 Hz), 6.44 (1H, d, J=7.6 Hz), 7.35-7.49 (4H, m), 8.20 (1H, d, J=7.6 Hz).

Reference Example 116

Production of 6-ethyl-1-(4-fluorophenyl)-2-oxo-1,2-dihydropyridine-3-carboxylic acid

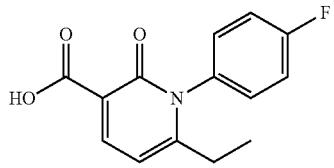 [SMILES: CCc1ccc(C(=O)O)c(=O)n1-c1ccc(F)cc1]

A solution of 6-ethyl-1-(4-fluorophenyl)-2-oxo-1,2-dihydropyridine-3-carbonitrile (410 mg, 1.69 mmol) in conc. sulfuric acid (2 mL)/water (2 mL) was stirred at 120° C. for 17 hr. The reaction solution was allowed to cool to room temperature, 6N aqueous sodium hydroxide solution was added, and the aqueous layer was washed with ethyl acetate. 1N Hydrochloric acid was added to the aqueous layer, and the precipitate was collected by filtration and washed with water to give the title compound (345 mg, 78%) as a white solid.

¹H-NMR (DMSO-d₆, 300 MHz) δ 1.05 (3H, t, J=7.4 Hz), 2.33 (2H, q, J=7.4 Hz), 6.76 (1H, d, J=7.7 Hz), 7.37-7.62 (4H, m), 8.45 (1H, d, J=7.7 Hz), 14.17 (1H, br s).

Reference Example 117

Production of 5-bromo-1-(4-fluorophenyl)-6-methyl-2-oxo-1,2-dihydropyridine-3-carbonitrile

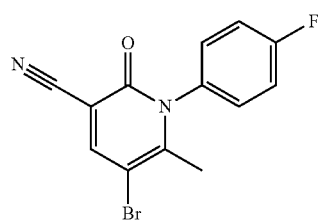 [SMILES: Cc1c(Br)cc(C#N)c(=O)n1-c1ccc(F)cc1]

To a solution of 1-(4-fluorophenyl)-6-methyl-2-oxo-1,2-dihydropyridine-3-carbonitrile (1 g, 4.05 mmol) in acetonitrile (10 mL)/tetrahydrofuran (5 mL) was added N-bromosuccinimide (792 mg, 4.46 mmol), and the mixture was stirred at 60° C. overnight. After cooling to room temperature, saturated aqueous sodium hydrogen carbonate solution and ethyl acetate were added to the reaction mixture, and the mixture was extracted 3 times with ethyl acetate. The organic layer was washed with saturated brine, dried over anhydrous magnesium sulfate and filtered. The solvent was evaporated under reduced pressure. The obtained residue was washed with diethyl ether and collected by filtration to give the title compound (1.07 g, 86%) as a slightly yellow solid.

¹H-NMR (DMSO-d₆, 300 MHz) δ 2.12 (3H, s), 6.95-7.77 (4H, m), 8.55 (1H, s).

Reference Example 118

Production of 1-(4-fluorophenyl)-5,6-dimethyl-2-oxo-1,2-dihydropyridine-3-carbonitrile

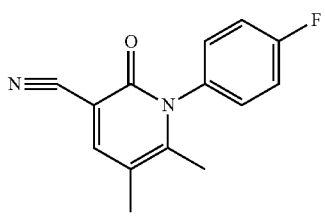 [SMILES: Cc1cc(C#N)c(=O)n(-c2ccc(F)cc2)c1C]

To a solution of 5-bromo-1-(4-fluorophenyl)-6-methyl-2-oxo-1,2-dihydropyridine-3-carbonitrile (200 mg, 0.651 mmol) in N,N-dimethylformamide (2 mL) were added tetramethyltin (582 mg, 3.255 mmol) and tetrakistriphenylphosphinepalladium(0) (22.3 mg, 0.019 mmol), and the mixture was stirred at 120° C. for 17 hr. Water and ethyl acetate were added to the reaction mixture, and the mixture was extracted 3 times with ethyl acetate. The organic layer was washed with saturated brine, and the solvent was evaporated under reduced pressure. The obtained residue was washed with diethyl ether and collected by filtration to give the title compound (94 mg, 60%) as a white solid.

¹H-NMR (DMSO-d₆, 300 MHz) δ 1.94 (3H, s), 2.10 (3H, s), 7.27-7.52 (4H, m), 8.13 (1H, s).

Reference Example 119

Production of 1-(4-fluorophenyl)-5,6-dimethyl-2-oxo-1,2-dihydropyridine-3-carboxylic acid

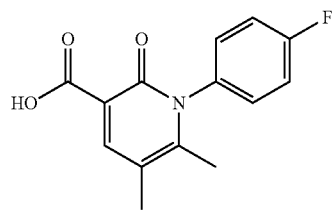 [SMILES: Cc1cc(C(=O)O)c(=O)n(-c2ccc(F)cc2)c1C]

A solution of 1-(4-fluorophenyl)-5,6-dimethyl-2-dihydropyridine-3-carbonitrile (90 mg, 0.324 mmol) in conc. sulfuric acid (0.5 mL) and water (0.5 mL) was stirred at 120° C. for 8 hr. The reaction solution was allowed to cool to room temperature and diluted with water. The precipitate was collected by filtration and washed with water to give the title compound (90 mg, 93%) as a white solid.

¹H-NMR (DMSO-d₆, 300 MHz) δ 2.03 (3H, s), 2.23 (3H, s), 7.37-7.52 (4H, m), 8.37 (1H, s), 14.44 (1H, br s).

Reference Example 120

Production of N-[3-fluoro-6-(2-fluoro-4-nitrophenoxy)imidazo[1,2-a]pyridin-2-yl]cyclopropanecarboxamide

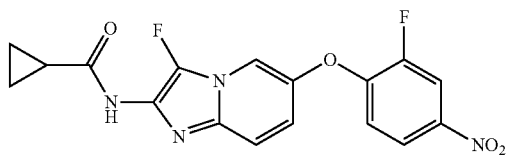 [SMILES: O=C(Nc1nc2ccc(Oc3ccc([N+](=O)[O-])cc3F)cn2c1F)C1CC1]

To a solution of N-[6-(2-fluoro-4-nitrophenoxy)imidazo[1,2-a]pyridin-2-yl]cyclopropanecarboxamide (121.6 mg, 0.341 mmol) in acetonitrile (0.5 mL)/tetrahydrofuran (0.5 mL) was added 1-fluoro-2,6-dichloropyridine triflate (129 mg, 0.409 mmol), and the mixture was stirred at room temperature for 2 hr. Tetrahydrofuran, ethyl acetate and 1N hydrochloric acid were added to the reaction mixture, and the mixture was extracted with ethyl acetate. The organic layer was washed with saturated brine, dried over anhydrous magnesium sulfate and filtered. The solvent was evaporated under reduced pressure. The obtained residue was purified by silica gel column chromatography (NH silica gel, ethyl acetate/hexane=1/2→1/1) to give the title compound (15.2 mg, 12%) as a white solid.

¹H-NMR (DMSO-d₆, 300 MHz) δ 0.69-0.89 (4H, m), 1.77-1.94 (1H, m), 7.10-7.37 (2H, m), 7.58 (1H, d, J=1.9 Hz), 7.94-8.16 (1H, m), 8.37 (1H, dd, J=10.9, 2.7 Hz), 8.56 (1H, d, J=2.3 Hz), 10.58 (1H, s).

Reference Example 121

1-(3-fluorophenyl)-6-methyl-2-oxo-1,2-dihydropyridine-3-carbonitrile

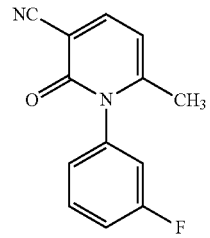 [SMILES: Cc1ccc(C#N)c(=O)n1-c1cccc(F)c1]

A solution (50 mL) of 2-cyano-N-(3-fluorophenyl)acetamide (6.60 g, 37.0 mmol), (3E)-4-methoxybut-3-en-2-one (5.60 g, 56.0 mmol) and 1,4-diazabicyclo[2.2.2]octane (6.20 g, 56.0 mmol) in 2-(2-methoxyethoxy)ethanol was stirred at 120° C. for 12 hr. The reaction solution was divided into two layers with ethyl acetate and water and subjected to extraction (3 times) with ethyl acetate. The organic layer was washed with water and saturated brine, dried over anhydrous magnesium sulfate and filtered. The solvent was evaporated under reduced pressure, and the obtained residue was washed with ethyl acetate and collected by filtration to give the title compound (2.60 g, 31%) as a brown solid.

¹H-NMR (DMSO-d₆, 300 MHz) δ 2.03 (3H, s), 6.50 (1H, d, J=7.6 Hz), 7.24 (1H, ddd, J=7.4, 1.1 0.9 Hz), 7.34-7.46 (2H, m), 7.54-7.71 (1H, m), 8.17 (1H, d, J=7.6 Hz).

Reference Example 122

1-(3-fluorophenyl)-6-methyl-2-oxo-1,2-dihydropyridine-3-carboxylic acid

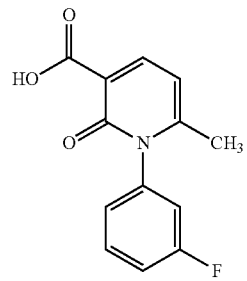

1-(3-Fluorophenyl)-2-oxo-1,2-dihydropyridine-3-carbonitrile (2.60 g, 11.0 mmol) was suspended in aqueous sulfuric acid solution (98% sulfuric acid 13 mL, water 13 mL), and the mixture was stirred at 130° C. for 10 hr. The reaction solution was allowed to cool to room temperature, water was added, and the precipitate was collected by filtration. The obtained solid was washed with ethyl acetate to give the title compound (2.20 g, 78%) as a brown solid.

$^1$H-NMR (DMSO-d$_6$, 300 MHz) δ 2.12 (3H, s), 6.81 (1H, dd, J=7.6, 0.8 Hz), 7.32 (1H, ddd, J=7.9, 1.9, 0.9 Hz), 7.38-7.53 (2H, m), 7.66 (1H, td, J=8.1, 6.4 Hz), 8.41 (1H, d, J=7.6 Hz).

Reference Example 123

2-cyano-N-(4-fluoro-3-methylphenyl)acetamide

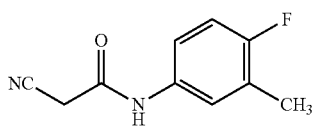

A mixture of 4-fluoro-3-methylaniline (2.50 g, 20.0 mmol) and ethyl cyanoacetate (2.70 g, 24.0 mmol) was stirred at 180° C. for 14 hr. After cooling to room temperature, the obtained solid was washed with hexane and collected by filtration to give the title compound (3.60 g, 95%) as a brownish-red solid.

$^1$H-NMR (DMSO-d$_6$, 300 MHz) δ 2.22 (3H, s), 3.88 (2H, s), 7.10 (1H, t, J=9.2 Hz), 7.28-7.55 (2H, m), 10.27 (1H, br s).

Reference Example 124

1-(4-fluoro-3-methylphenyl)-6-methyl-2-oxo-1,2-dihydropyridine-3-carbonitrile

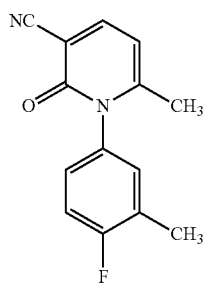 [SMILES: Cc1cc(-n2c(C)ccc(C#N)c2=O)ccc1F]

A solution (30 mL) of 2-cyano-N-(4-fluoro-3-methylphenyl)acetamide (3.60 g, 19.0 mmol), (3E)-4-methoxybut-3-en-2-one (2.80 g, 28.0 mmol) and 1,4-diazabicyclo[2.2.2]octane (3.20 g, 28.0 mmol) in 2-(2-methoxyethoxy)ethanol was stirred at 120° C. for 12 hr. After cooling to room temperature, the reaction solution was divided into two layers with ethyl acetate and water and subjected to extraction (3 times) with ethyl acetate. The organic layer was washed with water and saturated brine, dried over anhydrous magnesium sulfate and filtered. The solvent was evaporated under reduced pressure, and the obtained residue was washed with ethyl acetate and collected by filtration to give the title compound (1.60 g, 34%) as a brown solid.

$^1$H-NMR (DMSO-d$_6$, 300 MHz) δ 2.02 (3H, s), 2.27 (3H, d, J=1.9 Hz), 6.43-6.53 (1H, m), 7.17-7.38 (3H, m), 8.14 (1H, d, J=7.4 Hz).

Reference Example 125

1-(4-fluoro-3-methylphenyl)-6-methyl-2-oxo-1,2-dihydropyridine-3-carboxylic acid

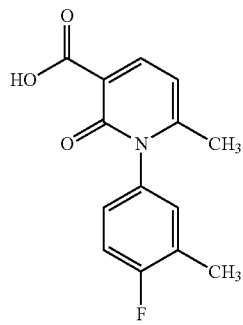 [SMILES: Cc1cc(-n2c(C)ccc(C(=O)O)c2=O)ccc1F]

1-(4-Fluoro-3-methylphenyl)-6-methyl-2-oxo-1,2-dihydropyridine-3-carbonitrile (1.60 g, 6.60 mmol) was suspended in aqueous sulfuric acid solution (98% sulfuric acid 8 mL, water 8 mL), and the mixture was stirred at 130° C. for 10 hr. The reaction solution was cooled to room temperature, water was added, and the precipitated solid was collected by filtration. The obtained solid was washed with ethyl acetate to give the title compound (1.00 g, 58%) as a brown solid.

$^1$H-NMR (DMSO-d$_6$, 300 MHz) δ 2.11 (3H, s), 2.29 (3H, d, J=1.9 Hz), 6.80 (1H, d, J=7.6 Hz), 7.27-7.48 (3H, m), 8.40 (1H, d, J=7.6 Hz).

Reference Example 126

1-(3,5-difluorophenyl)-6-methyl-2-oxo-1,2-dihydropyridine-3-carbonitrile

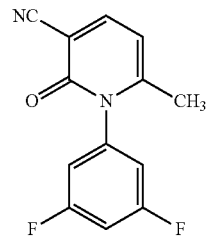 [SMILES: Cc1ccc(C#N)c(=O)n1-c1cc(F)cc(F)c1]

A solution (30 mL) of 2-cyano-N-(3,5-difluorophenyl)acetamide (3.10 g, 16.0 mmol), (3E)-4-methoxybut-3-en-2-one (2.40 g, 24.0 mmol) and 1,4-diazabicyclo[2.2.2]octane (2.70 g, 24.0 mmol) in 2-(2-methoxyethoxy)ethanol was stirred at 130° C. for 12 hr. After cooling to room temperature, the reaction solution was divided into two layers with ethyl acetate and water and subjected to extraction (3 times) with ethyl acetate. The organic layer was washed with water and saturated brine, dried over anhydrous magnesium sulfate and filtered. The solvent was evaporated under reduced pressure, and the obtained residue was washed with ethyl acetate and collected by filtration to give the title compound (1.60 g, 40%) as a brown solid.

$^1$H-NMR (DMSO-d$_6$, 300 MHz) δ 2.07 (3H, s), 6.51 (1H, dd, J=7.6, 0.8 Hz), 7.24-7.42 (2H, m), 7.49 (1H, tt, J=9.4, 2.4 Hz), 8.18 (1H, d, J=7.6 Hz).

Reference Example 127

1-(3,5-difluorophenyl)-6-methyl-2-oxo-1,2-dihydropyridine-3-carboxylic acid

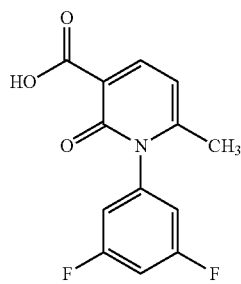 [SMILES: Cc1ccc(C(=O)O)c(=O)n1-c1cc(F)cc(F)c1]

1-(3,5-Difluorophenyl)-6-methyl-2-oxo-1,2-dihydropyridine-3-carbonitrile (1.50 g, 6.20 mmol) was suspended in aqueous sulfuric acid solution (98% sulfuric acid 8 mL, water 8 mL), and the mixture was stirred at 120° C. for 10 hr. The reaction solution was cooled to room temperature and poured into water, and the precipitate was collected by filtration. The obtained solid was washed with ethyl acetate to give the title compound (1.00 g, 61%) as a brown solid.

$^1$H-NMR (DMSO-d$_6$, 300 MHz) δ 2.15 (3H, s), 6.80 (1H, dd, J=7.6, 0.8 Hz), 7.35-7.47 (2H, m), 7.53 (1H, tt, J=9.4, 2.4 Hz), 8.42 (1H, d, J=7.6).

Reference Example 128

Production of methyl 1-(4-fluoro-2-methylphenyl)-2-oxo-1,2-dihydropyridine-3-carboxylate

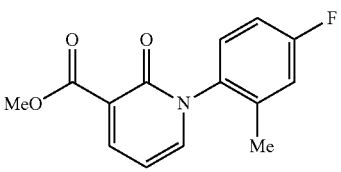 [SMILES: COC(=O)c1cccn(-c2ccc(F)cc2C)c1=O]

To a solution of methyl 2-oxo-2H-pyran-3-carboxylate (3 g, 19.5 mmol) in N,N-dimethylformamide, (18 mL) was added 4-fluoro-2-methylaniline (2.44 g, 19.5 mmol), and the mixture was stirred at room temperature for 3 hr. 4-Dimethylaminopyridine (119 mg, 0.974 mmol) and 1-ethyl-3-(3-dimethylaminopropyl)carbodiimide hydrochloride (4.48 g, 23.4 mmol) were added to the reaction mixture, and the mixture was further stirred at room temperature for 16 hr. 2N Hydrochloric acid was added to the reaction solution, and the mixture was extracted with ethyl acetate. The organic layer was washed with water and saturated brine, dried over anhydrous magnesium sulfate and filtered. The solvent was evaporated under reduced pressure. The obtained residue was purified by silica gel column chromatography (ethyl acetate/hexane=1/1), and the obtained solid was washed with hexane/ethyl acetate (=1/1) and collected by filtration to give the title compound (0.40 g, 8%) as a yellow solid.

$^1$H-NMR (DMSO-d$_6$, 300 MHz) δ 2.04 (3H, s), 3.75 (3H, s), 6.43 (1H, t, J=6.9 Hz), 7.15-7.23 (1H, m), 7.27-7.37 (2H, m), 7.86 (1H, dd, J=7.1, 2.4 Hz) 8.16 (1H, dd, J=7.1, 2.4 Hz).

Reference Example 129

Production of 1-(4-fluoro-2-methylphenyl)-2-oxo-1,2-dihydropyridine-3-carboxylic acid

To a suspension of methyl 1-(4-fluoro-2-methylphenyl)-2-oxo-1,2-dihydropyridine-3-carboxylate (0.40 g, 1.53 mmol) in methanol (9 mL) was added 2N aqueous sodium hydroxide solution (1.15 mL), and the mixture was stirred at room temperature for 3 hr. 6N Hydrochloric acid (0.5 mL) was added to the reaction mixture, and the mixture was extracted with ethyl acetate. The organic layer was washed with saturated brine, dried over anhydrous magnesium sulfate and filtered. The solvent was evaporated under reduced pressure, and the obtained residue was washed with hexane/ethyl acetate (=1/1) to give the title compound (704 mg, 85%) as a yellow solid.

$^1$H-NMR (300 MHz, DMSO-d$_6$) δ 2.07 (3H, s), 6.81 (1H, t, J=6.9 Hz), 7.20-7.29 (1H, m), 7.32-7.38 (1H, m), 7.46-7.52 (1H, m), 8.13 (1H, dd, J=6.9, 2.1 Hz), 8.51 (1H, dd, J=6.9, 2.1 Hz), 14.16 (1H, br s).

Reference Example 130

Production of 2-cyano-N-(3,4-difluorophenyl)acetamide

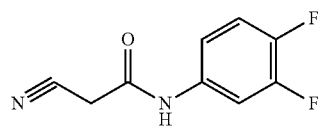 [SMILES: N#CCC(=O)Nc1ccc(F)c(F)c1]

A mixed solution of 3,4-difluoroaniline (10 g, 77.5 mmol) and ethyl cyanoacetate (10.5 g, 92.9 mmol) was heated to 180° C. and stirred for 8 hr. After cooling to room temperature, the mixture was dissolved in ethyl acetate/tetrahydrofuran and washed with water and saturated brine in this order. The mixture was dried over anhydrous magnesium sulfate and filtered. The solvent was evaporated under reduced pressure, and the obtained residue was washed with ethyl acetate and collected by filtration to give the title compound (7.6 g, 56%) as a yellow solid.

¹H-NMR (DMSO-d₆, 300 MHz) δ 3.92 (2H, s), 7.22-7.28 (1H, m), 7.36-7.47 (1H, m), 7.68-7.75 (1H, m), 10.53 (1H, s).

Reference Example 131

Production of 1-(3,4-difluorophenyl)-6-methyl-2-oxo-1,2-dihydropyridine-3-carbonitrile

A mixture of 2-cyano-N-(3,4-difluorophenyl)acetamide (6.0 g, 30.6 mmol), (3E)-4-methoxybut-3-en-2-one (4.29 g, 42.8 mmol) and 2-(2-methoxyethoxy)ethanol (60 mL) was stirred at 90° C. for 20 min. 1,4-Diazabicyclo[2.2.2]octane (3.77 g, 33.6 mmol) was added, and the mixture was stirred at 125° C. for 5 hr. After cooling to room temperature, the mixture was adjusted to pH 5 with 2N hydrochloric acid and extracted with ethyl acetate. The organic layer was washed with water and saturated brine, dried over anhydrous magnesium sulfate and filtered. The solvent was evaporated under reduced pressure, and the obtained residue was washed with ethyl acetate/hexane (=1/1) and collected by filtration to give the title compound (3.69 g, 49%) as a pale-yellow solid.

¹H-NMR (DMSO-d₆, 300 MHz) δ 2.05 (3H, s), 6.48-6.51 (1H, m), 7.25-7.35 (1H, m), 7.61-7.73 (2H, m), 8.17 (1H, d, J=7.5 Hz).

Reference Example 132

Production of 1-(3,4-difluorophenyl)-6-methyl-2-oxo-1,2-dihydropyridine-3-carboxylic acid

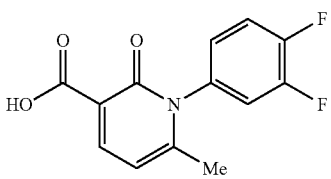 [SMILES: Cc1ccc(C(=O)O)c(=O)n1-c1ccc(F)c(F)c1]

Water (7.2 mL) and conc. sulfuric acid (7.2 mL) were added to 1-(3,4-difluorophenyl)-6-methyl-2-oxo-1,2-dihydropyridine-3-carbonitrile (3.6 g, 14.6 mmol), and the mixture was stirred at 100° C. for 20 hr. The mixture was basified (pH 10) with 8N aqueous sodium hydroxide solution at 0° C. and washed with ethyl acetate. The aqueous layer was acidified (pH 3) with 6N hydrochloric acid and extracted with ethyl acetate. The organic layer was washed with water and saturated brine, dried over anhydrous magnesium sulfate and filtered. The solvent was evaporated under reduced pressure, and the obtained residue was washed with ethyl acetate/hexane (=1/1) and collected by filtration to give the title compound (2.49 g, 64%) as a thin-yellow powder.

¹H-NMR (DMSO-d₆, 300 MHz) δ 2.13 (3H, s), 6.80 (1H, d, J=8.1 Hz), 7.34-7.43 (1H, m), 7.65-7.80 (2H, m), 8.41 (1H, d, J=7.5 Hz), 14.06 (1H, br s).

Reference Example 133

Production of N-[6-(2-fluoro-4-nitrophenoxy)imidazo[1,2-a]pyridin-2-yl]cyclopropanecarboxamide

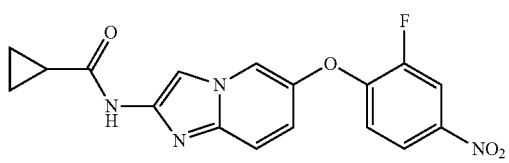

To a solution of N-(6-hydroxyimidazo[1,2-a]pyridin-2-yl)cyclopropanecarboxamide (30 g, 138 mmol) and 1,2-difluoro-4-nitrobenzene (24.2 g, 152 mmol) in dimethyl sulfoxide (180 mL) was added cesium carbonate (58.5 g, 180 mmol), and the mixture was stirred at room temperature for 5 hr under an argon atmosphere. Water (1080 mL) was added to the reaction mixture, and the mixture was stirred for 20 min. The precipitate was collected by filtration and washed with water and ethyl acetate. After air drying for one day, the mixture was dried under reduced pressure at 100° C. for 5 hr to give the title compound (46.5 g, 95%) as a yellow solid.

¹H-NMR (DMSO-d₆, 300 MHz) δ 0.76-0.84 (4H, m), 1.88-1.99 (1H, m), 7.22 (1H, d, J=9.5 Hz), 7.21-7.27 (1H, m), 7.54 (1H, d, J=9.5 Hz), 8.01-8.08 (1H, m), 8.08 (1H, s), 8.36 (1H, dd, J=11.1, 2.9 Hz), 8.74 (1H, d, J=1.8 Hz), 11.02 (1H, s).

Reference Example 134

Production of N-[6-(4-amino-2-fluorophenoxy)imidazo[1,2-a]pyridin-2-yl]cyclopropanecarboxamide

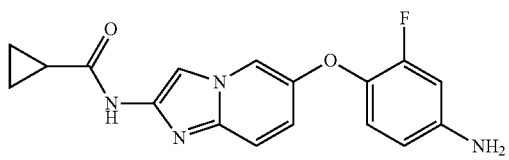

To a suspension of N-[6-(2-fluoro-4-nitrophenoxy)imidazo[1,2-a]pyridin-2-yl]cyclopropanecarboxamide (10 g, 28.1 mmol) in tetrahydrofuran (80 mL)/methanol (80 mL) were added iron chloride•hexahydrate (0.5 g), hydrazine•monohydrate (8.2 mL, 168 mmol) and activated carbon (1.0 g), and the mixture was heated under reflux for 16 hr. After cooling to 40° C., the mixture was filtered through celite and washed with methanol. The solvent of the filtrate was evaporated under reduced pressure, and the precipitate was washed with water/methanol (=10/1) and collected by filtration to give the title compound (8.4 g, 92%) as a white solid.

¹H-NMR (DMSO-d₆, 300 MHz) δ 0.75-0.81 (4H, m), 1.85-1.96 (1H, m), 5.34 (2H, s), 6.34-6.40 (1H, m), 6.49 (1H, dd, J=135.5, 2.7 Hz), 7.00-7.05 (1H, m), 7.38 (1H, d, J=9.5 Hz), 8.00 (1H, s), 8.21 (1H, d, J=2.1 Hz), 10.88 (1H, s).

Reference Example 135

Production of 4-[(6,7-dimethoxyquinolin-4-yl)oxy]aniline

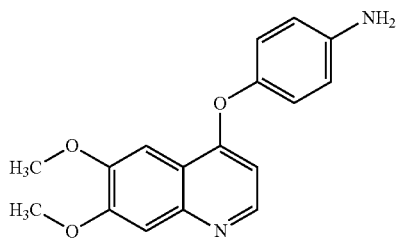 [SMILES: COc1cc2nccc(Oc3ccc(N)cc3)c2cc1OC]

A suspension of 4-chloro-6,7-dimethoxyquinoline (1566 mg, 7.00 mmol), 4-aminophenol (917 mg, 8.40 mmol) and cesium carbonate (4561 mg, 14.0 mmol) in dimethyl sulfoxide (14 ml) was stirred at 100° C. for 18 hr. Water was added to the reaction mixture, and the mixture was extracted 3 times with ethyl acetate/tetrahydrofuran (=1/1). The solvent was evaporated under reduced pressure, and the residue was purified by silica gel column chromatography (ethyl acetate→ethyl acetate/methanol=60/40). Ethyl acetate was added to the obtained residue and the mixture was filtrated to give the title compound (1267 mg, 61%) as a white powder.

$^1$H-NMR (DMSO-d$_6$, 300 MHz) δ 3.93 (6H, s), 5.16 (2H, s), 6.37 (1H, d, J=5.4 Hz), 6.67 (2H, d, J=8.7 Hz), 6.93 (2H, d, J=8.7 Hz), 7.36 (1H, s), 7.50 (1H, s), 8.43 (1H, d, J=5.4 Hz).

Reference Example 136

Production of N-{4-[(6,7-dimethoxyquinolin-4-yl]phenyl}-N'-phenylcyclopropanedicarboxamide

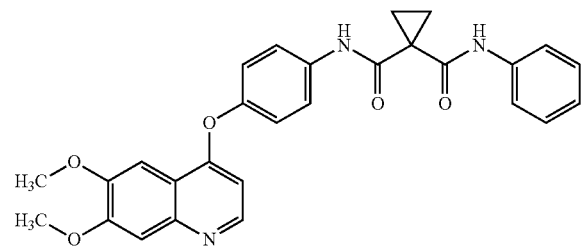 [SMILES: COc1cc2nccc(Oc3ccc(NC(=O)C4(C(=O)Nc5ccccc5)CC4)cc3)c2cc1OC]

To a solution of 1-(phenylcarbamoyl)cyclopropanecarboxylic acid (237 mg, 1.04 mmol) in tetrahydron (10 mL) were added N,N-dimethylformamide (1 drop) and oxalyl chloride (178 µL, 2.08 mmol), and the mixture was stirred at room temperature for 2 hr. The solvent was evaporated under reduced pressure, N,N-dimethylacetamide (3 ml) and 4-[(6, 7-dimethoxyquinolin-4-yl)oxy]aniline (213 mg, 1.04 mmol) were added to the obtained residue, and the mixture was stirred at room temperature for 18 hr. Water was added to the reaction mixture, and the mixture was extracted with ethyl acetate/tetrahydrofuran. The solvent was evaporated under reduced pressure, and the obtained residue was purified by silica gel column chromatography (ethyl acetate→ethyl acetate/methanol=75/25). The obtained powder was recrystallized from ethyl acetate/diisopropyl ether to give the title compound (286 mg, 74%) as white crystals.

$^1$H-NMR (DMSO-d$_6$, 300 MHz) δ 1.49 (4H, s), 3.93 (3H, s), 3.95 (3H, s), 6.43 (1H, d, J=5.3 Hz), 7.07 (1H, t, J=7.4 Hz), 7.23 (2H, d, J=9.2 Hz), 7.27-7.35 (2H, m), 7.39 (1H, s), 7.51 (1H, s), 7.63 (2H, d, J=7.4 Hz), 8.47 (1H, d, J=5.3 Hz), 10.05 (1H, brs), 10.26 (1H, brs).

Reference Example 137

Production of 1-(2-fluorophenyl)-6-methyl-2-oxo-1, 2-dihydropyridine-3-carboxylic acid

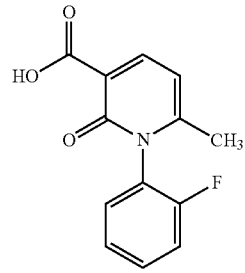 [SMILES: Cc1ccc(C(=O)O)c(=O)n1-c1ccccc1F]

An aqueous solution (98% sulfuric acid 3 mL, water 3 mL) of 1-(2-fluorophenyl)-6-methyl-2-oxo-1,2-dihydropyridine-3-carbonitrile (660 mg, 3.08 mmol) in sulfuric acid was stirred at 130° C. for 6 hr. The reaction solution was cooled to room temperature, water was added, and the precipitated solid was collected by filtration. The obtained solid was washed with ethyl acetate to give the title compound (550 mg, 72%) as a brown solid.

$^1$H-NMR (DMSO-d$_6$, 300 MHz) δ 2.14 (3H, s), 6.84 (1H, d, J=8.1 Hz), 7.41-7.70 (4H, m), 8.45 (1H, d, J=7.6 Hz), 13.87 (1H, br s).

Reference Example 138

Production of 2-cyano-N-(4-fluoro-3-methylphenyl)acetamide

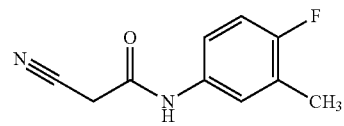

A mixture of 4-fluoro-3-methylaniline (2.50 g, 20.0 mmol) and ethyl cyanoacetate (2.70 g, 24.0 mmol) was stirred at 180° C. for 14 hr. After the reaction, the mixture was cooled to room temperature, and the obtained solid was washed with hexane and collected by filtration to give the title compound (3.60 g, 95%) as a brownish-red solid.

$^1$H-NMR (DMSO-d$_6$, 300 MHz) δ 2.22 (3H, s), 3.88 (2H, s), 7.10 (1H, t, J=9.2 Hz), 7.28-7.55 (2H, m), 10.27 (1H, br s).

Reference Example 139

Production of 1-(4-fluoro-3-methylphenyl)-6-methyl-2-oxo-1,2-dihydropyridine-3-carbonitrile

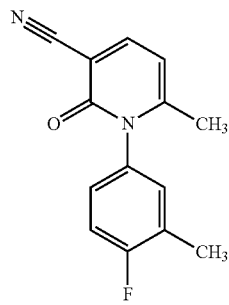 [SMILES: Cc1cc(-n2c(C)ccc(C#N)c2=O)ccc1F]

A solution (30 mL) of 2-cyano-N-(4-fluoro-3-methylphenyl)acetamide (3.60 g, 19.0 mmol), (3E)-4-methoxybut-3-en-2-one (2.80 g, 28.0 mmol) and 1,4-diazabicyclo[2.2.2]octane (3.20 g, 28.0 mmol) in 2-(2-methoxyethoxy)ethanol was stirred at 120° C. for 12 hr. After cooling to room temperature, the reaction solution was divided into two layers with ethyl acetate and water and subjected to extraction (3 times) with ethyl acetate. The organic layer was washed with water and saturated brine, dried over anhydrous magnesium sulfate and filtered. The solvent was evaporated under reduced pressure, and the obtained residue was washed with ethyl acetate and collected by filtration to give the title compound (1.60 g, 34%) as a brown solid.
$^1$H-NMR (DMSO-d$_6$, 300 MHz) δ 2.02 (3H, s), 2.27 (3H, d, J=1.9 Hz), 6.43-6.53 (1H, m), 7.17-7.38 (3H, m), 8.14 (1H, d, J=7.4 Hz).

Reference Example 140

Production of 1-(4-fluoro-3-methylphenyl)-6-methyl-2-oxo-1,2-dihydropyridine-3-carboxylic acid

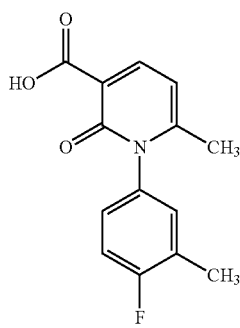 [SMILES: Cc1cc(-n2c(C)ccc(C(=O)O)c2=O)ccc1F]

An aqueous solution (98% sulfuric acid 8 mL, water 8 mL) of 1-(4-fluoro-3-methylphenyl)-6-methyl-2-oxo-1,2-dihydropyridine-3-carbonitrile (1.60 g, 6.60 mmol) in sulfuric acid was stirred at 130° C. for 10 hr. The reaction solution was cooled to room temperature, water was added, and the precipitated solid was collected by filtration. The obtained solid was washed with ethyl acetate to give the title compound (1.00 g, 58%) as a brown solid.
$^1$H-NMR (DMSO-d$_6$, 300 MHz) δ 2.11 (3H, s), 2.29 (3H, d, J=1.9 Hz), 6.80 (1H, d, J=7.6 Hz), 7.27-7.48 (3H, m), 8.40 (1H, d, J=7.6 Hz).

Reference Example 141

Production of 2-(3-fluorophenyl)-3-methylpyridine 1-oxide

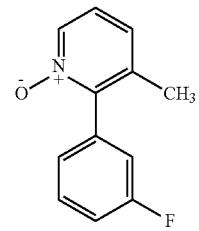

To a solution (100 mL) of 2-(3-fluorophenyl)-3-methylpyridine (4.83 g, 25.8 mmol) in ethyl acetate was added 3-chloroperbenzoic acid (7.1 g, 28.4 mmol), and the mixture was stirred at 50° C. for 5 hr. The disappearance of 3-chloroperbenzoic acid was confirmed using potassium iodide starch paper (manufactured by ADVANTEC MFS, INC), and the solvent was evaporated under reduced pressure. The residue was purified by silica gel column chromatography to give the title compound (4.26 g, 81%).
$^1$H-NMR (DMSO-d$_6$, 300 MHz) δ 2.05 (3H, s), 7.17 (1H, dt, J=7.6, 1.2 Hz), 7.21-7.40 (4H, m), 7.54 (1H, td, J=7.8, 5.9 Hz), 8.20 (1H, dd, J=5.4, 1.6 Hz).

Reference Example 142

Production of 6-(3-fluorophenyl)-5-methylpyridine-2-carbonitrile

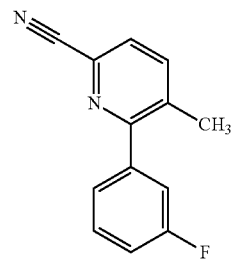 [SMILES: Cc1ccc(C#N)nc1-c1cccc(F)c1]

A solution (40 mL) of 2-(3-fluorophenyl)-3-methylpyridine 1-oxide (4.26 g, 21.0 mmol), dimethylcarbamic acid chloride (2.94 g, 27.3 mmol) and trimethylsilanecarbonitrile (2.71 g, 27.3 mmol) in tetrahydrofuran was heated under reflux, and the mixture was stirred for 2 hr. After cooling to room temperature, the reaction solution was divided into two layers with ethyl acetate and saturated aqueous sodium hydrogen carbonate solution and subjected to extraction (3 times) with ethyl acetate. The organic layer was washed with saturated brine, dried over anhydrous magnesium sulfate and filtered. The solvent was evaporated under reduced pressure, and the residue was purified by silica gel chromatography to give the title compound (4.42 g, 99%).

¹H-NMR (DMSO-d₆, 300 MHz) δ 2.41 (3H, s), 7.27-7.39 (1H, m), 7.39-7.48 (2H, m), 7.50-7.62 (1H, m), 7.93-8.09 (2H, m).

Reference Example 143

Production of 6-(3-fluorophenyl)-5-methylpyridine-2-carbonitrile 1-oxide

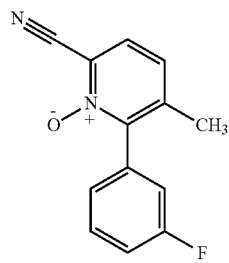

To a solution (50 mL) of 6-(3-fluorophenyl)-5-methylpyridine-2-carbonitrile (4.42 g, 20.8 mmol) in acetonitrile were added trifluoroacetic acid anhydride (17.6 g, 62.4 mmol) and sodium percarbonate (6.5 g, 41.6 mmol) at 0° C., and the mixture was stirred at 0° C. for 1 hr and at room temperature overnight. The reaction solution was divided into two layers with ethyl acetate and saturated aqueous sodium hydrogen carbonate solution and subjected to extraction (3 times) with ethyl acetate. The organic layer was washed with saturated brine, dried over anhydrous magnesium sulfate and filtered. The disappearance of sodium percarbonate was confirmed, and the solvent was evaporated under reduced pressure. The residue was purified by silica gel chromatography to give the title compound (1.4 g, 29%) as a white solid.

¹H-NMR (DMSO-d₆, 300 MHz) δ 2.11 (3H, s), 7.23 (1H, dt, J=7.7, 1.2 Hz), 7.29-7.39 (2H, m), 7.48-7.53 (1H, m), 7.53-7.64 (1H, m), 8.05 (1H, d, J=8.3 Hz).

Reference Example 144

Production of 6-(3-fluorophenyl)-5-methylpyridine-2-carboxylic acid 1-oxide

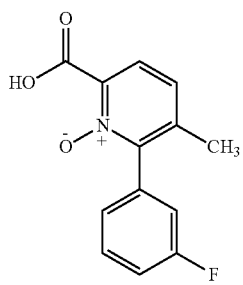

An aqueous solution (98% sulfuric acid 6 mL, water 6 mL) of 6-(3-fluorophenyl)-5-methylpyridine-2-carbonitrile 1-oxide (1.4 g, 6.13 mmol) in sulfuric acid was stirred at 120° C. for 10 hr. The reaction solution was cooled to room temperature and added to water, and the precipitated solid was collected by filtration. The obtained solid was washed with ethyl acetate to give the title compound (1.07 g, 71%) as a brown solid.

¹H-NMR (DMSO-d₆, 300 MHz) δ 2.18 (3H, s), 7.26-7.47 (3H, m), 7.54-7.73 (1H, m), 7.87-8.01 (1H, m), 8.31 (1H, d, J=8.3 Hz).

Example 1

Production of benzyl [4-({2-[(cyclopropylcarbonyl)amino]imidazo[1,2-a]pyridin-6-yl}oxy)phenyl]carbamate

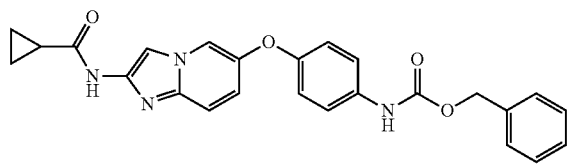 [SMILES: O=C(Nc1ccc(Oc2ccc3nc(NC(=O)C4CC4)cn3c2)cc1)OCc1ccccc1]

To a solution of benzylcarbamate {4-[(2-aminoimidazo[1,2-a]pyridin-6-yl)oxy]phenyl}carbamate (8.7 g, 22.2 mmol) in N,N-dimethylacetamide (70 mL) was added cyclopropanecarbonyl chloride (2.21 mL, 24.4 mmol) at room temperature, and the mixture was stirred at room temperature for 1 hr. Saturated aqueous sodium hydrogen carbonate was added to the reaction mixture, and the mixture was extracted with ethyl acetate/tetrahydrofuran. The organic layer was washed with saturated brine, dried over anhydrous magnesium sulfate and filtered. The solvent was evaporated under reduced pressure, and the residue was washed with hexane/ethyl acetate (=1/1) and collected by filtration to give the title compound (8.5 g, 87%) as a thin-brown solid.

¹H-NMR (DMSO-d₆, 300 MHz) δ 0.76-0.82 (4H, m), 1.85-1.95 (1H, m), 5.14 (2H, s), 6.97-7.09 (3H, m), 7.27-7.50 (8H, m), 8.03 (1H, s), 8.44 (1H, d, J=1.8 Hz), 9.75 (1H, s), 10.97 (1H, s).

Example 2

Production of N-[6-(4-{[(phenylacetyl)carbamothioyl]amino}phenoxy)imidazo[1,2-a]pyridin-2-yl]cyclopropanecarboxamide

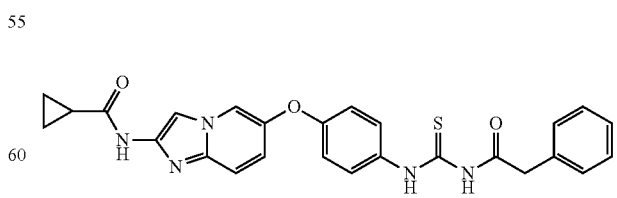

To a solution of phenylacetyl chloride (422 mg, 2.59 mmol) in acetonitrile (8 mL) was added potassium thiocyanate (317 mg, 3.24 mmol), and the mixture was stirred at 50° C. for 1 hr. The reaction solution was cooled to room temperature, saturated aqueous sodium hydrogen carbonate was added, and the mixture was extracted with ethyl acetate. The organic layer was washed with saturated aqueous sodium hydrogen carbonate and saturated brine, dried over anhydrous magnesium sulfate and concentrated. The obtained residue was dissolved in toluene (2 mL)/ethanol (2 mL), N-[6-(4-aminophenoxy)imidazo[1,2-a]pyridin-2-yl]cyclopropanecarboxamide (200 mg, 649 µmol) was added, and the mixture was stirred at room temperature for 1 hr. Saturated aqueous sodium hydrogen carbonate was added to the reaction solution, and the mixture was extracted with ethyl acetate. The organic layer was washed with 1N aqueous sodium hydroxide solution, water and saturated brine, dried over anhydrous magnesium sulfate and concentrated. The obtained residue was purified by silica gel column chromatography (ethyl acetate/hexane) and recrystallized from ethanol/water to give the title compound (98 mg, 31%) as a pale-yellow powder.

$^1$H-NMR (DMSO-d$_6$, 300 MHz) δ 0.68-0.93 (4H, m), 1.82-2.05 (1H, m), 3.81 (2H, s), 7.02 (2H, d, J=8.9 Hz), 7.08 (1H, dd, J=9.6, 2.1 Hz), 7.22-7.41 (5H, m), 7.46 (1H, d, J=9.6 Hz), 7.57 (2H, d, J=8.9 Hz), 8.05 (1H, s), 8.57 (1H, d, J=2.1 Hz), 10.97 (1H, s), 11.69 (1H, s), 12.30 (1H, s).

Example 3

Production of N-[4-({2-[(cyclopropylcarbonyl)amino]imidazo[1,2-a]pyridin-6-yl}oxy)phenyl]-5-methyl-1-phenyl-1H-pyrazole-3-carboxamide

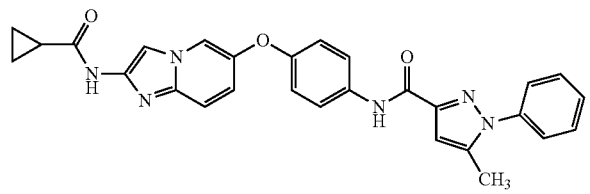 [SMILES: Cc1cc(C(=O)Nc2ccc(Oc3ccc4nc(NC(=O)C5CC5)cn4c3)cc2)nn1-c1ccccc1]

To a solution of 5-methyl-1-phenyl-1H-pyrazole-3-carboxylic acid (197 mg, 973 µmol) in tetrahydrofuran (2 mL) were added oxalyl chloride (80 µL, 973 µmol) and N,N-dimethylformamide (2 drops) under ice-cooling, and the mixture was stirred at room temperature for 1 hr. A solution of N-[6-(4-aminophenoxy)imidazo[1,2-a]pyridin-2-yl]cyclopropanecarboxamide (200 mg, 649 µmol) in N,N-dimethylacetamide (2 mL) was added to the reaction solution, and the mixture was stirred at room temperature for 2 hr. Saturated aqueous sodium hydrogen carbonate was added to the reaction solution, and the mixture was extracted with ethyl acetate. The organic layer was washed with 1N aqueous sodium hydroxide solution, water and saturated brine, dried over anhydrous magnesium sulfate and concentrated. The obtained residue was recrystallized from ethanol/water to give the title compound (187 mg, 39%) as a white powder.

$^1$H-NMR (DMSO-d$_6$, 300 MHz) δ 0.75-0.86 (4H, m), 1.86-1.98 (1H, m), 2.30 (3H, s), 6.83 (1H, s), 7.03 (2H, d, J=9.1 Hz), 7.02-7.08 (1H, m), 7.31-7.50 (6H, m), 7.65 (2H, d, J=9.1 Hz), 8.04 (1H, s), 8.48 (1H, d, J=1.7 Hz), 10.53 (1H, s), 10.95 (1H, s).

Example 4

Production of N-[4-({2-[(cyclopropylcarbonyl)amino]imidazo[1,2-a]pyridin-6-yl}oxy)phenyl]-3-methyl-1-phenyl-1H-pyrazole-5-carboxamide

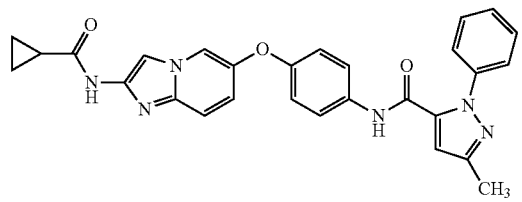 [SMILES: Cc1cc(C(=O)Nc2ccc(Oc3ccc4nc(NC(=O)C5CC5)cn4c3)cc2)n(-c2ccccc2)n1]

To a solution of 3-methyl-1-phenyl-1H-pyrazole-5-carboxylic acid (197 mg, 973 µmol) in tetrahydrofuran (2 mL) were added oxalyl chloride (80 µL, 973 µmol) and N,N-dimethylformamide under ice-cooling, and the mixture was stirred at room temperature for 1 hr. A solution of N-[6-(4-aminophenoxy)imidazo[1,2-a]pyridin-2-yl]cyclopropanecarboxamide (200 mg, 649 µmol) in N,N-dimethylacetamide (2 mL) was added to the reaction solution, and the mixture was stirred at room temperature for 2 hr. Saturated aqueous sodium hydrogen carbonate was added to the reaction solution, and the mixture was extracted with ethyl acetate. The organic layer was washed with 1N aqueous sodium hydroxide solution, water and saturated brine, dried over anhydrous magnesium sulfate and concentrated. The obtained residue was recrystallized from ethanol/water to give the title compound (138 mg, 29%) as a white powder.

$^1$H-NMR (DMSO-d$_6$, 300 MHz) δ 0.74-0.87 (4H, m), 1.83-2.05 (1H, m), 2.36 (3H, s), 6.79 (1H, s), 7.02 (2H, d, J=9.1 Hz), 7.07 (1H, dd, J=9.6, 2.2 Hz), 7.45 (1H, d, J=9.6 Hz), 7.47-7.68 (5H, m), 7.82 (2H, d, J=8.9 Hz), 8.05 (1H, s), 8.49 (1H, d, J=1.7 Hz), 10.08 (1H, s), 10.95 (1H, s).

Example 5

Production of benzyl [4-({2-[(cyclopropylcarbonyl)amino]imidazo[1,2-a]pyridin-6-yl}oxy)-3-fluorophenyl]carbamate

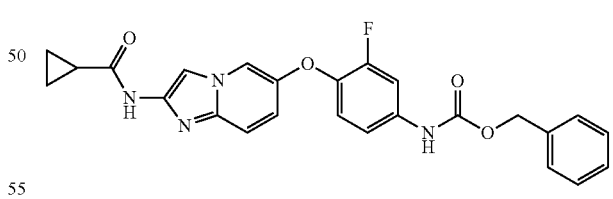

To a solution of benzyl {4-[(2-aminoimidazo[1,2-a]pyridin-6-yl)oxy]-3-fluorophenyl}carbamate (10.0 g, 25.5 mmol) in N,N-dimethylacetamide (100 mL) was added cyclopropanecarbonyl chloride (2.77 mL, 30.6 mmol) at 0° C., and the mixture was stirred at room temperature for 2 hr. Water and saturated aqueous sodium hydrogen carbonate were added to the reaction mixture, and the mixture was extracted with ethyl acetate/tetrahydrofuran. The organic layer was washed with saturated brine, dried over anhydrous magnesium sulfate and filtered. The solvent was evaporated under reduced pressure, and the residue was washed with ethyl acetate and collected by filtration to give the title compound (9.2 g, 78%) as a thin-brown solid.

¹H-NMR (DMSO-d₆, 300 MHz) δ 0.76-0.81 (4H, m), 1.85-1.96 (1H, m), 5.17 (2H, s), 7.05-7.25 (4H, m), 7.30-7.45 (5H, m), 7.52-7.60 (1H, m), 8.01 (1H, s), 8.38 (1H, d, J=2.1 Hz), 10.02 (1H, s), 10.93 (1H, s).

Example 6

Production of benzyl [4-({2-[(cyclopropylcarbonyl)amino]imidazo[1,2-a]pyridin-6-yl}oxy)-2-fluorophenyl]carbamate

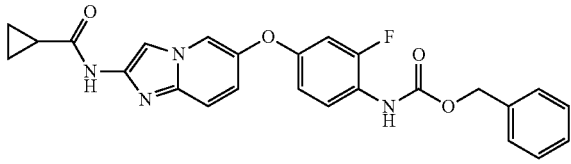 [SMILES: O=C(Nc1ccc(Oc2ccc3nc(NC(=O)C4CC4)cn3c2)cc1F)OCc1ccccc1]

To a solution of benzyl {4-[(2-aminoimidazo[1,2-a]pyridin-6-yl)oxy]-2-fluorophenyl}carbamate (12.1 g, 30.9 mmol) in N,N-dimethylacetamide (84.7 mL) was added cyclopropanecarbonyl chloride (3.36 mL, 37.0 mmol) at 0° C., and the mixture was stirred at room temperature for 2 hr. Water and saturated aqueous sodium hydrogen carbonate were added to the reaction mixture, and the mixture was extracted with ethyl acetate/tetrahydrofuran. The organic layer was washed with saturated brine, dried over anhydrous magnesium sulfate and filtered. The solvent was evaporated under reduced pressure, and the residue was washed with ethyl acetate and collected by filtration to give the title compound (9.7 g, 68%) as a thin-brown solid.

¹H-NMR (DMSO-d₆, 300 MHz) δ 0.77-0.83 (4H, m), 1.86-1.96 (1H, m), 5.14 (2H, s), 6.81-6.86 (1H, m), 6.97-7.11 (2H, m), 7.31-7.56 (7H, m), 8.05 (1H, s), 8.57 (1H, d, J=1.5 Hz), 9.37 (1H, br s), 10.97 (1H, s).

Example 7

Production of N-(6-{(4-[(cyclopropylcarbonyl)amino]-2-fluorophenoxy}imidazo[1,2-a]pyridin-2-yl)cyclopropanecarboxamide

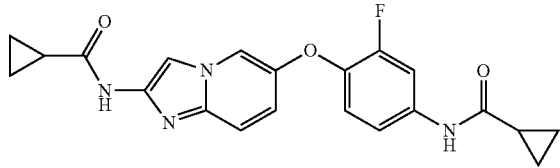 [SMILES: O=C(Nc1ccc(Oc2ccc3nc(NC(=O)C4CC4)cn3c2)c(F)c1)C1CC1]

To a solution of N-[6-(4-amino-2-fluorophenoxy)imidazo[1,2-a]pyridin-2-yl]cyclopropanecarboxamide (150 mg, 0.46 mmol) in N,N-dimethylacetamide (1.5 mL) was added cyclopropanecarbonyl chloride (50.1 μL, 0.55 mmol) at room temperature, and the mixture was stirred at room temperature for 30 min. Saturated aqueous sodium hydrogen carbonate was added to the reaction mixture, and the mixture was extracted with ethyl acetate/tetrahydrofuran. The organic layer was washed with saturated brine, dried over anhydrous magnesium sulfate and filtered. The solvent was evaporated under reduced pressure, and the residue was purified by silica gel column chromatography (hexane/ethyl acetate=40/60→0/100). The obtained powder was washed with ethyl acetate and collected by filtration to give the title compound (150 mg, 83%) as a white solid.

¹H-NMR (DMSO-d₆, 300 MHz) δ 0.76-0.84 (8H, m), 1.71-1.80 (1H, m), 1.86-1.96 (1H, m), 7.09 (1H, dd, J=9.6, 2.4 Hz), 7.16 (1H, d, J=9.0 Hz), 7.24-7.30 (1H, m), 7.43 (1H, d, J=9.6 Hz), 7.78 (1H, dd, J=13.5, 2.4 Hz), 8.02 (1H, s), 8.41 (1H, d, J=2.1 Hz), 10.41 (1H, s), 10.93 (1H, s).

Example 8

Production of N-[4-({2-[(cyclopropylcarbonyl)amino]imidazo[1,2-a]pyridin-6-yl}oxy)phenyl]-N'-phenylcyclopropane-1,1-dicarboxamide

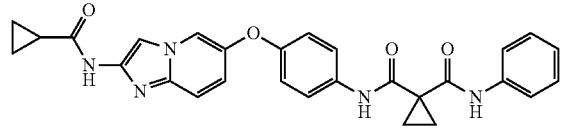 [SMILES: O=C(Nc1cn2cc(Oc3ccc(NC(=O)C4(C(=O)Nc5ccccc5)CC4)cc3)ccc2n1)C1CC1]

To a solution of N-[6-(4-aminophenoxy)imidazo[1,2-a]pyridin-2-yl]cyclopropanecarboxamide (142 mg, 0.461 mmol) in N,N-dimethylacetamide (2.8 mL) were added 1-(phenylcarbamoyl)cyclopropanecarboxylic acid (142 mg, 0.691 mmol), HATU (263 mg, 0.691 mmol) and N,N-diisopropylethylamine (120 μL, 0.691 mmol), and the mixture was stirred at room temperature for 4 hr. Saturated aqueous sodium hydrogen carbonate was added to the reaction mixture, and the mixture was extracted with ethyl acetate/tetrahydrofuran. The organic layer was washed with saturated brine, dried over anhydrous magnesium sulfate and filtered. The solvent was evaporated under reduced pressure, and the residue was purified by silica gel column chromatography (hexane/ethyl acetate=40/60→0/100), washed with hexane/ethyl acetate and collected by filtration to give the title compound (130 mg, 57%) as a white solid.

¹H-NMR (DMSO-d₆, 300 MHz) δ 0.75-0.82 (4H, m), 1.46 (4H, s), 1.86-1.96 (1H, m), 6.96-7.09 (4H, m), 7.27-7.33 (2H, m), 7.44 (1H, d, J=9.6 Hz), 7.57-7.62 (4H, m), 8.04 (1H, s), 8.47 (1H, d, J=1.5 Hz), 10.00 (1H, br s), 10.07 (1H, br s), 10.94 (1H, s).

Example 9

Production of N-[4-({2-[(cyclopropylcarbonyl)amino]imidazo[1,2-a]pyridin-6-yl}oxy)phenyl]-N'-(4-fluorophenyl)cyclopropane-1,1-dicarboxamide

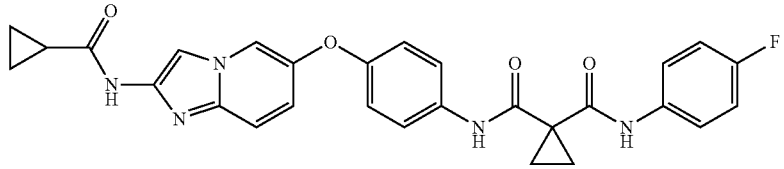 [SMILES: O=C(Nc1cn2cc(Oc3ccc(NC(=O)C4(C(=O)Nc5ccc(F)cc5)CC4)cc3)ccc2n1)C1CC1]

Using N-[6-(4-aminophenoxy)imidazo[1,2-a]pyridin-2-yl]cyclopropanecarboxamide (150 mg, 0.486 mmol), N,N-dimethylacetamide (3.0 mL), 1-[(4-fluorophenyl)carbamoyl]cyclopropanecarboxylic acid (163 mg, 0.730 mmol), HATU (277 mg, 0.730 mmol) and N,N-diisopropylethylamine (127 μL, 0.730 mmol) and in the same manner as in Example 8, the title compound (111 mg, 44%) was obtained as a white solid.

¹H-NMR (DMSO-d₆, 300 MHz) δ 0.75-0.82 (4H, m), 1.44 (4H, s), 1.86-1.96 (1H, m), 6.96-7.17 (5H, m), 7.44 (1H, d, J=9.6 Hz), 7.57-7.65 (4H, m), 8.03 (1H, s), 8.47 (1H, d, J=1.8 Hz), 10.03 (1H, br s), 10.06 (1H, br s), 10.94 (1H, s).

Example 10

Production of N-[4-({2-[(cyclopropylcarbonyl)amino]imidazo[1,2-a]pyridin-6-yl}oxy)-3-fluorophenyl]-1-(4-fluorophenyl)-2-oxo-1,2-dihydropyridine-3-carboxamide

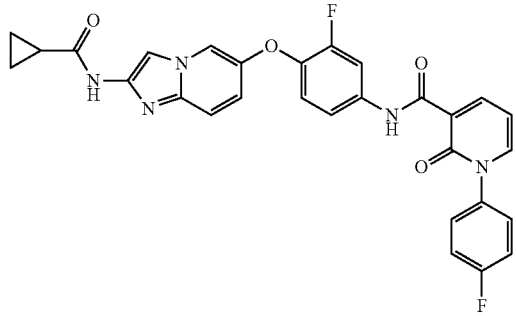 [SMILES: O=C(Nc1ccc(Oc2ccc3nc(NC(=O)C4CC4)cn3c2)c(F)c1)c1cccn(-c2ccc(F)cc2)c1=O]

To a solution of N-[6-(4-amino-2-fluorophenoxy)imidazo[1,2-a]pyridin-2-yl]cyclopropanecarboxamide (150 mg, 0.460 mmol) in N,N-dimethylacetamide (3.0 mL) were added 1-(4-fluorophenyl)-2-oxo-1,2-dihydropyridine-3-carboxylic acid (161 mg, 0.689 mmol), HATU (262 mg, 0.689 mmol) and N,N-diisopropylethylamine (120 μL, 0.689 mmol), and the mixture was stirred at room temperature for 2 hr. Water and saturated aqueous sodium hydrogen carbonate were added to the reaction mixture, and the mixture was extracted with ethyl acetate. The organic layer was washed with saturated brine, dried over anhydrous magnesium sulfate and filtered. The solvent was evaporated under reduced pressure, and the residue was washed with ethyl acetate and collected by filtration to give the title compound (269 mg, 81%) as a pale-yellow solid.

¹H-NMR (DMSO-d₆, 300 MHz) δ 0.76-0.81 (4H, m), 1.85-1.96 (1H, m), 6.69-6.75 (1H, m), 7.08-7.19 (2H, m), 7.34-7.45 (4H, m), 7.58-7.63 (2H, m), 7.94-7.99 (1H, m), 8.03 (1H, s), 8.10-8.14 (1H, m), 8.47 (1H, d, J=1.8 Hz), 8.57 (1H, dd, J=7.4, 2.3 Hz), 10.94 (1H, br s), 12.03 (1H, s).

Example 11

N-[4-({2-[(cyclopropylcarbonyl)amino]imidazo[1,2-a]pyridin-6-yl}oxy)-3-fluorophenyl]-N'-(4-fluorophenyl)cyclopropane-1,1-dicarboxamide

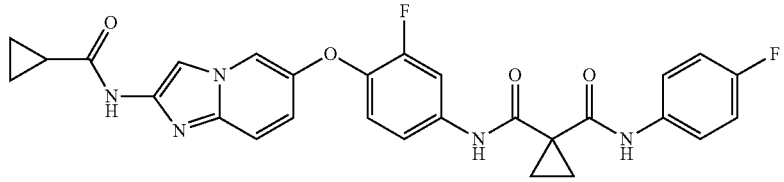 [SMILES: O=C(Nc1cn2cc(Oc3ccc(NC(=O)C4(C(=O)Nc5ccc(F)cc5)CC4)cc3F)ccc2n1)C1CC1]

To a solution of N-[6-(4-amino-2-fluorophenoxy)imidazo[1,2-a]pyridin-2-yl]cyclopropanecarboxamide (150 mg, 0.460 mmol) in N,N-dimethylacetamide (3.0 mL) were added 1-[(4-fluorophenyl)carbamoyl]cyclopropanecarboxylic acid (154 mg, 0.689 mmol), HATU (262 mg, 0.689 mmol) and N,N-diisopropylethylamine (120 μL, 0.689 mmol), and the mixture was stirred at room temperature for 4 hr. Saturated aqueous sodium hydrogen carbonate was added to the reaction mixture, and the mixture was extracted with ethyl acetate/tetrahydrofuran. The organic layer was washed with saturated brine, dried over anhydrous magnesium sulfate and filtered. The solvent was evaporated under reduced pressure, and the residue was purified by silica gel column chromatography (hexane/ethyl acetate=40/60→0/100), washed with hexane/ethyl acetate and collected by filtration to give the title compound (99 mg, 41%) as a white solid.

¹H-NMR (DMSO-d₆, 300 MHz) δ 0.76-0.81 (4H, m), 1.42-1.47 (4H, m), 1.86-1.96 (1H, m), 7.05-7.18 (4H, m), 7.33-7.45 (2H, m), 7.60-7.66 (2H, m), 7.81 (1H, dd, J=13.8, 2.4 Hz), 8.02 (1H, s), 8.43 (1H, d, J=2.1 Hz), 9.99 (1H, br s), 10.24 (1H, br s), 10.93 (1H, s).

Example 12

Production of N-[4-({2-[(cyclopropylcarbonyl)amino]imidazo[1,2-a]pyridin-6-yl}oxy)-3-fluorophenyl]-2-oxo-1-phenyl-1,2-dihydropyridine-3-carboxamide

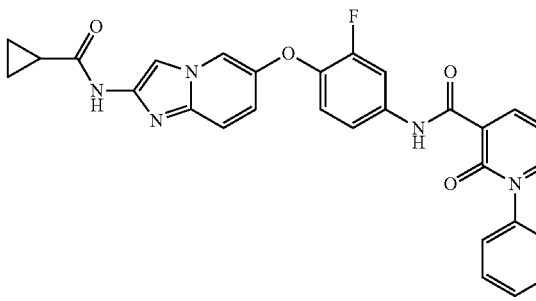

Example 13

Production of N-[4-({2-[(cyclopropylcarbonyl)amino]imidazo[1,2-a]pyridin-6-yl}oxy)phenyl]-2-oxo-1-(4-fluorophenyl)-1,2-dihydropyridine-3-carboxamide

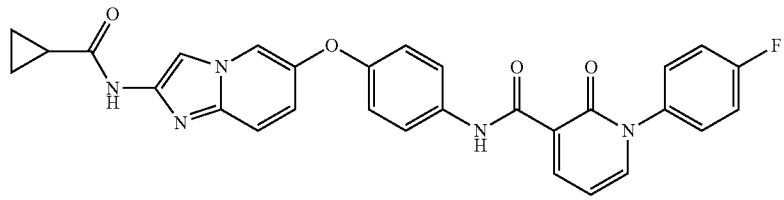 [SMILES: O=C(Nc1ccc(Oc2ccc3nc(NC(=O)C4CC4)cn3c2)cc1)c1cccn(-c2ccc(F)cc2)c1=O]

Using N-[6-(4-aminophenoxy)imidazo[1,2-a]pyridin-2-yl]cyclopropanecarboxamide (150 mg, 0.486 mmol), N,N-dimethylacetamide (3.0 mL), 1-(4-fluorophenyl)-2-oxo-1,2-dihydropyridine-3-carboxylic acid (170 mg, 0.729 mmol), HATU (277 mg, 0.729 mmol) and N,N-diisopropylethylamine (127 µL, 0.729 mmol) and in the same manner as in Example 10, the title compound (181 mg, 71%) was obtained as a white solid.

$^1$H-NMR (DMSO-$d_6$, 300 MHz) δ 0.76-0.82 (4H, m), 1.85-1.96 (1H, m), 6.68-6.74 (1H, m), 7.00-7.10 (3H, m), 7.37-7.48 (3H, m), 7.56-7.72 (4H, m), 8.04 (1H, s), 8.08-8.12 (1H, m), 8.50-8.51 (1H, m), 8.54-8.58 (1H, m), 10.95 (1H, s), 11.89 (1H, s).

Example 14

Production of N-[4-({2-[(cyclopropylcarbonyl)amino]imidazo[1,2-a]pyridin-6-yl}oxy)-3-fluorophenyl]-N'-phenylcyclopropane-1,1-dicarboxamide

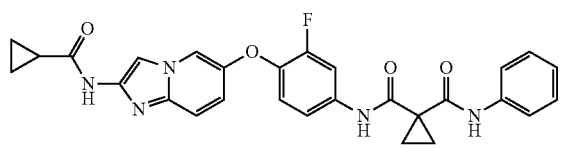 [SMILES: O=C(Nc1cn2cc(Oc3ccc(NC(=O)C4(C(=O)Nc5ccccc5)CC4)cc3F)ccc2n1)C1CC1]

To a solution of N-[6-(4-amino-2-fluorophenoxy)imidazo[1,2-a]pyridin-2-yl]cyclopropanecarboxamide (400 mg, 1.23 mmol) in N,N-dimethylacetamide (4.0 mL) were added 1-(phenylcarbamoyl)cyclopropanecarboxylic acid (352 mg, 1.72 mmol), HATU (699 mg, 1.84 mmol) and N,N-diisopropylethylamine (320 µL, 1.84 mmol), and the mixture was stirred at room temperature for 3 hr. Water and saturated aqueous sodium hydrogen carbonate were added to the reaction mixture, and the mixture was extracted with ethyl acetate/tetrahydrofuran. The organic layer was washed with saturated brine, dried over anhydrous magnesium sulfate and filtered. The solvent was evaporated under reduced pressure, and the residue was purified by silica gel column chromatography (hexane/ethyl acetate=40/60→0/100). The obtained powder was recrystallized from methyl ethyl ketone/water (=20/1) to give the title compound (294 mg, 47%) as white crystals.

$^1$H-NMR (DMSO-$d_6$, 300 MHz) δ 0.75-0.83 (4H, m), 1.43-1.48 (4H, m), 1.85-1.96 (1H, m), 7.02-7.18 (3H, m), 7.26-7.46 (4H, m), 7.62 (2H, dd, J=8.6, 1.1 Hz), 7.81 (1H, dd, J=13.5, 2.7 Hz), 8.03 (1H, s), 8.42-8.44 (1H, m), 9.98 (1H, br s), 10.22 (1H, s), 10.94 (1H, s).

Example 15

Production of N-[4-({2-[(cyclopropylcarbonyl)amino]imidazo[1,2-a]pyridin-6-yl}oxy)-3-fluorophenyl]-N'-phenylcyclopropane-1,1-dicarboxamide hydrochloride

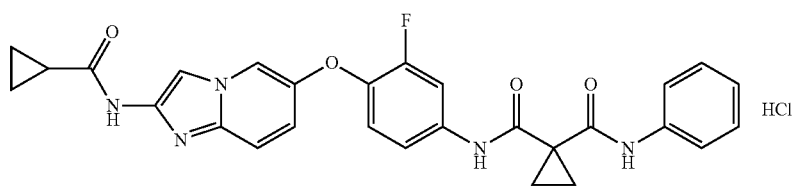 [SMILES: O=C(Nc1cn2cc(Oc3ccc(NC(=O)C4(C(=O)Nc5ccccc5)CC4)cc3F)ccc2n1)C1CC1 ; Cl]

A suspension of N-[4-({2-[(cyclopropylcarbonyl)amino]imidazo[1,2-a]pyridin-6-yl}oxy)-3-fluorophenyl]-N'-phenylcyclopropane-1,1-dicarboxamide (960 mg, 1.87 mmol) in methyl ethyl ketone (9.6 mL) was stirred with heating at 60° C., and 6N hydrochloric acid was added. The mixture was cooled to room temperature and left standing for 20 hr. The precipitate was filtered and washed with methyl ethyl ketone to give the title compound (697 mg, 68%) as white crystals.

$^1$H-NMR (DMSO-$d_6$, 300 MHz) δ 0.85-0.94 (4H, m), 1.44-1.51 (4H, m), 1.90-1.99 (1H, m), 7.03-7.10 (1H, m), 7.21-7.34 (3H, m), 7.41-7.52 (2H, m), 7.60-7.64 (2H, m), 7.70 (1H, d, J=9.6 Hz), 7.82-7.87 (1H, m), 8.06 (1H, s), 8.57 (1H, d, J=1.8 Hz), 9.99 (1H, s), 10.32 (1H, s), 11.66 (1H, s).

Example 16

Production of N-[4-({2-[(cyclopropylcarbonyl)amino]imidazo[1,2-a]pyridin-6-yl}oxy)-2-fluorophenyl]-1-(4-fluorophenyl)-6-methyl-2-oxo-1,2-dihydropyridine-3-carboxamide

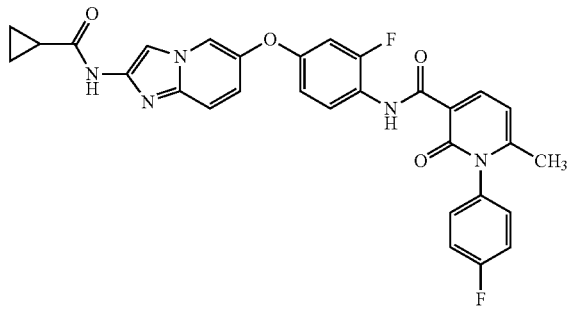 [SMILES: Cc1ccc(C(=O)Nc2ccc(Oc3ccc4nc(NC(=O)C5CC5)cn4c3)cc2F)c(=O)n1-c1ccc(F)cc1]

To a solution of N-[6-(4-amino-3-fluorophenoxy)imidazo[1,2-a]pyridin-2-yl]cyclopropanecarboxamide (150 mg, 0.46 mmol) in N,N-dimethylacetamide (3.0 mL) were added 1-(4-fluorophenyl)-6-methyl-2-oxo-1,2-dihydropyridine-3-carboxylic acid (170 mg, 0.689 mmol), HATU (262 mg, 0.689 mmol) and N,N-diisopropylethylamine (120 µL, 0.689 mmol), and the mixture was stirred at room temperature for 20 hr. Saturated aqueous sodium hydrogen carbonate was added to the reaction mixture, and the mixture was extracted with ethyl acetate/tetrahydrofuran. The organic layer was washed with saturated brine, dried over anhydrous magnesium sulfate and filtered. The solvent was evaporated under reduced pressure, and the residue was washed with ethyl acetate and collected by filtration to give the title compound (208 mg, 81%) as a white solid.

$^1$H-NMR (DMSO-$d_6$, 300 MHz) δ 0.77-0.81 (4H, m), 1.86-1.96 (1H, m), 2.07 (3H, s), 6.70 (1H, d, J=8.1 Hz), 6.86-6.92 (1H, m), 7.06-7.12 (2H, m), 7.40-7.52 (5H, m), 8.04 (1H, s), 8.37-8.56 (3H, m), 10.97 (1H, s), 12.04 (1H, s).

Example 17

Production of N-[4-({2-[(cyclopropylcarbonyl)amino]imidazo[1,2-a]pyridin-6-yl}oxy)-2-fluorophenyl]-N'-(4-fluorophenyl)cyclopropane-1,1-dicarboxamide

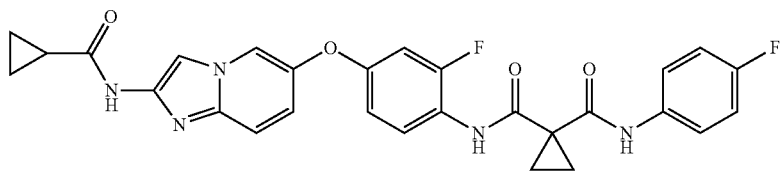 [SMILES: O=C(Nc1cn2cc(Oc3ccc(NC(=O)C4(C(=O)Nc5ccc(F)cc5)CC4)c(F)c3)ccc2n1)C1CC1]

To a solution of N-[6-(4-amino-3-fluorophenoxy)imidazo[1,2-a]pyridin-2-yl]cyclopropanecarboxamide (150 mg, 0.46 mmol) in N,N-dimethylacetamide (3.0 mL) were added 1-[(4-fluorophenyl)carbamoyl]cyclopropanecarboxylic acid (170 mg, 0.689 mmol), HATU (262 mg, 0.689 mmol) and N,N-diisopropylethylamine (120 µL, 0.689 mmol), and the mixture was stirred at room temperature for 20 hr. Saturated aqueous sodium hydrogen carbonate was added to the reaction mixture, and the mixture was extracted with ethyl acetate/tetrahydrofuran. The organic layer was washed with saturated brine, dried over anhydrous magnesium sulfate and filtered. The solvent was evaporated under reduced pressure, and the residue was purified by silica gel column chromatography (NH silica gel, ethyl acetate alone). The obtained powder was washed with hexane/ethyl acetate and collected by filtration to give the title compound (115 mg, 47%) as a white solid.

$^1$H-NMR (DMSO-$d_6$, 300 MHz) δ 0.77-0.82 (4H, m), 1.51-1.59 (4H, s), 1.87-1.96 (1H, m), 6.82-6.88 (1H, m), 7.00-7.20 (4H, m), 7.47 (1H, d, J=9.6 Hz), 7.56-7.63 (2H, m), 7.72-7.80 (1H, m), 8.05 (1H, s), 8.57 (1H, d, J=1.5 Hz), 10.00 (1H, s), 10.37 (1H, s), 10.97 (1H, s).

Example 18

Production of N-[4-({2-[(cyclopropylcarbonyl)amino]-1,3-benzothiazol-6-yl}oxy)-3-fluorophenyl]-N'-phenylcyclopropane-1,1-dicarboxamide

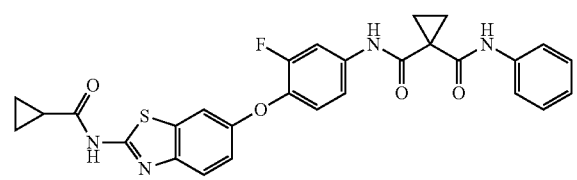 [SMILES: O=C(Nc1nc2ccc(Oc3ccc(NC(=O)C4(C(=O)Nc5ccccc5)CC4)cc3F)cc2s1)C1CC1]

To a solution of 1-(phenylcarbamoyl)cyclopropanecarboxylic acid (214 mg, 1.04 mmol) in tetrahydrofuran (2 mL) were added oxalyl chloride (178 μL, 2.08 μmol) and N,N-dimethylformamide (2 drops) under ice-cooling, and the mixture was stirred at room temperature for 3 hr. The solvent was evaporated under reduced pressure. To a solution of the obtained residue in N,N-dimethylacetamide (5 mL) was added N-[6-(4-amino-2-fluorophenoxy)-1,3-benzothiazol-2-yl]cyclopropanecarboxamide (275 mg, 0.80 mmol), and the mixture was stirred at room temperature for 18 hr. Water was added to the reaction solution, and the mixture was extracted with ethyl acetate. The solvent was evaporated under reduced pressure, and the residue was purified by silica gel column chromatography (hexane/ethyl acetate=80/20→20/80, NH silica gel, hexane/ethyl acetate=50/50→0/100) and recrystallized from ethyl acetate to give the title compound (241 mg, 57%) as white crystals.

$^1$H-NMR (DMSO-d$_6$, 300 MHz) δ 0.89-0.97 (4H, m), 1.44-1.47 (4H, m), 1.95-2.06 (1H, m), 7.03-7.19 (3H, m), 7.25-7.43 (3H, m), 7.56 (1H, d, J=2.7 Hz), 7.60-7.64 (2H, m), 7.70 (1H, d, J=8.7 Hz), 7.81 (1H, dd, J=13.5, 2.4 Hz), 9.99 (1H, s), 10.24 (1H, s), 12.59 (1H, s).

Example 19

Production of tert-butyl [4-({2-[(cyclopropylcarbonyl)amino][1,3]thiazolo[5,4-b]pyridin-5-yl}oxy)-3-fluorophenyl]carbamate

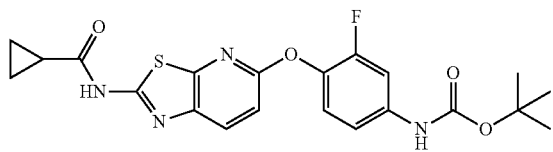 [SMILES: CC(C)(C)OC(=O)Nc1ccc(Oc2ccc3nc(NC(=O)C4CC4)sc3n2)c(F)c1]

To a solution of tert-butyl {4-[(2-amino[1,3]thiazolo[5,4-b]pyridin-5-yl)oxy]-3-fluorophenyl}carbamate (2.02 g, 5.37 mmol) in N,N-dimethylacetamide (20.2 mL) were added cyclopropanecarbonyl chloride (0.97 mL, 10.7 mmol) and triethylamine (2.24 mL, 16.1 mmol), and the mixture was stirred at room temperature for 24 hr. Water was added to the reaction mixture, and the mixture was extracted with ethyl acetate. The organic layer was washed with saturated brine, dried over anhydrous magnesium sulfate and filtered. The solvent was evaporated under reduced pressure, methanol (20 mL) and 5% aqueous sodium carbonate solution (10 mL) were added to the residue, and the mixture was stirred at room temperature for 3 hr. The reaction mixture was extracted with ethyl acetate/tetrahydrofuran. The organic layer was washed with saturated brine, dried over anhydrous magnesium sulfate and filtered. The solvent was evaporated under reduced pressure, and the residue was washed with hexane/ethyl acetate (=1/1) and collected by filtration to give the title compound (1.33 g, 56%).

$^1$H-NMR (DMSO-d$_6$, 300 MHz) δ 0.92-0.99 (4H, m), 1.49 (9H, s), 1.85-1.95 (1H, m), 7.16 (1H, d, J=8.7 Hz), 7.24-7.27 (2H, m), 7.50-7.58 (1H, m), 8.16 (1H, d, J=8.7 Hz), 9.63 (1H, s), 12.67 (1H, br s).

Example 20

Production of N-[4-({2-[(cyclopropylcarbonyl)amino][1,3]thiazolo[5,4-b]pyridin-5-yl}oxy)-3-fluorophenyl]-N'-phenylcyclopropane-1,1-dicarboxamide

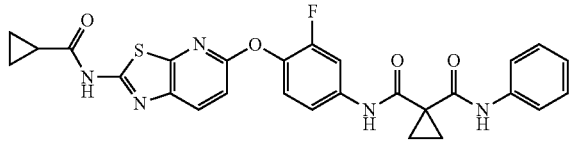 [SMILES: O=C(Nc1nc2ccc(Oc3ccc(NC(=O)C4(C(=O)Nc5ccccc5)CC4)cc3F)nc2s1)C1CC1]

To a solution of N-[5-(4-amino-2-fluorophenoxy)[1,3]thiazolo[5,4-b]pyridin-2-yl]cyclopropanecarboxamide (150 mg, 0.436 mmol) in N,N-dimethylacetamide (3.0 mL) were added 1-(phenylcarbamoyl)cyclopropanecarboxylic acid (134 mg, 0.653 mmol), HATU (248 mg, 0.653 mmol) and N,N-diisopropylethylamine (114 μL, 0.653 mmol), and the mixture was stirred at room temperature for 2 hr. Saturated aqueous sodium hydrogen carbonate was added to the reaction mixture, and the mixture was extracted with ethyl acetate/tetrahydrofuran. The organic layer was washed with saturated brine, dried over anhydrous magnesium sulfate and filtered. The solvent was evaporated under reduced pressure, and the residue was purified by silica gel column chromatography (ethyl acetate alone). The obtained powder was washed with hexane/ethyl acetate and collected by filtration to give the title compound (175 mg, 76%).

$^1$H-NMR (DMSO-d$_6$, 300 MHz) δ 0.89-0.98 (4H, m), 1.47 (4H, s), 1.94-2.03 (1H, m), 7.03-7.09 (1H, m), 7.18 (1H, d, J=8.9 Hz), 7.25-7.34 (3H, m), 7.40-7.46 (1H, m), 7.61-7.65 (2H, m), 7.79 (1H, dd, J=13.1, 2.3 Hz), 8.17 (1H, d, J=8.9 Hz), 10.01 (1H, s), 10.26 (1H, s), 12.68 (1H, br s).

Example 21

Production of N-[4-({2-[(cyclopropylcarbonyl)amino][1,3]thiazolo[5,4-b]pyridin-5-yl}oxy)-3-fluorophenyl]-1-(4-fluorophenyl)-6-methyl-2-oxo-1,2-dihydropyridine-3-carboxamide

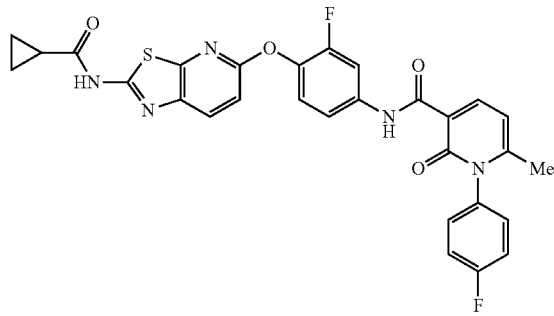 [SMILES: Cc1ccc(C(=O)Nc2ccc(Oc3ccc4nc(NC(=O)C5CC5)sc4n3)c(F)c2)c(=O)n1-c1ccc(F)cc1]

N-[5-(4-Amino-2-fluorophenoxy)[1,3]thiazolo[5,4-b]pyridin-2-yl]cyclopropanecarboxamide (240 mg, 0.70 mmol), 1-(4-fluorophenyl)-6-methyl-2-oxo-1,2-dihydropyridine-3-carboxylic acid (190 mg, 0.77 mmol) and HATU (340 mg, 0.91 mmol) were suspended in N,N'-dimethylformamide (3.0 mL), and N,N-diisopropylethylamine (0.24 mL, 1.4 mmol) was added. After stirring at room temperature for 8 hr, the mixture was diluted with ethyl acetate (5.0 mL) and tetrahydrofuran (5.0 mL). The mixture was washed twice with saturated aqueous sodium hydrogen carbonate solution, and the organic layer was dried over anhydrous sodium sulfate. The solvent was evaporated under reduced pressure, and ethyl acetate was added to the residue. The resulting precipitate was collected by filtration to give the title compound (350 mg, 0.61 mmol, 88%) as a pale-yellow solid.

$^1$H-NMR (DMSO-d$_6$, 300 MHz) δ 0.89-0.99 (4H, m), 1.93-2.03 (1H, m), 2.08 (3H, s), 6.71 (1H, d, J=8.3 Hz), 7.19 (1H, d, J=8.7 Hz), 7.32 (1H, t, J=8.8 Hz), 7.40-7.55 (5H, m), 7.95 (1H, dd, J=12.9, 2.4 Hz), 8.17 (1H, d, J=8.7 Hz), 8.50 (1H, d, J=7.6 Hz), 12.03 (1H, s), 12.69 (1H, s).

Example 22

Production of N-[4-({2-[(cyclopropylcarbonyl)amino]imidazo[1,2-a]pyridin-6-yl}oxy)-3-fluorophenyl]-1-(4-fluoro-2-methylphenyl)-6-methyl-2-oxo-1,2-dihydropyridine-3-carboxamide

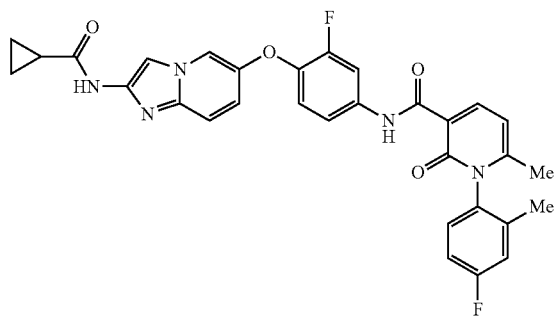 [SMILES: Cc1cc(F)ccc1-n1c(C)ccc(C(=O)Nc2ccc(Oc3ccc4nc(NC(=O)C5CC5)cn4c3)c(F)c2)c1=O]

N-[6-(4-Amino-2-fluorophenoxy)imidazo[1,2-a]pyridin-2-yl]cyclopropanecarboxamide (150 mg, 0.46 mmol), 1-(4-fluoro-2-methylphenyl)-6-methyl-2-oxo-1,2-dihydropyridine-3-carboxylic acid (130 mg, 0.51 mmol) and HATU (230 mg, 0.60 mmol) were suspended in N,N-dimethylformamide (3.0 mL), and N,N-diisopropylethylamine (0.16 mL, 0.92 mmol) was added. After stirring at room temperature for 8 hr, the reaction mixture was diluted with ethyl acetate (5.0 mL) and tetrahydrofuran (5.0 ml). The mixture was washed twice with saturated aqueous sodium hydrogen carbonate solution, and the organic layer was dried over anhydrous sodium sulfate. The solvent was evaporated under reduced pressure, ethyl acetate was added to the residue, and the resulting precipitate was collected by filtration. The obtained precipitate was recrystallized from ethanol/water to give the title compound (130 mg, 50%) as a white solid.

$^1$H-NMR (DMSO-d$_6$, 300 MHz) δ 0.74-0.83 (4H, m), 1.86-1.97 (1H, m), 2.00 (3H, s), 2.03 (3H, s), 6.75 (1H, d, J=8.1 Hz), 7.07-7.18 (2H, m), 7.21-7.30 (1H, m), 7.33-7.47 (4H, m), 7.97 (1H, dd, J=13.3, 2.4 Hz), 8.02 (1H, s), 8.45 (1H, d, J=1.9 Hz), 8.51 (1H, d, J=7.6 Hz), 10.93 (1H, s), 11.97 (1H, s).

Example 23

Production of N-[4-({2-[(cyclopropylcarbonyl)amino]imidazo[1,2-a]pyridin-6-yl}oxy)-3-fluorophenyl]-N'-(4-fluoro-2-methylphenyl)cyclopropane-1,1-dicarboxamide

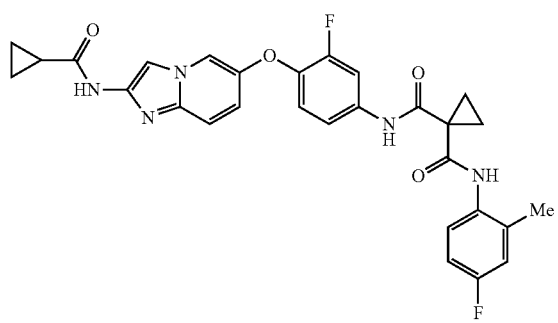 [SMILES: Cc1cc(F)ccc1NC(=O)C1(C(=O)Nc2ccc(Oc3ccc4nc(NC(=O)C5CC5)cn4c3)c(F)c2)CC1]

N-[6-(4-Amino-2-fluorophenoxy)imidazo[1,2-a]pyridin-2-yl]cyclopropanecarboxamide (150 mg, 0.46 mmol), 1-[(4-fluoro-2-methylphenyl)carbamoyl]cyclopropanecarboxylic acid (120 mg, 0.51 mmol) and HATU (230 mg, 0.60 mmol) were suspended in N,N-dimethylformamide (3.0 mL), and N,N-diisopropylethylamine (0.16 mL, 0.92 mmol) was added. After stirring at room temperature for 8 hr, the reaction mixture was diluted with ethyl acetate (5.0 mL) and tetrahydrofuran (5.0 mL). The mixture was washed twice with saturated aqueous sodium hydrogen carbonate solution, and the organic layer was dried over anhydrous sodium sulfate. The solvent was evaporated under reduced pressure, ethyl acetate was added to the residue, and the resulting precipitate was collected by filtration. The obtained precipitate was recrystallized from ethanol/water to give the title compound (110 mg, 45%) as a white solid.

$^1$H-NMR (DMSO-d$_6$, 300 MHz) δ 0.74-0.84 (4H, m), 1.52 (4H, s), 1.85-1.97 (1H, m), 2.20 (3H, s), 6.97-7.19 (4H, m), 7.34-7.40 (1H, m), 7.41-7.50 (2H, m), 7.75-7.85 (1H, m), 8.03 (1H, s), 8.44 (1H, d, J=1.9 Hz), 9.73 (1H, s), 10.41 (1H, s), 10.94 (1H, s).

Example 24

Production of N-[4-({2-[(cyclopropylcarbonyl)amino]imidazo[1,2-a]pyridin-6-yl}oxy)-3-fluorophenyl]-6-methyl-2-oxo-1-phenyl-1,2-dihydropyridine-3-carboxamide

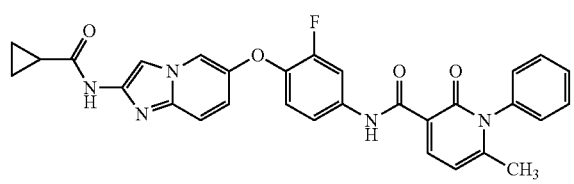 [SMILES: Cc1ccc(C(=O)Nc2ccc(Oc3ccc4nc(NC(=O)C5CC5)cn4c3)c(F)c2)c(=O)n1-c1ccccc1]

To a solution of N-[6-(4-amino-2-fluorophenoxy)imidazo[1,2-a]pyridin-2-yl]cyclopropanecarboxamide (70 mg, 0.215 mmol) and 6-methyl-2-oxo-1-phenyl-1,2-dihydropyridine-3-carboxylic acid (59.1 mg, 0.258 mmol) in N,N-dimethylformamide (1.0 mL) were added HATU (98 mg, 0.258 mmol) and N,N-diisopropylethylamine (74 μL, 0.43 mmol), and the mixture was stirred at room temperature for 17 hr. Ethyl acetate and saturated aqueous sodium hydrogen carbonate solution were added to the reaction mixture, and the mixture was extracted 3 times with ethyl acetate. The combined organic layer was washed with saturated brine, dried over anhydrous magnesium sulfate and filtered, and the solvent was evaporated under reduced pressure. The obtained residue was purified by silica gel column chromatography (ethyl acetate) to give a pale-yellow solid. The obtained pale-yellow solid was washed with ethyl acetate and collected by filtration to give the title compound (66 mg, 57%) as a white solid.

$^1$H-NMR (DMSO-d$_6$, 300 MHz) δ 0.70-0.85 (4H, m), 1.86-1.96 (1H, m), 2.06 (3H, s), 6.71 (1H, d, J=8.3 Hz), 7.07-7.17 (2H, m), 7.32-7.65 (7H, m), 7.96 (1H, dd, J=13.4, 2.5 Hz), 8.02 (1H, s), 8.42-8.52 (2H, m), 10.93 (1H, s), 12.02 (1H, s).

Example 25

Production of N-[4-({2-[(cyclopropylcarbonyl)amino]imidazo[1,2-a]pyridin-6-yl}oxy)-3-fluorophenyl]-5-methyl-6-phenylpyridine-2-carboxamide 1-oxide

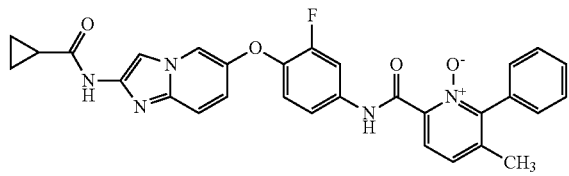 [SMILES: Cc1ccc(C(=O)Nc2ccc(Oc3ccc4nc(NC(=O)C5CC5)cn4c3)c(F)c2)[n+]([O-])c1-c1ccccc1]

To a solution of N-[6-(4-amino-2-fluorophenoxy)imidazo[1,2-a]pyridin-2-yl]cyclopropanecarboxamide (98.8 mg, 0.303 mmol) and 5-methyl-6-phenylpyridine-2-carboxylic acid 1-oxide (83.1 mg, 0.363 mmol) in N,N-dimethylformamide (1.0 mL) were added HATU (150 mg, 0.394 mmol) and N,N-diisopropylethylamine (104 μL, 0.606 mmol), and the mixture was stirred at room temperature for 3.5 hr. Ethyl acetate and saturated aqueous sodium hydrogen carbonate solution were added to the reaction mixture, and the mixture was extracted 3 times with ethyl acetate. The combined organic layer was washed with saturated brine, dried over anhydrous magnesium sulfate and filtered, and the solvent was evaporated under reduced pressure. The obtained residue was purified by silica gel column chromatography (NH silica gel, ethyl acetate) to give a white solid. The obtained solid was washed with ethyl acetate to give the title compound (100 mg, 61%) as a white solid.

$^1$H-NMR (DMSO-d$_6$, 300 MHz) δ 0.72-0.86 (4H, m), 1.85-1.98 (1H, m), 2.12 (3H, s), 7.05-7.21 (2H, m), 7.36-7.61 (7H, m), 7.70 (1H, d, J=8.9 Hz), 7.98 (1H, dd, J=13.0, 2.5 Hz), 8.03 (1H, s), 8.31 (1H, d, J=8.3 Hz), 8.49 (1H, d, J=1.7 Hz), 10.94 (1H, s), 13.79 (1H, s).

Example 26

Production of N-[4-({2-[(cyclopropylcarbonyl)amino]imidazo[1,2-a]pyridin-6-yl}oxy)-3-fluorophenyl]-6-ethyl-2-oxo-1-phenyl-1,2-dihydropyridine-3-carboxamide

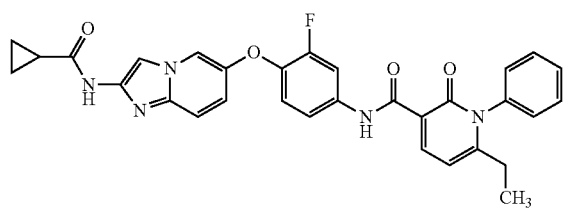 [SMILES: CCc1ccc(C(=O)Nc2ccc(Oc3ccc4nc(NC(=O)C5CC5)cn4c3)c(F)c2)c(=O)n1-c1ccccc1]

To a solution of N-[6-(4-amino-2-fluorophenoxy)imidazo[1,2-a]pyridin-2-yl]cyclopropanecarboxamide (100 mg, 0.306 mmol) and 6-ethyl-2-oxo-1-phenyl-1,2-dihydropyridine-3-carboxylic acid (89 mg, 0.366 mmol) in N,N-dimethylformamide (1.0 mL) were added HATU (151 mg, 0.397 mmol) and N,N-diisopropylethylamine (105 μL, 0.612 mmol), and the mixture was stirred at room temperature for 17 hr. Ethyl acetate and saturated aqueous sodium hydrogen carbonate solution were added to the reaction mixture, and the mixture was extracted with ethyl acetate. The organic layer was washed with saturated brine, dried over anhydrous magnesium sulfate and filtered, and the solvent was evaporated under reduced pressure. The obtained residue was purified by silica gel column chromatography (ethyl acetate) to give a white solid. The obtained white solid was washed with ethyl acetate to give the title compound (100 mg, 59%) as a white solid.

$^1$H-NMR (DMSO-d$_6$, 300 MHz) δ 0.73-0.85 (4H, m), 1.05 (3H, t, J=7.4 Hz), 1.82-2.01 (1H, m), 2.30 (2H, q, J=7.4 Hz), 6.68 (1H, d, J=7.7 Hz), 7.05-7.21 (2H, m), 7.31-7.48 (4H, m), 7.49-7.66 (3H, m), 7.97 (1H, dd, J=13.2, 2.5 Hz), 8.02 (1H, s), 8.45 (1H, d, J=1.7 Hz), 8.53 (1H, d, J=7.7 Hz), 10.94 (1H, s), 12.02 (1H, s).

Example 27

Production of N-[4-({2-[(cyclopropylcarbonyl)amino]imidazo[1,2-a]pyridin-6-yl}oxy)-3-fluorophenyl]-1-(4-fluorophenyl)-6-methyl-2-oxo-1,2-dihydropyridine-3-carboxamide

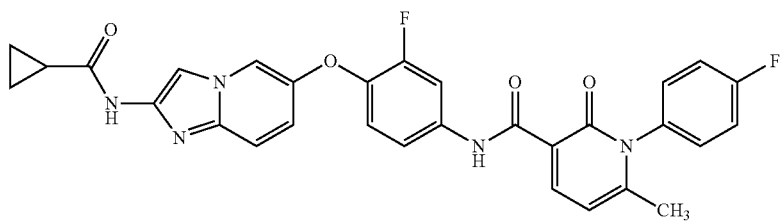 [SMILES: Cc1ccc(C(=O)Nc2ccc(Oc3ccc4nc(NC(=O)C5CC5)cn4c3)c(F)c2)c(=O)n1-c1ccc(F)cc1]

To a solution of N-[6-(4-amino-2-fluorophenoxy)imidazo[1,2-a]pyridin-2-yl]cyclopropanecarboxamide (100 mg, 0.306 mmol) and 1-(4-fluorophenyl)-6-methyl-2-oxo-1,2-dihydropyridine-3-carboxylic acid (90.8 mg, 0.367 mmol) in N,N-dimethylformamide (1.0 mL) were added HATU (151 mg, 0.397 mmol) and N,N-diisopropylethylamine (105 μL, 0.612 mmol), and the mixture was stirred at room temperature for 20 hr. Ethyl acetate and saturated aqueous sodium hydrogen carbonate solution were added to the reaction mixture, and the mixture was extracted 3 times with ethyl acetate. The combined organic layer was washed with saturated brine, dried over anhydrous magnesium sulfate and filtered, and the solvent was evaporated under reduced pressure. The obtained residue was purified by silica gel column chromatography (ethyl acetate) to give a white solid. The obtained white solid was washed with ethyl acetate to give the title compound (131 mg, 77%) as a white solid.

$^1$H-NMR (DMSO-d$_6$, 300 MHz) δ 0.66-0.92 (4H, m), 1.87-1.93 (1H, m), 2.07 (3H, s), 6.70 (1H, d, J=7.6 Hz), 7.01-7.18 (2H, m), 7.26-7.56 (6H, m), 7.97 (1H, d, J=13.4 Hz), 8.02 (1H, s), 8.40-8.54 (2H, m), 10.93 (1H, s), 11.98 (1H, s).

Example 28

Production of N-[4-({2-[(cyclopropylcarbonyl)amino]imidazo[1,2-a]pyridin-6-yl}oxy)phenyl]-1-(4-fluorophenyl)-6-methyl-2-oxo-1,2-dihydropyridine-3-carboxamide

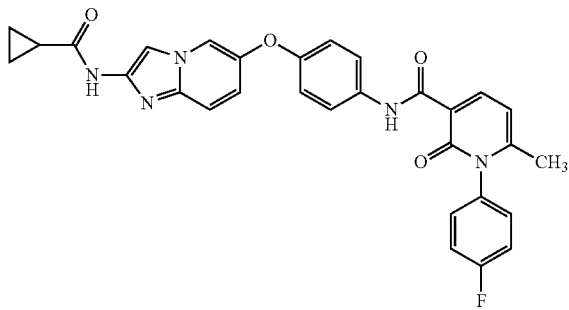 [SMILES: Cc1ccc(C(=O)Nc2ccc(Oc3ccc4nc(NC(=O)C5CC5)cn4c3)cc2)c(=O)n1-c1ccc(F)cc1]

To a solution of N-[6-(4-aminophenoxy)imidazo[1,2-a]pyridin-2-yl]cyclopropanecarboxamide (100 mg, 0.324 mmol) and 1-(4-fluorophenyl)-6-methyl-2-oxo-1,2-dihydropyridine-3-carboxylic acid (96.1 mg, 0.389 mmol) in N,N-dimethylformamide (1.0 mL) were added HATU (147.8 mg, 0.389 mmol) and N,N-diisopropylethylamine (111.6 μL, 0.648 mmol), and the mixture was stirred at room temperature for 20 hr. Tetrahydrofuran, ethyl acetate and saturated aqueous sodium hydrogen carbonate solution were added to the reaction mixture, and the mixture was extracted 3 times with ethyl acetate. The combined organic layer was washed with saturated brine, dried over anhydrous magnesium sulfate and filtered, and the solvent was evaporated under reduced pressure. The obtained residue was washed with tetrahydrofuran and collected by filtration to give the title compound (154 mg, 88%) as a white solid.

$^1$H-NMR (DMSO-d$_6$, 300 MHz) δ 0.68-0.86 (4H, m), 1.89-1.95 (1H, m), 2.06 (3H, s), 6.60-6.76 (1H, m), 6.93-7.12 (3H, m), 7.37-7.53 (5H, m), 7.63-7.73 (2H, m), 8.03 (1H, s), 8.40-8.54 (2H, m), 10.94 (1H, s), 11.83 (1H, s).

Example 29

Production of N-[4-({2-[(cyclopropylcarbonyl)amino]imidazo[1,2-a]pyridin-6-yl}oxy)-3-fluorophenyl]-6-(4-fluorophenyl)-5-methylpyridine-2-carboxamide 1-oxide

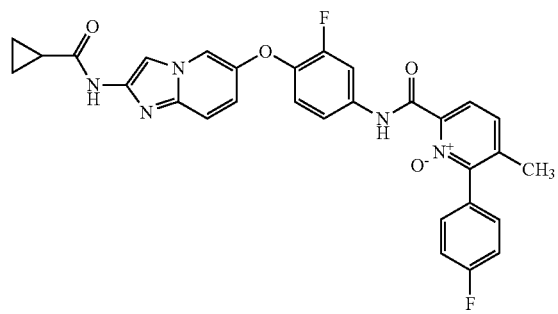

To a solution of N-[6-(4-amino-2-fluorophenoxy)imidazo[1,2-a]pyridin-2-yl]cyclopropanecarboxamide (100 mg, 0.306 mmol) and 6-(4-fluorophenyl)-5-methylpyridine-2-carboxylic acid 1-oxide (98.9 mg, 0.367 mmol) in N,N-dimethylformamide (1.0 mL) were added HATU (140 mg, 0.368 mmol) and N,N-diisopropylethylamine (105 μL, 0.612 mmol), and the mixture was stirred at room temperature for 3 hr. Ethyl acetate and saturated aqueous sodium hydrogen carbonate solution were added to the reaction mixture, and the mixture was extracted twice with ethyl acetate. The combined organic layer was washed with saturated brine, dried over anhydrous magnesium sulfate and filtered, and the solvent was evaporated under reduced pressure. The obtained residue was purified by silica gel column chromatography (ethyl acetate) to give a white solid. The obtained white solid was washed with ethyl acetate to give the title compound (80 mg, 47%) as white crystals.

$^1$H-NMR (DMSO-d$_6$, 300 MHz) δ 0.66-0.89 (4H, m), 1.87-1.97 (1H, m), 2.13 (3H, s), 7.07-7.22 (2H, m), 7.33-7.55 (6H, m), 7.69 (1H, d, J=8.9 Hz), 7.98 (1H, dd, J=13.0, 2.5 Hz), 8.03 (1H, s), 8.31 (1H, d, J=8.3 Hz), 8.48 (1H, d, J=1.7 Hz), 10.94 (1H, s), 13.73 (1H, s).

Example 30

Production of N-[4-({2-[(cyclopropylcarbonyl)amino]imidazo[1,2-a]pyridin-6-yl}oxy)-3-fluorophenyl]-6-methyl-2-oxo-1-phenyl-1,2-dihydropyridine-3-carboxamide hydrochloride

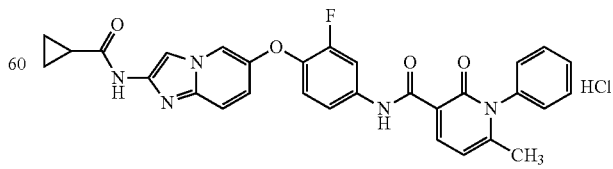

To a suspension of N-[4-({2-[(cyclopropylcarbonyl)amino]imidazo[1,2-a]pyridin-6-yl}oxy)-3-fluorophenyl]-6- methyl-2-oxo-1-phenyl-1,2-dihydropyridine-3-carboxamide (464 mg, 0.864 mmol) in ethanol was added and dissolved therein 6N hydrochloric acid (86.4 μL, 1.04 mmol). The solution was concentrated to a half amount, and left standing for 17 hr. The precipitate was collected by filtration and washed with ethanol to give a pale-yellow solid (458 mg).

A suspension of pale-yellow solid (100 mg) in methyl ethyl ketone (10 mL) was stirred at 60° C. for 17 hr. The precipitate was filtered, washed with methyl ethyl ketone and collected by filtration to give the title compound (80 mg).

To the title compound (80 mg) was added a pale-yellow solid (358 mg), after which methyl ethyl ketone (4 mL) was added, and the mixture was stirred at 60° C. for 6 hr. The precipitate was collected by filtration to give the title compound (330 mg, 67%) as a white solid.

$^1$H-NMR (DMSO-$d_6$, 300 MHz) δ 0.80-0.93 (4H, m), 1.88-2.00 (1H, m), 2.07 (3H, s), 6.72 (1H, d, J=8.3 Hz), 7.24 (1H, t, J=9.1 Hz), 7.37-7.75 (8H, m), 8.01 (1H, dd, J=13.2, 2.5 Hz), 8.06 (1H, s), 8.49 (1H, d, J=7.6 Hz), 8.59 (1H, d, J=2.1 Hz), 11.65 (1H, br s), 12.07 (1H, s).

Example 31

Production of N-[4-({2-[(cyclopropylcarbonyl)amino]imidazo[1,2-a]pyridin-6-yl}oxy)-3-fluorophenyl]-6-(4-fluorophenyl)-5-methylpyridine-2-carboxamide 1-oxide hydrochloride

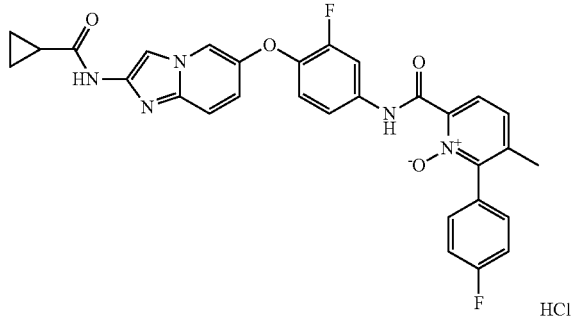

To a suspension of N-[4-({2-[(cyclopropylcarbonyl)amino]imidazo[1,2-a]pyridin-6-yl}oxy)-3-fluorophenyl]-6-(4-fluorophenyl)-5-methylpyridine-2-carboxamide 1-oxide (1.54 g, 2.77 mmol) in ethanol (15 mL) was added and dissolved therein 6N hydrochloric acid (554 μL, 3.32 mmol), and the mixture was left standing at room temperature overnight. The precipitate was collected by filtration and washed with ethanol to give a white powder. The white powder was dissolved in ethyl acetate, tetrahydrofuran and saturated aqueous sodium hydrogen carbonate solution, and the mixture was extracted twice with ethyl acetate. The combined organic layer was washed with saturated brine, dried over anhydrous magnesium sulfate and filtered, and the solvent was evaporated under reduced pressure. The residue was suspended in ethanol (30 mL) and heated to 80° C. 6N Hydrochloric acid (370 μL, 2.22 mmol) was added dropwise and dissolved therein. The solution was allowed to gradually cool to 50° C., and the mixture was stirred for 6 hr. The precipitate was collected by filtration and washed with ethanol to give a white solid. The white solid was suspended in methyl ethyl ketone (10 mL), and the suspension was stirred at 50° C. overnight. The precipitate was collected by filtration and washed with methyl ethyl ketone to give the title compound (747 mg, 46%) as white crystals.

$^1$H-NMR (300 MHz, DMSO-$d_6$) δ 0.80-0.97 (4H, m), 1.88-2.06 (1H, m), 2.13 (3H, s), 7.20-7.44 (3H, m), 7.46-7.82 (6H, m), 8.03 (1H, dd, J=13.1, 2.4 Hz), 8.09 (1H, s), 8.31 (1H, d, J=8.3 Hz), 8.66 (1H, d, J=1.7 Hz), 11.91 (1H, s), 13.77 (1H, s).

Example 32

Production of N-[4-({2-[(cyclopropylcarbonyl)amino]imidazo[1,2-a]pyridin-6-yl}oxy)-3-fluorophenyl]-1-(4-fluorophenyl)-6-methyl-2-oxo-1,2-dihydropyridine-3-carboxamide hydrochloride

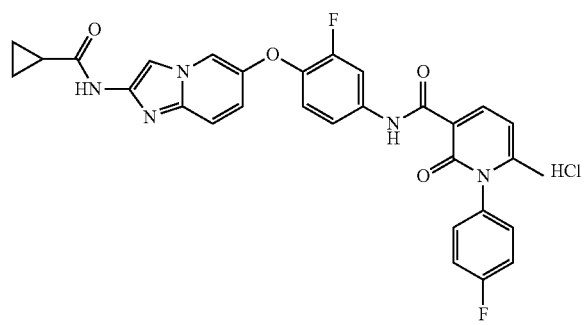 [SMILES: Cc1ccc(C(=O)Nc2ccc(Oc3ccc4nc(NC(=O)C5CC5)cn4c3)c(F)c2)c(=O)n1-c1ccc(F)cc1 ; Cl]

To a suspension of N-[4-({2-[(cyclopropylcarbonyl)amino]imidazo[1,2-a]pyridin-6-yl}oxy)-3-fluorophenyl]-1-(4-fluorophenyl)-6-methyl-2-oxo-1,2-dihydropyridine-3-carboxamide (1.42 g, 2.55 mmol) in ethanol (14 mL) and water (2 mL) was added and dissolved therein 6N hydrochloric acid (510 μL, 3.06 mmol), and the solution was concentrated to a half amount, and left standing for 1 hr. The precipitate was collected by filtration to give white crystals. The white crystals were suspended in ethanol (50 mL) again, 6N hydrochloric acid (205 μL, 1.53 mmol) was added, and the mixture was dissolved at 70° C. The solution was left standing at room temperature for 6 hr. The precipitate was collected by filtration to give a white solid. The white solid (850 mg) was dissolved in ethyl acetate, tetrahydrofuran and saturated aqueous sodium hydrogen carbonate solution, and the mixture was extracted 3 times with ethyl acetate. The combined organic layer was washed with saturated brine, dried over anhydrous magnesium sulfate and filtered, and the solvent was evaporated under reduced pressure. The residue was suspended in ethanol (20 mL), heated to 80° C. and dissolved by dropwise addition of 6N hydrochloric acid (358 μL, 2.15 mmol). The solution was allowed to gradually cool to 50° C., and the mixture was stirred overnight. The precipitate was collected by filtration and washed with ethanol to give a white solid. The white solid was suspended in methyl ethyl ketone (10 mL), and the mixture was stirred at 50° C. overnight. The precipitate was collected by filtration and washed with methyl ethyl ketone to give the title compound (590 mg, 39%) as white crystals.

$^1$H-NMR (300 MHz, DMSO-$d_6$) δ 0.83-0.97 (4H, m), 1.90-2.03 (1H, m), 2.08 (3H, s), 6.71 (1H, d, J=8.1 Hz), 7.25 (1H, t, J=9.1 Hz), 7.35-7.61 (6H, m), 7.75 (1H, d, J=9.8 Hz), 8.02 (1H, dd, J=13.2, 2.5 Hz), 8.08 (1H, s), 8.49 (1H, d, J=7.6 Hz), 8.62 (1H, d, J=1.9 Hz), 11.85 (1H, s), 12.03 (1H, s).

Example 33

Production of N-[4-({2-[(cyclopropylcarbonyl)amino]imidazo[1,2-a]pyridin-6-yl}oxy)-3-fluorophenyl]-1-(2-methylphenyl)-2-oxo-1,2-dihydropyridine-3-carboxamide

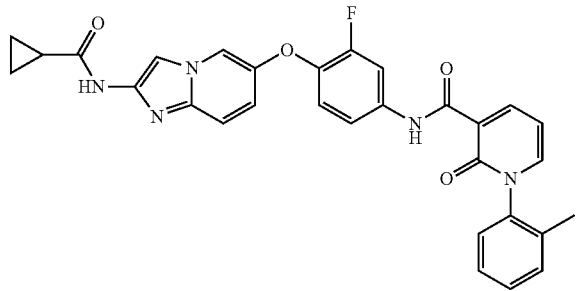 [SMILES: Cc1ccccc1-n1cccc(C(=O)Nc2ccc(Oc3ccc4nc(NC(=O)C5CC5)cn4c3)c(F)c2)c1=O]

Using N-[6-(4-amino-2-fluorophenoxy)imidazo[1,2-a]pyridin-2-yl]cyclopropanecarboxamide (200 mg, 0.613 mmol), 1-(2-methylphenyl)-2-oxo-1,2-dihydropyridine-3-carboxylic acid (169 mg, 0.735 mmol), N,N-dimethylformamide (2 mL), N,N-diisopropylethylamine (211 μL, 1.23 mmol) and HATU (280 mg, 0.735 mmol) and in the same manner as in Example 24, the title compound (177 mg, 54%) was obtained as pale-yellow crystals.

$^1$H-NMR (300 MHz, DMSO-$d_6$) δ 0.61-0.95 (4H, m), 1.87-1.95 (1H, m), 2.08 (3H, s), 6.64-6.83 (1H, m), 7.04-7.24 (2H, m), 7.33-7.53 (6H, m), 7.91-8.09 (3H, m), 8.46 (1H, d, J=1.7 Hz), 8.61 (1H, dd, J=7.3, 2.2 Hz), 10.94 (1H, s), 12.07 (1H, s).

Example 34

Production of N-[4-({2-[(cyclopropylcarbonyl)amino][1,2,4]triazolo[1,5-a]pyridin-6-yl}oxy)-3-fluorophenyl]-N'-phenylcyclopropane-1,1-dicarboxamide

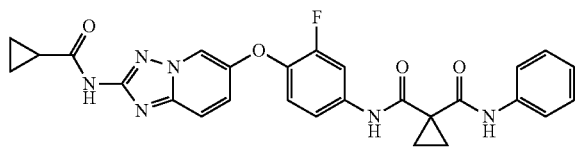

Using N-[6-(4-amino-2-fluorophenoxy) [1,2,4]triazolo[1,5-a]pyridin-2-yl]cyclopropanecarboxamide (120 mg, 0.367 mmol), 1-(phenylcarbamoyl)cyclopropanecarboxylic acid (90.4 mg, 0.440 mmol), N,N-dimethylformamide (1 mL), N,N-diisopropylethylamine (126 μL, 0.733 mmol) and HATU (209 mg, 0.550 mmol) and in the same manner as in Example 24, the title compound (151 mg, 80%) was obtained as white crystals.

$^1$H-NMR (300 MHz, DMSO-$d_6$) δ 0.71-0.86 (4H, m), 1.43-1.50 (4H, m), 1.97-2.09 (1H, m), 7.03-7.10 (1H, m), 7.19 (1H, t, J=9.2 Hz), 7.26-7.41 (3H, m), 7.51 (1H, dd, J=9.6, 2.3 Hz), 7.58-7.65 (2H, m), 7.71 (1H, d, J=9.6 Hz), 7.82 (1H, dd, J=13.5, 2.4 Hz), 8.78 (1H, d, J=1.7 Hz), 9.98 (1H, s), 10.24 (1H, s), 11.03 (1H, s).

Example 35

Production of N-[4-({2-[(cyclopropylcarbonyl)amino]imidazo[1,2-a]pyridin-6-yl}oxy)-3-fluorophenyl]-1-methyl-3-oxo-2-phenyl-5-(trifluoromethyl)-2,3-dihydro-1H-pyrazole-4-carboxamide

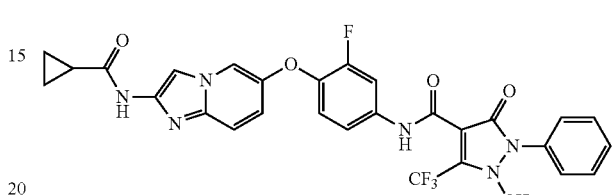

A mixture of 1-methyl-3-oxo-2-phenyl-5-(trifluoromethyl)-2,3-dihydro-1H-pyrazole-4-carboxylic acid (450 mg, 1.6 mmol), N-[6-(4-amino-2-fluorophenoxy)imidazo[1,2-a]pyridin-2-yl]cyclopropanecarboxamide (360 mg, 1.1 mmol), HATU (590 mg, 1.6 mmol), diisopropylethylamine (430 mg, 3.3 mmol) and N,N-dimethylformamide (7 mL) was stirred at room temperature for 13 hr. Ethyl acetate/tetrahydrofuran and saturated aqueous sodium hydrogen carbonate solution were added to the mixture, and the aqueous layer was extracted 4 times with ethyl acetate/tetrahydrofuran. The combined organic layer was washed with saturated brine, dried over anhydrous sodium sulfate and filtered. The filtrate was concentrated under reduced pressure, and the residue was purified by silica gel column chromatography (NH silica gel, ethyl acetate/hexane=40/60→100/0) to give the title compound (320 mg, 48%) as a pale-yellow solid.

$^1$H-NMR (DMSO-$d_6$, 300 MHz) δ 0.75-0.84 (4H, m), 1.85-1.97 (1H, m), 3.52 (3H, s), 7.11 (1H, dd, J=9.6, 2.5 Hz), 7.17 (1H, t, J=9.0 Hz), 7.26-7.32 (1H, m), 7.44 (1H, d, J=9.6 Hz), 7.53-7.69 (5H, m), 7.88 (1H, dd, J=13.1, 2.4 Hz), 8.03 (1H, s), 8.45 (1H, d, J=1.7 Hz), 10.93 (1H, s), 10.97 (1H, s).

Example 36

Production of N-[4-({2-[(cyclopropylcarbonyl)amino]imidazo[1,2-a]pyridin-6-yl}oxy)-3-fluorophenyl]-1-methyl-3-oxo-2-phenyl-2,3-dihydro-1H-pyrazole-4-carboxamide

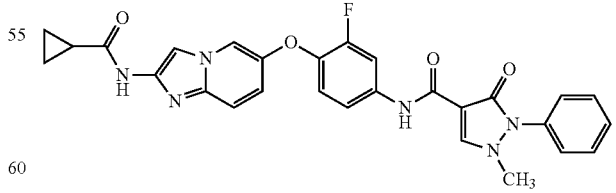

Using 1-methyl-3-oxo-2-phenyl-2,3-dihydro-1H-pyrazole-4-carboxylic acid (220 mg, 0.99 mmol), N-[6-(4-amino-2-fluorophenoxy)imidazo[1,2-a]pyridin-2-yl]cyclopropanecarboxamide (220 mg, 0.66 mmol), HATU (380 mg, 0.99 mmol), diisopropylethylamine (260 mg, 2.0 mmol) and N,N- dimethylformamide (6 mL) as starting materials and in the same manner as in Example 35, the title compound (50 mg, 15%) was obtained as a white solid.

$^1$H-NMR (DMSO-d$_6$, 300 MHz) δ 0.74-0.84 (4H, m), 1.86-1.97 (1H, m), 3.48 (3H, s), 7.11 (1H, dd, J=9.6, 2.5 Hz), 7.16 (1H, t, J=9.0 Hz), 7.21-7.27 (1H, m), 7.43 (1H, d, J=9.6 Hz), 7.46-7.64 (5H, m), 7.90 (1H, dd, J=13.3, 2.5 Hz), 8.02 (1H, s), 8.44 (1H, d, J=1.9 Hz), 8.62 (1H, s), 10.45 (1H, s), 10.93 (1H, s).

Example 37

Production of N-[4-({2-[(cyclopropylcarbonyl)amino]imidazo[1,2-a]pyridin-6-yl}oxy)-3-fluorophenyl]-3-oxo-2-phenyl-1-(2,2,2-trifluoroethyl)-2,3-dihydro-1H-pyrazole-4-carboxamide

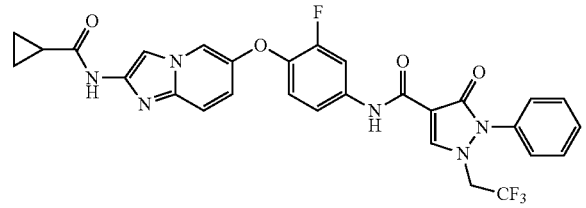 [SMILES: O=C(Nc1ccc(Oc2ccc3nc(NC(=O)C4CC4)cn3c2)c(F)c1)c1cn(CC(F)(F)F)n(-c2ccccc2)c1=O]

Using 3-oxo-2-phenyl-1-(2,2,2-trifluoroethyl)-2,3-dihydro-1H-pyrazole-4-carboxylic acid (210 mg, 0.72 mmol), N-[6-(4-amino-2-fluorophenoxy)imidazo[1,2-a]pyridin-2-yl]cyclopropanecarboxamide (170 mg, 0.52 mmol), HATU (280 mg, 0.72 mmol), diisopropylethylamine (200 mg, 1.6 mmol) and N,N-dimethylformamide (6 mL) as starting materials and in the same manner as in Example 35, the title compound (240 mg, 77%) was obtained as a white solid.

$^1$H-NMR (DMSO-d$_6$, 300 MHz) δ 0.74-0.84 (4H, m), 1.87-1.97 (1H, m), 4.90 (2H, q, J=8.5 Hz), 7.11 (1H, dd, J=9.6, 2.3 Hz), 7.17 (1H, t, J=9.0 Hz), 7.27-7.33 (1H, m), 7.40-7.46 (3H, m), 7.50-7.65 (3H, m), 7.89 (1H, dd, J=13.1, 2.3 Hz), 8.03 (1H, s), 8.46 (1H, d, J=1.9 Hz), 8.87 (1H, s), 10.26 (1H, s), 10.94 (1H, s).

Example 38

Production of N-[4-({2-[(cyclopropylcarbonyl)amino]imidazo[1,2-a]pyridin-6-yl}oxy)-3-fluorophenyl]-1-ethyl-3-oxo-2-phenyl-2,3-dihydro-1H-pyrazole-4-carboxamide

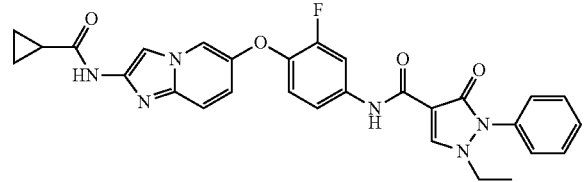 [SMILES: CCn1cc(C(=O)Nc2ccc(Oc3ccc4nc(NC(=O)C5CC5)cn4c3)c(F)c2)c(=O)n1-c1ccccc1]

Using 1-ethyl-3-oxo-2-phenyl-2,3-dihydro-1H-pyrazole-4-carboxylic acid (270 mg, 1.2 mmol), N-[6-(4-amino-2-fluorophenoxy)imidazo[1,2-a]pyridin-2-yl]cyclopropanecarboxamide (260 mg, 0.79 mmol), HATU (450 mg, 1.2 mmol), diisopropylethylamine (300 mg, 2.4 mmol) and N,N-dimethylformamide (6 mL) as starting materials and in the same manner as in Example 35, the title compound (140 mg, 34%) was obtained as a white solid.

$^1$H-NMR (DMSO-d$_6$, 300 MHz) δ 0.75-0.83 (4H, m), 1.07 (3H, t, J=7.2 Hz), 1.87-1.96 (1H, m), 3.88 (2H, q, J=7.2 Hz), 7.11 (1H, dd, J=9.7, 2.4 Hz), 7.16 (1H, t, J=8.9 Hz), 7.22-7.28 (1H, m), 7.40-7.66 (6H, m), 7.90 (1H, dd, J=13.3, 2.4 Hz), 8.02 (1H, s), 8.44 (1H, d, J=1.7 Hz), 8.71 (1H, s), 10.43 (1H, s), 10.93 (1H, s).

Example 39

Production of N-[4-({2-[(cyclopropylcarbonyl)amino]imidazo[1,2-a]pyridin-6-yl}oxy)-3-fluorophenyl]-1-(2,6-dimethylphenyl)-2-oxo-1,2-dihydropyridine-3-carboxamide

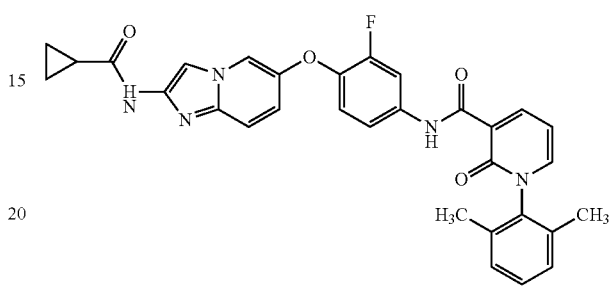

1-(2,6-Dimethylphenyl)-2-oxo-1,2-dihydropyridine-3-carboxylic acid (120 mg, 0.51 mmol), N-[6-(4-amino-2-fluorophenoxy)imidazo[1,2-a]pyridin-2-yl]cyclopropanecarboxamide (150 mg, 0.46 mmol) and HATU (340 mg, 0.91 mmol) were suspended in N,N-dimethylformamide (3.0 mL), and N,N-diisopropylethylamine (0.16 mL, 0.92 mmol) was added. After stirring at room temperature overnight, the mixture was diluted with ethyl acetate (5.0 mL) and tetrahydrofuran (5.0 mL). The mixture was washed twice with saturated aqueous sodium hydrogen carbonate solution, and the organic layer was dried over anhydrous sodium sulfate. The solvent was evaporated under reduced pressure, and the residue was purified by silica gel column chromatography (ethyl acetate/hexane=65/35→85/15). The fractions containing the object product were mixed. The solvent was evaporated under reduced pressure, and a small amount of hexane/ethyl acetate was added. The resulting precipitate was collected by filtration to give the title compound (130 mg, 49%) as a white solid.

$^1$H-NMR (DMSO-d$_6$, 300 MHz) δ 0.80 (4H, d, J=2.3 Hz), 1.86-1.97 (1H, m), 2.02 (6H, s), 6.81 (1H, d, J=7.0 Hz), 7.07-7.19 (2H, m), 7.24-7.41 (4H, m), 7.44 (1H, d, J=9.6 Hz), 7.93-8.04 (3H, m), 8.46 (1H, d, J=1.9 Hz), 8.64 (1H, dd, J=7.3, 2.2 Hz), 10.94 (1H, s), 12.07 (1H, s).

Example 40

Production of N-[4-({2-[(cyclopropylcarbonyl)amino]imidazo[1,2-a]pyridin-6-yl}oxy)-3-fluorophenyl]-1-[2-(1-methylethyl)phenyl]-2-oxo-1,2-dihydropyridine-3-carboxamide

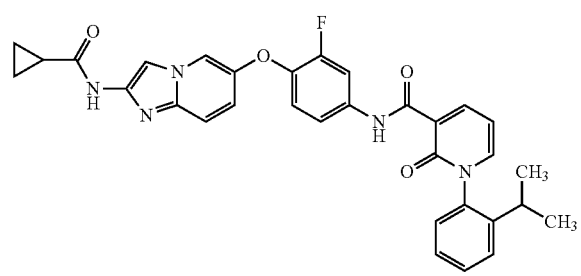 [SMILES: CC(C)c1ccccc1-n1cccc(C(=O)Nc2ccc(Oc3ccc4nc(NC(=O)C5CC5)cn4c3)c(F)c2)c1=O]

1-[2-(1-Methylethyl)phenyl]-2-oxo-1,2-dihydropyridine-3-carboxylic acid (100 mg, 0.39 mmol), N-[6-(4-amino-2-fluorophenoxy)imidazo[1,2-a]pyridin-2-yl]cyclopropanecarboxamide (120 mg, 0.35 mmol) and HATU (170 mg, 0.45 mmol) were suspended in N,N-dimethylformamide (3.0 mL), and N,N-diisopropylethylamine (0.12 mL, 0.71 mmol) was added. After stirring at room temperature overnight, the mixture was diluted with ethyl acetate (5.0 mL) and tetrahydrofuran (5.0 mL). The mixture was washed twice with saturated aqueous sodium hydrogen carbonate solution, and the organic layer was dried over anhydrous magnesium sulfate. The solvent was evaporated under reduced pressure, and the residue was purified by silica gel column chromatography (ethyl acetate/hexane=65/35→85/15). The fractions containing the object product were mixed. The solvent was evaporated under reduced pressure, and a small amount of hexane/ethyl acetate (=2/1) was added. The resulting precipitate was collected by filtration to give the title compound (53 mg, 27%) as a white solid.

$^1$H-NMR (DMSO-d$_6$, 300 MHz) δ 0.79 (4H, d, J=2.5 Hz), 1.12 (3H, d, J=6.8 Hz), 1.16 (3H, d, J=7.2 Hz), 1.86-1.97 (1H, m), 2.52-2.62 (1H, m), 6.75 (1H, d, J=7.2 Hz), 7.06-7.21 (2H, m), 7.31-7.47 (4H, m), 7.48-7.60 (2H, m), 7.97 (1H, dd, J=13.2, 2.5 Hz), 8.02 (1H, s), 8.10 (1H, dd, J=6.5, 2.2 Hz), 8.45 (1H, d, J=1.9 Hz), 8.62 (1H, dd, J=7.3, 2.2 Hz), 10.94 (1H, s), 12.08 (1H, s).

Example 41

Production of 1-(2-chloro-4-fluorophenyl)-N-[4-({2-[(cyclopropylcarbonyl)amino]imidazo[1,2-a]pyridin-6-yl}oxy)-3-fluorophenyl]-6-methyl-2-oxo-1,2-dihydropyridine-3-carboxamide

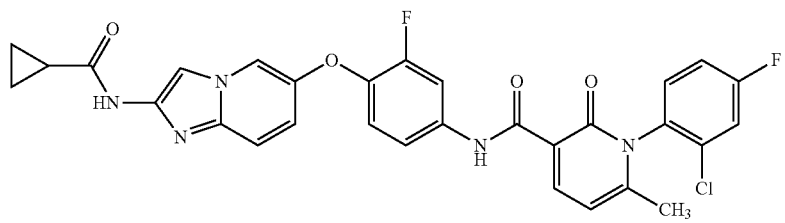 [SMILES: Cc1ccc(C(=O)Nc2ccc(Oc3ccc4nc(NC(=O)C5CC5)cn4c3)c(F)c2)c(=O)n1-c1ccc(F)cc1Cl]

A mixture of N-[6-(4-amino-2-fluorophenoxy)imidazo[1,2-a]pyridin-2-yl]cyclopropanecarboxamide (150 mg, 0.459 mmol), 1-(2-chloro-4-fluorophenyl)-6-methyl-2-oxo-1,2-dihydropyridine-3-carboxylic acid (168 mg, 0.597 mmol), HATU (262 mg, 0.689 mmol), N,N-diisopropylethylamine (160 μL, 0.919 mmol) and N,N-dimethylformamide (3 mL) was stirred at room temperature for 18 hr. After dilution with ethyl acetate, the mixture was washed with saturated aqueous sodium hydrogen carbonate solution and saturated brine, dried over anhydrous magnesium sulfate and filtered. The solvent was evaporated under reduced pressure, and the residue was purified by silica gel column chromatography (NH silica gel, 30 g, ethyl acetate/hexane=2/98→100/0), silica gel column chromatography (30 g, ethyl acetate/hexane=0/100→100/0) and preparative HPLC (acetonitrile/water=40/60→50/50, containing 0.1% trifluoroacetic acid) to give the title compound (101 mg, 37%) as a white solid.

$^1$H-NMR (DMSO-d$_6$, 300 MHz) δ 0.74-0.83 (4H, m), 1.86-1.97 (1H, m), 2.07 (3H, s), 6.75-6.80 (1H, m), 7.07-7.18 (2H, m), 7.35-7.41 (1H, m), 7.44 (1H, d, J=9.6 Hz), 7.47-7.55 (1H, m), 7.71-7.78 (1H, m), 7.83 (1H, dd, J=8.5, 2.8 Hz), 7.97 (1H, dd, J=13.4, 2.4 Hz), 8.02 (1H, s), 8.46 (1H, dd, J=2.4, 0.6 Hz), 8.54 (1H, d, J=7.5 Hz), 10.95 (1H, s), 11.81 (1H, s).

Example 42

Production of 1-(2-bromo-4-fluorophenyl)-N-[4-({2-[(cyclopropylcarbonyl)amino]imidazo[1,2-a]pyridin-6-yl}oxy)-3-fluorophenyl]-6-methyl-2-oxo-1,2-dihydropyridine-3-carboxamide

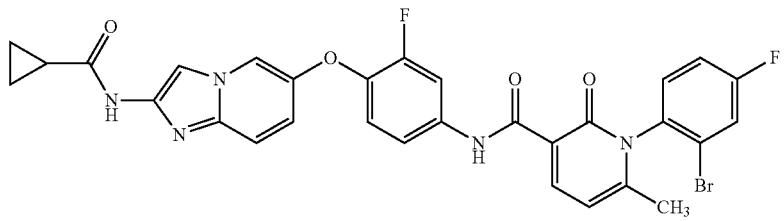 [SMILES: Cc1ccc(C(=O)Nc2ccc(Oc3ccc4nc(NC(=O)C5CC5)cn4c3)c(F)c2)c(=O)n1-c1ccc(F)cc1Br]

A mixture of N-[6-(4-amino-2-fluorophenoxy)imidazo[1,2-a]pyridin-2-yl]cyclopropanecarboxamide (150 mg, 0.459 mmol), 1-(2-bromo-4-fluorophenyl)-6-methyl-2-oxo-1,2-dihydropyridine-3-carboxylic acid (146 mg, 0.448 mmol), HATU (262 mg, 0.689 mmol), N,N-diisopropylethylamine (160 μl, 0.919 mmol) and N,N-dimethylformamide (3 mL) was stirred at room temperature for 3 days. After dilution with ethyl acetate, the mixture was washed with saturated aqueous sodium hydrogen carbonate solution and saturated brine, dried over anhydrous magnesium sulfate and filtered. The solvent was evaporated under reduced pressure, and the residue was purified by silica gel column chromatography (NH silica gel, 30 g, ethyl acetate/hexane=2/98→100/0) and preparative HPLC (acetonitrile/water=40/60→50/50, containing 0.1% trifluoroacetic acid) to give the title compound (152 mg, 52%) as a white solid.

$^1$H-NMR (DMSO-d$_6$, 300 MHz) δ 0.75-0.82 (4H, m), 1.86-1.97 (1H, m), 2.06 (3H, s), 6.75-6.80 (1H, m), 7.07-7.18 (2H, m), 7.35-7.47 (2H, m), 7.50-7.58 (1H, m), 7.69-7.76 (1H, m), 7.90-8.01 (2H, m), 8.02 (1H, s), 8.44-8.47 (1H, m), 8.54 (1H, d, J=7.5 Hz), 10.94 (1H, s), 11.84 (1H, s).

Example 43

Production of N-[4-({2-[(cyclopropylcarbonyl)amino]imidazo[1,2-a]pyridin-6-yl}oxy)-3-fluorophenyl]-1-(4-fluorophenyl)-6-(1-methylethyl)-2-oxo-1,2-dihydropyridine-3-carboxamide

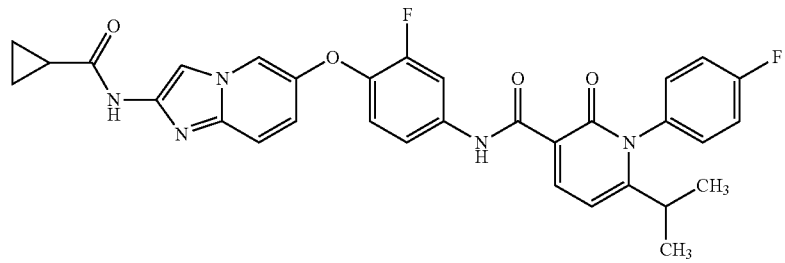 [SMILES: CC(C)c1ccc(C(=O)Nc2ccc(Oc3ccc4nc(NC(=O)C5CC5)cn4c3)c(F)c2)c(=O)n1-c1ccc(F)cc1]

A mixture of N-[6-(4-amino-2-fluorophenoxy)imidazo[1,2-a]pyridin-2-yl]cyclopropanecarboxamide (150 mg, 0.459 mmol), 1-(4-fluorophenyl)-6-(1-methylethyl)-2-oxo-1,2-dihydropyridine-3-carboxylic acid (151 mg, 0.551 mmol), HATU (262 mg, 0.689 mmol), N,N-diisopropylethylamine (240 μL, 1.37 mmol) and N,N-dimethylformamide (3 mL) was stirred at room temperature for 4 days. After dilution with ethyl acetate, the mixture was washed with saturated aqueous sodium hydrogen carbonate solution and saturated brine, dried over anhydrous magnesium sulfate and filtered. The solvent was evaporated under reduced pressure, and the residue was purified by silica gel column chromatography (NH silica gel, 30 g, ethyl acetate/hexane=2/98-+80/20) to give the title compound (157 mg, 58%) as a white powder.

$^1$H-NMR (DMSO-$d_6$, 300 MHz) δ 0.74-0.82 (4H, m), 1.12 (6H, d, J=6.8 Hz), 1.87-1.97 (1H, m), 2.44-2.56 (1H, m), 6.76 (1H, d, J=7.9 Hz), 7.07-7.18 (2H, m), 7.33-7.39 (1H, m), 7.39-7.49 (3H, m), 7.49-7.57 (2H, m), 7.97 (1H, dd, J=13.2, 2.4 Hz), 8.02 (1H, s), 8.45 (1H, dd, J=2.4, 0.6 Hz), 8.54 (1H, d, J=7.9 Hz), 10.93 (1H, s), 11.97 (1H, s).

Example 44

Production of N-[4-({2-[(cyclopropylcarbonyl)amino]imidazo[1,2-a]pyridin-6-yl}oxy)-2-fluorophenyl]-1-(2,4-difluorophenyl)-6-methyl-2-oxo-1,2-dihydropyridine-3-carboxamide

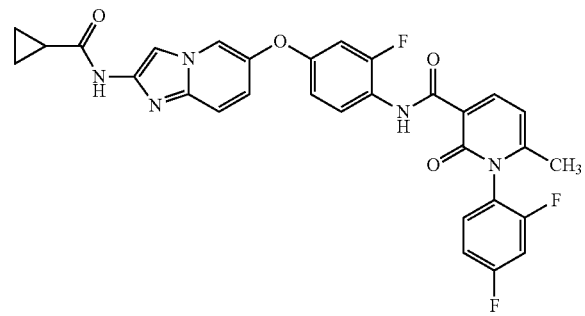 [SMILES: Cc1ccc(C(=O)Nc2ccc(Oc3ccc4nc(NC(=O)C5CC5)cn4c3)cc2F)c(=O)n1-c1ccc(F)cc1F]

To a solution of N-[6-(4-amino-2-fluorophenoxy)imidazo[1,2-a]pyridin-2-yl]cyclopropanecarboxamide (200 mg, 0.613 mmol) and 1-(2,4-difluorophenyl)-6-methyl-2-oxo-1,2-dihydropyridine-3-carboxylic acid (244 mg, 0.919 mmol) in N,N-dimethylacetamide (2.0 mL) were added HATU (350 mg, 0.919 mmol) and N,N-diisopropylethylamine (160 μL, 0.919 mmol), and the mixture was stirred at room temperature for 3 hr. Saturated aqueous sodium hydrogen carbonate solution was added to the reaction mixture, and the mixture was extracted with ethyl acetate/tetrahydrofuran, washed with saturated brine, dried over anhydrous magnesium sulfate and filtered. The solvent was evaporated under reduced pressure. The obtained residue was washed with ethyl acetate and collected by filtration to give the title compound (284 mg, 81%) as a white solid.

$^1$H-NMR (DMSO-$d_6$, 300 MHz) δ 0.77-0.81 (4H, m), 1.86-1.99 (1H, m), 2.12 (3H, s), 6.76 (1H, d, J=8.4 Hz), 6.87-6.94 (1H, m), 7.07-7.13 (2H, m), 7.31-7.40 (1H, m), 7.46 (1H, d, J=9.9 Hz), 7.58-7.76 (2H, m), 8.04 (1H, s), 8.39 (1H, t, J=9.2 Hz), 8.51-8.56 (2H, m), 10.96 (1H, s), 11.84 (1H, d, J=1.8 Hz).

Example 45

Production of N-[4-({2-[(cyclopropylcarbonyl)amino]imidazo[1,2-a]pyridin-6-yl}oxy)-3-fluorophenyl]-1-(3,4-difluorophenyl)-6-methyl-2-oxo-1,2-dihydropyridine-3-carboxamide

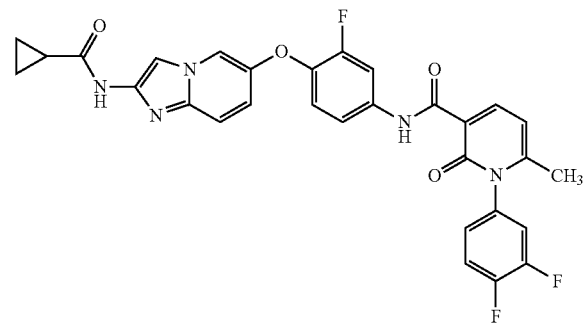 [SMILES: Cc1ccc(C(=O)Nc2ccc(Oc3ccc4nc(NC(=O)C5CC5)cn4c3)c(F)c2)c(=O)n1-c1ccc(F)c(F)c1]

Using a solution of N-[6-(4-amino-2-fluorophenoxy)imidazo[1,2-a]pyridin-2-yl]cyclopropanecarboxamide (200 mg, 0.613 mmol) and 1-(3,4-difluorophenyl)-6-methyl-2-oxo-1,2-dihydropyridine-3-carboxylic acid (244 mg, 0.919 mmol) in N,N-dimethylacetamide (2.0 mL), HATU (350 mg, 0.919 mmol) and N,N-diisopropylethylamine (160 μL, 0.919 mmol) and in the same manner as in Example 44, the title compound (301 mg, 86%) was obtained as a white solid.

¹H-NMR (DMSO-d₆, 300 MHz) δ 0.76-0.80 (4H, m), 1.87-1.97 (1H, m), 2.10 (3H, s), 6.71 (1H, d, J=7.8 Hz), 7.08-7.14 (2H, m), 7.33-7.46 (3H, m), 7.64-7.74 (2H, m), 7.94-7.97 (1H, m), 8.02 (1H, s), 8.44-8.50 (2H, m), 10.93 (1H, s), 11.91 (1H, d, J=1.8 Hz).

Example 46

Production of N-[4-({2-[(cyclopropylcarbonyl)amino]imidazo[1,2-a]pyridin-6-yl}oxy)-3-fluorophenyl]-1,5-dimethyl-3-oxo-2-phenyl-2,3-dihydro-1H-pyrazole-4-carboxamide

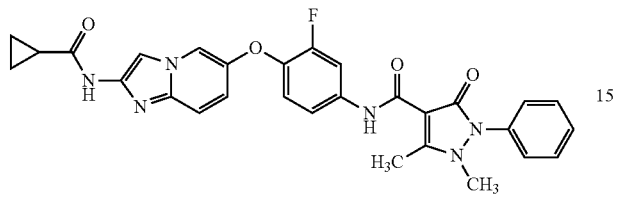

A mixture of 1,5-dimethyl-3-oxo-2-phenyl-2,3-dihydro-1H-pyrazole-4-carboxylic acid (279 mg, 1.2 mmol), N-[6-(4-amino-2-fluorophenoxy)imidazo[1,2-a]pyridin-2-yl]cyclopropanecarboxamide (265 mg, 0.81 mmol), HATU (460 mg, 1.2 mmol), N,N-diisopropylethylamine (320 mg, 2.4 mmol) and N,N-dimethylformamide (9 mL) was stirred at room temperature for 18 hr. Ethyl acetate/tetrahydrofuran and saturated aqueous sodium hydrogen carbonate solution were added to the mixture, and the aqueous layer was extracted with ethyl acetate/tetrahydrofuran (×3). The combined organic layer was washed with saturated brine, dried over anhydrous magnesium sulfate and filtered. The filtrate was concentrated under reduced pressure, and the residue was purified by silica gel column chromatography (NH silica gel, ethyl acetate/hexane=40/60→100/0) to give the title compound (300 mg, 69%) as a white solid.

¹H-NMR (DMSO-d₆, 300 MHz) δ 0.75-0.83 (4H, m), 1.86-1.97 (1H, m), 2.70 (3H, s), 3.36 (3H, s), 7.07-7.24 (3H, m), 7.40-7.46 (3H, m), 7.47-7.63 (3H, m), 7.90 (1H, dd, J=13.4, 2.3 Hz), 8.03 (1H, s), 8.44 (1H, d, J=1.9 Hz), 10.86 (1H, s), 10.93 (1H, s).

Example 47

Production of N-[4-({2-[(cyclopropylcarbonyl)amino]imidazo[1,2-a]pyridin-6-yl}oxy)-3-fluorophenyl]-1-methyl-3-oxo-2-phenyl-2,3-dihydro-1H-pyrazole-4-carboxamide•hydrochloride

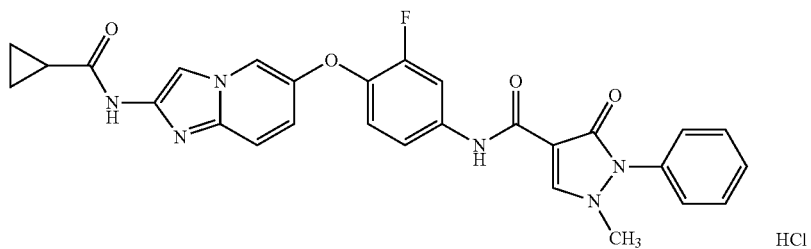 [SMILES: Cn1cc(C(=O)Nc2ccc(Oc3ccc4nc(NC(=O)C5CC5)cn4c3)c(F)c2)c(=O)n1-c1ccccc1 ; Cl]

To a suspension of N-[4-({2-[(cyclopropylcarbonyl)amino]imidazo[1,2-a]pyridin-6-yl}oxy)-3-fluorophenyl]-1-methyl-3-oxo-2-phenyl-2,3-dihydro-1H-pyrazole-4-carboxamide (480 mg, 0.92 mmol) in methyl ethyl ketone (7 mL) was slowly added 6N aqueous hydrochloric acid solution (4 mL) and then water (4 mL), and the mixture was stirred at 80° C. for 5 min. The mixture was cooled to room temperature and stirred at room temperature for 3 hr. The precipitated solid was collected by filtration, washed with methyl ethyl ketone and dried under reduced pressure to give the title compound (410 mg, 79%) as a white solid.

¹H-NMR (DMSO-d₆, 300 MHz) δ 0.83-0.93 (4H, m), 1.90-2.00 (1H, m), 3.49 (3H, s), 7.22-7.33 (2H, m), 7.45-7.64 (6H, m), 7.70 (1H, d, J=9.6 Hz), 7.95 (1H, dd, J=13.4, 1.9 Hz), 8.06 (1H, s), 8.57 (1H, d, J=1.9 Hz), 8.64 (1H, s), 10.50 (1H, s), 11.65 (1H, s).

Example 48

Production of N-[4-({2-[(cyclopropylcarbonyl)amino]imidazo[1,2-a]pyridin-6-yl}oxy)-3-fluorophenyl]-2-(4-fluorophenyl)-1-methyl-3-oxo-2,3-dihydro-1H-pyrazole-4-carboxamide

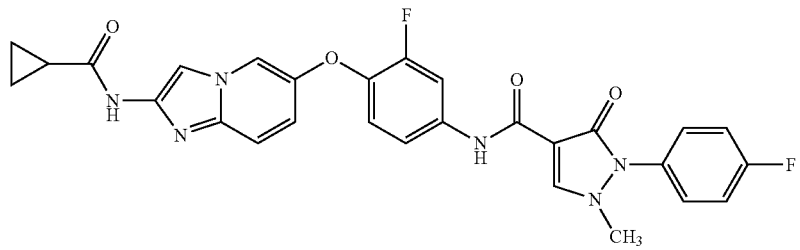

In the same manner as in Example 46 and using 2-(4-fluorophenyl)-1-methyl-3-oxo-2,3-dihydro-1H-pyrazole-4-carboxylic acid (280 mg, 1.2 mmol), N-[6-(4-amino-2-fluorophenoxy)imidazo[1,2-a]pyridin-2-yl]cyclopropanecarboxamide (260 mg, 0.80 mmol), HATU (460 mg, 1.2 mmol), N,N-diisopropylethylamine (310 mg, 2.4 mmol) and N,N-dimethylformamide (6 mL) as starting materials, the title compound (350 mg, 81%) was obtained as a white solid.

$^1$H-NMR (DMSO-$d_6$, 300 MHz) δ 0.72-0.85 (4H, m), 1.86-1.97 (1H, m), 3.48 (3H, s), 7.11 (1H, dd, J=9.6, 2.3 Hz), 7.16 (1H, t, J=8.9 Hz), 7.21-7.27 (1H, m), 7.40-7.50 (3H, m), 7.52-7.60 (2H, m), 7.90 (1H, dd, J=13.2, 2.3 Hz), 8.02 (1H, s), 8.44 (1H, d, J=1.9 Hz), 8.62 (1H, s), 10.43 (1H, s), 10.94 (1H, s).

Example 49

Production of N-[4-({2-[(cyclopropylcarbonyl)amino]imidazo[1,2-a]pyridin-6-yl}oxy)-3-fluorophenyl]-1-methyl-2-(2-methylphenyl)-3-oxo-2,3-dihydro-1H-pyrazole-4-carboxamide

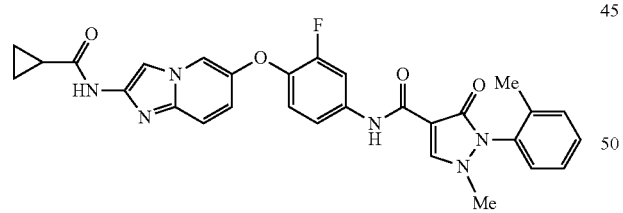

In the same manner as in Example 46 and using 1-methyl-2-(2-methylphenyl)-3-oxo-2,3-dihydro-1H-pyrazole-4-carboxylic acid (370 mg, 1.6 mmol), N-[6-(4-amino-2-fluorophenoxy)imidazo[1,2-a]pyridin-2-yl]cyclopropanecarboxamide (260 mg, 0.80 mmol), HATU (610 mg, 1.6 mmol), N,N-diisopropylethylamine (410 mg, 3.2 mmol) and N,N-dimethylformamide (12 mL) as starting materials, the title compound (300 mg, 70%) was obtained as a white solid.

$^1$H-NMR (DMSO-$d_6$, 300 MHz) δ 0.72-0.84 (4H; m), 1.86-1.96 (1H, m), 2.14 (3H, s), 3.38 (3H, s), 7.08-7.19 (2H, m), 7.20-7.25 (1H, m), 7.38-7.54 (5H, m), 7.91 (1H, dd, J=13.3, 2.4 Hz), 8.02 (1H, s), 8.44 (1H, d, J=1.7 Hz), 8.62 (1H, s), 10.47 (1H, s), 10.94 (1H, s).

Example 50

Production of 2-(2-chlorophenyl)-N-[4-({2-[(cyclopropylcarbonyl)amino]imidazo[1,2-a]pyridin-6-yl}oxy)-3-fluorophenyl]-1-methyl-3-oxo-2,3-dihydro-1H-pyrazole-4-carboxamide

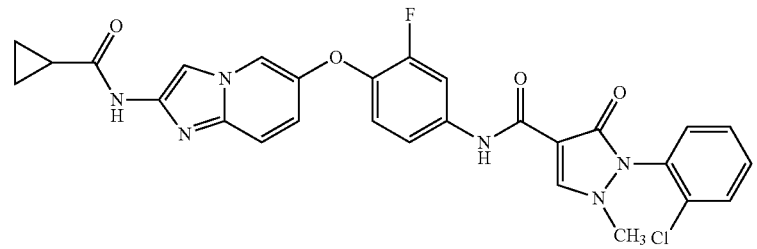 [SMILES: Cn1cc(C(=O)Nc2ccc(Oc3ccc4nc(NC(=O)C5CC5)cn4c3)c(F)c2)c(=O)n1-c1ccccc1Cl]

In the same manner as in Example 46 and using 2-(2-chlorophenyl)-1-methyl-3-oxo-2,3-dihydro-1H-pyrazole-4-carboxylic acid (330 mg, 1.3 mmol), N-[6-(4-amino-2-fluorophenoxy)imidazo[1,2-a]pyridin-2-yl]cyclopropanecarboxamide (250 mg, 0.77 mmol), HATU (490 mg, 1.3 mmol), N,N-diisopropylethylamine (340 mg, 2.6 mmol) and N,N-dimethylformamide (15 mL) as starting materials, the title compound (260 mg, 60%) was obtained as a white solid.

$^1$H-NMR (DMSO-$d_6$, 300 MHz) δ 0.71-0.85 (4H, m), 1.86-1.96 (1H, m), 3.41 (3H, s), 7.08-7.20 (2H, m), 7.21-7.27 (1H, m), 7.44 (1H, d, J=9.6 Hz), 7.57-7.73 (3H, m), 7.78 (1H, dd, J=7.8, 1.4 Hz), 7.90 (1H, dd, J=13.2, 2.5 Hz), 8.03 (1H, s), 8.44 (1H, d, J=1.9 Hz), 8.66 (1H, s), 10.33 (1H, s), 10.93 (1H, s).

Example 51

Production of N-[4-({2-[(cyclopropylcarbonyl)amino]imidazo[1,2-a]pyridin-6-yl}oxy)-3-fluorophenyl]-2-(2,4-difluorophenyl)-1-methyl-3-oxo-2,3-dihydro-1H-pyrazole-4-carboxamide In the same manner as in Example 46 and using 2-(2,4-difluorophenyl)-1-methyl-3-oxo-2,3-dihydro-1H-pyrazole-4-carboxylic acid (330 mg, 1.3 mmol), N-[6-(4-amino-2-fluorophenoxy)imidazo[1,2-a]pyridin-2-yl]cyclopropanecarboxamide (250 mg, 0.77 mmol), HATU (490 mg, 1.3 mmol), N,N-diisopropylethylamine (340 mg, 2.6 mmol) and N,N-dimethylformamide (15 mL) as starting materials, the title compound (330 mg, 76%) was obtained as a white solid.

$^1$H-NMR (DMSO-$d_6$, 300 MHz) δ 0.72-0.84 (4H, m), 1.87-1.97 (1H, m), 3.47 (3H, s), 7.08-7.20 (2H, m), 7.22-7.28 (1H, m), 7.33-7.41 (1H, m), 7.44 (1H, d, J=9.6 Hz), 7.61-7.70 (1H, m), 7.72-7.81 (1H, m), 7.89 (1H, dd, J=13.2, 2.5 Hz), 8.02 (1H, s), 8.44 (1H, d, J=1.7 Hz), 8.66 (1H, s), 10.27 (1H, s), 10.93 (1H, s).

Example 52

Production of N-[4-({2-[(cyclopropylcarbonyl)amino]imidazo[1,2-a]pyridin-6-yl}oxy)-3-fluorophenyl]-2-(2,6-dichlorophenyl)-1-methyl-3-oxo-2,3-dihydro-1H-pyrazole-4-carboxamide

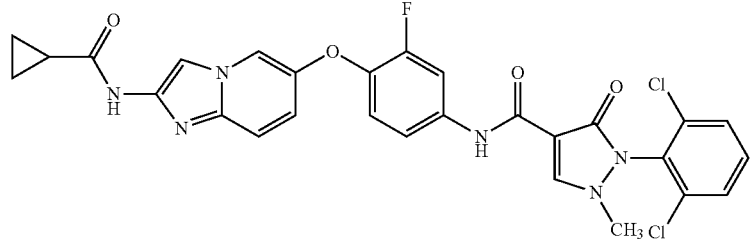

In the same manner as in Example 46 and using 2-(2,6-dichlorophenyl)-1-methyl-3-oxo-2,3-dihydro-1H-pyrazole-4-carboxylic acid (370 mg, 1.3 mmol), N-[6-(4-amino-2-fluorophenoxy)imidazo[1,2-a]pyridin-2-yl]cyclopropanecarboxamide (250 mg, 0.77 mmol), HATU (490 mg, 1.3 mmol), N,N-diisopropylethylamine (340 mg, 2.6 mmol) and N,N-dimethylformamide (15 mL) as starting materials, the title compound (330 mg, 72%) was obtained as a white solid.

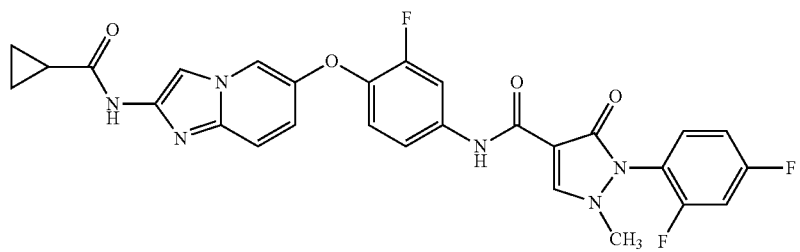 [SMILES: Cn1cc(C(=O)Nc2ccc(Oc3ccc4nc(NC(=O)C5CC5)cn4c3)c(F)c2)c(=O)n1-c1ccc(F)cc1F]

$^1$H-NMR (DMSO-$d_6$, 300 MHz) δ 0.71-0.84 (4H, m), 1.86-1.98 (1H, m), 3.44 (3H, s), 7.07-7.20 (2H, m), 7.23-7.29 (1H, m), 7.44 (1H, d, J=9.6 Hz), 7.69-7.76 (1H, m), 7.79-7.84 (2H, m), 7.89 (1H, dd, J=13.3, 2.4 Hz), 8.03 (1H, s), 8.44 (1H, d, J=1.9 Hz), 8.73 (1H, s), 10.18 (1H, s), 10.94 (1H, s).

Example 53

Production of N-[4-({2-[(cyclopropylcarbonyl)amino]imidazo[1,2-a]pyridin-6-yl}oxy)-3-s fluorophenyl]-3-(4-fluorophenyl)-2-oxoimidazolidine-1-carboxamide

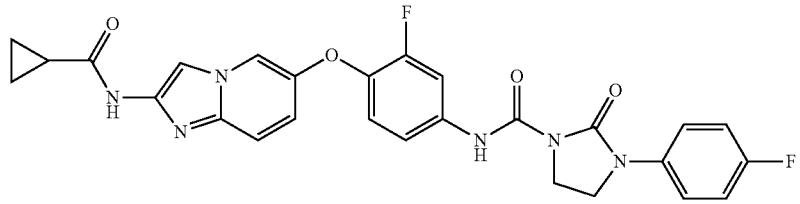 [SMILES: O=C(Nc1cn2cc(Oc3ccc(NC(=O)N4CCN(c5ccc(F)cc5)C4=O)cc3F)ccc2n1)C1CC1]

To a solution of 1-(4-fluorophenyl)imidazolidin-2-one (280 mg, 1.5 mmol) in tetrahydrofuran (5 mL) was added bis(trichloromethyl) carbonate (270 mg, 0.92 mmol), and the mixture was stirred at 70° C. for 5 hr. The mixture was cooled to room temperature, a solution of N-[6-(4-amino-2-fluorophenoxy)imidazo[1,2-a]pyridin-2-yl]cyclopropanecarboxamide (250 mg, 0.77 mmol) in tetrahydrofuran (5 mL) and N,N-diisopropylethylamine (300 mg, 2.3 mmol) were added to the mixture, and the mixture was stirred at room temperature for 40 min. Ethyl acetate/tetrahydrofuran and saturated aqueous sodium hydrogen carbonate solution were added to the mixture, and the aqueous layer was extracted with ethyl acetate/tetrahydrofuran (×3). The combined organic layer was washed with saturated brine, dried over anhydrous magnesium sulfate and filtered. The filtrate was concentrated under reduced pressure, and the residue was purified by silica gel column chromatography (NH silica gel, ethyl acetate/hexane=50/50→90/10) to give the title compound (120 mg, 30%) as a white solid.

$^1$H-NMR (DMSO-d$_6$, 300 MHz) δ 0.74-0.84 (4H, m), 1.85-1.97 (1H, m), 3.86-4.00 (4H, m), 7.10 (1H, dd, J=9.6, 2.5 Hz), 7.16 (1H, t, J=9.1 Hz), 7.23-7.32 (3H, m), 7.44 (1H, d, J=9.6 Hz), 7.61-7.67 (2H, m), 7.75 (1H, dd, J=13.2, 2.5 Hz), 8.03 (1H, s), 8.45 (1H, d, J=1.7 Hz), 10.42 (1H, s), 10.93 (1H, s).

Example 54

Production of N-[4-({2-[(cyclopropylcarbonyl)amino]imidazo[1,2-a]pyridin-6-yl}oxy)-3-fluorophenyl]-3-(4-fluorophenyl)-2-oxotetrahydropyrimidine-1(2H)-carboxamide

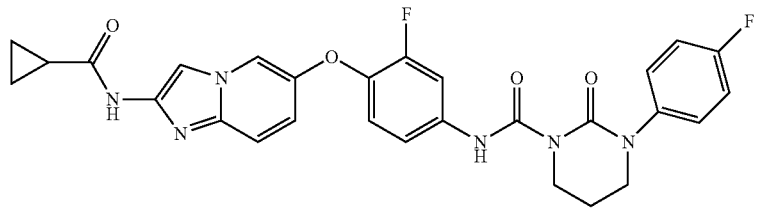 [SMILES: O=C(Nc1cn2cc(Oc3ccc(NC(=O)N4CCCN(c5ccc(F)cc5)C4=O)cc3F)ccc2n1)C1CC1]

To a solution of 1-(4-fluorophenyl)tetrahydropyrimidin-2 (1H)-one (360 mg, 1.8 mmol) in tetrahydrofuran (5 mL) was added bis(trichloromethyl) carbonate (330 mg, 1.1 mmol), and the mixture was stirred at 70° C. for 3.5 hr. The mixture was cooled to room temperature, a solution of N-[6-(4-amino-2-fluorophenoxy)imidazo[1,2-a]pyridin-2-yl]cyclopropanecarboxamide (300 mg, 0.92 mmol) in tetrahydrofuran (8 mL) and N,N-diisopropylethylamine (360 mg, 2.8 mmol) were added to the mixture, and the mixture was stirred at room temperature for 30 min. Ethyl acetate/tetrahydrofuran and saturated aqueous sodium hydrogen carbonate solution were added to the mixture, and the aqueous layer was extracted with ethyl acetate/tetrahydrofuran (×3). The combined organic layer was washed with saturated brine, dried over anhydrous magnesium sulfate and filtered. The filtrate was concentrated under reduced pressure, and the residue was purified by silica gel column chromatography (NH silica gel, ethyl acetate/hexane=40/60→90/10) to give the title compound (250 mg, 49%) as a white solid.

$^1$H-NMR (DMSO-d$_6$, 300 MHz) δ 0.73-0.85 (4H, m), 1.86-1.98 (1H, m), 2.06-2.16 (2H, m), 3.66 (2H, t, J=5.9 Hz), 3.85-3.96 (2H, m), 7.06-7.15 (2H, m), 7.15-7.32 (3H, m), 7.38-7.48 (3H, m), 7.71 (1H, dd, J=13.3, 2.4 Hz), 8.02 (1H, s), 8.44 (1H, d, J=1.7 Hz), 10.94 (1H, s), 11.78 (1H, s).

Example 55

Production of N-[4-({2-[(cyclopropylcarbonyl)amino]-3-methylimidazo[1,2-a]pyridin-6-yl}oxy)-3-fluorophenyl]-1-(4-fluorophenyl)-6-methyl-2-oxo-1,2-dihydropyridine-3-carboxamide

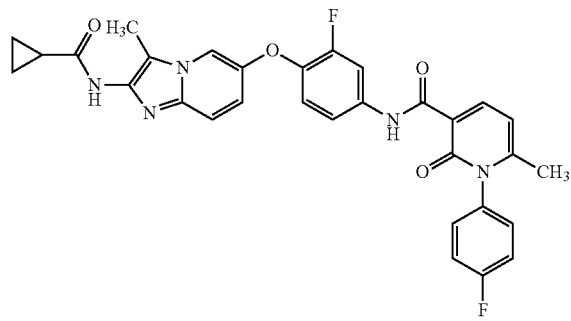 [SMILES: Cc1ccc(C(=O)Nc2ccc(Oc3ccc4nc(NC(=O)C5CC5)c(C)n4c3)c(F)c2)c(=O)n1-c1ccc(F)cc1]

To a solution of 1-(4-fluorophenyl)-6-methyl-2-oxo-1,2-dihydropyridine-3-carboxylic acid (56.7 mg, 0.229 mmol) and N-[6-(4-amino-2-fluorophenoxy)-3-methylimidazo[1,2-a]pyridin-2-yl]cyclopropanecarboxamide (60 mg, 0.176 mmol) in N,N-dimethylformamide (1 mL) were added N,N- diisopropylethylamine (61 μL, 0.352 mmol) and HATU (87 mg, 0.229 mmol), and the mixture was stirred at room temperature for 17 hr. Ethyl acetate and saturated aqueous sodium hydrogen carbonate solution were added to the reaction mixture, and the mixture was extracted 3 times with ethyl acetate. The organic layer was washed with saturated brine, dried over anhydrous magnesium sulfate and filtered, and the solvent was evaporated under reduced pressure. The obtained residue was purified by silica gel column chromatography (ethyl acetate alone) to give a yellow oil. The obtained oil was dissolved in ethyl acetate (1 mL) and left standing at room temperature for 17 hr. The precipitated solid was collected by filtration, washed with diethyl ether and collected by filtration to give the title compound (76 mg, 75%) as a white solid.

$^1$H-NMR (DMSO-d$_6$, 300 MHz) δ 0.78 (4H, m), 1.74-1.91 (1H, m), 2.07 (3H, s), 2.26 (3H, s), 6.61-6.79 (1H, m), 7.01-7.15 (2H, m), 7.28-7.37 (1H, m), 7.38-7.54 (5H, m), 7.97 (1H, dd, J=13.2, 2.5 Hz), 8.19 (1H, d, J=1.9 Hz), 8.48 (1H, d, J=7.6 Hz), 10.21 (1H, br s), 11.97 (1H, s).

Example 56

Production of N-[4-({2-[(cyclopropylcarbonyl)amino]imidazo[1,2-a]pyridin-6-yl}oxy)-2-methylphenyl]-1-(4-fluorophenyl)-6-methyl-2-oxo-1,2-dihydropyridine-3-carboxamide

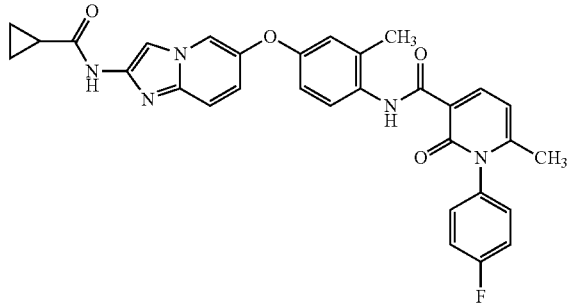 [SMILES: Cc1cc(Oc2ccc3nc(NC(=O)C4CC4)cn3c2)ccc1NC(=O)c1ccc(C)n(-c2ccc(F)cc2)c1=O]

A mixed solution of N-[6-(3-methyl-4-nitrophenoxy)imidazo[1,2-a]pyridin-2-yl]cyclopropanecarboxamide (200 mg, 0.568 mmol), reduced iron (166.9 mg, 2.84 mmol) and ammonium chloride (303 mg, 5.68 mmol) in ethanol (2 mL) and water (0.5 mL) was stirred at 80° C. for 6 hr. The reaction mixture was diluted with ethyl acetate and tetrahydrofuran, and filtered through celite. Water was added to the filtrate, and the mixture was extracted 3 times with ethyl acetate. The organic layer was washed with saturated brine, dried over anhydrous magnesium sulfate and filtered, and the solvent was evaporated under reduced pressure. The obtained residue was purified by silica gel column chromatography (ethyl acetate/hexane=50/50→100/0) to give a white solid.

To a solution of the obtained white solid and 1-(4-fluorophenyl)-6-methyl-2-oxo-1,2-dihydropyridine-3-carboxylic acid (45 mg, 0.182 mmol) in N,N-dimethylformamide (1 mL) were added N,N-diisopropylethylamine (48 μL, 0.28 mmol) and HATU (69 mg, 0.182 mmol), and the mixture was stirred at room temperature for 2 hr. Ethyl acetate, tetrahydrofuran and saturated aqueous sodium hydrogen carbonate solution were added to the reaction mixture, and the mixture was extracted 3 times with ethyl acetate. The organic layer was washed with saturated brine, dried over anhydrous magnesium sulfate and filtered, and the solvent was evaporated under reduced pressure. The obtained residue was purified by silica gel column chromatography (ethyl acetate alone) to give a yellow solid. The obtained solid was washed with ethyl acetate and collected by filtration to give the title compound (33 mg, 41%) as a slightly yellow solid.

$^1$H-NMR (DMSO-d$_6$, 300 MHz) δ 0.68-0.91 (4H, m), 1.89-1.96 (1H, m), 2.06 (3H, s), 2.19 (3H, s), 6.70 (1H, d, J=8.3 Hz), 6.83-6.97 (2H, m), 7.05 (1H, dd, J=9.6, 2.3 Hz), 7.35-7.56 (5H, m), 8.03 (1H, s), 8.23 (1H, d, J=8.9 Hz), 8.45-8.53 (2H, m), 10.94 (1H, s), 11.67 (1H, s).

Example 57

Production of N-[3-chloro-4-({2-[(cyclopropylcarbonyl)amino]imidazo[1,2-a]pyridin-6-yl}oxy)phenyl]-1-(4-fluorophenyl)-6-methyl-2-oxo-1,2-dihydropyridine-3-carboxamide

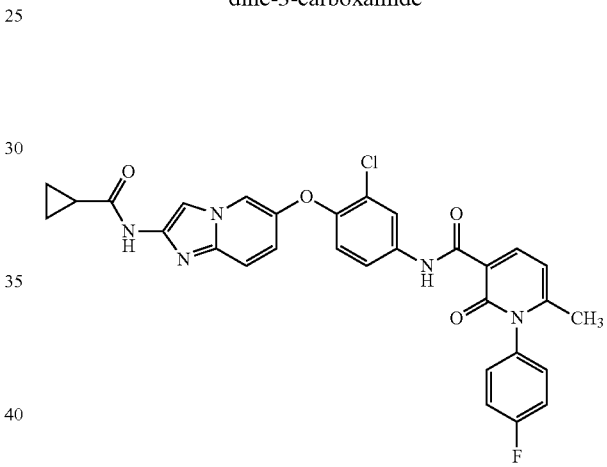

To a solution of N-[6-(4-amino-2-chlorophenoxy)imidazo[1,2-a]pyridin-2-yl]cyclopropanecarboxamide (100 mg, 0.292 mmol) and 1-(4-fluorophenyl)-6-methyl-2-oxo-1,2-dihydropyridine-3-carboxylic acid (94 mg, 0.38 mmol) in N,N-dimethylformamide (1 mL) were added N,N-diisopropylethylamine (100 μL, 0.583 mmol) and HATU (144 mg, 0.380 mmol), and the mixture was stirred at 60° C. for 4 hr. Ethyl acetate, tetrahydrofuran and saturated aqueous sodium hydrogen carbonate solution was added to the reaction mixture, and the mixture was extracted 3 times with ethyl acetate. The organic layer was washed with saturated brine, dried over anhydrous magnesium sulfate and filtered, and the solvent was evaporated under reduced pressure. The obtained residue was purified by silica gel column chromatography (ethyl acetate alone) to give a white solid. The obtained solid was washed with ethyl acetate and collected by filtration to give the title compound (120.2 mg, 72%) as a white solid.

$^1$H-NMR (DMSO-d$_6$, 300 MHz) δ 0.67-0.90 (4H, m), 1.85-1.96 (1H, m), 2.07 (3H, s), 6.71 (1H, d, J=8.3 Hz), 6.99-7.14 (2H, m), 7.35-7.57 (6H, m), 8.02 (1H, s), 8.16 (1H, d, J=2.5 Hz), 8.40-8.51 (2H, m), 10.94 (1H, s), 11.96 (1H, s).

Example 58

Production of N-[4-({2-[(cyclopropylcarbonyl)amino]imidazo[1,2-a]pyridin-6-yl}oxy)-3-fluorophenyl]-1-(4-fluoro-2-methylphenyl)-2-oxo-1,2-dihydropyridine-3-carboxamide

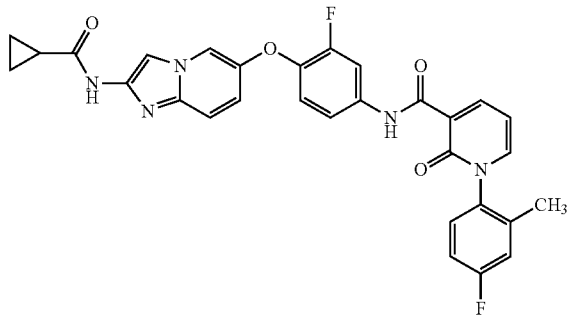 [SMILES: Cc1cc(F)ccc1-n1cccc(C(=O)Nc2ccc(Oc3ccc4nc(NC(=O)C5CC5)cn4c3)c(F)c2)c1=O]

To a solution of N-[6-(4-amino-2-fluorophenoxy)imidazo[1,2-a]pyridin-2-yl]cyclopropanecarboxamide (100 mg, 0.306 mmol) and 1-(4-fluoro-2-methylphenyl)-2-oxo-1,2-dihydropyridine-3-carboxylic acid (98 mg, 0.398 mmol) in N,N-dimethylformamide (2 mL) were added N,N-diisopropylethylamine (105 μL, 0.612 mmol) and HATU (151 mg, 0.398 mmol), and the mixture was stirred at room temperature for 4 hr. Ethyl acetate, tetrahydrofuran and saturated aqueous sodium hydrogen carbonate solution were added to the reaction mixture, and the mixture was extracted 3 times with ethyl acetate. The organic layer was washed with saturated brine, dried over anhydrous magnesium sulfate and filtered, and the solvent was evaporated under reduced pressure. The obtained residue was washed with ethyl acetate and collected by filtration to give the title compound (140 mg, 82%) as a slightly yellow solid.

$^1$H-NMR (DMSO-d$_6$, 300 MHz) δ 0.69-0.85 (4H, m), 1.86-1.96 (1H, m), 2.08 (3H, s), 6.67-6.81 (1H, m), 7.06-7.52 (7H, m), 7.88-8.11 (3H, m), 8.46 (1H, d, J=1.7 Hz), 8.61 (1H, dd, J=7.3, 2.2 Hz), 10.94 (1H, s), 12.02 (1H, s).

Example 59

Production of N-[6-({2-[(cyclopropylcarbonyl)amino]imidazo[1,2-a]pyridin-6-yl}oxy)pyridin-3-yl]-1-(4-fluorophenyl)-6-methyl-2-oxo-1,2-dihydropyridine-3-carboxamide

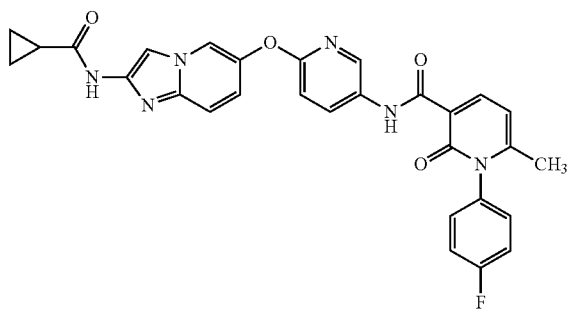 [SMILES: Cc1ccc(C(=O)Nc2ccc(Oc3ccc4nc(NC(=O)C5CC5)cn4c3)nc2)c(=O)n1-c1ccc(F)cc1]

A mixed solution of N-{6-[(5-nitropyridin-2-yl)oxy]imidazo[1,2-a]pyridin-2-yl}cyclopropanecarboxamide (111 mg, 0.327 mmol), reduced iron (96 mg, 1.64 mmol) and ammonium chloride (175 mg, 3.27 mmol) in ethanol (2 mL) and water (0.5 mL) was stirred at 70° C. for 1.5 hr. The reaction mixture was diluted with ethyl acetate and filtered through celite. Water was added to the filtrate, and the mixture was extracted twice with ethyl acetate. The organic layer was washed with saturated brine, dried over anhydrous magnesium sulfate and filtered, and the solvent was evaporated under reduced pressure. The obtained residue was washed with ethyl acetate and collected by filtration to give a yellow solid.

To a solution of the obtained yellow solid and 1-(4-fluorophenyl)-6-methyl-2-oxo-1,2-dihydropyridine-3-carboxylic acid (76.8 mg, 0.311 mmol) in N,N-dimethylformamide (1 mL) were added N,N-diisopropylethylamine (89 μL, 0.518 mmol) and HATU (128 mg, 0.337 mmol), and the mixture was stirred at room temperature for 7 hr. Ethyl acetate, tetrahydrofuran and saturated aqueous sodium hydrogen carbonate solution were added to the reaction mixture, and the mixture was extracted 3 times with ethyl acetate. The organic layer was washed with saturated brine, dried over anhydrous magnesium sulfate and filtered, and the solvent was evaporated under reduced pressure. The obtained residue was washed with ethyl acetate and collected by filtration to give the title compound (70 mg, 40%) as a white solid.

$^1$H-NMR (DMSO-d$_6$, 300 MHz) δ 0.64-0.91 (4H, m), 1.87-1.96 (1H, m), 2.08 (3H, s), 6.70 (1H, d, J=8.3 Hz), 7.03-7.18 (2H, m), 7.34-7.56 (5H, m), 8.04 (1H, s), 8.24 (1H, dd, J=8.9, 2.8 Hz), 8.42 (1H, d, J=2.3 Hz), 8.47 (1H, d, J=7.6 Hz), 8.56-8.61 (1H, m), 10.96 (1H, s), 11.85 (1H, s).

Example 60

Production of N-[5-({2-[(cyclopropylcarbonyl)amino]imidazo[1,2-a]pyridin-6-yl}oxy)pyridin-2-yl]-1-(4-fluorophenyl)-6-methyl-2-oxo-1,2-dihydropyridine-3-carboxamide

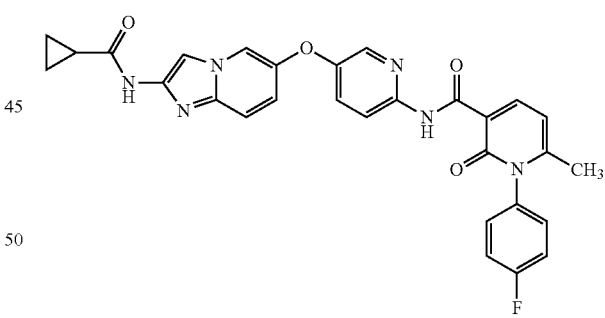

To a solution of N-{6-[(6-aminopyridin-3-yl)oxy]imidazo[1,2-a]pyridin-2-yl}cyclopropanecarboxamide (75 mg, 0.242 mmol) and 1-(4-fluorophenyl)-6-methyl-2-oxo-1,2-dihydropyridine-3-carboxylic acid (78 mg, 0.315 mmol) in N,N-dimethylformamide (1 mL) were added N,N-diisopropylethylamine (83 μL, 0.484 mmol) and HATU (120 mg, 0.315 mmol), and the mixture was stirred at room temperature for 17 hr. Ethyl acetate, tetrahydrofuran and saturated aqueous sodium hydrogen carbonate solution were added to the reaction mixture, and the mixture was extracted 3 times with ethyl acetate. The organic layer was washed with saturated brine, dried over anhydrous magnesium sulfate and filtered, and the solvent was evaporated under reduced pressure. The obtained residue was washed with ethyl acetate and collected by filtration to give the title compound (116 mg, 89%) as a white solid.

$^1$H-NMR (DMSO-d$_6$, 300 MHz) δ 0.70-0.88 (4H, m), 1.85-1.96 (1H, m), 2.07 (3H, s), 6.66-6.75 (1H, m), 7.12 (1H, dd, J=9.6, 2.5 Hz), 7.38-7.52 (5H, m), 7.58 (1H, dd, J=9.1, 3.0 Hz), 8.03 (1H, s), 8.16 (1H, d, J=2.5 Hz), 8.29 (1H, d, J=9.6 Hz), 8.46-8.56 (2H, m), 10.95 (1H, s), 12.22 (1H, s).

Example 61

Production of N-[5-({2-[(cyclopropylcarbonyl)amino]imidazo[1,2-a]pyridin-6-yl}oxy)pyridin-2-yl]-6-(4-fluorophenyl)-5-methylpyridine-2-carboxamide 1-oxide

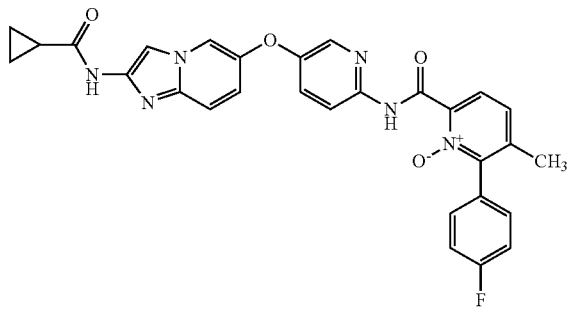

To a solution of N-{6-[(6-aminopyridin-3-yl)oxy]imidazo[1,2-a]pyridin-2-yl}cyclopropanecarboxamide (100 mg, 0.323 mmol) and 6-(4-fluorophenyl)-5-methylpyridine-2-carboxylic acid 1-oxide (103.8 mg, 0.42 mmol) in N,N-dimethylformamide (1 mL) were added N,N-diisopropylethylamine (111 μL, 0.646 mmol) and HATU (160 mg, 0.42 mmol), and the mixture was stirred at room temperature for 4 hr. Ethyl acetate, tetrahydrofuran and saturated aqueous sodium hydrogen carbonate solution were added to the reaction mixture, and the mixture was extracted 3 times with ethyl acetate. The organic layer was washed with saturated brine, dried over anhydrous magnesium sulfate and filtered, and the solvent was evaporated under reduced pressure. The obtained residue was washed with ethyl acetate and collected by filtration to give the title compound (140 mg, 80%) as a slightly yellow solid.

$^1$H-NMR (DMSO-d$_6$, 300 MHz) δ 0.60-0.87 (4H, m), 1.86-1.96 (1H, m), 2.13 (3H, s), 7.14 (1H, dd, J=9.5, 2.4 Hz), 7.33-7.55 (5H, m), 7.62 (1H, dd, J=9.1, 3.0 Hz), 7.69 (1H, d, J=208.9 Hz), 8.04 (1H, s), 8.21 (1H, d, J=2.5 Hz), 8.26-8.37 (2H, m), 8.57 (1H, dd, J=2.5, 0.8 Hz), 10.97 (1H, s), 13.99 (1H, s).

Example 62

Production of N-[4-({2-[(cyclopropylcarbonyl)amino]imidazo[1,2-a]pyridin-6-yl}oxy)-3-methylphenyl]-1-(4-fluorophenyl)-6-methyl-2-oxo-1,2-dihydropyridine-3-carboxamide

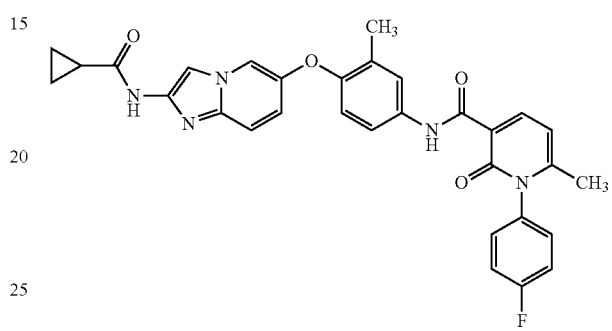

Using N-[6-(4-amino-2-methylphenoxy)imidazo[1,2-a]pyridin-2-yl]cyclopropanecarboxamide (100 mg, 0.31 mmol), 1-(4-fluorophenyl)-6-methyl-2-oxo-1,2-dihydropyridine-3-carboxylic acid (99.7 mg, 0.403 mmol), N,N-dimethylformamide (1 mL), N,N-diisopropylethylamine (107 μL, 0.620 mmol) and HATU (153 mg, 0.403 mmol) and in the same manner as in Example 57, the title compound (125.7 mg, 74%) was obtained as a white solid.

$^1$H-NMR (DMSO-d$_6$, 300 MHz) δ 0.67-0.88 (4H, m), 1.86-1.95 (1H, m), 2.07 (3H, s), 2.23 (3H, s), 6.69 (1H, d, J=8.1 Hz), 6.85 (1H, d, J=8.9 Hz), 7.03 (1H, dd, J=9.6, 2.3 Hz), 7.37-7.68 (7H, m), 8.01 (1H, s), 8.32 (1H, d, J=1.7 Hz), 8.46 (1H, d, J=7.6 Hz), 10.92 (1H, s), 11.85 (1H, s).

Example 63

Production of N-[5-({2-[(cyclopropylcarbonyl)amino]imidazo[1,2-a]pyridin-6-yl}oxy)pyridin-2-yl]-6-(4-fluorophenyl)-5-methylpyridine-2-carboxamide 1-oxide•hydrochloride•monohydrate

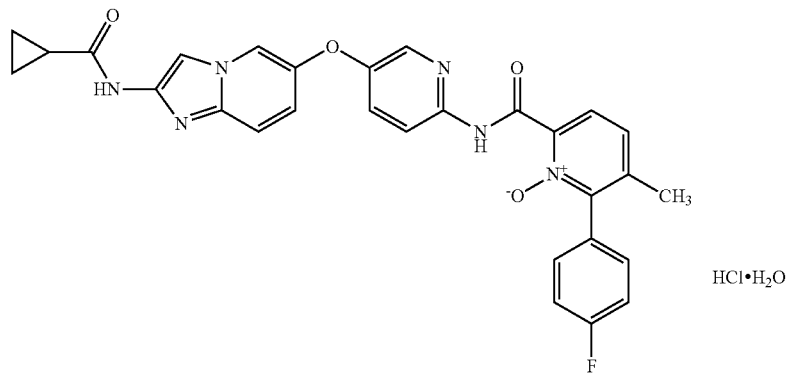

To a suspension of N-[5-({2-[(cyclopropylcarbonyl)amino]imidazo[1,2-a]pyridin-6-yl}oxy)pyridin-2-yl]-6-(4-fluorophenyl)-5-methylpyridine-2-carboxamide 1-oxide (530 mg, 0.984 mmol) in ethanol (8 mL) were added 6N hydrochloric acid (0.984 mL, 5.9 mmol) and water (0.984 mL) at 80° C. The reaction solution was stirred at 70° C. for 7 hr, and the precipitate was collected by filtration to give the title compound (197.6 mg, 34%) as a white solid.

$^1$H-NMR (DMSO-$d_6$, 300 MHz) δ 0.79-0.98 (4H, m), 1.86-2.01 (1H, m), 2.14 (3H, s), 7.28-7.57 (5H, m), 7.61-7.77 (3H, m), 8.06 (1H, s), 8.26 (1H, d, J=2.5 Hz), 8.29-8.37 (2H, m), 8.67 (1H, d, J=1.7 Hz), 11.48 (1H, br s), 14.02 (1H, s).

Example 64

Production of N-[2-chloro-4-({2-[(cyclopropylcarbonyl)amino]imidazo[1,2-a]pyridin-6-yl}oxy)phenyl]-1-(4-fluorophenyl)-6-methyl-2-oxo-1,2-dihydropyridine-3-carboxamide

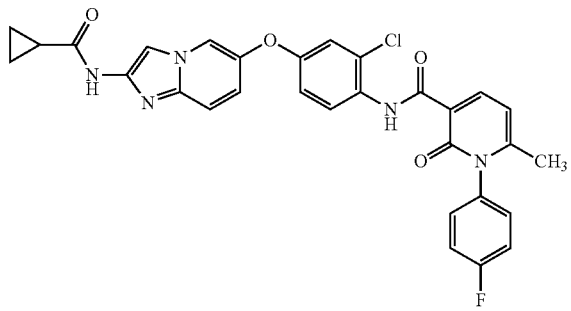 [SMILES: Cc1ccc(C(=O)Nc2ccc(Oc3ccc4nc(NC(=O)C5CC5)cn4c3)cc2Cl)c(=O)n1-c1ccc(F)cc1]

Using N-[6-(4-amino-3-chlorophenoxy)imidazo[1,2-a]pyridin-2-yl]cyclopropanecarboxamide (160 mg, 0.467 mmol), 1-(4-fluorophenyl)-6-methyl-2-oxo-1,2-dihydropyridine-3-carboxylic acid (150 mg, 0.607 mmol), N,N-dimethylformamide (2 mL), N,N-diisopropylethylamine (161 μL, 0.934 mmol) and HATU (230.8 mg, 0.607 mmol) and in the same manner as in Example 60, the title compound (250 mg, 94%) was obtained as a white solid.

$^1$H-NMR (DMSO-$d_6$, 300 MHz) δ 0.74-0.86 (4H, m), 1.86-1.97 (1H, m), 2.06 (3H, s), 6.64-6.77 (1H, m), 7.02-7.14 (2H, m), 7.24 (1H, d, J=3.0 Hz), 7.38-7.54 (5H, m), 8.04 (1H, s), 8.43-8.58 (3H, m), 10.96 (1H, s), 12.15 (1H, s).

Example 65

Production of N-[5-({2-[(cyclopropylcarbonyl)amino]imidazo[1,2-a]pyridin-6-yl}oxy)pyridin-2-yl]-6-methyl-2-oxo-1-phenyl-1,2-dihydropyridine-3-carboxamide

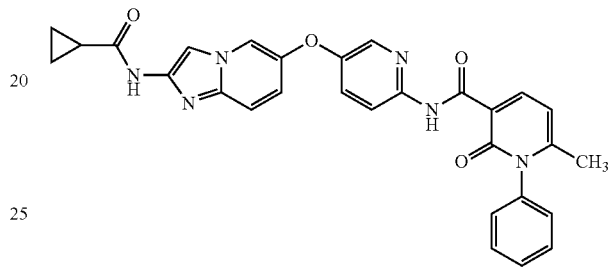

To a solution of N-{6-[(6-aminopyridin-3-yl)oxy]imidazo[1,2-a]pyridin-2-yl}cyclopropanecarboxamide (200 mg, 0.647 mmol) and 6-methyl-2-oxo-1-phenyl-1,2-dihydropyridine-3-carboxylic acid (178 mg, 0.776 mmol) in N,N-dimethylformamide (3 mL) were added N,N-diisopropylethylamine (233 μL, 1.29 mmol) and HATU (320 mg, 0.841 mmol), and the mixture was stirred at room temperature for 6 hr. Ethyl acetate, tetrahydrofuran and saturated aqueous sodium hydrogen carbonate solution were added to the reaction mixture, and the mixture was extracted 3 times with ethyl acetate. The organic layer was washed with saturated brine, dried over anhydrous magnesium sulfate and filtered, and the solvent was evaporated under reduced pressure. The obtained residue was washed with ethyl acetate and collected by filtration. The obtained white solid was suspended in methyl ethyl ketone (2 mL), and the mixture was stirred at 80° C. for 17 hr. The suspension was collected by filtration to give the title compound (175 mg, 52%) as a white solid.

$^1$H-NMR (DMSO-$d_6$, 300 MHz) δ 0.72-0.84 (4H, m), 1.86-1.98 (1H, m), 2.06 (3H, s), 6.70 (1H, d, J=8.3 Hz), 7.12 (1H, dd, J=9.6, 2.5 Hz), 7.29-7.70 (7H, m), 8.03 (1H, s), 8.16 (1H, d, J=2.5 Hz), 8.29 (1H, d, J=9.1 Hz), 8.45-8.55 (2H, m), 10.95 (1H, s), 12.24 (1H, s).

Example 66

Production of N-[4-({2-[(cyclopropylcarbonyl)amino]imidazo[1,2-a]pyridin-6-yl}oxy)-3-fluorophenyl]-1-(4-fluorophenyl)-5-methyl-2-oxo-1,2-dihydropyridine-3-carboxamide

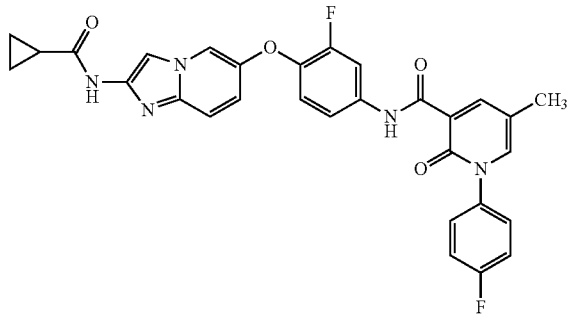 [SMILES: Cc1cc(C(=O)Nc2ccc(Oc3ccc4nc(NC(=O)C5CC5)cn4c3)c(F)c2)c(=O)n(-c2ccc(F)cc2)c1]

To a solution of N-[6-(4-amino-2-fluorophenoxy)imidazo[1,2-a]pyridin-2-yl]cyclopropanecarboxamide (100 mg, 0.306 mmol) and 1-(4-fluorophenyl)-5-methyl-2-oxo-1,2-dihydropyridine-3-carboxylic acid (90.8 mg, 0.367 mmol) in N,N-dimethylformamide (1 mL) were added N,N-diisopropylethylamine (105 μL, 0.612 mmol) and HATU (151 mg, 0.40 mmol), and the mixture was stirred at room temperature for 6 hr. Ethyl acetate, tetrahydrofuran and saturated aqueous sodium hydrogen carbonate solution were added to the reaction mixture, and the mixture was extracted 3 times with ethyl acetate. The organic layer was washed with saturated brine, dried over anhydrous magnesium sulfate and filtered, and the solvent was evaporated under reduced pressure. The obtained residue was washed with ethyl acetate and collected by filtration. The obtained slightly yellow solid was suspended in methanol (3 mL), and the mixture was stirred at 70° C. for 10 min. The suspension was collected by filtration, and the obtained solid was washed with methanol to give the title compound (122 mg, 72%) as a slightly yellow solid.

$^1$H-NMR (DMSO-$d_6$, 300 MHz) δ 0.71-0.85 (4H, m), 1.92 (1H, m), 2.20 (3H, s), 7.02-7.23 (2H, m), 7.30-7.50 (4H, m), 7.53-7.67 (2H, m), 7.88-8.06 (3H, m), 8.46 (2H, s), 10.93 (1H, s), 12.16 (1H, s).

Example 67

Production of N-[4-({2-[(cyclopropylcarbonyl)amino]imidazo[1,2-a]pyridin-6-yl}oxy)-3-fluorophenyl]-1-(2,4-difluorophenyl)-6-methyl-2-oxo-1,2-dihydropyridine-3-carboxamide

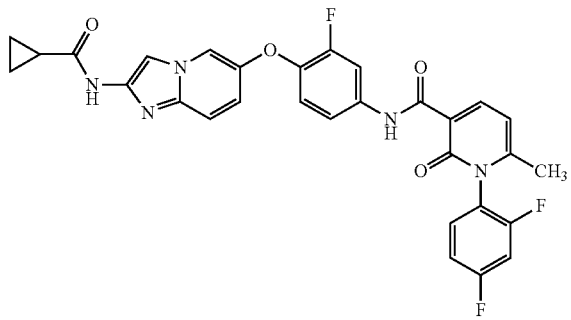 [SMILES: Cc1ccc(C(=O)Nc2ccc(Oc3ccc4nc(NC(=O)C5CC5)cn4c3)c(F)c2)c(=O)n1-c1ccc(F)cc1F]

Using N-[6-(4-amino-2-fluorophenoxy)imidazo[1,2-a]pyridin-2-yl]cyclopropanecarboxamide (100 mg, 0.306 mmol), 1-(2,4-difluorophenyl)-6-methyl-2-oxo-1,2-dihydropyridine-3-carboxylic acid (97.4 mg, 0.367 mmol), N,N-dimethylformamide (1 mL), N,N-diisopropylethylamine (105 μL, 0.612 mmol) and HATU (151 mg, 0.40 mmol) and in the same manner as in Example 65, the title compound (115 mg, 66%) was obtained as a white solid.

$^1$H-NMR (DMSO-$d_6$, 300 MHz) δ 0.67-0.83 (4H, m), 1.85-1.96 (1H, m), 2.13 (3H, s), 6.71-6.86 (1H, m), 7.04-7.22 (2H, m), 7.30-7.48 (3H, m), 7.57-7.79 (2H, m), 7.96 (1H, dd, J=13.2, 2.5 Hz), 8.02 (1H, s), 8.46 (1H, d, J=1.9 Hz), 8.52 (1H, d, J=7.6 Hz), 10.93 (1H, s), 11.76 (1H, s).

Example 68

Production of N-[4-({2-[(cyclopropylcarbonyl)amino]imidazo[1,2-a]pyridin-6-yl}oxy)-3-fluorophenyl]-1-(4-fluorophenyl)-2-oxo-6-(trifluoromethyl)-1,2-dihydropyridine-3-carboxamide

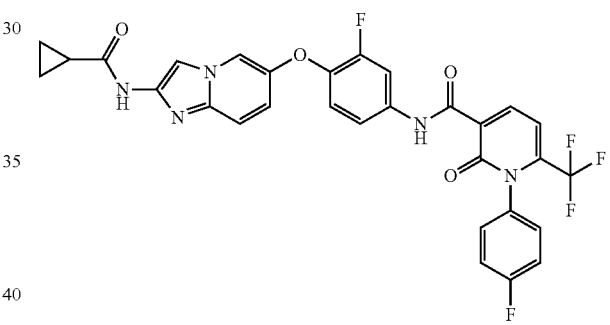

To a solution of N-[6-(4-amino-2-fluorophenoxy)imidazo[1,2-a]pyridin-2-yl]cyclopropanecarboxamide (90 mg, 0.276 mmol) and 1-(4-fluorophenyl)-2-oxo-6-(trifluoromethyl)-1,2-dihydropyridine-3-carboxylic acid (100 mg, 0.331 mmol) in N,N-dimethylformamide (2 mL) were added N,N-diisopropylethylamine (95 μL, 0.552 mmol) and HATU (126 mg, 0.331 mmol), and the mixture was stirred at room temperature for 6 hr. Ethyl acetate, tetrahydrofuran and saturated aqueous sodium hydrogen carbonate solution were added to the reaction mixture, and the mixture was extracted 3 times with ethyl acetate. The organic layer was washed with saturated brine, dried over anhydrous magnesium sulfate and filtered, and the solvent was evaporated under reduced pressure. The obtained residue was washed with ethyl acetate and collected by filtration. The obtained slightly yellow solid was suspended in ethanol (3 mL), and the mixture was stirred at 70° C. for 17 hr. The suspension was collected by filtration and washed with ethanol to give the title compound (32.7 mg, 19%) as a slightly yellow solid.

¹H-NMR (DMSO-d₆, 300 MHz) δ 0.61-0.91 (4H, m), 1.86-1.97 (1H, m), 7.04-7.20 (2H, m), 7.31 (1H, d, J=7.7 Hz), 7.38-7.48 (4H, m), 7.57 (2H, d, J=4.5 Hz), 7.97 (1H, dd, J=13.0, 2.5 Hz), 8.02 (1H, s), 8.47 (1H, d, J=1.7 Hz), 8.63 (1H, d, J=7.6 Hz), 10.93 (1H, s), 11.66 (1H, s).

Example 69

Production of N-[4-({2-[(cyclopropylcarbonyl)amino]imidazo[1,2-a]pyridin-6-yl}oxy)-3-fluorophenyl]-6-ethyl-1-(4-fluorophenyl)-2-oxo-1,2-dihydropyridine-3-carboxamide

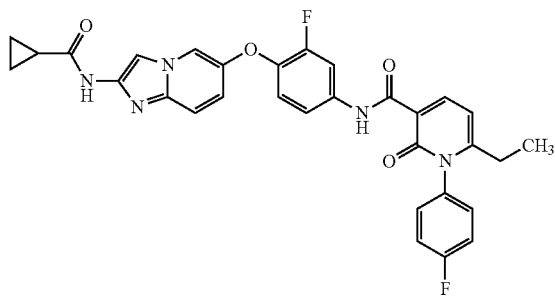 [SMILES: CCc1ccc(C(=O)Nc2ccc(Oc3ccc4nc(NC(=O)C5CC5)cn4c3)c(F)c2)c(=O)n1-c1ccc(F)cc1]

Using N-[6-(4-amino-2-fluorophenoxy)imidazo[1,2-a]pyridin-2-yl]cyclopropanecarboxamide (100 mg, 0.306 mmol), 6-ethyl-1-(4-fluorophenyl)-2-oxo-1,2-dihydropyridine-3-carboxylic acid (95.9 mg, 0.367 mmol), N,N-dimethylformamide (1 mL), N,N-diisopropylethylamine (105 μL, 0.612 mmol) and HATU (151 mg, 0.40 mmol) and in the same manner as in Example 68, the title compound (64.1 mg, 37%) was obtained as a white solid.

¹H-NMR (DMSO-d₆, 300 MHz) δ 0.70-0.87 (4H, m), 1.06 (3H, t, J=7.3 Hz), 1.81-2.01 (1H, m), 2.30 (2H, q, J=7.5 Hz), 6.68 (1H, d, J=7.7 Hz), 7.01-7.22 (2H, m), 7.30-7.56 (6H, m), 7.87-8.06 (2H, m), 8.45 (1H, d, J=1.7 Hz), 8.53 (1H, d, J=7.7 Hz), 10.93 (1H, s), 11.98 (1H, s).

Example 70

Production of N-[4-({2-[(cyclopropylcarbonyl)amino]imidazo[1,2-a]pyridin-6-yl}oxy)-3-fluorophenyl]-1-(4-fluorophenyl)-5,6-dimethyl-2-oxo-1,2-dihydropyridine-3-carboxamide

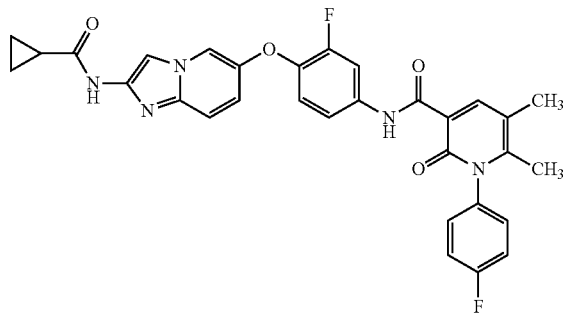 [SMILES: Cc1cc(C(=O)Nc2ccc(Oc3ccc4nc(NC(=O)C5CC5)cn4c3)c(F)c2)c(=O)n(-c2ccc(F)cc2)c1C]

To a solution of N-[6-(4-amino-2-fluorophenoxy)imidazo[1,2-a]pyridin-2-yl]cyclopropanecarboxamide (83 mg, 0.255 mmol) and 1-(4-fluorophenyl)-5,6-dimethyl-2-oxo-1,2-dihydropyridine-3-carboxylic acid (80 mg, 0.306 mmol) in N,N-dimethylformamide (1 mL) were added N,N-diisopropylethylamine (88 μL, 0.51 mmol) and HATU (116 mg, 0.306 mmol), and the mixture was stirred at room temperature for 6 hr. Ethyl acetate, tetrahydrofuran and saturated aqueous sodium hydrogen carbonate solution were added to the reaction mixture, and the mixture was extracted 3 times with ethyl acetate. The organic layer was washed with saturated brine, dried over anhydrous magnesium sulfate and filtered, and the solvent was evaporated under reduced pressure. The obtained residue was purified by silica gel column chromatography (ethyl acetate alone) to give a white solid. The obtained solid was suspended in methyl ethyl ketone, stirred at 80° C. and collected by filtration to give the title compound (90 mg, 62%) as a white solid.

¹H-NMR (DMSO-d₆, 300 MHz) δ 0.69-0.85 (4H, m), 1.82-1.96 (1H, m), 2.01 (3H, s), 2.23 (3H, s), 7.05-7.20 (2H, m), 7.30-7.50 (6H, m), 7.91-8.08 (2H, m), 8.35-8.48 (2H, m), 10.93 (1H, s), 12.11 (1H, s).

Example 71

Production of N-[4-({2-[(cyclopropylcarbonyl)amino]imidazo[1,2-a]pyridin-6-yl}oxy)phenyl]-6-ethyl-1-(4-fluorophenyl)-2-oxo-1,2-dihydropyridine-3-carboxamide

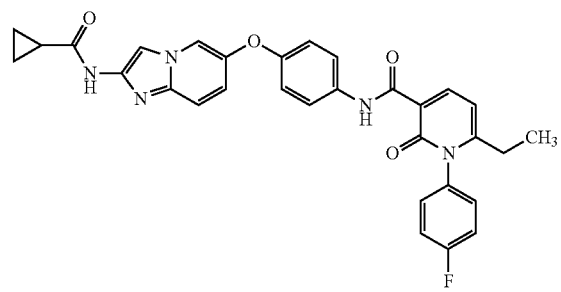 [SMILES: CCc1ccc(C(=O)Nc2ccc(Oc3ccc4nc(NC(=O)C5CC5)cn4c3)cc2)c(=O)n1-c1ccc(F)cc1]

Using N-[6-(4-aminophenoxy)imidazo[1,2-a]pyridin-2-yl]cyclopropanecarboxamide (100 mg, 0.324 mmol), 6-ethyl-1-(4-fluorophenyl)-2-oxo-1,2-dihydropyridine-3-carboxylic acid (101.5 mg, 0.389 mmol), N,N-dimethylformamide (1 mL), N,N-diisopropylethylamine (111 μL, 0.648 mmol) and HATU (148 mg, 0.389 mmol) and in the same manner as in Example 57, the title compound (133 mg, 74%) was obtained as a white solid.

¹H-NMR (DMSO-d₆, 300 MHz) δ 0.68-0.87 (4H, m), 1.05 (3H, t, J=7.4 Hz), 1.86-1.96 (1H, m), 2.30 (2H, q, J=7.4 Hz), 6.66 (1H, d, J=7.9 Hz), 6.93-7.16 (3H, m), 7.36-7.55 (5H, m), 7.63-7.75 (2H, m), 8.03 (1H, s), 8.44-8.59 (2H, m), 10.94 (1H, s), 11.83 (1H, s).

Example 72

Production of N-[4-({2-[(cyclopropylcarbonyl)amino]imidazo[1,2-a]pyridin-6-yl}oxy)phenyl]-6-(4-fluorophenyl)-5-methylpyridine-2-carboxamide 1-oxide

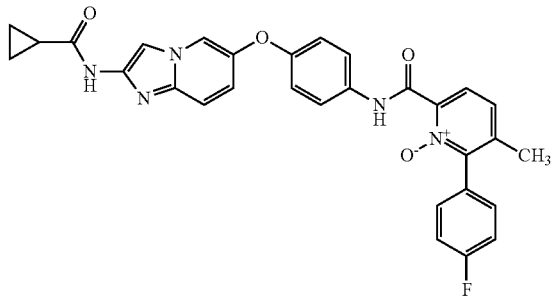 [SMILES: Cc1ccc(C(=O)Nc2ccc(Oc3ccc4nc(NC(=O)C5CC5)cn4c3)cc2)[n+]([O-])c1-c1ccc(F)cc1]

Using N-[6-(4-aminophenoxy)imidazo[1,2-a]pyridin-2-yl]cyclopropanecarboxamide (200 mg, 0.649 mmol), 6-(4-fluorophenyl)-5-methylpyridine-2-carboxylic acid 1-oxide (192.5 mg, 0.779 mmol), N,N-dimethylformamide (2 mL), N,N-diisopropylethylamine (224 μL, 1.30 mmol) and HATU (296 mg, 0.779 mmol) and in the same manner as in Example 58, the title compound (254 mg, 73%) was obtained as a white solid.

$^1$H-NMR (DMSO-$d_6$, 300 MHz) δ 0.70-0.87 (4H, m), 1.86-1.98 (1H, m), 2.12 (3H, s), 6.94-7.15 (3H, m), 7.32-7.56 (5H, m), 7.65-7.80 (3H, m), 8.04 (1H, s), 8.31 (1H, d, J=8.3 Hz), 8.50-8.56 (1H, m), 10.95 (1H, s), 13.60 (1H, s).

Example 73

Production of N-[4-({2-[(cyclopropylcarbonyl)amino]-3-fluoroimidazo[1,2-a]pyridin-6-yl}oxy)-3-fluorophenyl]-1-(4-fluorophenyl)-6-methyl-2-oxo-1,2-dihydropyridine-3-carboxamide

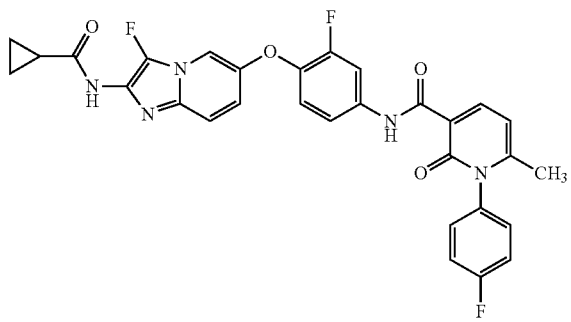 [SMILES: Cc1ccc(C(=O)Nc2ccc(Oc3ccc4nc(NC(=O)C5CC5)c(F)n4c3)c(F)c2)c(=O)n1-c1ccc(F)cc1]

A mixed solution of N-[3-fluoro-6-(2-fluoro-4-nitrophenoxy)imidazo[1,2-a]pyridin-2-yl]cyclopropanecarboxamide (15.2 mg, 0.041 mmol), reduced iron (12.1 mg, 0.205 mmol) and ammonium chloride (21.9 mg, 0.41 mmol) in ethanol (1 mL) and water (0.2 mL) was stirred at 90° C. for 5 hr. The reaction mixture was diluted with ethyl acetate and saturated aqueous ammonium chloride solution and extracted twice with ethyl acetate. The organic layer was washed with saturated brine, dried over anhydrous magnesium sulfate and filtered, and the solvent was evaporated under reduced pressure. To a solution of the obtained residue and 1-(4-fluorophenyl)-6-methyl-2-oxo-1,2-dihydropyridine-3-carboxylic acid (12.2 mg, 0.0492 mmol) in N,N-dimethylformamide (1 mL) were added N,N-diisopropylethylamine (14 μL, 0.082 mmol) and HATU (18.7 mg, 0.0492 mmol), and the mixture was stirred at room temperature for 17 hr. Ethyl acetate and saturated aqueous sodium hydrogen carbonate solution were added to the reaction mixture, and the mixture was extracted 3 times with ethyl acetate. The organic layer was washed with saturated brine, dried over anhydrous magnesium sulfate and filtered, and the solvent was evaporated under reduced pressure. The obtained residue was purified by silica gel column chromatography (ethyl acetate/hexane=2/1→ethyl acetate alone) to give a white solid. The obtained solid was washed with ethyl acetate and collected by filtration to give the title compound (8 mg, 34%) as a white solid.

$^1$H-NMR (DMSO-$d_6$, 300 MHz) δ 0.68-0.90 (4H, m), 1.77-1.93 (1H, m), 2.07 (3H, s), 6.66-6.78 (1H, m), 7.07-7.25 (2H, m), 7.32-7.59 (6H, m), 7.97 (1H, dd, J=13.3, 2.4 Hz), 8.13 (1H, d, J=2.3 Hz), 8.48 (1H, d, J=7.6 Hz), 10.51 (1H, s), 11.99 (1H, s).

Example 74

Production of N-[4-({2-[(cyclopropylcarbonyl)amino]imidazo[1,2-a]pyridin-6-yl}oxy)-3-fluorophenyl]-6-methyl-1-(3-methylphenyl)-2-oxo-1,2-dihydropyridine-3-carboxamide

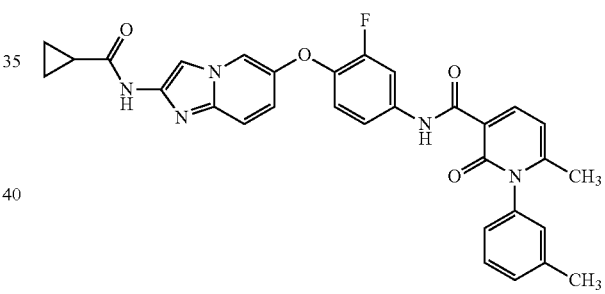

To a solution (3 mL) of 6-methyl-1-(3-methylphenyl)-2-oxo-1,2-dihydropyridine-3-carboxylic acid (120 mg, 0.50 mmol) in tetrahydrofuran were added oxalyl dichloride (130 mg, 1.0 mmol) and N,N-dimethylformamide (1 drop), and the mixture was stirred at room temperature for 1 hr. The mixture was concentrated under reduced pressure, and the solvent was evaporated. N,N-Dimethylformamide (3.0 mL) and a solution (2.0 mL) of N-[6-(4-amino-2-fluorophenoxy)imidazo[1,2-a]pyridin-2-yl]cyclopropanecarboxamide (130 mg, 0.40 mmol) in N,N-dimethylformamide were successively added, and the mixture was stirred at room temperature for 5 hr. Saturated aqueous sodium hydrogen carbonate solution was added to the reaction solution, and the mixture was extracted with ethyl acetate. The organic layer was washed with water and saturated brine, dried over anhydrous magnesium sulfate and filtered. The solvent was evaporated under reduced pressure, and the obtained residue was washed with ethyl acetate and collected by filtration to give the title compound (150 mg, 69%) as a brown solid.

$^1$H-NMR (DMSO-$d_6$, 300 MHz) δ 0.70-0.86 (4H, m), 1.85-1.96 (1H, m), 2.07 (3H, s), 2.38 (3H, s), 6.69 (1H, d,

J=8.1 Hz), 7.05-7.55 (8H, m), 7.96 (1H, dd, J=13.2, 2.5 Hz), 8.02 (1H, s), 8.43-8.53 (2H, m), 10.93 (1H, s), 12.03 (1H, s).

Example 75

Production of N-[4-({2-[(cyclopropylcarbonyl)amino]imidazo[1,2-a]pyridin-6-yl}oxy)-3-fluorophenyl]-1-(3-fluorophenyl)-6-methyl-2-oxo-1,2-dihydropyridine-3-carboxamide

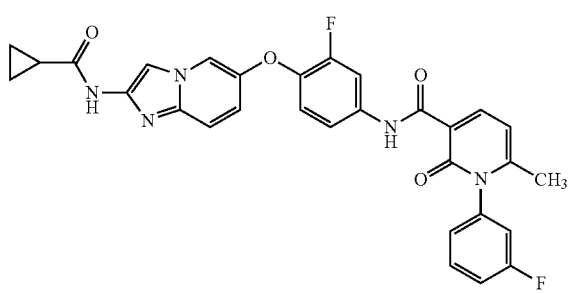 [SMILES: Cc1ccc(C(=O)Nc2ccc(Oc3ccc4nc(NC(=O)C5CC5)cn4c3)c(F)c2)c(=O)n1-c1cccc(F)c1]

A solution (5 mL) of N-[6-(4-amino-2-fluorophenoxy)imidazo[1,2-a]pyridin-2-yl]cyclopropanecarboxamide (130 mg, 0.40 mmol), 1-(3-fluorophenyl)-6-methyl-2-oxo-1,2-dihydropyridine-3-carboxylic acid (120 mg, 0.48 mmol), HATU (180 mg, 0.48 mmol) and N,N-diisopropylethylamine (100 mg, 0.80 mmol) in N,N-dimethylformamide was stirred at room temperature for 5 hr. The reaction solution was divided into two layers with tetrahydrofuran (10 mL) and saturated aqueous sodium hydrogen carbonate solution (10 mL) and the aqueous layer was subjected to extraction (3 times) with ethyl acetate (15 ml). The combined organic layer was washed with water (15 mL) and saturated brine (15 mL), dried over anhydrous magnesium sulfate and filtered. The solvent was evaporated under reduced pressure, and the obtained residue was washed with ethyl acetate and collected by filtration to give the title compound (80 mg, 35%) as a brown solid.

$^1$H-NMR (DMSO-d$_6$, 300 MHz) δ 0.77-0.93 (4H, m), 1.88-1.98 (1H, m), 2.10 (3H, s), 6.72 (1H, d, J=8.3 Hz), 7.22 (1H, t, J=9.1 Hz), 7.30 (1H, dt, J=7.8, 1.0 Hz), 7.35-7.52 (4H, m), 7.65 (2H, d, J=8.7 Hz), 8.00 (1H, dd, J=13.2, 2.5 Hz), 8.05 (1H, s), 8.49 (1H, d, J=7.6 Hz), 8.57 (1H, d, J=2.1 Hz), 11.52 (1H, br s), 11.98 (1H, s).

Example 76

Production of N-[4-({2-[(cyclopropylcarbonyl)amino][1,2,4]triazolo[1,5-a]pyridine-7-yl}oxy)-3-fluorophenyl]-1-(4-fluorophenyl)-6-methyl-2-oxo-1,2-dihydropyridine-3-carboxamide

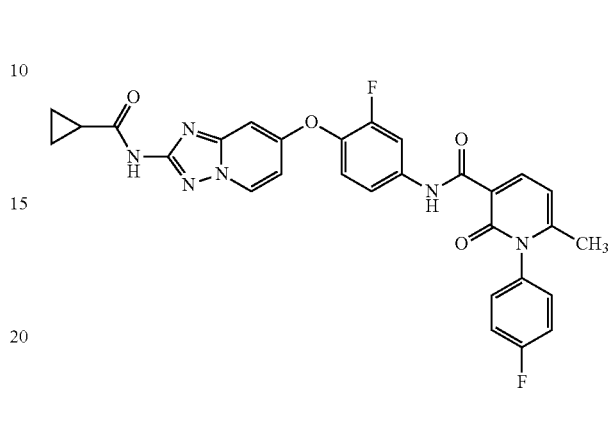

To a solution of N-[6-(4-amino-2-fluorophenoxy)imidazo[1,2-a]pyridin-2-yl]cyclopropanecarboxamide (150 mg, 0.458 mmol) and 1-(4-fluorophenyl)-6-methyl-2-oxo-1,2-dihydropyridine-3-carboxylic acid (170 mg, 0.687 mmol) in N,N-dimethylacetamide (3.0 mL) were added HATU (261 mg, 0.687 mmol) and N,N-diisopropylethylamine (120 μL, 0.687 mmol), and the mixture was stirred at room temperature for 16 hr. Saturated aqueous sodium hydrogen carbonate solution was added to the reaction mixture, and the mixture was extracted with ethyl acetate/tetrahydrofuran. The extract was washed with saturated brine, dried over anhydrous magnesium sulfate and filtered, and the solvent was evaporated under reduced pressure. The obtained residue was purified by silica gel column chromatography (ethyl acetate/hexane=25/75→100/0) and the obtained solid was washed with ethyl acetate and collected by filtration to give the title compound (111 mg, 44%) as a white solid.

$^1$H-NMR (DMSO-d$_6$, 300 MHz) δ 0.78-0.83 (4H, m), 1.98-2.07 (1H, m), 2.08 (3H, s), 6.72 (1H, d, J=8.4 Hz), 6.84 (1H, d, J=2.7 Hz), 6.91-6.96 (1H, m), 7.34-7.54 (6H, m), 8.03 (1H, dd, J=12.9, 2.4 Hz), 8.50 (1H, d, J=7.5 Hz), 8.80 (1H, d, J=6.9 Hz), 10.99 (1H, s), 12.08 (1H, s).

Example 77

Production of N-[4-({2-[(cyclopropylcarbonyl)amino]imidazo[1,2-a]pyridin-6-yl}oxy)-3-fluorophenyl]-2-(4-fluorophenyl)-1,5-dimethyl-3-oxo-2,3-dihydro-1H-pyrazole-4-carboxamide

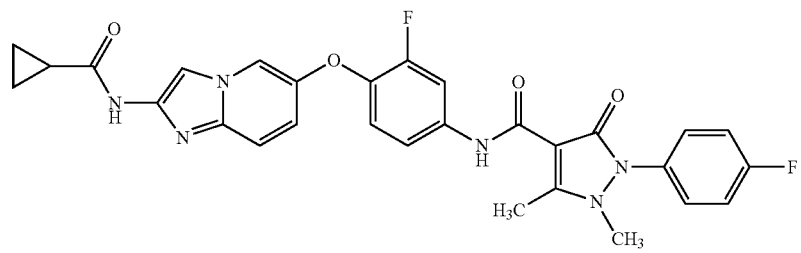 [SMILES: Cc1c(C(=O)Nc2ccc(Oc3ccc4nc(NC(=O)C5CC5)cn4c3)c(F)c2)c(=O)n(-c2ccc(F)cc2)n1C]

To a solution of 2-(4-fluorophenyl)-1,5-dimethyl-3-oxo-2,3-dihydro-1H-pyrazole-4-carboxylic acid (1130 mg, 4.5 mmol) in tetrahydrofuran (75 mL) were added N,N-dimethylformamide (6 drops) and oxalyl dichloride (780 μL, 9.1 mmol), and the mixture was stirred at room temperature for 1 hr. The solvent was evaporated under reduced pressure, and the obtained residue was dissolved in N,N-dimethylacetamide (10 mL). The solution was added to a solution of N-[6-(4-amino-2-fluorophenoxy)imidazo[1,2-a]pyridin-2-yl]cyclopropanecarboxamide (1230 mg, 3.8 mmol) in N,N-dimethylacetamide (30 mL), and the mixture was stirred at room temperature for 4 hr. Ethyl acetate/tetrahydrofuran and saturated aqueous sodium hydrogen carbonate solution were added to the mixture, and the aqueous layer was extracted 4 times with ethyl acetate/tetrahydrofuran. The combined organic layer was washed with water and saturated brine, dried over anhydrous magnesium sulfate and filtered. The solvent was evaporated under reduced pressure, and the residue was washed with ethyl acetate and collected by filtration to give the title compound (1640 mg, 67%) as a white solid.

$^1$H-NMR (DMSO-$d_6$, 300 MHz) δ 0.75-0.84 (4H, m), 1.86-1.97 (1H, m), 2.69 (3H, s), 3.35 (3H, s), 7.05-7.24 (3H, m), 7.38-7.55 (5H, m), 7.90 (1H, dd, J=13.4, 2.3 Hz), 8.02 (1H, s), 8.44 (1H, d, J=1.9 Hz), 10.84 (1H, s), 10.94 (1H, s).

Example 78

Production of N-[4-({2-[(cyclopropylcarbonyl)amino]imidazo[1,2-a]pyridin-6-yl}oxy)-3-fluorophenyl]-2-(4-fluorophenyl)-1,5-dimethyl-3-oxo-2,3-dihydro-1H-pyrazole-4-carboxamide hydrochloride monohydrate

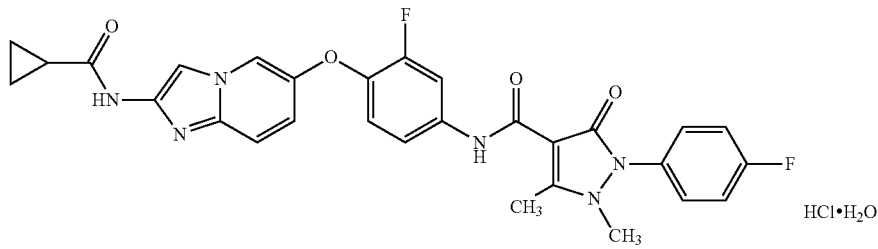

To a suspension of N-[4-({2-[(cyclopropylcarbonyl)amino]imidazo[1,2-a]pyridin-6-yl}oxy)-3-fluorophenyl]-2-(4-fluorophenyl)-1,5-dimethyl-3-oxo-2,3-dihydro-1H-pyrazole-4-carboxamide (400 mg, 0.72 mmol) in methyl ethyl ketone (7 mL) and water (5 mL) was slowly added 6N aqueous hydrochloric acid solution (240 μL), and the mixture was stirred at room temperature for 1 hr. The precipitated solid was collected by filtration, washed with methyl ethyl ketone and suspended in ethanol (5 mL), and the suspension was stirred at 70° C. for 10 min. The solid was collected by filtration, washed with ethanol and dried under reduced pressure to give the title compound (120 mg, 27%) as a white solid.

$^1$H-NMR (DMSO-$d_6$, 300 MHz) δ 0.84-0.95 (4H, m), 1.90-2.01 (1H, m), 2.69 (3H, s), 3.36 (3H, s), 7.25-7.28 (2H, m), 7.41-7.54 (4H, m), 7.57 (1H, dd, J=9.6, 2.1 Hz), 7.75 (1H, d, J=9.6 Hz), 7.90-7.99 (1H, m), 8.08 (1H, s), 8.61 (1H, d, J=2.1 Hz), 10.89 (1H, s), 11.85 (1H, s).

Example 79

Production of N-[4-({2-[(cyclopropylcarbonyl)amino]imidazo[1,2-a]pyridin-6-yl}oxy)-3-fluorophenyl]-5-ethyl-2-(4-fluorophenyl)-1-methyl-3-oxo-2,3-dihydro-1H-pyrazole-4-carboxamide

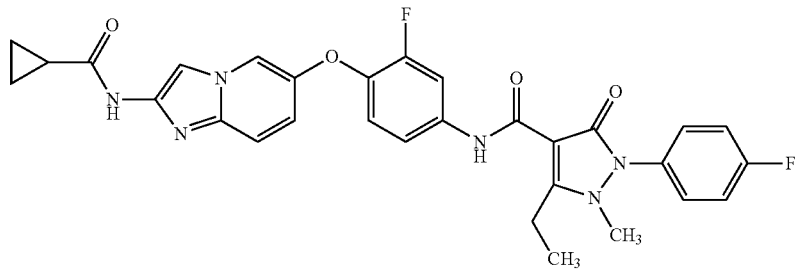 [SMILES: CCc1c(C(=O)Nc2ccc(Oc3ccc4nc(NC(=O)C5CC5)cn4c3)c(F)c2)c(=O)n(-c2ccc(F)cc2)n1C]

In the same manner as in Example 77 and using 5-ethyl-2-(4-fluorophenyl)-1-methyl-3-oxo-2,3-dihydro-1H-pyrazole-4-carboxylic acid (250 mg, 0.94 mmol), tetrahydrofuran (9 mL), N,N-dimethylformamide (1 drop), oxalyl dichloride (160 μL, 1.9 mmol), N-[6-(4-amino-2-fluorophenoxy)imidazo[1,2-a]pyridin-2-yl]cyclopropanecarboxamide (250 mg, 0.78 mmol) and N,N-dimethylacetamide (12 mL) as starting materials, the title compound (210 mg, 47%) was obtained as a white solid.

$^1$H-NMR (DMSO-$d_6$, 300 MHz) δ 0.75-0.83 (3H, m), 1.20-1.29 (4H, m), 1.85-1.96 (1H, m), 3.15 (2H, q, J=7.5 Hz), 3.39 (3H, s), 7.06-7.23 (3H, m), 7.39-7.48 (3H, m), 7.49-7.58 (2H, m), 7.91 (1H, dd, J=13.4, 2.3 Hz), 8.03 (1H, s), 8.42-8.47 (1H, m), 10.87 (1H, s), 10.94 (1H, s).

Example 80

Production of N-[4-({2-[(cyclopropylcarbonyl)amino]imidazo[1,2-a]pyridin-6-yl}oxy)-3-fluorophenyl]-3-(4-fluorophenyl)-4-methyl-2-oxotetrahydropyrimidine-1(2H)-carboxamide

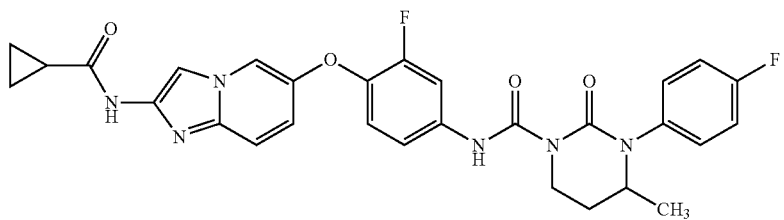 [SMILES: CC1CCN(C(=O)Nc2ccc(Oc3ccc4nc(NC(=O)C5CC5)cn4c3)c(F)c2)C(=O)N1c1ccc(F)cc1]

To a solution of 1-(4-fluorophenyl)-6-methyltetrahydropyrimidin-2(1H)-one (240 mg, 1.1 mmol) in tetrahydrofuran (5 mL) was added bis(trichloromethyl) carbonate (170 mg, 0.57 mmol), and the mixture was stirred at 70° C. for 3.5 hr. The mixture was cooled to room temperature, a solution of N-[6-(4-amino-2-fluorophenoxy)imidazo[1,2-a]pyridin-2-yl]cyclopropanecarboxamide (250 mg, 0.76 mmol) in tetrahydrofuran (8 mL) and N,N-diisopropylethylamine (300 mg, 2.3 mmol) were added to the mixture, and the mixture was stirred at room temperature for 1 hr. Ethyl acetate/tetrahydrofuran and saturated aqueous sodium hydrogen carbonate solution were added to the mixture, and the aqueous layer was extracted 3 times with ethyl acetate/tetrahydrofuran. The combined organic layer was washed with saturated brine, dried over anhydrous magnesium sulfate and filtered. The filtrate was concentrated under reduced pressure, and the residue was purified by silica gel column chromatography (NH silica gel, ethyl acetate/hexane=50/50→100/0) to give the title compound (29 mg, 7%) as a white solid.

Example 81

Production of N-[4-({2-[(cyclopropylcarbonyl)amino]imidazo[1,2-a]pyridin-6-yl}oxy)-3-fluorophenyl]-5-(4-fluorophenyl)-4-methyl-6-oxo-3,6-dihydropyridine-1(2H)-carboxamide

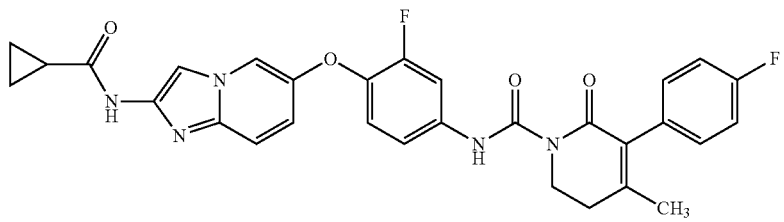 [SMILES: CC1=C(c2ccc(F)cc2)C(=O)N(C(=O)Nc2ccc(Oc3ccc4nc(NC(=O)C5CC5)cn4c3)c(F)c2)CC1]

To a solution of bis(trichloromethyl) carbonate (127 mg, 0.43 mmol) in tetrahydrofuran (4 mL) were slowly added a solution of 3-(4-fluorophenyl)-4-methyl-5,6-dihydropyridin-2(1H)-one (240 mg, 1.2 mmol) and triethylamine (240 mg, 2.3 mmol) in tetrahydrofuran (2 mL) under ice-cooling, and the mixture was stirred at 0° C. for 40 min and at room temperature for 15 min. A solution of N-[6-(4-amino-2-fluorophenoxy)imidazo[1,2-a]pyridin-2-yl]cyclopropanecarboxamide (250 mg, 0.78 mmol) in tetrahydrofuran (4 mL) and triethylamine (79 mg, 0.78 mmol) were added to the mixture, and the mixture was stirred at room temperature for 2 hr. Ethyl acetate/tetrahydrofuran and saturated brine were added to the mixture, and the aqueous layer was extracted 3 times with ethyl acetate/tetrahydrofuran. The combined organic layer was washed with saturated brine, dried over anhydrous magnesium sulfate and filtered. The solvent was evaporated under reduced pressure, and the residue was purified by silica gel column chromatography (NH silica gel, ethyl acetate/hexane=40/60→90/10) to give the title compound (170 mg, 39%) as a white solid.

$^1$H-NMR (DMSO-$d_6$, 300 MHz) δ 0.72-0.85 (4H, m), 1.82 (3H, s), 1.87-1.96 (1H, m), 2.60 (2H, t, J=6.5 Hz), 4.02 (2H, t, J=6.5 Hz), 7.06-7.17 (2H, m), 7.19-7.32 (5H, m), 7.43 (1H, d, J=9.6 Hz), 7.74 (1H, dd, J=13.3, 2.5 Hz), 8.02 (1H, s), 8.45 (1H, d, J=1.7 Hz), 10.94 (1H, s), 11.51 (1H, s).

Example 82

Production of N-[4-({2-[(cyclopropylcarbonyl)amino]imidazo[1,2-a]pyridin-6-yl}oxy)-3-fluorophenyl]-1-(4-fluorophenyl)-4,6-dimethyl-2-oxo-1,2-dihydropyridine-3-carboxamide

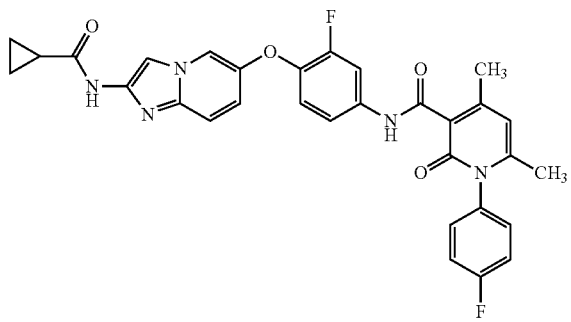 [SMILES: Cc1cc(C)n(-c2ccc(F)cc2)c(=O)c1C(=O)Nc1ccc(Oc2ccc3nc(NC(=O)C4CC4)cn3c2)c(F)c1]

To a solution of N-[6-(4-amino-2-fluorophenoxy)imidazo[1,2-a]pyridin-2-yl]cyclopropanecarboxamide (116 mg, 0.357 mmol) and 1-(4-fluorophenyl)-4,6-dimethyl-2-oxo-1,2-dihydropyridine-3-carboxylic acid (112 mg, 0.429 mmol) in N,N-dimethylformamide (1 mL) were added N,N-diisopropylethylamine (123 μL, 0.714 mmol) and HATU (163 mg, 0.428 mmol), and the mixture was stirred at room temperature for 4 hr. Ethyl acetate and saturated aqueous sodium hydrogen carbonate solution were added to the reaction mixture, and the mixture was extracted 3 times with ethyl acetate. The organic layer was washed with saturated brine, dried over anhydrous magnesium sulfate and filtered, and the solvent was evaporated under reduced pressure. The obtained residue was purified by silica gel column chromatography (ethyl acetate) to give a white solid. The obtained solid was washed with ethyl acetate and collected by filtration to give the title compound (110 mg, 54%) as a white solid.

$^1$H-NMR (DMSO-$d_6$, 300 MHz) δ 0.38-1.08 (4H, m), 1.54-2.17 (4H, m), 2.36 (3H, s), 6.37 (1H, s), 6.91-7.24 (2H, m), 7.24-7.58 (6H, m), 7.88 (1H, dd, J=13.4, 2.5 Hz), 8.02 (1H, s), 8.42 (1H, d, J=1.9 Hz), 10.93 (1H, s), 11.11 (1H, s).

Example 83

Production of N-[4-({2-[(cyclopropylcarbonyl)amino]imidazo[1,2-a]pyridin-6-yl}oxy)phenyl]-1-(4-fluorophenyl)-6-methyl-2-oxo-1,2-dihydropyridine-3-carboxamide benzenesulfonate monohydrate

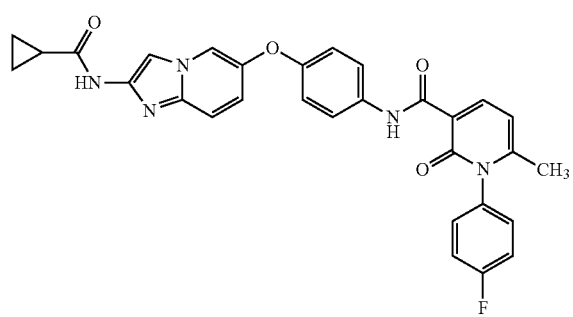

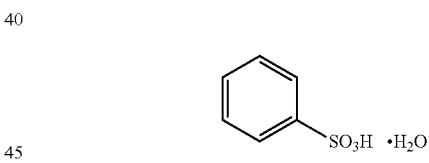

To a solution (90 mL) of N-[4-({2-[(cyclopropylcarbonyl)amino]imidazo[1,2-a]pyridin-6-yl}oxy)phenyl]-1-(4-fluorophenyl)-6-methyl-2-oxo-1,2-dihydropyridine-3-carboxamide (400 mg, 0.744 mmol) in tetrahydrofuran was added benzenesulfonic acid monohydrate (197 mg, 1.12 mmol) at 80° C. The mixture was filtered, and the filtrate was gradually cooled to room temperature. The solution at room temperature was distilled off at 110° C. to evaporate tetrahydrofuran to about half, and gradually cooled again to room temperature. The precipitate was collected by filtration, and the solid was washed with tetrahydrofuran and dried to give the title compound (309 mg, 58%) as a white solid.

$^1$H-NMR (DMSO-$d_6$, 300 MHz) δ 0.78-0.99 (4H, m), 1.90 (1H, s), 2.07 (3H, s), 6.70 (1H, d, J=8.3 Hz), 7.01-7.16 (2H, m), 7.25-7.35 (3H, m), 7.38-7.53 (5H, m), 7.56-7.64 (2H, m), 7.65-7.78 (3H, m), 8.05 (1H, s), 8.48 (1H, d, J=7.6 Hz), 8.60 (1H, d, J=1.7 Hz), 11.43 (1H, s), 11.88 (1H, s).

Example 84

Production of N-[4-({2-[(cyclopropylcarbonyl)amino]imidazo[1,2-a]pyridin-6-yl}oxy)-2-fluorophenyl]-6-(4-fluorophenyl)-5-methylpyridine-2-carboxamide 1-oxide

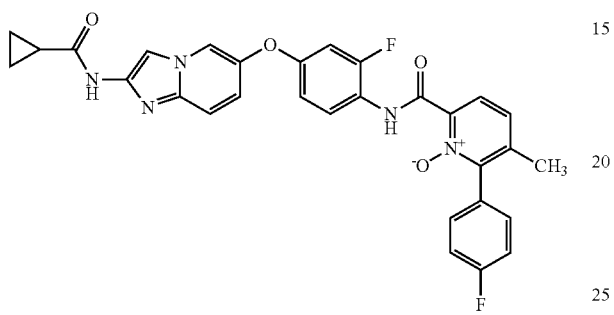

To a solution of N-[6-(4-amino-2-fluorophenoxy)imidazo[1,2-a]pyridin-2-yl]cyclopropanecarboxamide (200 mg, 0.613 mmol) and 6-(4-fluorophenyl)-5-methylpyridine-2-carboxylic acid 1-oxide (212 mg, 0.858 mmol) in N,N-dimethylacetamide (2.0 mL) were added HATU (350 mg, 0.919 mmol) and N,N-diisopropylethylamine (160 μL, 0.919 mmol), and the mixture was stirred at room temperature for 6 hr. Ethyl acetate/tetrahydrofuran was added and the mixture was washed with saturated aqueous sodium hydrogen carbonate solution and saturated brine, dried over anhydrous magnesium sulfate and filtered. The solvent was evaporated under reduced pressure and the obtained residue was recrystallized from tetrahydrofuran to give the title compound (109 mg, 32%) as a white solid.

$^1$H-NMR (DMSO-d$_6$, 300 MHz) δ 0.78-0.82 (4H, m), 1.88-1.97 (1H, m), 2.13 (3H, s), 6.90-6.95 (1H, m), 7.08-7.16 (2H, m), 7.28-7.52 (5H, m), 7.70-7.73 (1H, m), 8.05 (1H, s), 8.30-8.40 (2H, m), 8.58 (1H, s), 10.97 (1H, s), 14.01 (1H, s).

Example 85

Production of N-[4-({2-[(cyclopropylcarbonyl)amino]imidazo[1,2-a]pyridin-6-yl}oxy)-2-fluorophenyl]-1-(4-fluorophenyl)-6-methyl-2-oxo-1,2-dihydropyridine-3-carboxamide p-toluenesulfonate To N-[4-({2-[(cyclopropylcarbonyl)amino]imidazo[1,2-a]pyridin-6-yl}oxy)-2-fluorophenyl]-1-(4-fluorophenyl)-6-methyl-2-oxo-1,2-dihydropyridine-3-carboxamide (300 mg, 0.54 mmol) was added tetrahydrofuran (15 mL), and the mixture was dissolved by heating at 60° C. p-Toluenesulfonic acid monohydrate (123.3 mg, 0.65 mmol) was added. The mixture was stirred at 50° C. for 1 hr and at 40° C. for 12 hr. After cooling to room temperature, the precipitate was collected by filtration, washed with tetrahydrofuran and dried at 100° C. for 3 hr under reduced pressure to give the title compound (259 mg, 66%) as a white powder.

$^1$H-NMR (DMSO-d$_6$, 300 MHz) δ 0.85-0.90 (4H, m), 1.86-1.94 (1H, m), 2.07 (3H, s), 2.29 (3H, s), 6.71 (1H, d, J=8.1 Hz), 6.95-7.00 (1H, m), 7.11 (2H, d, J=7.8 Hz), 7.13-7.18 (1H, m), 7.40-7.52 (7H, m), 7.66 (1H, d, J=9.6 Hz), 8.05 (1H, s), 8.42-8.50 (2H, m), 8.66 (1H, s), 11.35 (1H, s), 12.09 (1H, s).

Example 86

Production of N-[4-({2-[(cyclopropylcarbonyl)amino]imidazo[1,2-a]pyridin-6-yl}oxy)-3-fluorophenyl]-6-methyl-2-oxo-1-phenyl-1,2-dihydropyridine-3-carboxamide acetate

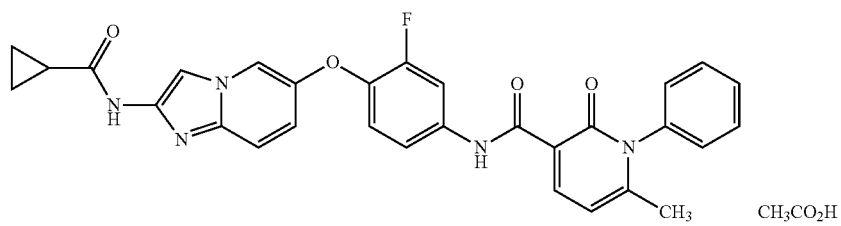

To a solution of N-[4-({2-[(cyclopropylcarbonyl)amino]imidazo[1,2-a]pyridin-6-yl}oxy)-3-fluorophenyl]-6-methyl-2-oxo-1-phenyl-1,2-dihydropyridine-3-carboxamide (500 mg, 0.93 mmol) in acetic acid (3 ml) was added diisopropyl ether (15 ml) at room temperature. The reaction solution was stirred at 70° C. for 3 hr, and the precipitate was collected by filtration and washed with diisopropyl ether to give a white solid (420 mg). To a solution (4 ml) of the white solid (400 mg) in acetic acid was added water (3 ml) at 80° C., and the mixture was cooled to room temperature and stirred for 17 hr. The precipitate was collected by filtration and washed with water to give the title compound (330 mg, 59%) as white crystals.

$^1$H-NMR (DMSO-d$_6$, 300 MHz) δ 0.80 (4H, m), 1.91 (4H, s), 2.06 (3H, s), 6.71 (1H, d, J=7.4 Hz), 6.89-7.25 (2H, m), 7.25-7.48 (4H, m), 7.48-7.74 (3H, m), 7.74-8.15 (2H, m), 8.15-8.66 (2H, m), 10.93 (1H, s), 12.02 (2H, s).

Example 87

Production of N-[4-({2-[(cyclopropylcarbonyl)amino]imidazo[1,2-a]pyridin-6-yl}oxy)-3-fluorophenyl]-6-methyl-2-oxo-1-phenyl-1,2-dihydropyridine-3-carboxamide p-toluenesulonate

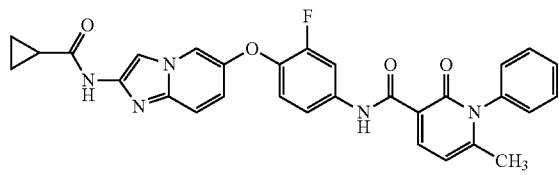

To a suspension of N-[4-({2-[(cyclopropylcarbonyl)amino]imidazo[1,2-a]pyridin-6-yl}oxy)-3-fluorophenyl]-6-methyl-2-oxo-1-phenyl-1,2-dihydropyridine-3-carboxamide (650 mg, 1.21 mmol) in ethanol (6.5 ml) was added p-toluenesulfonic acid monohydrate (276 mg, 1.45 mmol) at 70° C. The reaction solution was stirred at 70° C. for 1 hr, and the precipitate was collected by filtration and washed with ethanol to give the title compound (702 mg, 82%) as white crystals.

$^1$H-NMR (DMSO-d$_6$, 300 MHz) δ 0.48-0.96 (4H, m), 1.90 (1H, br s), 2.07 (3H, s), 2.29 (3H, s), 6.71 (1H, d, J=7.9 Hz), 6.98-7.26 (3H, m), 7.27-7.73 (10H, m), 7.83-8.15 (2H, m), 8.27-8.69 (2H, m), 11.23 (1H, br s), 12.05 (1H, s).

Example 88

Production of N-[4-({2-[(cyclopropylcarbonyl)amino]imidazo[1,2-a]pyridin-6-yl}oxy)-3-fluorophenyl]-6-methyl-2-oxo-1-phenyl-1,2-dihydropyridine-3-carboxamide hydrochloride

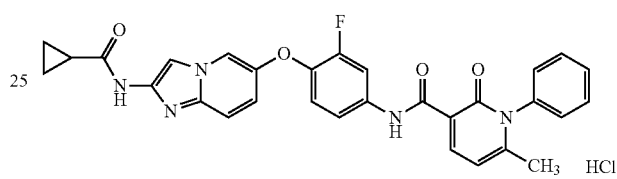

A solution (5 to 10%) of hydrogen chloride/methanol was heated to 50° C., and N-[4-({2-[(cyclopropylcarbonyl)amino]imidazo[1,2-a]pyridin-6-yl}oxy)-3-fluorophenyl]-6-methyl-2-oxo-1-phenyl-1,2-dihydropyridine-3-carboxamide (500 mg, 0.93 mmol) was added. The mixture was stirred for 5 min and at room temperature for 30 min. The precipitate was collected by filtration and washed with methanol to give the title compound (420 mg, 79%) as white crystals.

$^1$H-NMR (DMSO-d$_6$, 300 MHz) δ 0.35-1.61 (4H, m), 1.77-2.04 (1H, m), 2.07 (3H, s), 6.72 (1H, d, J=8.3 Hz), 7.04-7.36 (1H, m), 7.36-7.49 (4H, m), 7.49-7.80 (4H, m), 7.93-8.26 (2H, m), 8.49 (1H, d, J=7.6 Hz), 8.56 (1H, d, J=1.9 Hz), 11.49 (1H, br s), 12.06 (1H, s).

Example 89

Production of N-[4-({2-[(cyclopropylcarbonyl)amino]imidazo[1,2-a]pyridin-6-yl}oxy)-3-fluorophenyl]-6-methyl-2-oxo-1-phenyl-1,2-dihydropyridine-3-carboxamide methanesulfonate

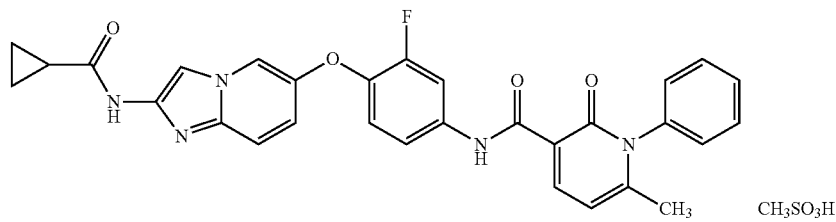

Example 90

Production of N-[4-({2-[(cyclopropylcarbonyl)amino]imidazo[1,2-a]pyridin-6-yl}oxy)-3-fluorophenyl]-1-(4-fluorophenyl)-6-methyl-2-oxo-1,2-dihydropyridine-3-carboxamide acetate

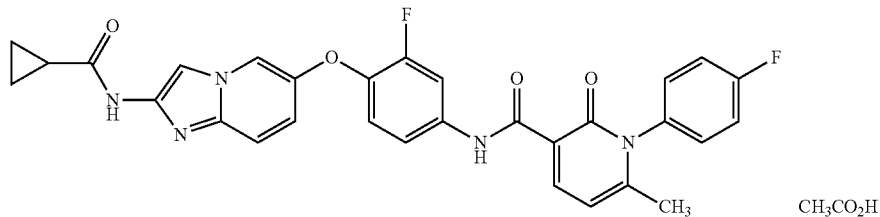 [SMILES: Cc1ccc(C(=O)Nc2ccc(Oc3ccc4nc(NC(=O)C5CC5)cn4c3)c(F)c2)c(=O)n1-c1ccc(F)cc1 ; "CH3CO2H"] 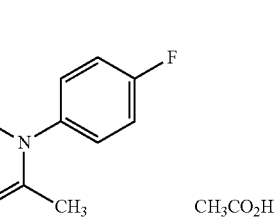

To N-[4-({2-[(cyclopropylcarbonyl)amino]imidazo[1,2-a]pyridin-6-yl}oxy)-3-fluorophenyl]-1-(4-fluorophenyl)-6-methyl-2-oxo-1,2-dihydropyridine-3-carboxamide (700 mg, 1.26 mmol) was added acetic acid (3.5 mL), and the mixture was heated to 60° C. Methylethylketone (2.1 mL) and water (3.5 mL) were added, and the mixture was cooled to room temperature and stirred at room temperature for 16 hr. The precipitate was collected by filtration and washed with water to give the title compound (512 mg, 66%) as white crystals.

$^1$H-NMR (DMSO-d$_6$, 300 MHz) δ 0.75-0.82 (4H, m), 1.85-1.96 (1H, m), 1.91 (3H, s), 2.07 (3H, s), 6.75 (1H, d, J=8.1 Hz), 7.10-7.17 (2H, m), 7.34-7.53 (6H, m), 7.97 (1H, dd, J=13.2, 2.7 Hz), 8.02 (1H, s), 8.45-8.50 (2H, m), 10.94 (1H, s), 11.99 (1H, s).

Example 91

Production of N-[4-({2-[(cyclopropylcarbonyl)amino]imidazo[1,2-a]pyridin-6-yl}oxy)-3-fluorophenyl]-1-(2-fluorophenyl)-6-methyl-2-oxo-1,2-dihydropyridine-3-carboxamide

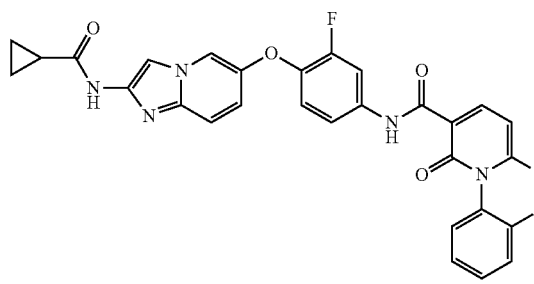

A solution (5 mL) of N-[6-(4-amino-2-fluorophenoxy)imidazo[1,2-a]pyridin-2-yl]cyclopropanecarboxamide (131 mg, 0.40 mmol), 1-(2-fluorophenyl)-6-methyl-2-oxo-1,2-dihydropyridine-3-carboxylic acid (119 mg, 0.48 mmol), HATU (183 mg, 0.48 mmol) and N,N-diisopropylethylamine (103 mg, 0.80 mmol) in N,N-dimethylformamide was stirred at room temperature for 5 hr. The reaction solution was divided into two layers with tetrahydrofuran and sodium hydrogen carbonate saturated aqueous solution and the aqueous layer was subjected to extraction (3 times) with ethyl acetate. The combined organic layer was washed with water and saturated brine, dried over anhydrous magnesium sulfate and filtered. The solvent was evaporated under reduced pressure, and the residue was purified by silica gel column chromatography (basic silica) and recrystallized from ethanol to give the title compound (80 mg, 36%) as a white solid.

$^1$H-NMR (DMSO-d$_6$, 300 MHz) δ 0.68-0.89 (4H, m), 1.83-1.98 (1H, m), 2.12 (3H, s), 6.71-6.82 (1H, m), 7.07-7.19 (2H, m), 7.35-7.68 (6H, m), 7.96 (1H, dd, J=13.2, 2.5 Hz), 8.02 (1H, s), 8.46 (1H, d, J=1.7 Hz), 8.53 (1H, d, J=7.6 Hz), 10.94 (1H, s), 11.81 (1H, s).

Example 92

Production of N-[4-({2-[(cyclopropylcarbonyl)amino]imidazo[1,2-a]pyridin-6-yl}oxy)-3-fluorophenyl]-1-(4-fluoro-3-methylphenyl)-6-methyl-2-oxo-1,2-dihydropyridine-3-carboxamide

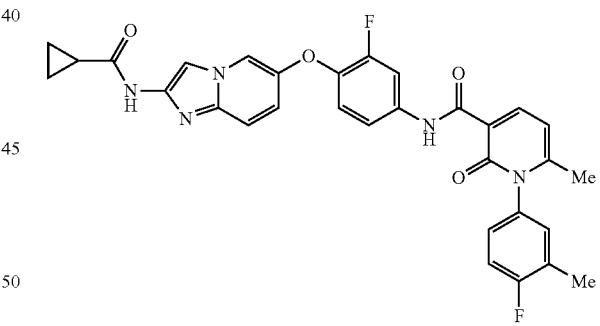

A solution (5 mL) of N-[6-(4-amino-2-fluorophenoxy)imidazo[1,2-a]pyridin-2-yl]cyclopropanecarboxamide (131 mg, 0.40 mmol), 1-(4-fluoro-3-methylphenyl)-6-methyl-2-oxo-1,2-dihydropyridine-3-carboxylic acid (125 mg, 0.48 mmol), HATU (183 mg, 0.48 mmol) and N,N-diisopropylethylamine (103 mg, 0.80 mmol) in N,N-dimethylformamide was stirred at room temperature for 5 hr. The reaction solution was divided into two layers with tetrahydrofuran and sodium hydrogen carbonate saturated aqueous solution and the aqueous layer was subjected to extraction (3 times) with ethyl acetate. The combined organic layer was washed with water and saturated brine, dried over anhydrous magnesium sulfate and filtered. The solvent was evaporated under reduced pressure, and the residue was purified by silica gel column chromatography (basic silica) and recrystallized from ethanol to give the title compound (100 mg, 44%) as a white solid.

$^1$H-NMR (DMSO-$d_6$, 300 MHz) δ 0.69-0.87 (4H, m), 1.84-1.98 (1H, m), 2.09 (3H, s), 2.29 (3H, d, J=1.5 Hz), 6.70 (1H, d, J=8.3 Hz), 7.05-7.19 (2H, m), 7.24-7.41 (4H, m), 7.43 (1H, d, J=9.6 Hz), 7.97 (1H, dd, J=13.2, 2.5 Hz), 8.02 (1H, s), 8.35-8.57 (2H, m), 10.94 (1H, s), 12.00 (1H, s).

Example 93

Production of N-[4-({2-[(cyclopropylcarbonyl)amino]imidazo[1,2-a]pyridin-6-yl}oxy)-3-fluorophenyl]-6-(3-fluorophenyl)-5-methylpyridin-2-carboxamide 1-oxide

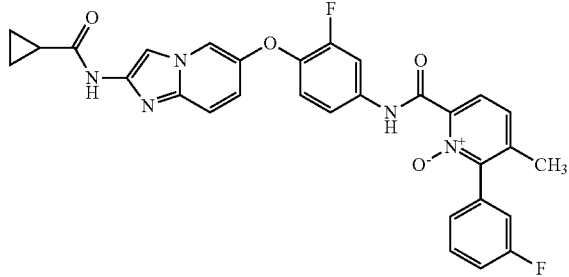 [SMILES: Cc1ccc(C(=O)Nc2ccc(Oc3ccc4nc(NC(=O)C5CC5)cn4c3)c(F)c2)[n+]([O-])c1-c1cccc(F)c1]

A solution (5 mL) of N-[6-(4-amino-2-fluorophenoxy)imidazo[1,2-a]pyridin-2-yl]cyclopropanecarboxamide (196 mg, 0.60 mmol), 6-(3-fluorophenyl)-5-methylpyridine-2-carboxylic acid 1-oxide (178 mg, 0.72 mmol), HATU (273 mg, 0.72 mmol) and N,N-diisopropylethylamine (155 mg, 1.20 mmol) in N,N-dimethylformamide was stirred at room temperature for 5 hr. The reaction solution was divided into two layers with tetrahydrofuran and sodium hydrogen carbonate saturated aqueous solution and the aqueous layer was subjected to extraction (3 times) with ethyl acetate. The combined organic layer was washed with water and saturated brine, dried over anhydrous magnesium sulfate and filtered. The solvent was evaporated under reduced pressure, and the residue was purified by silica gel column chromatography (basic silica) and recrystallized from ethanol/water to give the title compound (250 mg, 75%) as a white solid.

$^1$H-NMR (DMSO-$d_6$, 300 MHz) δ 0.74-0.85 (4H, m), 1.85-1.98 (1H, m), 2.13 (3H, s), 7.08-7.21 (2H, m), 7.24-7.30 (1H, m), 7.30-7.40 (2H, m), 7.41-7.52 (2H, m), 7.54-7.65 (1H, m), 7.71 (1H, d, J=9.1 Hz), 7.98 (1H, dd, J=13.0, 2.5 Hz), 8.03 (1H, s), 8.32 (1H, d, J=8.3 Hz), 8.49 (1H, d, J=1.7 Hz), 10.94 (1H, s), 13.69 (1H, s).

Example 94

Production of N-[4-({2-[(cyclopropylcarbonyl)amino]imidazo[1,2-a]pyridin-6-yl}oxy)-3-fluorophenyl]-6-(3-fluorophenyl)-5-methylpyridine-2-carboxamide 1-oxide p-tluenesulfonate

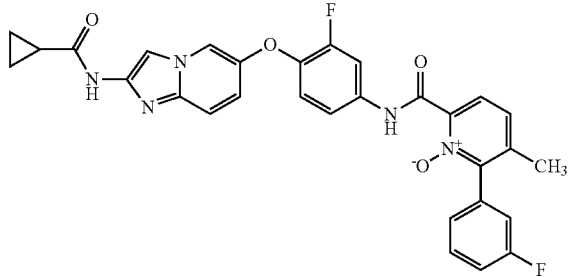

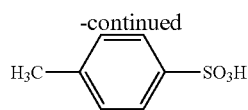

An ethanol (20 mL) suspension containing N-[4-({2-[(cyclopropylcarbonyl)amino]imidazo[1,2-a]pyridin-6-yl}oxy)-3-fluorophenyl]-6-(3-fluorophenyl)-5-methylpyridine-2-carboxamide 1-oxide (833 mg, 1.50 mmol) was heated to 90° C., and p-toluenesulfonic acid monohydrate (314 mg, 1.65 mmol) was added. When the mixture became a uniform transparent solution, the precipitated solid was collected by filtration and washed with ethanol to give the title compound (870 mg, 80%) as a white solid.

$^1$H-NMR (DMSO-$d_6$, 300 MHz) δ 0.79-0.96 (4H, m), 1.83-1.97 (1H, m), 2.14 (3H, s), 2.29 (3H, s), 7.11 (2H, d, J=7.7 Hz), 7.21-7.41 (4H, m), 7.43-7.66 (5H, m), 7.66-7.76 (2H, m), 7.96-8.10 (2H, m), 8.33 (1H, d, J=8.3 Hz), 8.60 (1H, d, J=1.9 Hz), 11.42 (1H, s), 13.73 (1H, s).

Example 95

Production of N-[4-({2-[(cyclopropylcarbonyl)amino]imidazo[1,2-a]pyridin-6-yl}oxy)-3-s fluorophenyl]-6-methyl-2-oxo-1-phenyl-1,2-dihydropyridine-3-carboxamide

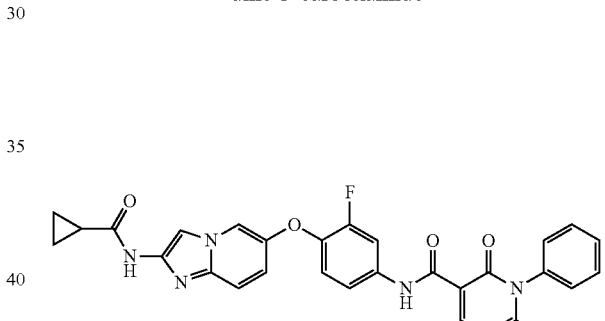

To a solution of N-[6-(4-amino-2-fluorophenoxy)imidazo[1,2-a]pyridin-2-yl]cyclopropanecarboxamide (1.0 g, 3.06 mmol) and 6-methyl-2-oxo-1-phenyl-1,2-dihydropyridine-3-carboxylic acid (843 mg, 3.68 mmol) in N,N-dimethylacetamide (10 mL) were added 1-ethyl-3-(3-dimethylaminopropyl)carbodiimide hydrochloride (822 mg, 4.29 mmol), 1-hydroxybenzotriazole (580 mg, 4.29 mmol) and triethylamine (854 μL, 6.13 mmol), and the mixture was stirred at room temperature for 16 hr. Water (60 mL) was added to the reaction mixture, and the mixture was stirred for 20 min. The precipitate was collected by filtration and washed with water and ethyl acetate. The obtained powder was recrystallized from methyl ethyl ketone/water to give the title compound (1.08 g, 66%) as white crystals.

$^1$H-NMR (DMSO-$d_6$, 300 MHz) δ 0.70-0.85 (4H, m), 1.86-1.96 (1H, m), 2.06 (3H, s), 6.71 (1H, d, J=8.3 Hz), 7.07-7.17 (2H, m), 7.32-7.65 (7H, m), 7.96 (1H, dd, J=13.4, 2.5 Hz), 8.02 (1H, s), 8.42-8.52 (2H, m), 10.93 (1H, s), 12.02 (1H, s).

Formulation Example 1

A pharmaceutical agent containing the compound of the present invention as an active ingredient can be produced, for example, according to the following formulation.

1. Capsule

| | |
|---|---|
| (1) compound obtained in Example 2 | 40 mg |
| (2) lactose | 70 mg |
| (3) crystalline cellulose | 9 mg |
| (4) magnesium stearate | 1 mg |
| 1 capsule | 120 mg |

(1), (2), (3) and ½ of (4) are blended, granulated and the rest of (4) is added thereto. The whole mixture is sealed in a gelatin capsule.

2. Tablet

| | |
|---|---|
| (1) compound obtained in Example 2 | 40 mg |
| (2) lactose | 58 mg |
| (3) cornstarch | 18 mg |
| (4) crystalline cellulose | 3.5 mg |
| (5) magnesium stearate | 0.5 mg |
| 1 tablet | 120 mg |

(1), (2), (3), ⅔ of (4), and ½ of (5) are blended and granulated. The rest of (4) and (5) are added to the granules. The mixture is compression-formed into a tablet.

Formulation Example 2

The compound (50 mg) obtained Example 2 is dissolved in Japanese Pharmacopoeia distilled water for injection (50 mL), and the Japanese Pharmacopoeia distilled water for injection is added to 100 mL. This solution is filtrated under sterile conditions. The solution (1 mL) is taken, filled in a vial for injection under sterile conditions, freeze-dried and sealed.

Experimental Example 1

Cloning of Human Vascular Endothelial Growth Factor Receptor 2 (VEGFR2) Gene and Preparation of Recombinant Baculovirus Human vascular endothelial growth factor receptor 2 (hereinafter to be referred to as VEGFR2) gene was cloned by PCR using cDNA Libraries Human Placenta (Clontech) as a template. The primer used for PCR was prepared from base sequence (Genbank Accession AF035121) information of VEGFR2 gene by adding a base sequence encoding flag peptide and a recognition sequence of the restriction enzyme to a base sequence (2671-4374 of Genbank Accession AF035121) encoding the VEGFR2 intracellular domain region, so that the protein contains an N-terminal Flag tag. The primer base sequence is shown below.

VEGFR2-U:
(SEQ ID NO: 1)
5'-AATTAAGTCGACATGGACTACAAGGATGACGATGACAAGAAGCGG
GCCAATGGAGGGGAACTGAAGACA-3'
and

VEGFR2-L:
(SEQ ID NO: 2)
5'-AATTAAGCATGCTTAAACAGGAGGAGAGCTCAGTGTGGTCCC-3'

The base sequence of primer VEGFR2-U is shown in SEQUENCE LISTING SEQ ID NO: 1, and the base sequence of primer VEGFR2-L is shown in SEQUENCE LISTING SEQ ID NO: 2.

The PCR reaction was conducted using a KOD-plus kit (TOYOBO). The obtained PCR product was electrophoresed on agarose gel (1%), the DNA fragment amplified by PCR was recovered from the gel, and then digested with restriction enzymes Sal I and Sph I. The DNA treated with the restriction enzymes was electrophoresed on agarose gel (1%), and the obtained DNA fragment was recovered and ligated to plasmid pFASTBAC1 (Invitrogen) digested with restriction enzymes Sal I and Sph I to give expression plasmid pFB-VEGFR2. The base sequence of the insert fragment was confirmed and found to be identical with the base sequence (2671-4374 of Genbank Accession AF035121) of VEGFR2 intracellular domain. Furthermore, using BAC-TO-BAC Baculovirus Expression System (Invitrogen), virus stock BAC-VEGFR2 of recombinant baculovirus was prepared.

Experimental Example 2

Preparation of Vascular Endothelial Growth Factor Receptor 2 (VEGFR2) Intracellular Domain Protein SF-21 cells were sown at $1\times10^6$ cells/mL to Sf-900II SFM medium (1 L, Invitrogen) containing 10% fetal bovine serum (trace), 50 mg/L Gentamicin (Invitrogen) and 0.1% Pluronic F-68 (Invitrogen), and shaking culture was performed using a 2 L volume Erlenmeyer flask at 27° C., 100 rpm. After culturing for 24 hrs, recombinant baculovirus BAC-VEGFR2 (13.4 mL) was added to the mixture, and the mixture was further cultured for 3 days. The culture medium was centrifuged at 2,000 rpm for 5 min to give virus-infected cells. The infected cells were washed with a phosphate buffered saline (Invitrogen), centrifuged under the same conditions, and the cells were preserved at −80° C. The cryopreserved cells were thawed in ice, suspended in buffer A (50 mM Tris buffer (30 mL, pH 7.4) containing 20% glycerol, 0.15 M NaCl) supplemented with Complete Protease Inhibitor (Boehringer), and ruptured 3 times with a Polytron homogenizer (Kinematica) at 20,000 rpm for 30 sec. The ruptured medium was clarified by centrifugation at 40,000 rpm for 30 min and filtered with a 0.45 μm filter. The filtrate was passed through a column packed with Anti-FLAG M2 Affinity Gel (4 mL, Sigma) at a flow rate of about 0.5 mL/min. The column was washed with buffer A, and eluted with buffer A containing 100 μg/mL of FLAG peptide. The eluate was concentrated with Vivaspin 20 (Vivascience) having a molecular weight cut off of 30K. The buffer of this concentrate was exchanged using NAP™ 25 column (Amersham Bioscience) equilibrated with buffer A. The fractions containing intracellular domain protein of VEGFR2 were collected, glycerol was added to the final concentration of 50% and cryopreserved at −80° C.

Test Example 1

Determination of Vascular Endothelial Growth Factor Receptor 2 (VEGFR2) Kinase Inhibitory Activity A test compound dissolved in dimethyl sulfoxide (DMSO) was diluted with a buffer (50 mM Tris-HCl (pH 7.5), 5 mM MgCl$_2$, 5 mM MnCl$_2$, 2 mM dithiothreitol, 0.01% Tween-20). To this compound solution (5 µL) was added a buffer (10 µL) containing 50 ng/mL of VEGFR2 intracellular domain protein and 250 ng/mL of biotin labeled polypeptide biotinyl-poly-Glu:Tyr (4:1) (CIS bio International). To the obtained mixture was added a buffer (10 µL) containing ATP (25 µM), the mixture was allowed to react at 25° C. for 5 min and the reaction was quenched with 25 µL of a stop solution (100 mM EDTA disodium salt, 62.5 mM HEPES buffer (pH 7.4), 250 mM NaCl, 0.1% bovine serum albumin, 10 µg/mL AlphaScreen assay streptavidin donor beads (Streptavidin Donor beads: PerkinElmer), 10 µg/mL AlphaScreen assay anti-phosphotyrosine recognition antibody PY-100 binding acceptor beads (Anti-phosphotyrosine (P-Tyr-100) Acceptor beads: PerkinElmer)). The reaction solution was allowed to stand at 25° C. for 16 hrs, and the wells were counted using a plate reader (Fusion™ (PerkinElmer)). The kinase inhibitory rate (%) of the test compound was calculated by the following formula:

Inhibitory rate (%)=(1−(count of test compound−blank)÷(control−blank))×100

The count of the solution reacted without addition of the compound was used as a "control", and the count of the solution without the compound and ATP was used as a "blank".

As shown in Table 1, the inhibitory rates of the compounds of Examples 10, 11, 14, 18, 20, 24, 27, 28, 29, 32, 45, 46, 53, 57, 60, 61, 66, 70, 72, 75, 76, 77, 80, 81, 82, 84, 86, 87, 88, 90, 93 and 94 at 1 µM were not less than 70%.

In addition, the IC$_{50}$ values of the compounds of Examples 10, 11, 14, 18, 20, 24, 27, 28, 29, 32, 45, 46, 53, 57, 60, 61, 66, 70, 72, 75, 76, 77, 80, 81, 82, 84, 86, 87, 88, 90, 93 and 94 were not more than 1 µM.

TABLE 1

| Example | inhibitory rate (%) at 1 µM |
|---|---|
| 10 | 97 |
| 11 | 99 |
| 14 | 99 |
| 18 | 91 |
| 20 | 73 |
| 24 | 100 |
| 27 | 100 |
| 28 | 96 |
| 29 | 100 |
| 32 | 100 |
| 45 | 99 |
| 46 | 100 |
| 53 | 92 |
| 57 | 100 |
| 60 | 98 |
| 61 | 99 |
| 66 | 100 |
| 70 | 99 |
| 72 | 100 |
| 75 | 100 |
| 76 | 99 |
| 77 | 100 |
| 80 | 100 |
| 81 | 99 |
| 82 | 100 |
| 84 | 99 |
| 86 | 100 |
| 87 | 100 |
| 88 | 100 |
| 90 | 100 |
| 93 | 100 |
| 94 | 100 |

Test Example 2

Vascular Endothelial Cell Proliferation Inhibitory Test

Human umbilical vein-derived vascular endothelial cells (HUVEC purchased from KURABO INDUSTRIES LTD.) were cultured in an incubator at 37° C., 5% carbon dioxide in a vascular endothelial cell medium (Invitrogen) containing 3% bovine fetal serum and 2.5 ng/mL basic fibroblast growth factor. To be specific, HUVEC was suspended in a vascular endothelial cell medium containing the aforementioned 3% bovine fetal serum and plated on a 96 well flat bottom plate by 50 µL (3000 cells) each well. After culture overnight, various concentrations of the test substance and 120 ng/mL of vascular endothelial growth factor (VEGF) were dissolved in a vascular endothelial cell medium containing 3% bovine fetal serum and added to each well by 50 µL. After 5 days of culture, a Cell counting kit-8 reagent (DOJINDO LABORATORIES) was added to each well by 10 µL, and the mixture was reacted in an incubator at 37° C., 5% carbon dioxide for 2-3 hr. The absorbance at 450 nm was measured by a microtiter plate reader and the cell proliferation inhibitory activity was determined. Using the absorbance with addition of a test substance at each concentration and based on the nonlinear least-squares analysis using a logistic curve of SAS system NLIN procedure, the concentration of the test substance (IC$_{50}$ value) necessary for showing 50% of the value obtained without addition of the test substance was calculated.

The inhibitory rates of the compounds of Example 10, 11, 14, 18, 20, 24, 27, 28, 29, 32, 45, 46, 53, 57, 60, 61, 66, 70, 72, 75, 76, 77, 80, 81, 82, 84, 86, 87, 88, 90, 93 and 94 at 1 µM were not less than 40%.

In addition, the IC$_{50}$ values of the compounds of Examples 10, 11, 14, 18, 20, 24, 27, 28, 29, 32, 45, 46, 53, 57, 60, 61, 66, 70, 72, 75, 76, 77, 80, 81, 82, 84, 86, 87, 88, 90, 93 and 94 were not more than 2 µM.

TABLE 2

| Example | inhibitory rate (%) at 1 µM |
|---|---|
| 10 | 92 |
| 11 | 92 |
| 14 | 92 |
| 18 | 87 |
| 20 | 48 |
| 24 | 83 |
| 27 | 89 |
| 28 | 85 |
| 29 | 87 |
| 32 | 87 |
| 45 | 89 |
| 46 | 80 |
| 53 | 89 |
| 57 | 83 |
| 60 | 89 |
| 61 | 89 |
| 66 | 94 |
| 70 | 90 |
| 72 | 91 |
| 75 | 91 |
| 76 | 83 |
| 77 | 91 |
| 80 | 88 |
| 81 | 88 |
| 82 | 88 |
| 84 | 91 |
| 86 | 88 |
| 87 | 88 |
| 88 | 99 |
| 90 | 89 |

TABLE 2-continued

| Example | inhibitory rate (%) at 1 μM |
|---|---|
| 93 | 91 |
| 94 | 86 |

Test Example 3

Determination of Hepatocyte Growth Factor Receptor (c-Met) Kinase Inhibitory Activity A test compound dissolved in dimethyl sulfoxide (DMSO) was diluted with a buffer (50 mM Tris-HCl (pH 7.5), 5 mM $MgCl_2$, 5 mM $MnCl_2$, 2 mM dithiothreitol, 0.01% Tween-20). To this compound solution (5 μL) was added a buffer (10 μL) containing 2.5 ng/ml of c-Met intracellular domain protein (Millipore) and 250 ng/mL of biotin labeled polypeptide biotinyl-poly-Glu:Tyr (4:1) (CIS bio International). At 5 min after mixing kinase enzyme and the compound and biotin labeled polypeptide, to the obtained mixture was added a buffer (10 μL) containing ATP (5 μM), the mixture was allowed to react at 25° C. for 10 min and the reaction was quenched with 25 μL of a stop solution (100 mM EDTA disodium salt, 62.5 mM HEPES buffer (pH 7.4), 250 mM NaCl, 0.1% bovine serum albumin, 10 μg/mL AlphaScreen assay streptavidin donor beads (Streptavidin Donor beads: PerkinElmer), 10 μg/mL AlphaScreen assay anti-phosphotyrosine recognition antibody PT-66 binding acceptor beads (Anti-phosphotyrosine (PT-66) Acceptor beads: PerkinElmer)). The reaction solution was allowed to stand at 25° C. for 16 hrs, and the wells were counted using a plate reader (Fusion™ (PerkinElmer)). The kinase inhibitory rate (%) of the test compound was calculated by the following formula:

Inhibitory rate (%)=(1−(count of test compound−blank)÷(control−blank))×100

The count of the solution reacted without addition of the compound was used as a "control", and the count of the solution without the compound and ATP was used as a "blank".

As shown in Table 3, the inhibitory rates of the compounds of Examples 10, 11, 14, 18, 20, 24, 27, 28, 29, 32, 45, 46, 53, 57, 60, 61, 66, 70, 72, 75, 76, 77, 80, 81, 82, 84, 86, 87, 88, 90, 93, and 94 at 1 μM were not less than 80%.

In addition, the $IC_{50}$ values of the compounds of Examples 10, 11, 14, 18, 20, 24, 27, 28, 29, 32, 45, 46, 53, 57, 60, 61, 66, 70, 72, 75, 76, 77, 80, 81, 82, 84, 86, 87, 88, 90, 93 and 94 were not more than 1 μM.

TABLE 3

| Example | inhibitory rate (%) at 1 μM |
|---|---|
| 10 | 99 |
| 11 | 100 |
| 14 | 100 |
| 18 | 100 |
| 20 | 98 |
| 24 | 100 |
| 27 | 100 |
| 28 | 100 |
| 29 | 100 |
| 32 | 100 |
| 45 | 100 |
| 46 | 100 |
| 53 | 100 |
| 57 | 100 |
| 60 | 99 |
| 61 | 100 |
| 66 | 100 |
| 70 | 100 |
| 72 | 100 |
| 75 | 100 |
| 76 | 100 |
| 77 | 100 |
| 80 | 100 |
| 81 | 100 |
| 82 | 100 |
| 84 | 100 |
| 86 | 100 |
| 87 | 100 |
| 88 | 100 |
| 90 | 100 |
| 93 | 100 |
| 94 | 100 |

Test Example 4

Human Gastric Cancer Cell Line MKN-45 Growth Inhibitory Test

Human gastric cancer cell line MKN-45 (RIKEN BioResource Center) was cultured in RPMI1640 (Invitrogen) containing 10% bovine fetal serum in a gas incubator at 37° C., 5% $CO_2$. MKN-45 cells were treated with trypsin/EDTA and recovered. The cells were suspended in RPMI1640 containing 0.3% bovine fetal serum, plated on a 96 well flat bottom plate at a cells density of 3000 cells/50 μL per well. After culturing overnight, various concentrations of test substance were dissolved in RPMI1640 containing 0.3% bovine fetal serum and added to each well by 50 μL. After culture for 3 days, a Cell counting kit-8 reagent (DOJINDO LABORATORIES) was added to each well by 10 μL, and reacted in an incubator at 37° C., 5% $CO_2$ for 2-3 hr. After the reaction, the absorbance of each well at 450 nm was measured by a microtiter plate reader. The concentration of a test substance necessary for inhibiting the growth by 50% ($IC_{50}$ value) was calculated using a cell proliferation rate with addition of the test substance at each concentration and according to the nonlinear regression analysis using GraphPad Prism [Sigmoidal dose response (variable slope)]. The cell proliferation rate (%) with addition of a test substance at each concentration was calculated by the following formula. As a positive control (100% growth), dimethyl sulfoxide was added instead of a test substance. As a negative control (0% growth), the compound of Reference Example 136 (WO2005/030140, Entry 104), which is a known c-Met inhibitor, was added in large excess (10 μM) instead of a test substance.

As shown in Table 4, the inhibitory rates of the compounds of Examples 10, 11, 14, 18, 20, 24, 27, 28, 29, 32, 45, 46, 53, 57, 60, 61, 66, 70, 72, 75, 76, 77, 80, 81, 82, 84, 86, 87, 88, 90, 93 and 94 at 1 μM were not less than 80%.

In addition, the $IC_{50}$ values of the compounds of Examples 10, 11, 14, 18, 20, 24, 27, 28, 29, 32, 45, 46, 53, 57, 60, 61, 66, 70, 72, 75, 76, 77, 80, 81, 82, 84, 86, 87, 88, 90, 93 and 94 were not more than 1 μM.

TABLE 4

| Example | inhibitory rate (%) at 1 μM |
|---|---|
| 10 | 100 |
| 11 | 100 |

TABLE 4-continued

| Example | inhibitory rate (%) at 1 μM |
|---|---|
| 14 | 100 |
| 18 | 96 |
| 20 | 99 |
| 24 | 91 |
| 27 | 100 |
| 28 | 100 |
| 29 | 100 |
| 32 | 97 |
| 45 | 99 |
| 46 | 100 |
| 53 | 97 |
| 57 | 98 |
| 60 | 100 |
| 61 | 100 |
| 66 | 88 |
| 70 | 97 |
| 72 | 99 |
| 75 | 96 |
| 76 | 99 |
| 77 | 92 |
| 80 | 82 |
| 81 | 89 |
| 82 | 100 |
| 84 | 93 |
| 86 | 100 |
| 87 | 100 |
| 88 | 93 |
| 90 | 95 |
| 93 | 99 |
| 94 | 99 |

TABLE 5

| Example | dose (mg/kg) | tumor growth rate (%) |
|---|---|---|
| 15 | 2 | 85 |
| 32 | 2 | 14 |
| 63 | 1 | 24 |
| 87 | 2 | 17 |
| 88 | 2 | 17 |

TABLE 6

| Example | dose (mg/kg) | tumor growth rate (%) |
|---|---|---|
| 15 | 2 | 17 |
| 32 | 2 | <0 |
| 63 | 2 | <0 |
| 87 | 2 | <0 |
| 88 | 2 | <0 |

Test Example 5

Antitumor Test (MKN-45 and MV-4-11)

Cancer cells were cultured in a culture medium containing 10% bovine fetal serum in an incubator at 37° C., 5% $CO_2$. MKN-45 cells were treated with trypsin/EDTA and isolated. MKN-45 and MV-4-11 cells were washed with HBSS (HANK's Balanced Saline Solution). When MKN-45 cells were transplanted, they were adjusted with HBSS to a cell density of $1.2 \times 10^8$ cells/mL, and transplanted by subcutaneous injection of 0.05 mL of a mixed suspension ($3 \times 10^6$ cells) of the cell suspension and the same amount of Matrigel into the abdomen of 6 or 7-week-old female nude mouse (BALB/c nu/nu, CLEA Japan, Inc.). When MV-4-11 cells were transplanted, they were adjusted with HESS to a cell density of $1.2 \times 10^8$ cells/mL, and transplanted by subcutaneous injection of 0.05 mL of a mixed suspension ($3 \times 10^6$ cells) of the cell suspension and the same amount of Matrigel into the abdomen of 7-week-old female nude mouse (BALB/c nu/nu, CLEA Japan, Inc.). When the average tumor volume reached 100-250 $mm^3$, the mice were grouped, and various doses of test substance were orally administered for 14 consecutive days starting from the next day. The length of the major axis and the length of the minor axis of the tumor were measured over time and the tumor volume was calculated by tumor volume=major axis length×minor axis length×minor axis length×0.5. The ratio of an increase in the average tumor volume of the control group to an increase in the average tumor volume of the drug administration group was taken as the tumor growth rate (%) of the drug administration group. Table 5 showed MKN-45 tumor growth rate (%) and table 6 showed MV-4-11 tumor growth rate (%).

Test Example 6

Determination of Fms Like Tyrosine Kinase 3 (FLT3) Kinase Inhibitory Activity A test compound dissolved in dimethyl sulfoxide (DMSO) was diluted with a buffer (50 mM Tris-HCl (pH 7.5), 5 mM $MgCl_2$, 5 mM $MnCl_2$, 2 mM dithiothreitol, 0.01% Tween-20). To this compound solution (5 μL) was added a buffer (10 μL) containing 7.5 ng/ml of FLT3 intracellular domain protein (Millipore) and 250 ng/mL of biotin labeled polypeptide biotinyl-poly-Glu:Tyr (4:1) (CIS bio International). At 5 min after mixing kinase enzyme and the compound and biotin labeled polypeptide, to the obtained mixture was added a buffer (10 μL) containing ATP (5 μM), the mixture was allowed to react at 25° C. for 10 min and the reaction was quenched with 25 μL of a stop solution (100 mM EDTA disodium salt, 62.5 mM HEPES buffer (pH 7.4), 250 mM NaCl, 0.1% bovine serum albumin, 10 μg/mL AlphaScreen assay streptavidin donor beads (Streptavidin Donor Beads: PerkinElmer), 10 μg/mL AlphaScreen assay anti-phosphotyrosine recognition antibody Y-100 binding acceptor beads (Anti-phosphotyrosine (P-Tyr-100) Acceptor beads: PerkinElmer)). The reaction solution was allowed to stand at 25° C. for 16 hrs, and the wells were counted using a plate reader (Envision™ (PerkinElmer)). The kinase inhibitory rate (%) of the test compound was calculated by the following formula:

Inhibitory rate (%)=(1−(count of test compound−blank)÷(control−blank))×100

The count of the solution reacted without addition of the compound was used as a "control", and the count of the solution without the compound and ATP was used as a "blank".

As shown in Table 7, the inhibitory rates of the compounds of Examples 10, 11, 14, 18, 24, 27, 28, 29, 32, 45, 46, 53, 57, 60, 61, 66, 70, 72, 75, 76, 77, 80, 81, 82, 84, 86, 87, 88, 90, 93 and 94 at 1 μM were not less than 50%.

In addition, the $IC_{50}$ values of the compounds of Examples 10, 11, 14, 18, 24, 27, 28, 29, 32, 45, 46, 53, 57, 60, 61, 66, 70, 72, 75, 76, 77, 80, 81, 82, 84, 86, 87, 88, 90, 93 and 94 were not more than 1 μM.

TABLE 7

| Example | inhibitory rate (%) at 1 μM |
|---|---|
| 10 | 63 |
| 11 | 88 |
| 14 | 88 |
| 18 | 55 |
| 24 | 87 |
| 27 | 73 |
| 28 | 63 |
| 29 | 96 |
| 32 | 75 |
| 45 | 93 |
| 46 | 92 |
| 53 | 66 |
| 57 | 93 |
| 60 | 89 |
| 61 | 71 |
| 66 | 75 |
| 70 | 94 |
| 72 | 91 |
| 75 | 92 |
| 76 | 86 |
| 77 | 96 |
| 80 | 93 |
| 81 | 90 |
| 82 | 79 |
| 84 | 96 |
| 86 | 97 |
| 87 | 96 |
| 88 | 96 |
| 90 | 69 |
| 93 | 93 |
| 94 | 94 |

Test Example 7

Determination of TIE2 Kinase Inhibitory Activity

A test compound dissolved in dimethyl sulfoxide (DMSO) was diluted with a buffer (50 mM Tris-HCl (pH 7.5), 5 mM $MgCl_2$, 5 mM $MnCl_2$, 2 mM dithiothreitol, 0.01% Tween-20). A buffer (10 μL) containing 50 ng/mL of Tie2 intracellular domain protein (Millipore) and 250 ng/ml, of biotin labeled polypeptide biotinyl-poly-Glu:Tyr (4:1) (CIS bio International) was added to the compound solution (5 μL). At 5 min from the mixing of the kinase enzyme, the compound and the biotin labeled polypeptide, a buffer (10 μL) containing 5 μM ATP was added, and the mixture was reacted at 25° C. for 10 min. The reaction was quenched by the addition of 25 μL of a stop solution (100 mM EDTA disodium salt, 62.5 mM HEPES buffer (pH 7.4), 250 mM NaCl, 0.1% bovine serum albumin, 10 μg/ml AlphaScreen assay streptavidin donor beads (Streptavidin Donor beads: PerkinElmer), 10 μg/ml, AlphaScreen assay anti-phosphotyrosine recognition antibody PT-66 binding acceptor beads (Anti-phosphotyrosine (PT-66) Acceptor beads: PerkinElmer)). The reaction solution was allowed to stand at 25° C. for 16 hrs, and the cells were counted using a plate reader (Fusion™ (PerkinElmer)). The kinase inhibitory rate (%) of the test compound was calculated by the following formula:

Inhibitory rate (%)=(1−(count of test compound−blank)÷(control−blank))×100

The count of the solution reacted without addition of the compound was used as a "control", and the count of the solution without the compound and ATP was used as a "blank".

As shown in Table 8, the inhibitory rates of the compounds of Examples 10, 11, 14, 18, 24, 27, 28, 29, 32, 45, 46, 53, 57, 60, 61, 66, 70, 72, 75, 76, 77, 80, 81, 82, 84, 86, 87, 88, 90, 93 and 94 at 1 μM were not less than 50%.

In addition, the $IC_{50}$ values of the compounds of Examples 10, 11, 14, 18, 24, 27, 28, 29, 32, 45, 46, 53, 57, 60, 61, 66, 70, 72, 75, 76, 77, 80, 81, 82, 84, 86, 87, 88, 90, 93 and 94 were not more than 1 μM.

TABLE 8

| Example | inhibitory rate (%) at 1 μM |
|---|---|
| 10 | 99 |
| 11 | 100 |
| 14 | 98 |
| 18 | 77 |
| 24 | 100 |
| 27 | 100 |
| 28 | 100 |
| 29 | 100 |
| 32 | 99 |
| 45 | 100 |
| 46 | 100 |
| 53 | 56 |
| 57 | 100 |
| 60 | 100 |
| 61 | 99 |
| 66 | 100 |
| 70 | 99 |
| 72 | 100 |
| 75 | 100 |
| 76 | 100 |
| 77 | 100 |
| 80 | 100 |
| 81 | 100 |
| 82 | 100 |
| 84 | 100 |
| 86 | 100 |
| 87 | 100 |
| 88 | 100 |
| 90 | 100 |
| 93 | 100 |
| 94 | 100 |

Test Example 8

Human Blood Cell Cancer Cell Line MV-4-11 Growth Inhibitory Test

Human blood cell cancer cell line MV-4-11 (ATCC) was cultured in IMDM (Invitrogen) containing 10% bovine fetal serum in an incubator at 37° C., 5% $CO_2$. MV-4-11 cells were treated with trypsin/EDTA and recovered. The cells were suspended in IMDM containing 10% bovine fetal serum, plated on a 96 well flat bottom plate at a cells density of 30,000 cells/50 μL per well. After culturing overnight, various concentrations of test substance were dissolved in IMDM containing 10% bovine fetal serum and added to each well by 50 μL. After culture for 3 days, a Cell counting kit-8 reagent (DOJINDO LABORATORIES) was added to each well by 10 μL, and reacted in an incubator at 37° C., 5% $CO_2$ for 2-3 hr. After the reaction, the absorbance of each well at 450 nm was measured by a microtiter plate reader. The concentration of a test substance necessary for inhibiting the growth by 50% ($IC_{50}$ value) was calculated using a cell proliferation rate with addition of the test substance at each concentration and according to the nonlinear regression analysis using GraphPad Prism [Sigmoidal dose response (variable slope)].

As shown in Table 9, the inhibitory rates of the compounds of Examples 10, 11, 14, 18, 20, 24, 27, 28, 29, 32, 45, 46, 53, 57, 60, 61, 66, 70, 72, 75, 76, 77, 80, 81, 82, 84, 86, 87, 88, 90, 93 and 94 at 1 μM were not less than 90%.

The $IC_{50}$ values of the compounds of Examples 10, 11, 14, 18, 20, 24, 27, 28, 29, 32, 45, 46, 53, 57, 60, 61, 66, 70, 72, 75, 76, 77, 80, 81, 82, 84, 86, 87, 88, 90, 93 and 94 were not more than 1 μM.

TABLE 9

| Example | inhibitory rate (%) at 1 μM |
|---|---|
| 10 | 96 |
| 11 | 97 |
| 14 | 97 |
| 18 | 96 |
| 20 | 96 |
| 24 | 98 |
| 27 | 96 |
| 28 | 97 |
| 29 | 97 |
| 32 | 92 |
| 45 | 97 |
| 46 | 97 |
| 53 | 97 |
| 57 | 97 |
| 60 | 97 |
| 61 | 97 |
| 66 | 98 |
| 70 | 98 |
| 72 | 97 |
| 75 | 97 |
| 76 | 97 |
| 77 | 97 |
| 80 | 97 |
| 81 | 98 |
| 82 | 97 |
| 84 | 98 |
| 86 | 91 |
| 87 | 92 |
| 88 | 91 |
| 90 | 92 |
| 93 | 91 |
| 94 | 92 |

SEQUENCE LISTING FREE TEXT

[SEQ ID NO: 1]

Designed Oligonucleotide Primer to Amplify DNA Encoding Human VEGFR2

[SEQ ID NO: 2]

Designed Oligonucleotide Primer to Amplify DNA Encoding Human VEGFR2

INDUSTRIAL APPLICABILITY

The compound of the present invention show superior inhibitory activity on kinases such as vascular endothelial growth factor receptor, hepatocyte growth factor receptor, angiopoietin receptor (TIE2), Fms Like Tyrosine Kinase 3 (FLT3) and the like. Therefore, a clinically useful agent for the prophylaxis or treatment of diseases related to the action of vascular endothelial growth factor, hepatocyte growth factor, angiopoietin, FLT3 ligand (FL) in the living body (e.g., cancer etc.) can be provided. Moreover, since the compound of the present invention are also superior in efficacy expression, pharmacokinetics, solubility, interaction with other pharmaceutical products, safety and stability, they are useful as pharmaceutical agents.

This application is based on patent application Nos. 2008-122789 and 2008-306661 filed in Japan, the contents of which are incorporated in full herein by this reference.

---

The invention claimed is:
1. A compound represented by the formula

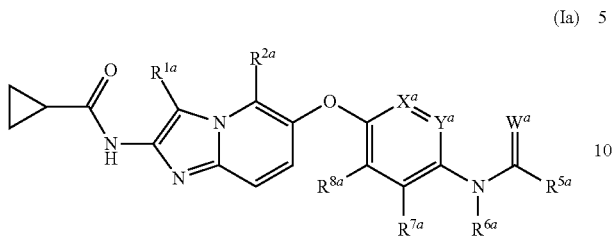

(Ia)

wherein $R^{1a}$ and $R^{2a}$ are the same or different and each is
(1) a hydrogen atom,
(2) a halogen atom,
(3) a group bonded via a carbon atom,
(4) a group bonded via a nitrogen atom,
(5) a group bonded via an oxygen atom, or
(6) a group bonded via a sulfur atom;
$W^a$ is O or S;
$X^a$ is $CR^{3a}$ ($R^{3a}$ is a hydrogen atom, a halogen atom or $C_{1-6}$ alkyl), or N;
$Y^a$ is $CR^{4a}$ ($R^{4a}$ is a hydrogen atom, a halogen atom or $C_{1-6}$ alkyl), or N;
$R^{5a}$ is
  (1) $C_{3-6}$ cycloalkyl optionally having one $C_{6-10}$ arylaminocarbonyl optionally having 1 to 3 substituents selected from a halogen atom and $C_{1-6}$ alkyl,
  (2) $C_{1-6}$ alkyl-carbonylamino optionally having one $C_{6-10}$ aryl,
  (3) $C_{1-6}$ alkoxy optionally having one $C_{6-10}$ aryl, or
  (4) a nitrogen-containing heterocyclic group or an N-oxide thereof optionally having 1 to 4 substituents selected from
    (a) $C_{6-10}$ aryl optionally having 1 to 3 substituents selected from a halogen atom and $C_{1-6}$ alkyl,
    (b) $C_{1-6}$ alkyl optionally having 1 to 3 halogen atoms, and
    (c) oxo;
$R^{6a}$ is a hydrogen atom;
$R^{7a}$ is a hydrogen atom, a halogen atom or $C_{1-6}$ alkyl;
$R^{8a}$ is a hydrogen atom, a halogen atom or $C_{1-6}$ alkyl, or a salt thereof.

2. The compound of claim 1 wherein
$R^{1a}$ is a hydrogen atom, a fluorine atom or methyl;
$R^{2a}$ is a hydrogen atom;
$W^a$ is O or S;
$X^a$ is CH, CF, CCl, C(CH$_3$) or N;
$Y^a$ is CH, CF, CCl, C(CH$_3$) or N;
$R^{5a}$ is
  (1) cyclopropyl optionally having one phenylaminocarbonyl optionally having 1 to 3 substituents selected from a fluorine atom and methyl,
  (2) acetylamino optionally having one phenyl,
  (3) methoxy optionally having one phenyl,
  (4) tert-butoxy, or
  (5) a nitrogen-containing heterocyclic group or an N-oxide thereof optionally having 1 to 4 substituents selected from
    (a) phenyl optionally having 1 to 3 substituents selected from a fluorine atom, a chlorine atom, a bromine atom, methyl and isopropyl,
    (b) methyl optionally having 1 to 3 fluorine atoms,
    (c) ethyl optionally having 1 to 3 fluorine atoms,
    (d) isopropyl, and
    (e) oxo;
$R^{6a}$ is a hydrogen atom;
$R^{7a}$ is a hydrogen atom; and
$R^{8a}$ is a hydrogen atom.

3. N-[4-({2-[(Cyclopropylcarbonyl)amino]imidazo[1,2-a]pyridin-6-yl}oxy)-3-fluorophenyl]-N'-phenylcyclopropane-1,1-dicarboxamide or a salt thereof.

4. N-[4-({2-[(Cyclopropylcarbonyl)amino]imidazo[1,2-a]pyridin-6-yl}oxy)-3-fluorophenyl]-6-methyl-2-oxo-1-phenyl-1,2-dihydropyridine-3-carboxamide or a salt thereof.

5. N-[4-({2-[(Cyclopropylcarbonyl)amino]imidazo[1,2-a]pyridin-6-yl}oxy)-3-fluorophenyl]-1-(4-fluorophenyl)-6-methyl-2-oxo-1,2-dihydropyridine-3-carboxamide or a salt thereof.

6. N-[5-({2-[(Cyclopropylcarbonyl)amino]imidazo[1,2-a]pyridin-6-yl}oxy)pyridin-2-yl]-6-(4-fluorophenyl)-5-methylpyridine-2-carboxamide 1-oxide or a salt thereof.

7. A pharmaceutical agent comprising the compound of claim 1 and a pharmacologically acceptable carrier.

8. The pharmaceutical agent of claim 7, which is a kinase inhibitor.

* * * * *

SEQUENCE LISTING

```
<160> NUMBER OF SEQ ID NOS: 2

<210> SEQ ID NO 1
<211> LENGTH: 69
<212> TYPE: DNA
<213> ORGANISM: Artificial Sequence
<220> FEATURE:
<223> OTHER INFORMATION: Designed oligonucleotide primer to amplify DNA
      encoding human VEGFR2

<400> SEQUENCE: 1
aattaagtcg acatggacta caaggatgac gatgacaaga agcgggccaa tggaggggaa      60
ctgaagaca                                                              69

<210> SEQ ID NO 2
<211> LENGTH: 42
<212> TYPE: DNA
<213> ORGANISM: Artificial Sequence
<220> FEATURE:
<223> OTHER INFORMATION: Designed oligonucleotide primer to amplify DNA
      encoding human VEGFR2

<400> SEQUENCE: 2
aattaagcat gcttaaacag gaggagagct cagtgtggtc cc                         42
```